(12) United States Patent
Fukuda

(10) Patent No.: US 7,462,633 B2
(45) Date of Patent: Dec. 9, 2008

(54) CYCLOPROPYL GROUP SUBSTITUTED OXAZOLIDINONE ANTIBIOTICS AND DERIVATIVES THEREOF

(75) Inventor: Yasumichi Fukuda, Tochigi (JP)

(73) Assignees: Merck & Co., Inc., Rahway, NJ (US); Kyorin Pharmaceutical Co., Ltd., Tokyo (JP)

( * ) Notice: Subject to any disclaimer, the term of this patent is extended or adjusted under 35 U.S.C. 154(b) by 517 days.

(21) Appl. No.: 10/878,637

(22) Filed: Jun. 29, 2004

(65) Prior Publication Data

US 2005/0038092 A1 Feb. 17, 2005

Related U.S. Application Data

(60) Provisional application No. 60/546,984, filed on Feb. 24, 2004, provisional application No. 60/483,904, filed on Jul. 2, 2003.

(51) Int. Cl.
- A61K 31/44 (2006.01)
- A61K 31/42 (2006.01)
- C07D 413/00 (2006.01)
- C07D 498/00 (2006.01)

(52) U.S. Cl. .................... 514/340; 514/376; 546/271.4; 548/229

(58) Field of Classification Search ................. 514/340, 514/376; 546/271.4; 548/229
See application file for complete search history.

(56) References Cited

U.S. PATENT DOCUMENTS

| | | | |
|---|---|---|---|
| 4,053,593 | A | 10/1977 | Frumoff |
| 5,523,403 | A | 6/1996 | Barbachyn |
| 5,565,571 | A | 10/1996 | Barbachyn et al. |
| 5,627,181 | A | 5/1997 | Riedl et al. |
| 5,736,545 | A | 4/1998 | Gadwood et al. |
| 6,069,160 | A | 5/2000 | Stolle et al. |
| 6,686,363 | B2 | 2/2004 | Fukuda |
| 6,689,779 | B2 * | 2/2004 | Lee et al. .................. 514/235.8 |
| 7,192,974 | B2 | 3/2007 | Gravestock et al. |
| 2002/0103186 | A1 | 8/2002 | Mehta et al. |
| 2002/0161029 | A1 | 10/2002 | Paget et al. |
| 2003/0125367 | A1 | 7/2003 | Fukuda et al. |
| 2003/0225107 | A1 | 12/2003 | Fukuda et al. |
| 2004/0147760 | A1 | 7/2004 | Thomas et al. |
| 2005/0203144 | A1 | 9/2005 | Fukuda et al. |
| 2007/0185132 | A1 | 8/2007 | Fukuda |
| 2007/0203187 | A1 | 8/2007 | Fukuda |
| 2007/0293493 | A1 | 12/2007 | Hammond et al. |

FOREIGN PATENT DOCUMENTS

| | | |
|---|---|---|
| CA | 2 415 965 A1 | 1/2002 |
| EP | 0 352 0 781 A3 | 1/1990 |
| EP | 0 352 0781 A2 | 1/1990 |
| EP | 0 657 440 A1 | 6/1995 |
| WO | WO 94/13649 | 6/1994 |
| WO | WO 96/35691 | 11/1996 |
| WO | WO 01/58885 A1 | 8/2001 |
| WO | WO 01/81350 A1 | 11/2001 |
| WO | WO 01/94342 A1 | 12/2001 |
| WO | WO 02/06278 A1 | 1/2002 |
| WO | WO 02/051819 A2 | 7/2002 |
| WO | WO 02/059116 A2 | 8/2002 |
| WO | WO 03/027083 A1 | 4/2003 |
| WO | WO 03/048136 A1 | 6/2003 |
| WO | WO 03/063862 A1 | 8/2003 |
| WO | WO 03/072553 A1 | 9/2003 |
| WO | WO 03/072575 A1 | 9/2003 |
| WO | WO 03/097059 A1 | 11/2003 |
| WO | WO 2004/033451 A1 | 4/2004 |
| WO | WO 2004/048350 | 6/2004 |
| WO | WO 2004/089943 A1 | 10/2004 |
| WO | WO 2004/099199 A1 | 11/2004 |
| WO | WO 2005/005398 | 1/2005 |
| WO | WO 2005/005399 | 1/2005 |
| WO | WO 2005/005420 | 1/2005 |
| WO | WO 2005/005422 | 1/2005 |

OTHER PUBLICATIONS

CAPLUS 2003:576097; 556801-55-9, 556801-57-1, 556801-58-2, 556801-59-3, 556801-62-8, 556801-63-9, 556801-64-0; 556801-61-7P.
Riedl et al., Exp. Opin. Ther. Patents (1999) 9(5).
Ford et al., Trends in Microbilogy, 196. vol. 5, May 1997.
Wolff, Manfred, Burger's Medicinal Chemistry 5th Ed. Part I, John Wiley & Sons, 1995, pp. 975-77
Banker, GS, et al., "Modern Pharmaceuticals" 3rd Ed. Marcel Dekker, New York, 1996, pp. 451 & 596.

(Continued)

*Primary Examiner*—Golam M. M. Shameem
*Assistant Examiner*—Susannah Chung
(74) *Attorney, Agent, or Firm*—McDermott Will & Emery LLP

(57) ABSTRACT

This invention relates to new oxazolidinones having a cyclopropyl moiety, which are effective against aerobic and anerobic pathogens such as multi-resistant *staphylococci, streptococci* and *enterococci, Bacteroides* spp., *Clostridia* spp. species, as well as acid-fast organisms such as *Mycobacterium tuberculosis* and other mycobacterial species.

The compounds are represented by structural formula I:

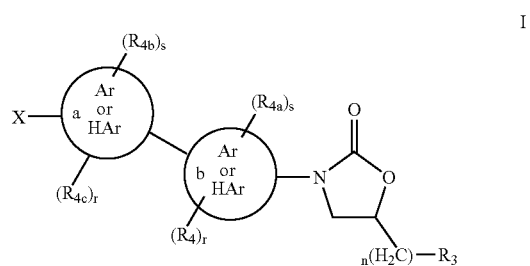

its enantiomer, diastereomer, or pharmaceutically acceptable salt or ester thereof.

29 Claims, No Drawings

OTHER PUBLICATIONS

West, Anthony R., Solid State Chemistry and its Applications, Wiley, New York, 1988, pp. 358 & 365.

Fleming et al., Expert Opinion on Pharmacotherapy, 2007, 8(4) 415-426.

Vippangunta et al., Advanced Drug delivery Reviews, 2001, 48: 3-26.

March, Jerry, Advanced Org. Chemistry, 1992, New York; John Wiley & Sons, pp. 771 & 1224.

Gladstone et al., Newer Formations of the Tripants, Drugs, 2003, 63(21) pp. 2285-2305.

Carey et al., Advanced Org. Chemistry, 3rd Ed. 1990, New York: Plenum Press, pp. 617-618.

Ammazzolorso et al., II Farmaco, 2004, pp. 686-690.

CAPLUS Database aceesion # 139: 85332.

Database Caplus, Chemical Abstracts Service, Columbus Ohio, US; XP002302363, retrieved from CAPLUS accension No. 2003:576097, Database accesion No. 139:85332 (Equivalent to CN1355165).

M.D. Mashkovsy, "Medicaments" part 1, p. 8 (Moscow 1993).

\* cited by examiner

CYCLOPROPYL GROUP SUBSTITUTED OXAZOLIDINONE ANTIBIOTICS AND DERIVATIVES THEREOF

CROSS REFERENCE TO RELATED APPLICATIONS

This application claims the benefit of U.S. Provisional Application No. 60/483,904, filed Jul. 2, 2003, entitled CYCLOPROPYL GROUP SUBSTITUTED OXAZOLIDINONE ANTIBIOTICS AND DERIVATIVES THEREOF, and U.S. Provisional Application No. 60/546,984, filed Feb. 24, 2004, entitled CYCLOPROPYL GROUP SUBSTITUTED OXAZOLIDINONE ANTIBIOTICS AND DERIVATIVES THEREOF, which are hereby incorporated herein by reference it their entirety.

BACKGROUND OF THE INVENTION

Oxazolidinones represent the first new class of antibacterials to be developed since the quinolones. The oxazolidinones are synthetic antibacterial compounds that are orally or intravenously active against problematic multidrug resistant Gram positive organisms and are not cross-resistant with other antibiotics. See Riedl et al, Recent Developments with Oxazolidinone Antibiotics, *Exp. Opin. Ther. Patents* (1999) 9(5), Ford et al., Oxazolidinones: New Antibacterial Agents, *Trends in Microbiology* 196 Vol.5, No. 5, May 1997 and WO 96/35691. See also WO 03/063862, WO 01/81350, WO 01/94342, WO 03/072553, EP 0352781 and U.S. Pat. Nos. 5,565,571 and 4,053,593.

This invention relates to new oxazolidinones having a cyclopropyl moiety, which are effective against aerobic and anerobic pathogens such as multi-resistant *staphylococci, streptococci* and *enterococci, Bacteroides* spp., *Clostridia* spp. species, as well as acid-fast organisms such as *Mycobacterium tuberculosis* and other mycobacterial species.

SUMMARY OF THE INVENTION

The present invention relates to compounds of formula I:

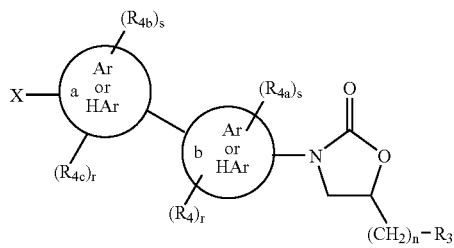

I its enantiomer, diastereomer, or pharmaceutically acceptable salt, hydrate or prodrug thereof wherein:

$R_1$ represents
  i) hydrogen,
  ii) $(CH_2)_n NR_5 R_6$,
  iii) $CR_7 R_8 R_9$, $C(R)_2 OR_{14}$, $CH_2 NHR_{14}$,
  iv) $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $NRCO_2R$, $(C=NH)R_7$, $N(R_{13})C(=X_1)N(R_{13})_2$, $COOR_{13}$, $SO_2 R_{14}$, $N(R_{13})SO_2 R_{14}$, $N(R_{13})COR_{14}$,
  v) $(C_{1-6}alkyl)CN$, $CN$, $CH=C(R)_2$, $(CH_2)_p OH$, $C(=O)CHR_{13}$, $C(=NR_{13})R_{13}$, $NR_{10}C(=X_1)R_{13}$; or
  vi) $C_{5-10}$ heterocycle optionally substituted with 1-3 groups of $R_7$, which may be attached through either a carbon or a heteroatom;

X represents

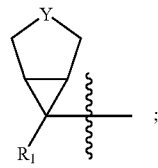

or a $C_{5-10}$ heteroaryl represented by

which represents an optionally substituted aromatic heterocyclic group containing 1 to 4 nitrogen atoms and at least one double bond, and which is connected through a bond on any nitrogen said heteroaryl optionally substituted with 1 to 3 substitutents selected from $R_7$ Y represents $NR^*$, O, CN, or $S(O)p$;

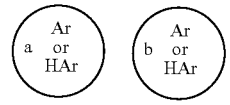

represents aryl or heteroaryl, heterocycle, heterocyclyl or heterocyclic;

$R_x$ represents hydrogen or $C_{1-6}$ alkyl;

$R_3$ represent $NR(C=X_2)R_{12}$, $NR^*R_{12}$, $C_{6-10}$ aryl, or $—(O)_n$ $C_{5-10}$ heterocyclyl which may be attached through either a carbon or a heteroatom; said aryl and heterocyclyl optionally substituted with 1-3 groups of $R_7$, $R_4$, $R_{4a}$, $R_{4b}$, and $R_{4c}$ independently represent
  i) hydrogen,
  ii) halogen,
  iii) $C_{1-6}$ alkoxy, or
  iv) $C_{1-6}$ alkyl;

r and s independently are 1-3, with the provision that when $(R_{4a})_s$ and $(R_4)_r$ or $(R_{4b})$ and $(R_{4c})_s$ are attached to an Ar or HAr ring the sum of r and s is less than or equal to 4;

$R_5$ and $R_6$ independently represent
  i) hydrogen,
  ii) $C_{1-6}$ alkyl optionally substituted with 1-3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1-3 halogen, CN, OH, $CF_3$, $C_{1-6}$ alkyl or $C_{1-6}$ alkoxy;
  iii) $C_{1-6}$ acyl optionally substituted with 1-3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1-3 groups of halo, OH, CN, $C_{1-6}$ alkoxy, amino, $C_{1-6}$ acylamino, $CF_3$ or $C_{1-6}$ alkyl;

iv) $C_{1-6}$ alkylsulfonyl optionally substituted with 1-3 groups of halogen, OH, $C_{1-6}$ alkoxy, amino, hydroxylamino, alkoxylamino, $C_{1-6}$ acyloxy, or phenyl; said phenyl optionally substituted with 1-3 groups of halo, OH, $C_{1-6}$ alkoxy, amino, $C_{1-6}$ acylamino, $CF_3$ or $C_{1-6}$ alkyl;

v) arylsulfonyl optionally substituted with 1-3 of halogen, $C_{1-6}$ alkoxy, OH or $C_{1-6}$ alkyl;

vi) $C_{1-6}$ alkoxycarbonyl optionally substituted with 1-3 of halogen, OH, $C_{1-6}$ alkoxy, $C_{1-6}$ acyloxy, or phenyl, said phenyl optionally substituted with 1-3 groups of halo, OH, $C_{1-6}$ alkoxy, amino, $C_{1-6}$ acylamino, $CF_3$ or $C_{1-6}$ alkyl;

vii) aminocarbonyl, $C_{1-6}$ alkylaminocarbonyl or $C_{1-6}$ dialkylaminocarbonyl, said alkyl groups optionally substituted with 1-3 groups of halogen, OH, $C_{1-6}$ alkoxy or phenyl viii) five to six membered heterocycles optionally substituted with 1-3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1-3 groups of halogen, or $C_{1-6}$ alkoxy;

ix) $C_{3-6}$ cycloalkylcarbonyl optionally substituted with 1-3 groups of halogen, OH, $C_{1-6}$ alkoxy or CN;

x) benzoyl optionally substituted with 1-3 groups of halogen, OH, $C_{1-6}$ alkoxy, $C_{1-6}$ alkyl, $CF_3$, $C_{1-6}$ alkanoyl, amino or $C_{1-6}$ acylamino;

xi) pyrrolylcarbonyl optionally substituted with 1-3 of $C_{1-6}$ alkyl;

xii) $C_{1-2}$ acyloxyacetyl where the acyl is optionally substituted with amino, $C_{1-6}$ alkylamino, $C_{1-6}$ dialkylamino, 4-morpholino, 4-aminophenyl, 4-(dialkylamino)phenyl, 4-(glycylamino)phenyl; or $R_5$ and $R_6$ taken together with any intervening atoms can form a 3 to 7 membered heterocyclic ring containing carbon atoms and 1-2 heteroatoms independently chosen from O, S, SO, $SO_2$, N, or $NR_8$;

$R_7$ represent
i) hydrogen, halogen, $(CH2)_pC_{5-10}$ heterocyclyl, CN, $CO_2R$, $CON(R)_2$, CHO, $(CH_2)_{0-3}NHAc$, C(=NOR), OH, $C_{1-6}$ alkoxy, $C_{1-6}$ alkyl, alkenyl, hydroxy $C_{1-6}$ alkyl, $(CH_2)_{1-3}NHC(O)C_{1-6}$ alkyl, $(CH_2)_{0-3}N(C_{1-6}$ alkyl$)_2$, $NHCO_2R$, —$OCOC_{1-6}$ alkyl;

ii) $(CH_2)_n$amino, $(CH_2)_nC1-6$ alkylamino, $C_{1-6}$ acylamino, $C_{1-6}$ dialkylamino, hydroxylamino or $C_{1-2}$ alkoxyamino all of which can be optionally substituted on the nitrogen with $C_{1-6}$ acyl, $C_{1-6}$ alkylsulfonyl or $C_{1-6}$ alkoxycarbonyl, said acyl and alkylsulfonyl optionally substituted with 1-2 of halogen or OH;

$R_8$ and $R_9$ independently represent
i) H, CN,
ii) $C_{1-6}$ alkyl optionally substituted with 1-3 halogen, CN, OH, $C_{1-6}$ alkoxy, $C_{1-6}$ acyloxy, or amino,
iii) phenyl optionally substituted with 1-3 groups of halogen, OH, $C_{1-6}$ alkoxy; or $R_7$ and $R_8$ taken together can form a 3-7 membered carbon ring optionally interrupted with 1-2 heteroatoms chosen from O, S, SO, $SO_2$, NH, and $NR_8$;

$X_1$ represents O, S or $NR_{13}$, NCN, $NCO_2R_{16}$, or $NSO_2R_{14}$ $X_2$ represents O, S, NH or $NSO_2R_{14}$;

$R_{10}$ represents hydrogen, $C_{1-6}$ alkyl or $CO_2R_{15}$;

$R_{12}$ represents hydrogen, $C_{1-6}$ alkyl, $NH_2$, OR, $CHF_2$, $CHCl_2$, $C(R)_2Cl$, $(CH_2)_nSR$, $(CH_2)_nCN$, $(CH_2)_nSO_2R$, $(CH_2)_nS(O)R$, $C_{1-6}$ alkylamino, $C_{3-6}$ cycloalkyl, $C_{5-10}$ heterocyclyl or $C_{1-6}$ dialkylamino, where said alkyl, and cycloalkyl may be substituted with 1-3 groups of halo, CN, OH or $C_{1-6}$ alkoxy, said heterocyclyl optionally substituted with 1-3 groups of $R_7$;

Each $R_{13}$ represents independently hydrogen, $C_{1-6}$ alkyl, $C_{6-10}$ aryl, $NR_5R_6$, $SR_8$, $S(O)R_8$, $S(O)_2R_8$, CN, OH, $C_{1-6}$ alkylS(O)R, $C_{1-6}$ alkoxycarbonyl, hydroxycarbonyl, —OCOaryl, $C_{1-6}$ acyl, $C_{3-7}$ membered carbon ring optionally interrupted with 1-4 heteroatoms chosen from O, S, SO, $SO_2$, NH and $NR_8$ where said $C_{1-6}$ alkyl, aryl or $C_{1-6}$ acyl groups may be independently substituted with 0-3 halogens, hydroxy, $N(R)_2$, $CO_2R$, $C_{6-10}$ aryl, $C_{5-10}$ heteroaryl, or $C_{1-6}$ alkoxy groups;

When two $R_{13}$ groups are attached to the same atom or two adjacent atoms they may be taken together to form a 3-7 membered carbon ring optionally interrupted with 1-2 heteroatoms chosen from O, S, SO, $SO_2$, NH, and $NR_8$;

R represents hydrogen or $C_{1-6}$ alkyl;

R* represents hydrogen, CN, C(=O)$R_{14}$, $(CH_2)_pCO_2C_{1-6}$ alkyl, $(CH_2)_pC_{5-10}$heterocyclyl, or $C_{1-6}$ alkyl, said alkyl and heterocyclyl optionally substituted with 1 to 3 groups of $R_7$;

$R_{14}$ represents amino, $C_{1-6}$ alkyl, $C_{3-6}$ cycloalkyl, $(CH_2)_p C_{5-10}$ heterocyclyl, $C_{1-6}$ haloalkyl, phenyl, said alkyl, cycloalkyl, phenyl, heterocyclyl optionally substituted with 1-3 group of $R_7$, when $R_7$ is an amino or hydroxyl group or a nitrogen that forms part of the heterocycle, said amino and hydroxy optionally protected with an amino or hydroxy protecting group;

$R_{15}$ is $C_{1-6}$ alkyl or benzyl said benzyl optionally substituted with 1-3 groups of halo, OH, $C_{1-6}$ alkoxy, amino, $C_{1-6}$ acylamino, or $C_{1-6}$ alkyl;

$R_{16}$ is hydrogen, $C_{5-10}$heteroaryl, $C_{6-10}$aryl, said heteroaryl and aryl optionally substituted with 1-3 groups of $R_7$;

p represents 0-2 and m, n and q independently represent 0-1.

Another aspect of the invention is concerned with the use of the novel antibiotic compositions in the treatment of bacterial infections.

DETAILED DESCRIPTION OF THE INVENTION

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen Stereochemistry of Carbon Compounds (John Wiley and Sons, New York 1994, in particular pages 1119-1190).

When any variable (e.g. aryl, heterocycle, $R_5$, $R_6$ etc.) occurs more than once, its definition on each occurrence is independent at every other occurrence. Also combinations of substituents/or variables are permissible only if such combinations result in stable compounds.

The term "alkyl" refers to a monovalent alkane (hydrocarbon) derived radical containing from 1 to 15 carbon atoms unless otherwise defined. It may be straight or branched. Preferred alkyl groups include lower alkyls which have from 1 to 6 carbon atoms such as methyl, ethyl, propyl, isopropyl, butyl and t-butyl. When substituted, alkyl groups may be substituted with up to 3 substituent groups, selected from the groups as herein defined, at any available point of attachment. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings which are fused. Preferred cycloalkyl groups are cyclopropyl, cyclobutyl, cyclopentyl and cyclohexyl. When substituted, cycloalkyl groups may be substituted with up to 3 substituents which are defined herein by the definition of alkyl.

Alkanoyl refers to a group derived from an aliphatic carboxylic acid of 2 to 4 carbon atoms. Examples are acetyl, propionyl, butyryl and the like.

The term "alkoxy" refers to those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

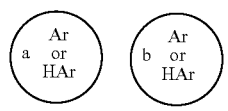

refers to aryl or heteroaryl, heterocycle, Het, heterocyclyl or heterocyclic as described immediately below.

Aryl refers to any stable monocyclic or bicyclic carbon ring of up to 7 atoms in each ring, wherein at least one ring is aromatic. Examples of such aryl elements include phenyl, napthyl, tetrahydronaphthyl, indanyl, indanonyl, biphenyl, tetralilnyl, tetralonyl, fluorenonyl, phenanthryl, anthryl, acenaphthyl, and the like substituted phenyl and the like. Aryl groups may likewise be substituted as defined. Preferred substituted aryls include phenyl and naphthyl.

The term heterocycle, heteroaryl, Het, heterocyclyl or heterocyclic, as used herein except where noted, represents a stable 5- to 7-membered mono- or bicyclic or stable 8- to 11-membered bicyclic heterocyclic ring system, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized (in which case it is properly balanced by a counterion), and including any bicyclic group in which any of the above-defined heterocyclic rings is fused to a benzene ring. The heterocyclic ring may be attached at any heteroatom or carbon atom, which results in the creation of a stable structure. The term heterocycle or heterocyclic includes heteroaryl moieties. "Heterocycle" or "heterocyclyl" therefore includes the above mentioned heteroaryls, as well as dihydro and tetrahydro analogs thereof. The heterocycle, heteroaryl, Het or heterocyclic may be substituted with 1-3 groups of $R_7$. Examples of such heterocyclic elements include, but are not limited to the following: piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyrimidonyl, pyridinonyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thiophenyl, imidazopyridinyl, triazolyl, tetrazolyl, triazinyl, thienyl, benzothienyl, thiamorpholinyl sulfoxide, thiamorpholinyl sulfone, naphthpyridinyl, dihydropyrimidinyl, dihydropyrrolyl, dihydroquinolinyl, dihydrotetrazolyl, dihydrotriazolyl, dihydrothienyl, dihydrooxazolyl, dihydrobenzothiophenyl, dihydrofuranyl, benzothiazolyl, benzothienyl, benzoimidazolyl, benzopyranyl, benzothiofuranyl, carbolinyl, chromanyl, cinnolinyl, benzopyrazolyl, benzodioxolyl and oxadiazolyl. Additional examples of heteroaryls are illustrated by formulas a, b, c and d:

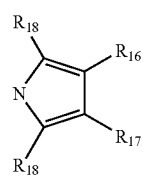

a

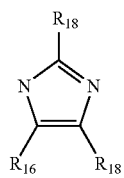

b

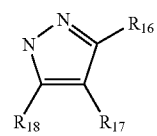

c

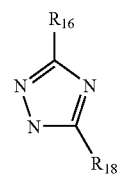

d wherein $R_{16}$ and $R_{17}$ are independently selected from hydrogen, halogen, $C_{1-6}$ alkyl, $C_{2-4}$ alkanoyl, $C_{1-6}$ alkoxy; and $R_{18}$ represents hydrogen, $C_{1-6}$ alkyl, $C_{2-4}$ alkanoyl, $C_{1-6}$ alkoxycarbonyl and carbamoyl.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The terms "quaternary nitrogen" and "positive charge" refer to tetravalent, positively charged nitrogen atoms (balanced as needed by a counterion known in the art) including, e.g., the positively charged nitrogen in a tetraalkylammonium group (e.g. tetramethylammonium), heteroarylium, (e.g., N-methylpyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

The term "prodrug" refers to compounds which are drug precursors which, following administration and absorption, release the drug in vivo via some metabolic process. Exemplary prodrugs include acyl amides of the amino compounds of this inventon such as amides of alkanoic($C_{1-6}$)acids, amides of aryl acids (e.g., benzoic acid) and alkane($C_{1-6}$) dioic acids.

Halogen and "halo" refer to bromine, chlorine, fluorine and iodine.

When a group is termed "substituted", unless otherwise indicated, this means that the group contains from 1 to 3 substituents thereon.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

Examples of suitable hydroxyl and amino protecting groups are: trimethylsilyl, triethylsilyl, o-nitrobenzyloxycarbonyl, p-nitrobenzyloxycarbonyl, t-butyidiphenylsilyl, t-butyldimethylsilyl, benzyloxycarbonyl, t-butyloxycarbonyl, 2,2,2-trichloroethyloxycarbonyl, allyloxycarbonyl and the like. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyidimethylsilyl, t-butidiphenylsilyl, 2-(trimethylsilyl)ethyl, phenacyl, p-methoxybenzyl, acetonyl, p-methoxyphenyl, 4-pyridylmethyl, t-butyl and the like.

The cyclopropyl containing oxazolidinone compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel cyclopropyl containing oxazolidinone compounds.

The pharmaceutically acceptable salts referred to above also include acid addition salts. Thus, when the Formula I compounds are basic, salts may be prepared from pharmaceutically acceptable non-toxic acids, including inorganic or organic acids. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonic, isethionic, lactate, maleate, mandelic, malic, maleic, methanesulfonate, mucic, 2-naphthalenesulfonate, nicotinate, nitric oxalate, pamoate, pectinate, persulfate, 3-phenylpropionate, picrate, pivalate, propionate, phosphate, pantothenic, pamoic, sulfate, succinate, tartrate, thiocyanate, tosylate and undecanoate.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium zinc and the like. Particularly preferred are the ammonium, calcium, magnesium, potassium and sodium salts. Salts derived from pharmaceutically acceptable inorganic non-toxic bases include salts of primary, secondary and teritary amines, substituted amines including naturally occurring substituted amines, cyclic amines and basic ion exchange resins, such as arginine, betaine caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The pharmaceutically acceptable esters are such as would be readily apparent to a medicinal chemist, and include those which are hydrolyzed under physiological conditions, such as "biolabile esters", pivaloyloxymethyl, acetoxymethyl, phthalidyl, indanyl and methoxymethyl, and others.

Biolabile esters are biologically hydrolizable, and may be suitable for oral administration, due to good absorption through the stomach or intenstinal niucosa, resistance to gastric acid degrada-tion and other factors. Examples of biolabile esters include compounds.

An embodiment of this invention is realized when $R_1$ independently represent H, $NR_5R_6$, CN, OH, or $CR_7R_8R_9$ and all other variables are as described herein.

Another embodiment of this invention is realized when

independently are phenyl, pyridyl, pyrimidinyl, or piperidinyl and all other variables are as described herein.

Another embodiment of this invention is realized when $R_1$ is CN and all other variables are as described herein.

An embodiment of this invention is realized when Y is NR* and all other variables are as described herein.

Another embodiment of this invention is realized when X is $C_{5-10}$ heteroaryl represented by

which represents an optionally substituted aromatic heterocyclic group containing 1 to 4 nitrogen atoms and at least one double bond, and which is connected through a bond on any nitrogen. Exemplary groups are 1,2,3-triazole, 1,2,4-triazole, 1,2,5-triazole, tetrazole, pyrazole, and imidazole, any of which may contain 1 to 3 substitutents selected from $R_7$.

Another embodiment of this invention is realized when X is

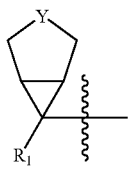

and all other variables are as described herein. A sub-embodiment of this invention is realized when Y is NR* and $R_1$ is CN or $NH_2$.

Another embodiment of this invention is realized when $R_3$ is $C_{5-10}$ heteroaryl, said heteroaryl optionally substituted with 1-3 groups of $R_7$ and all other variables are as described herein.

Another embodiment of this invention is realized when $R_3$ is a $C_{5-10}$ heteroaryl represented by

which represents an optionally substituted aromatic heterocyclic group containing 1 to 4 nitrogen atoms and at least one double bond, and which is connected through a bond on any nitrogen. Exemplary groups are 1,2,3-triazole, 1,2,4-triazole, 1,2,5-triazole, tetrazole, pyrazole, and imidazole, any of which may contain 1 to 3 substitutents selected from $R_7$.

Still another embodiment of this invention is realized when $R_5$ and $R_6$ independently are:
  i) H,
  ii) $C_{1-6}$ alkyl optionally substituted with 1-3 groups of halogen, CN, OH, $C_{1-6}$ alkoxy, amino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethyenyloxy, or ethynyl, said phenyl and pyridine optionally substituted with 1-3 halogen, CN, OH, $CF_3$, $C_{1-6}$ alkyl or $C_{1-6}$ alkoxy;
  iii) $C_{1-6}$ acyl optionally substituted with 1-3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1-3 groups of halo, OH, CN, $C_{1-6}$ alkoxy, amino, $C_{1-6}$ acylamino, $CF_3$ or $C_{1-6}$ alkyl; or
  iv) benzoyl optionally substituted with 1-3 groups of halogen, OH, $C_{1-6}$ alkoxy, $C_{1-6}$ alkyl, $CF_3$, $C_{1-6}$ alkanoyl, amino or $C_{1-6}$ acylamino and all other variables are as described herein.

Yet another embodiment of this invention is realized when $X_1$ represents O and all other variables are as described herein.

A preferred embodiment of this invention is realized when the structural formula is III:

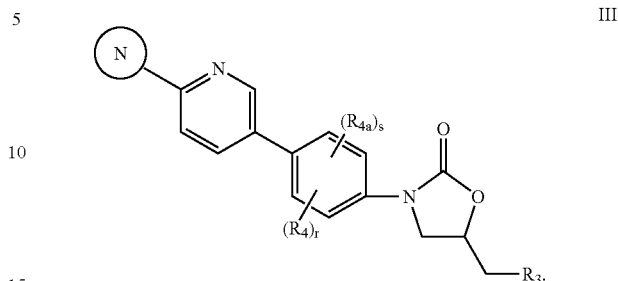

III wherein $R_4$, $R_{4a}$, and $R_3$ are as described herein and

is 1,2,3-triazole, 1,2,4-triazole, 1,2,5-triazole, tetrazole, pyrazole, or imidazole, any of which may contain 1 to 3 substitutents selected from $R_7$.

A subembodiment of this invention is realized when $R_3$ is a $C_{5-10}$ heteroaryl represented by

which represents an optionally substituted aromatic heterocyclic group containing 1 to 4 nitrogen atoms and at least one double bond, and which is connected through a bond on any nitrogen.

Another preferred embodiment of this invention is realized when the structural formula is IV:

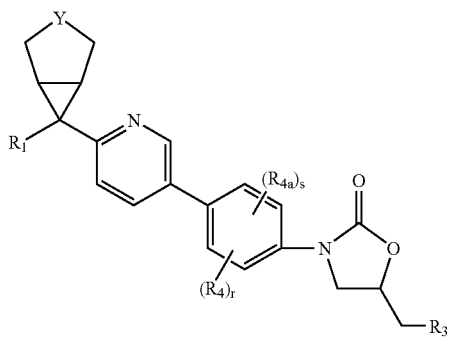

Formula IV wherein $R_1$, $R_4$, $R_{4a}$, Y and $R_3$ are as described herein. A subembodiment of this invention is realized when R3 is a $C_{5-10}$ heteroaryl represented by

which represents an optionally substituted aromatic heterocyclic group containing 1 to 4 nitrogen atoms and at least one double bond, and which is connected through a bond on any nitrogen.

Preferred compounds of this invention are:
1-[5(R)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]-1,2,3-triazole,
1-[5(R)-3-[4-[2-[(1α,5α,6β)-6-cyano-3-azabicyclo[3.1.0]hexan-6-yl]pyridin-5-yl]phenyl]-2-oxooxazolidin-5-ylmethyl]-1,2,3-triazole hydrochloride,
1-[5(R)-3-[4-[4-[(1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]-1,2,3-triazole,
1-[5(R)-3-[4-[4-[(1α,5α,6β)-6-cyano-3-azabicyclo[3.1.0]hexan-6yl]-3-fluorophenyl]phenyl]-2-oxooxazolidin-5-ylmethyl]-1,2,3-triazole hydrochloride,
1-[5(R)-3-[4-[4-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]-1,2,3-triazole,
1-[5(R)-3-[4-[4-[(1α,5α,6β)-6-cyano-3-azabicyclo[3.1.0]hexan-6-yl]-3-fluorophenyl]-3-fluorophenyl]-2-oxooxazol idin-5-ylmethyl]-1,2,3-triazole hydrochloride,
1-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole hydrochloride,
N-[5(S)-3-[4-[4-[(1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]acetamide,
N-[5(S)-3-[4-[4-[(1α,5α,6β)-6-cyano-3-azabicyclo[3.1.0]hexan-6-yl]-3-fluorophenyl]phenyl]-2-oxooxazolidin-5-ylmethyl]acetamide hydrochloride,
N-[5(S)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]acetamide,
N-[5(S)-3-[4-[2-[(1α,5α,6β)-6-cyano-3-azabicyclo[3.1.0]hexan-6-yl]pyridin-5-yl]phenyl]-2-oxooxazolidin-5-ylmethyl]acetamide hydrochloride,
N-[5(S)-3-[4-[4-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]acetamide,
N-[5(S)-3-[4-[2-[(1α,5α,6β)-6-cyano-3-azabicyclo[3.1.0]hexan-6-yl]-3-fluorophenyl]-3-fluorophenyl]-2-oxooxazolidin-5-ylmethyl]acetamide hydrochloride,
N-[5(S)-3-[4-[4-[(1α,5=,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]acetamide,
N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]acetamide hydrochloride,
N-[5(S)-3-[4-[2-[(1α,5α,6β)-6-t-butoxycarbonylamino-3-oxabicyclo[3.1.0]hexan-6-yl]pyridin-5-yl]-3-fluorophenyl]-2-oxooxazolidin-5-ylmethyl]acetamide,
N-[5(S)-3-[4-[2-[(1α,5α,6β)-6-amino-3-oxabicyclo[3.1.0]hexan-6-yl]pyridin-5-yl]-3-fluorophenyl]-2-oxooxazolidin-5-ylmethyl]acetamide,
1-[5(R)-3-[4-[2-[(1α,5α,6β)-6-t-butoxycarbonylamino-3-oxabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-amino-3-oxabicyclo[3.1.0]hexan-6-yl]pyridin-5-yl]-3-fluorophenyl]-2-oxooxazolidin-5-ylmethyl]-1,2,3-triazole,
N-[5(S)-3-[4-[4-[(1α,5α,6β)-6-cyano-3-oxabicyclo[3.1.0]hexan-6yl]pyridin-5-yl]-3-fluorophenyl]-2-oxooxazolidin-5-ylmethyl]acetamide,
1-[5(R)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]-1,2,3-triazole,
N-[5(S)-3-[4-[2-[(1α,5α,6β)-6-t-butoxycarbonylamino-3-oxabicyclo[3.1.0]hexan-6-yl]pyridin-5-yl]phenyl]-2-oxooxazolidin-5-ylmethyl]acetamide,
N-[5(S)-3-[4-[2-[(1α,5α,6β)-6-amino-3-oxabicyclo[3.1.0]hexan-6-yl]pyridin-5-yl]phenyl]-2-oxooxazolidin-5-ylmethyl]acetamide,
1-[5(R)-3-[4-[2-[(1α,5α,6β)-6-t-butoxycarbonylamino-3-oxabicyclo[3.1.0]hexan-6yl]pyridin-5-yl]phenyl]-2-oxooxazolidin-5-ylmethyl]-1,2,3-triazole,
1-[5(R)-3-[4-[2-[(1α,5α,6β)-6-amino-3-oxabicyclo[3.1.0]hexan-6-yl]pyridin -5-yl]phenyl]-2-oxooxazolidin-5-ylmethyl]-1,2,3-triazole,
N-[5(S)-3-[4-[4-[(1α,5α,6β)-6-cyano-3-oxabicyclo[3.1.0]hexan-6-yl]pyridin-5-yl]phenyl]-2-oxooxazolidin-5-ylmethyl]acetamide,
1-[5(R)-3-[4-[2-[(1α,5α,6β)-6-cyano-3-oxabicyclo[3.1.0]hexan-6-yl]pyridin-5-yl]phenyl]-2-oxooxazolidin-5-ylmethyl]-1,2,3-triazole,
1-[5(R)-3-[3-Fluoro-4-[2-(1-methyltetrazol-5-yl)pyridin-5-yl]phenyl]-2-oxooxazolidin-5-ylmethyl]-1,2,3-triazole,
1-[5(R)-3-[3,5-Difluoro-4-[2-(1-methyltetrazol-5-yl)pyridin-5-yl]phenyl]-2-oxooxazolidiin-5-ylmethyl]-1,2,3-triazole,
1-[5(R)-3-[4-[4-[(1α,5α,6β)-3-t-butoxycarbonyl-6-cyano-3-azabicyclo[3.1.0]hexan-6-yl]-3,5-difluorophenyl]-3-fluorophenyl]-2-oxooxazolidin-5-ylmethyl]-1, 2,3-triazole,
1-[5(R)-3-[4-[4-[(1α,5α,6β)-6-cyano-3-azabicyclo[3.1.0]hexan-6-yl]-3,5-difluorophenyl]-3-fluorophenyl]-2-oxooxazolidin-5-ylmethyl]-1,2,3-triazole,
N-[5(S)-3-[4-[4-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]acetamide,
N-[5(S)-3-[4-[4-[(1α,5α,6β)-6-cyano-3-azabicyclo[3.1.0]hexan-6-yl]pyridin-5-yl]-3,5-difluorophenyl]-2-oxooxazolidin-5-ylmethyl]acetamide hydrochloride,
N-[5(S)-3-[4-[4-[(1α,5α,6β)-3-t-butoxycarbonyl-6-cyano-3-azabicyclo[3.1.0]hexan-6-yl]-3,5-difluorophenyl]-3-fluorophenyl]-2-oxooxazolidin-5-ylmethyl]acetamide,
N-[5(S)-3-[4-[4-[(1α,5α,6β)-6-cyano-3-azabicyclo[3.1.0]hexan-6-yl]-3,5-difluorophenyl]-3-fluorophenyl]-2-oxooxazolidin-5-ylmethyl]acetamide hydrochloride,
N-[5(S)-3-[4-[4-[(1α,5α,6β)-3-t-butoxycarbonyl-6-cyano-3-azabicyclo[3.1.0]hexan-6-yl]phenyl]-3-fluorophenyl]-2-oxooxazolidin-5-ylmethyl]acetamide,
N-[5(S)-3-[4-[4-[(1α,5α,6β)-6-cyano-3-azabicyclo[3.1.0]hexan-6-yl]phenyl]-3-fluorophenyl]-2-oxooxazolidin-5-ylmethyl]acetamide,
N-[5(S)-3-[4-[4-[(1α,5α,6β)-3-t-butoxycarbonyl-6-cyano-3-azabicyclo[3.1.0]hexan-6-yl]-3-fluorophenyl]-3,5-difluorophenyl]-2-oxooxazolidin-5-ylmethyl]acetamide,
N-[5(S)-3-[4-[4-[(1α,5α,6β)-6-cyano-3-azabicyclo[3.1.0]hexan-6-yl]-3-fluorophenyl]-3,5-difluorophenyl]-2-oxooxazolidin-5-ylmethyl]acetamide, 1-[5(R)-3-[4-[4-[(1α,5α,6β)-3-t-butoxycarbonyl-6-cyano-3-azabicyclo[3.1.0]hexan-6-yl]-3-fluorophenyl]-3,5-difluorophenyl]-2-oxooxazolidin-5-ylmethyl]-1,2,3-triazole, 1-[5(R)-3-[4-[4-[(1α, 5α,6β)-6-cyano-3-azabicyclo[3.1.0]hexan-6-yl]-3-fluorophenyl]-3,5-difluorophenyl]-2-oxooxazolidin-5-ylmethyl]-1,2,3-triazole hydrochloride, 1-[5(R)-3-[4-[4-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]pyridin-5-yl]-3,5-difluorophenyl]-2-oxooxazolidin-5-ylmethyl]-1,2,3-triazole 1-[5(R)-3-[4-[4-[(1α, 5α,6β)-3-t-butoxycarbonyl-6-cyano-3-azabicyclo[3.1.0]hexan-6-yl]phenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]phenyl]-3-fluorophenyl]-2-oxooxazolidin-5-ylmethyl]-1,2,3-triazole, 1-[5(R)-3-[4-[2-[(1α,5α,6β)-6-t-butoxycarbonylamino-3-oxabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-amino-3-oxabicyclo[3.1.0]hexan-6-yl]pyridin-5-yl]-3,5-difluorophenyl]-2-oxooxazolidin-5-ylmethyl]-1,2,3-triazole, N-[5(S)-3-[4-[2-[(1α,5α,6β)-6-t-butoxycarbonylamino-3-oxabicyclo[3.1.0]hexan-6-yl]pyridin-5-yl]-3,5-difluorophenyl]-2-oxooxazolidin-5-ylmethyl]acetamide, N-[5(S)-3-[4-[2-[(1α,5=,6β)-6-amino-3-oxabicyclo[3.1.0]hexan-6-yl]pyridin-5-yl]-3,5-difluorophenyl]-2-oxooxazolidin-5-ylmethyl]acetamide, N-[5(S)-3-[4-[2-[(1α,5α,6β)-6-cyano-3-oxabicyclo[3.1.0]hexan-6-yl]pyridin-5-yl]-3,5-difluorophenyl]-2-oxooxazolidin-5-ylmethyl]acetamide, 1-[5(R)-3-[4-[2-[(1α, 5α,6β)-6-cyano-3-oxabicyclo[3.1.0]hexan-6-yl]pyridin-5-yl]-3,5-difluorophenyl]-2-oxooxazolidin-5-ylmethyl]-1,2,3-triazole, N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide, N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide S-oxide, N-[5(S)-3-[4-[2-[(1α, 5α,6βp)-6-cyano-3-thiabicyclo[3.1.0]hexan-6-yl]pyridin-5-yl]-3-flurophenyl-]-2-oxooxazolidin-5-ylmethyl]acetamide S,S-dioxide, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S,S-dioxide, 4-[5(R)-3-[4-[2-[(1α, 5α,6β)-3-t-butoxycarbonyl-6-cyano-3-azabicyclo[3.1.0]hexan-6yl]pyridin-5-yl]-3-fluorophenyl]-2-oxooxazolidin-5-ylmethyl]-1,2,4-triazole, 4-[5(R)-3-[4-[2-[(1α, 5α,6β)-6-cyano-3-azabicyclo[3.1.0]hexan-6-yl]pyridin-5-yl]-3-fluorophenyl]-2-oxooxazolidin-5-ylmethyl]-1,2,4-triazole, 5(R)-3-[4-[2-[(1α, 5α,6β)-3-t-butoxycarbonyl-6-cyano-3-azabicyclo[3.1.0]hexan-6-yl]pyridin-5-yl]-3-fluorophenyl]-5-[(isoxazol-3-yl)oxy]methyloxazolidin-2-one, 5(R)-3-[4-[2-[(1α, 5α,6β)-6-cyano-3-azabicyclo[3.1.0]hexan-6-yl]pyridin-5-yl]-3-fluorphenyl]-5-[(isoxazol-3-yl)oxy]methyloxazolidin-2-one, 5(R)-3-[4-[2-[(1α, 5α,6β)-3-t-butoxycarbonyl-6-cyano-3-azabicyclo[3.1.0]hexan-6-yl]pyridin-5-yl]-3-fluorophenyl]-5-[N-(t-butoxycarbonyl)-N-(isoxazol-3-yl)]aminomethyloxazolidin-2-one, 5(R)-3-[4-[2-[(1α,5α,6β)-6-cyano-3-azabicyclo[3.1.0]hexan-6-yl]pyridin-5-yl]-3-fluorophenyl]-5-[N-(isoxazol-3-yl)]aminomethyloxazolidin-2-one, 5(R)-3-[4-[2-[(1α,5α,6β)-6-cyano-3-oxabicyclo[3.1.0]hexan-6-yl]pyridin-5-yl]-3-fluorophenyl]-5-[(isoxazol-3-yl)oxy]methyloxazolidin-2-one, 5(R)-5-[N-(t-butoxycarbonyl)-N-(isoxazol-3-yl)]aminomethyl-3-[4-[2-[(1α,5α,6β)-6-cyano-3-oxabicyclo[3.1.0]hexan-6-yl]pyridin-5-yl]-3-fluorophenyl]oxazolidin-2-one, 5(R)-3-[4-[2-[(1α,5α,6β)-6-cyano-3-oxabicyclo[3.1.0]hexan-6-yl]pyridin-5-yl]-3-fluorophenyl]-5-[N-(isoxazol-3-yl)]aminomethyloxazolidin-2-one, N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]propionamide, N-[5(S)-3-[4-[2-[(1α, 5α,6β)-6-cyano-3-oxabicyclo[3.1.0]hexan-6-yl]pyridin-5-yl]-3-fluorophenyl]-2-oxooxazolidin-5-ylmethyl]difluoroacetamide, N-[5(S)-3-[4-[2-[(1α, 5α,6β)-6-cyano-3-oxabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α, 5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]propionamide, N-[5(S)-3-[4-[2-[(1α, 5α,6β)-6-cyano-3-azabicyclo[3.1.0]hexan-6-yl]pyridin-5-yl]-3-fluorophenyl]-2-oxooxazolidin-5-ylmethyl]propionamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α, 5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]difluoroacetamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]difluoroacetamide, 1-[5(R)-3-[4-[2-[(1α, 5α,6β)-6-cyano-3-methyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3,6-dicyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[(1-t-butoxycarbonylaminocyclopropan-1-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[(1-aminocyclopropan-1-yl)carbonyl]-6-cyano-3-azabicylco [3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[2-(phthalimid-2-yl)ethyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-(2-aminoethyl)-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[2-(1,2,4-triazol-4-yl)ethyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-bromoacetyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(morpholin-4-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α, 5α,6β)-6-cyano-3-(5-cyanopyridin-2-yl)-3azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α, 5α,6β)-6-cyano-3-(1,3-dihydroxypropan-2-yl)-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[((2S)-pyrrolidin-2-yl)carbonyl]-3-azabicylco[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S,4R)-1-t-butoxycabonyl-4-hydroxypyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α, 5α,6β)-6-cyano-3-[((2S,4R)-4-hydroxypyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α, 5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1═,5α,6β)-6-cyano-3-[((2S,4S)-4-fluoropyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[4-[(1α,5α,6β)-3-t-butoxycarbonyl-6-(t-butoxycarbonyl)amino-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[4-[(1α,5α,6β)-6-amino-3-azabicyclo[3.1.0]hexan-6-yl]pyridin-5-yl]-3-fluorophenyl]-2-oxooxazolidin-5-ylmethyl]-1,2,3-triazole dihydrochloride, 1-[5(R)-3-[4-[2-[(1α,5α,6β)-3-acetoxyacetyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-hydroxyacetyl-3-azabicyclo[3.1.0]-6-yl]pyridin-5-yl]-3-fluorophenyl]-2-oxooxazolidin-5-ylmethyl]-1,2,3-triazole, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide, N-[5(S)-3-[4-[2-[(1α, 5α,6β)-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide, O-methyl-N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]carbamate, O-methyl-N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]carbamate, 1-[5(R)-3-[4-[2-[(1α,5α,6β)-3,6-dicyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-methyl-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[3-fluoro-4-[2-[(1α,5α,6β)-6-hydroxymethyl-3-oxabicyclo[3.1.0]hexan-6-yl]pyridin-5-yl]phenyl]-2-oxooxazolidin-5-ylmethyl]-1,2,3-triazole, 1-[5(R)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[(1α,5α,6β)-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole, 1-[5(R)-3-[4-[(1α,5α,6β)-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole, 1-[5(R)-3-[4-[2-[(1α,5α,6β)-3-(4-t-butoxycarbonylpiperazin-1-yl)acetyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(piperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole dihydrochloride, 1-[5(R)-3-[4-[2-[(1α,5α,6β)-6-cyano-3-oxabicyclo[3.1.0]hexan-6-yl]thiophen-4-yl]-3fluorophenyl]-2-oxooxazolidin-5-ylmethyl]-1,2,3-triazole, 1-[5(R)-3-[4-[2-[(1α,5α,6β)-6-cyano-3-(piperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(pyrrolidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(4-dimethylaminopiperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S)-pyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S,4R)-4-hydroxypyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole hydrochloride, 1-[5(R)-3-[4-[2-[(1α,5α,6β)-3-[((2S,4R)-1-t-butoxycabonyl-4-hydroxypyrrolidin-2-yl(carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S,4S)-4-fluoropyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3triazole, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole S,S-dioxide, 1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole S,S-dioxide, 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-amino-3-thiabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole S-oxide, 1-[5(R)-3-[4-[2-[(1α,5α,6β)-6-amino-3-thiabicyclo[3.1.0]hexan-6-yl]pyridin-5-yl]-3,5-difluorophenyl]-2-oxooxazolidin-5-ylmethyl]-1,2,3-triazole S-oxide, 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole S,S-dioxide, 1-[5(R)-3-[4-[2-[(1α,5=,6β)-6-amino-3-thiabicyclo[3.1.0]hexan-6-yl]pyridin-5-yl]-3,5-difluorophenyl]-2-oxooxazolidin-5-ylmethyl]-1,2,3-triazole S,S-dioxide, 5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[(isoxazol-3-yl)oxy]methyloxazolidin-2-one, 5(R)-3-[4-[2-[(1α,5α,6β)-6-cyano-3-azabicyclo[3.1.0]hexan-6-yl]pyridin-5-yl]-3,5-difluorophenyl]-5-[(isoxazol-3-yl)oxy]methyloxazolidin-2-one, 1-[5(R)-3-[4-[2-[(1α,5α,6β)-6-cyano-3-(4-methylpiperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole, 1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole S-oxide, 1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole S,S-dioxide, 1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole S-oxide, 1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole S,S-dioxide, 1-[5(R)-3-[4-[2-[(1α,5α,6β)-6-cyano-3-(1,3-diacetoxypropan-2-yl)-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[(3R,4S)-1-azabicyclo[2.2.1]hepan-3-yl]carbonyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(pyridin-2-yl)-3-azabicyclo[3.1.0]hexan-6-yl]pyridin-5-yl]-3-fluorophenyl]-2-oxooxazolidin-5-ylmethyl]-1,2,3-triazole, 5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[N-(t-butoxycarbonyl)-N-(isoxazol-3-yl)]aminomethyloxazolidin-2-one, 5(R)-3-[4-[2-[(1α,5α,6β)-6-cyano-3-azabicyclo[3.1.0]hexan-6-yl]pyridin-5-yl]-3,5-difluorophenyl]-5-[N-(isoxazol-3-yl)]aminomethyloxazolidin-2-one, 1-[5(R)-3-[4-[2-[(1α,5α,6β)-6-cyano-3-(thiatriazol-2-yl)-3-azabicyclo[3.1.0]hexan-6-yl]pyridin-5-yl]-3-fluorophenyl]-2-oxooxazolidin-5-ylmethyl]-1,2,3-triazole, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]thioacetamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]thioacetamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]isothiocyanate, O-methyl-N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]thiocarbamate, O-methyl-N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]thiocarbamate, or their enantiomer, diastereomer, or pharmaceutically acceptable salt, hydrate or prodrug thereof.

Suitable subjects for the administration of the formulation of the present invention include mammals, primates, man, and other animals. In vitro antibacterial activity is predictive of in vivo activity when the compositions are administered to a mammal infected with a susceptible bacterial organism.

Using standard susceptibility tests, the compositions of the invention are determined to be active against MRSA and enterococcal infections.

The compounds of the invention are formulated in pharmaceutical compositions by combining the compounds with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The novel antibiotic compositions of this invention for human delivery per unit dosage, whether liquid or solid, comprise from about 0.01% to as high as about 99% of the cyclopropyl containing oxazolidinone compounds discussed herein, the preferred range being from about 10-60% and from about 1% to about 99.99% of one or more of other antibiotics such as those discussed herein, preferably from about 40% to about 90%. The composition will generally contain from about 125 mg to about 3.0 g of the cyclopropyl containing oxazolidinone compounds discussed herein; however, in general, it is preferable to employ dosage amounts in the range of from about 250 mg to 1000 mg and from about 200 mg to about 5 g of the other antibiotics discussed herein; preferably from about 250 mg to about 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal the claimed composition in an amount effective to treat said infection.

Oxazolidinones have been known at times to cause side effects such as sideroblastic anemia, peripheral sensory neuropathy, optic neuropathy, seizures, thrombocytopenia, cheilosis, seborrheic dermatitis, hypo-regenerative anemia, megaloblastic anemia or normocytic anemia. The compounds of the invention may be combined with an effective amount of one or more vitamins to prevent or reduce the occurrence of oxazolidinone-associated side effects in patients. The vitamins that can be combined are vitamin B2, vitamin B6, vitaimin B12 and folic acid. The vitamins may be administered with the oxazolidinones as separate compositions or the vitamins and oxazolidinones may be present in the same composition.

Thus another aspect of this invention is a method of treating or preventing an oxazolidinone-associated side effect by administering an effective amount of the oxazolidinone of structural formula I and an effective amount of one or more of vitamin B2, vitamin B6, vitaimin B12 and folic acid to a patient in need thereof.

A further aspect of this invention relates to a method of treating or preventing oxazolidinone-associated normocyctic anemia or peripheral sensory neuropathy by administering an effective amount of vitamin B2 to a patient in need thereof.

Yet another aspect of this invention relates to a method of treating or preventing oxazolidinone-associated sideroblastic anemia, peripheral sensory neuropathy, optic neuropathy, seizures, thrombocytopenia, cheilosis, and seborrheic dermatitis by administering an effective amount of vitamin B6 to a patient in need thereof.

Still another aspect of this invention relates to a method of treating or preventing oxazolidinone-associated hypo-regenerative anemia, megaloblastic anemia by administering an effective amount of vitamin B12 and folic acid to a patient in need thereof.

Still another aspect of this invention relates to a method of treating or preventing bacterial infection by administering an effective amount of a compound of formula I and an effective amount of one or more of the group selected from the group consisting of vitamin B2, vitamin B6, vitaimin B12 and folic acid to a patient in need thereof.

The preferred methods of administration of the claimed compositions include oral and parenteral, e.g., i.v. infusion, i.v. bolus and i.m. injection formulated so that a unit dosage comprises a therapeutically effective amount of each active component or some submultiple thereof.

For adults, about 5-50 mg/kg of body weight, preferably about 250 mg to about 1000 mg per person of the cyclopropyl containing oxazolidinone antibacterial compound and about 250 mg, to about 1000 mg per person of the other antibiotic(s) given one to four times daily is preferred. More specifically, for mild infections a dose of about 250 mg two or three times daily of the cyclopropyl containing oxazolidinone antibacterial compound and about 250 mg two or three times daily of the other antibiotic is recommended. For moderate infections against highly susceptible gram positive organisms a dose of about 500 mg each of the cyclopropyl containing oxazolidinone and the other antibiotics, three or four times daily is recommended. For severe, life-threatening infections against organisms at the upper limits of sensitivity to the antibiotic, a dose of about 500-2000 mg each of the cyclopropyl-containing oxazolidinone compound and the other antibiotics, three to four times daily may be recommended.

For children, a dose of about 5-25 mg/kg of body weight given 2, 3, or 4 times per day is preferred; a dose of 10 mg/kg is typically recommended.

The compounds of the present invention can be prepared according to the procedures of the following scheme and general examples, using appropriate materials, and are further exemplified by the following specific examples. The compounds illustrated in the examples are not, however, to be construed as forming the only genus that is considered as the invention. The following examples further illustrate details for the preparation of compounds of the present invention. Those skilled in the art will readily understand that known variations of the conditions and processes of the following preparative procedures can be used to prepare the compounds of the present invention. All temperatures are in degrees Celsius unless otherwise noted.

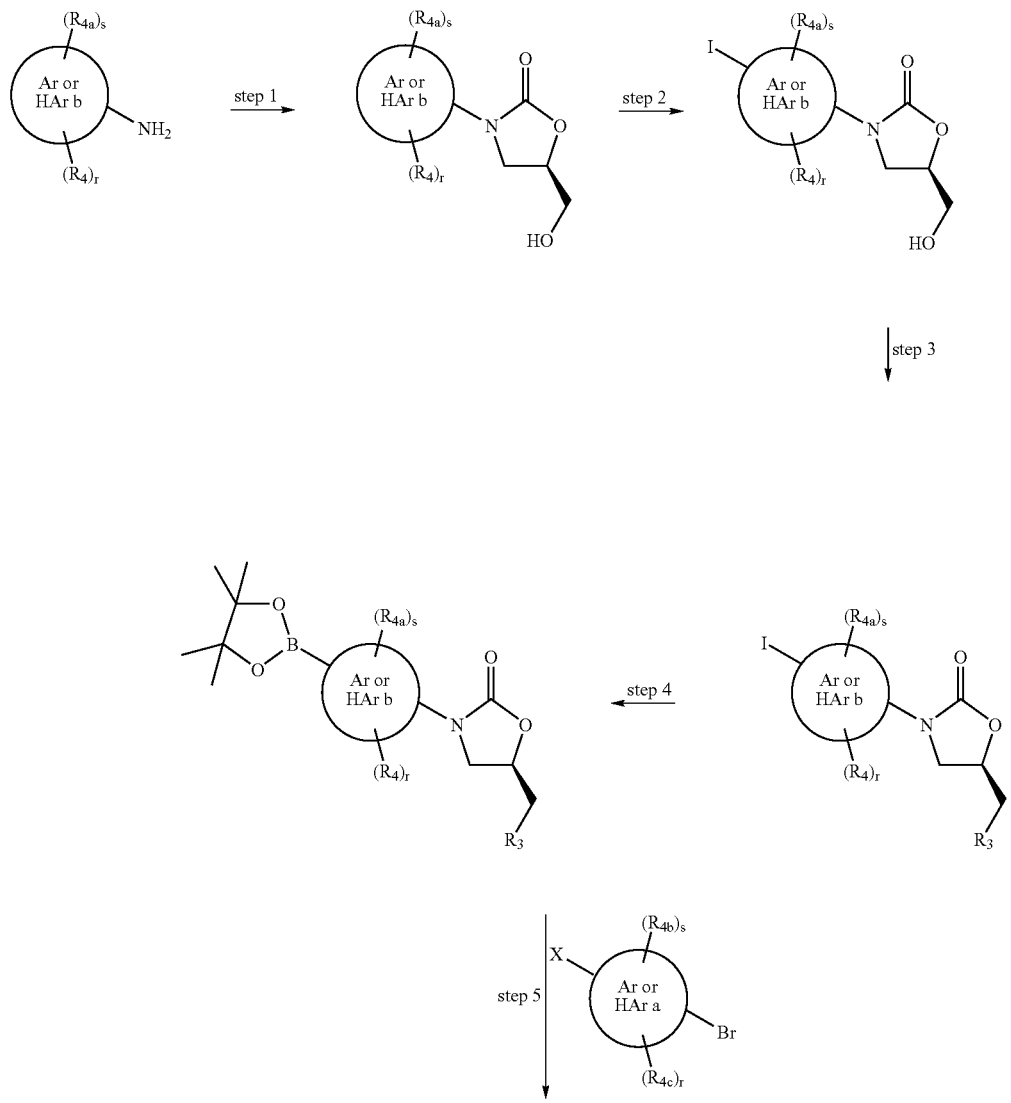

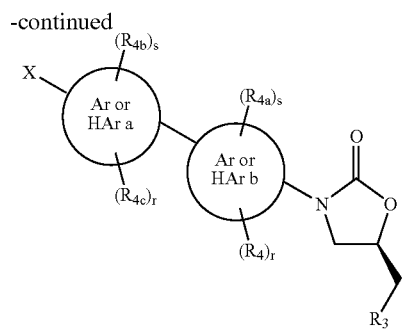

The compounds of the present invention can be prepared according to Scheme I, using appropriate materials, and are further exemplified by the following specific examples. The compounds illustrated in the examples are not, however, to be construed as forming the only genus that is considered as the invention. The following examples fuirther illustrate details for the preparation of compounds of the present invention. Those skilled in the art will readily understand that known variations of the conditions and processes of the following preparative procedures can be used to prepare the compounds of the present invention. All temperatures are in degrees Celsius unless otherwise noted.

In step 1 aromatic or heteroaromatic amines are converted to the corresponding 5-hydroxyoxazolidinones by methods well known to those skilled in the art. Typical conditions include acylation of the amine with a benzyloxycarbonyl chloride to afford the corresponding carbamate which is then deprotonated with a suitable strong base such n-butyl lithium, lithium t-butoxide or the like and the resulting anion quenched with the requisite glycidylbutyrate or other suitable glycidyl ester. Upon workup and purification the hydroxymethyloxazolidinone is obtained. It will be recognized to one skilled in the art that the requisite acylation may be catalyzed at the discretion of the experimenter by a number of suitable organic or inorganic bases and that likewise a number of suitable acylating agents can be envisaged for the performance of step 1. Moreover it should also be noted that if step 1 is performed using an R-glycidyl ester then the resulting 5-hydroxymethyl oxazolidinone will the S-configuration while performance of step 1 with an S-glycidyl ester will result in a 5-hydroxymethyl oxazolidinone with the R-configuration.

In step 2 the aromatic ring is halogenated using a suitable electrophilic halogenating agent undaer appropriate conditions. An example of such a halogenatiiong agent is iodine monochloride, but one skilled in the art will be quick to recognize that other halogenating agents could be used. One will recognize that if the desired halogen is an iodide, then an iodinating agent will be used but if another halogen is desired, then an appropriate halogenating agent will need to be chosen. These are well known to those of only ordinary skill in the art.

Step 3 describes the modification of the hydroxyl group to the $R_3$ substituent as described in the specification. It will be recognized that the exact procedures, conditions, and reagents will vary depending on the precise chemical nature of the $R_3$ substituent desired and representative transformations are described, but not limited to, those in the specific examples.

Step 4 describes the conversion of the aromatic halogen to a suitable boronate or boronic acid which is a suitable precursor for the subsequent coupling to AR or HAr a. These conditions are well known to one skilled in the art and include treatment of the starting halide with bispinacolato diboron or another suitable boron precursor in the presence of an appropriate Pd(II) catalyst such as [bis-(diphenylphosphino)ferrocene]palladium II dichloride methylene chloride complex or the like and a suitable base.

Step 5 describes the coupling of the HAr(or AR)b component with a suitable HAr(or AR)a component as detailed in the specification. This transformation, commonly referred to a Suzuki coupling by this skilled in the art is catalyzed by a palladium (0) species such as tetrakis(triphenylphosphine) palladium (0) in the presence ao a suitable base such as alkali metal carbonate to give the compounds iof the present invention. Subsequent chemical transformations, well known to those skilled in the art, can be used to interconvert various members of the broad genus described and delineated as X in the specification.

The invention is further described in connection with the following non-limiting examples.

EXAMPLE 1

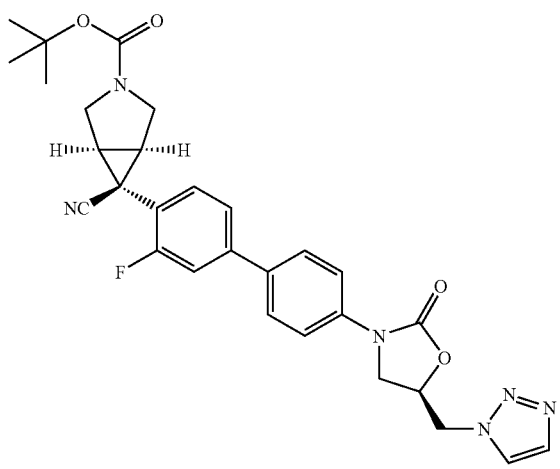

1-[5(R)-3-[4-[4-[(1α,5α,6β)-3-t-Butoxycarbonyl-6-cyano-3-azabicyclo[3.1.0]hexan-6-yl]-3-fluorophenyl]phenyl]-2-oxooxazolidin-5-ylmethyl]-1,2,3-triazole The mixture of 1-[5(R)-3-[4-(4,4,5,5-tetramethyl-1,3,2-dioxaborolyl)phenyl]-2-oxooxazolidin-5-ylmethyl]-1,2,3- triazole (20.0 mg), 1-bromo-4-[(1α,5α,6β)-3-t-butoxycarbonyl-6-cyano-3-azabicyclo[3.1.0]hexan-6-yl]-3-fluorobenzene (19.7 mg) and tetrakis(triphenylphosphine) palladium (0) (6.2 mg) in dioxane (0.5 mL) and 2M sodium carbonate solution (135 μL) was heated at 80° C. for 4 hours. The mixture was diluted with ethyl acetate and washed with saturated sodium hydrogencarbonate solution. The organic extracts were washed with brine, dried over anhydrous magnesium sulfate, and then concentrated in vacuo. Preparative thin-layer chromatography (silica, ethyl acetate:acetone=9:1) of the residue gave title compound 1 (19.4 mg)

MS (FAB+) m/z: 545 (MH+). HRMS (FAB+) for C29H30FN6O4 (MH+): calcd, 545.2313; found, 545.2341.

EXAMPLE 2

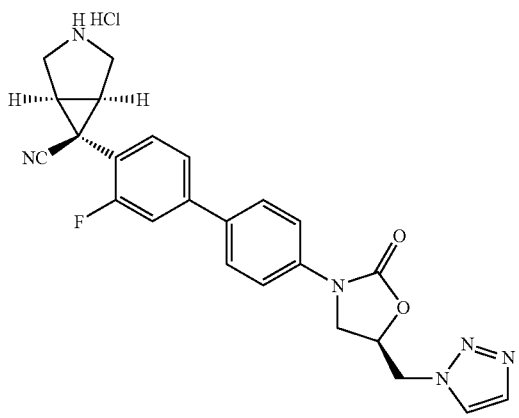

1-[5(R)-3-[4-[4-[(1α,5α,6β)-6-Cyano-3-azabicyclo[3.1.0]hexan-6-yl]-3fluorophenyl]phenyl]-2-oxooxazolidin-5-ylmethyl]-1,2,3-triazole Hydrochloride To a solution of 1-[5(R)-3-[4-[4-[(1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]-1,2,3-triazole (316 mg) in dichloromethane-methanol (10:1) solution (2.5 mL) was added a solution of hydrogen chloride in dioxane (4M, 2.5 mL) was stirred at room temperature for 3.5 hours, then concentrated in vacuo. Treatment with ethanol of the residue gave title compound 2 (236 mg).

MS (FAB+) m/z: 445 (MH+) (as free base). HRMS (FAB+) for C24H22FN6O2 (MH+): calcd, 445.1788; found, 445.1765.

EXAMPLE 3

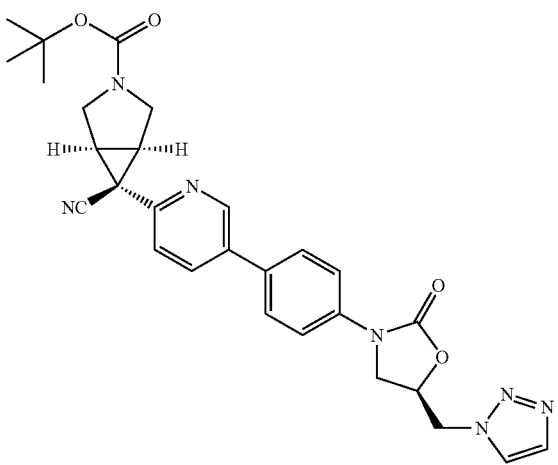

1-[5(R)-3-[4-[2-[(1α,5α,6β)-3-t-Butoxycarbonyl-6-cyano-3-azabicyclo[3.1.0]hexan-6-yl]pyridin-5-yl]phenyl]-2-oxooxazolidin-5-ylmethyl]-1,2,3-triazole Title compound 3 (22.3 mg) was prepared from 1-[5(R)-3-[4-(4,4,5,5-tetramethyl-1,3,2-dioxaborolyl)phenyl]-2-oxooxazolidin-5-ylmethyl]-1,2,3-triazole (20.0 mg) and 5-bromo-2-[(1α,5α,6β)-3-t-butoxycarbonyl-6-cyano-3-azabicyclo[3.1.0]hexan-6-yl]pyridine (19.7 mg) in the same manner as described for EXAMPLE 1.

MS (FAB+) m/z: 528 (MH+). HRMS (FAB+) for C28H30N7O4 (MH+): calcd, 528.2359; found, 528.2352.

EXAMPLE 4

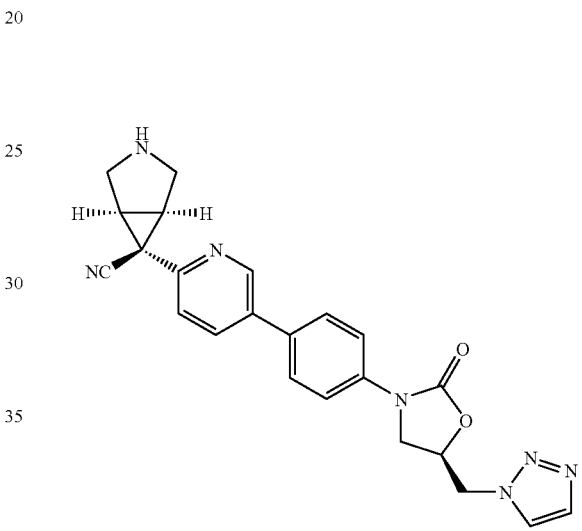

1-[5(R)-3-[4-[2-[(1α,5α,6β)-6-Cyano-3-azabicyclo[3.1.0]hexan-6-yl]pyridin-5-yl]phenyl]-2-oxooxazolidin-5-ylmethyl]-1,2,3-triazole To a solution of 1-[5(R)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]-1,2,3-triazole (209 mg) in dichloromethane-methanol (10:1) solution (1.7 mL) was added a solution of hydrogen chloride in dioxane (4M, 1.7 mL), the mixture was stirred at room temperature for 2.5 hours, then concentrated in vacuo. After dilution of the residue with dichloromethane-methanol (10:1) solution, the mixture was made to alkaline by the addition of 2 N. sodium hydroxide solution. The resulting mixture was extracted with dichloromethane-methanol (10:1) solution. The organic extracts were dried over anhydrous magnesium sulfate, and then concentrated in vacuo. Flash chromatography (silica, dichloromethane:methanol=10:1) of the residue gave title compound 5 (134 mg).

EXAMPLE 5

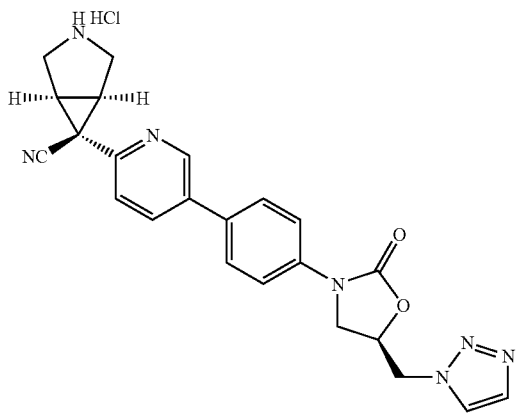

1-[5(R)-3-[4-[2-[(1α,5α,6β)-6-Cyano-3-azabicyclo[3.1.0]hexan-6-yl]pyridin-5-yl]phenyl]-2-oxooxazolidin-5-ylmethyl]-1,2,3-triazole Hydrochloride To a solution of 1-[5(R)-3-[4-[2-[(1α,5α,6β)-6-cyano-3-azabicyclo[3.1.0]hexan-6-yl]pyridin-5-yl]phenyl]-2-oxooxazolidin-5-ylmethyl]-1,2,3-triazole (287 mg) in dichloromethane-methanol (10:1) solution (2.5 mL) was added a solution of hydrogen chloride in dioxane (4M, 168 μL) at 0° C., the mixture was concentrated in vacuo. Treatment of the residue with ethanol gave title compound 5 (292 mg).

MS (EI$^+$) m/z: 428 (M$^+$) (as free base). HRMS (EI$^+$) for $C_{23}H_{22}N_7O_2$ (M$^+$): calcd, 428.1835; found, 428.1848.

EXAMPLE 6

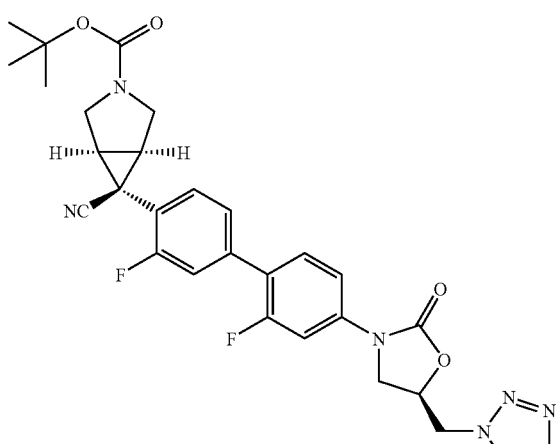

1-[5(R)-3-[4-[4-[(1α,5α,6β)-3-t-Butoxycarbonyl-6-cyano-3-azabicyclo[3.1.0]hexan-6-yl]-3-fluorophenyl]-3-fluorophenyl]-2-oxooxazolidin-5-ylmethyl]-1,2,3-triazole The title compound 6 was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (20.0 mg) and 1-bromo-4-[(1α,5α,6β)-3-t-butoxycarbonyl-6-cyano-3-azabicyclo[3.1.0]hexan-6-yl]-3-fluorobenzene (19.6 mg) in the same manner as described for EXAMPLE 1.

MS (FAB$^+$) m/z: 563 (MH$^+$). HRMS (FAB$^+$) for $C_{29}H_{29}F_2N_6O_4$(MH$^+$): calcd, 563.2218; found, 563.2222.

EXAMPLE 7

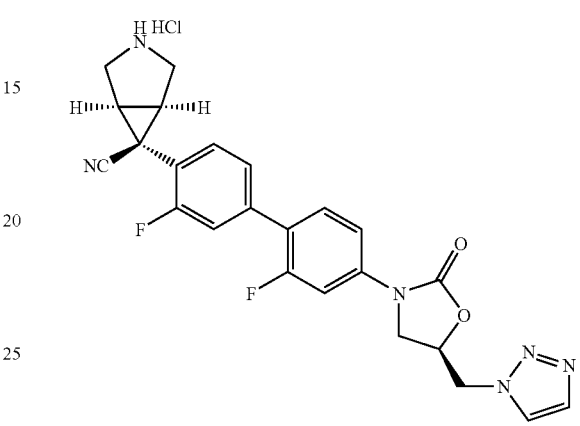

1-[5(R)-3-[4-[4-[(1α,5α,6β)-6-Cyano-3-azabicyclo[3.1.0]hexan-6-yl]-3-fluorophenyl]-3-fluorophenyl]-2-oxooxazolidin-5-ylmethyl]-1,2,3-triazole Hydrochloride Title compound 7 (212 mg) was prepared from 1-[5(R)-3-[4-[4-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]-1,2,3-triazole (273 mg) in the same manner as described for EXAMPLE 2.

MS,(EI$^+$) m/z: 462 (M$^+$) (as free base). HRMS (EI$^+$) for $C_{24}H_{20}F_2N_6O_2$ (M$^+$): calcd, 462.1616; found, 462.1631.

EXAMPLE 8

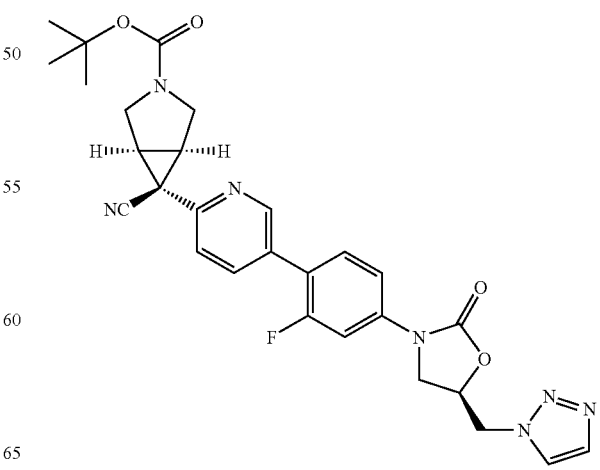

1-[5(R)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]-1,2,3-triazole The title compound 8 (15.8 mg) was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (20.0 mg) and 5-bromo-2-[(1α,5α,6β)-3-t-butoxycarbonyl-6-cyano-3-azabicyclo[3.1.0]hexan-6-yl]pyridine (18.8 mg) in the same manner as described for EXAMPLE 1.

MS (FAB$^+$) m/z: 546 (MH$^+$). HRMS (FAB$^+$) for C$_{28}$H$_{29}$FN$_7$O$_4$(MH$^+$): calcd, 546.2265; found, 546.2247.

EXAMPLE 9

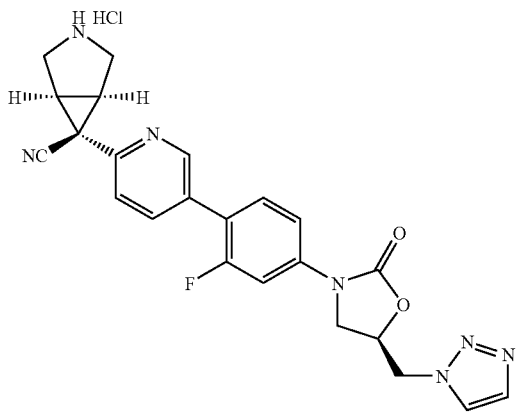

1-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-1,2,3-triazole Hydrochloride The title compound 9 (278 mg) was prepared from 1-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-1,2,3-triazole (500 mg) in the same manner as described for EXAMPLE 2.

MS (FAB$^+$) m/z: 446 (MH$^+$) (as free base). HRMS (FAB$^+$) for C$_{23}$H$_{21}$FN$_7$O$_2$ (MH$^+$): calcd, 446.1741; found, 446.1733.

EXAMPLE 10

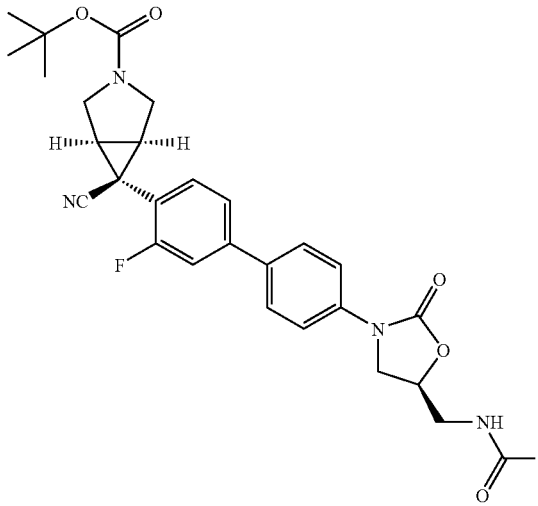

N-[5(S)-3-[4-[4-[(1α,5α,6β)-3-t-Butoxycarbonyl-6-cyano-3-azabicyclo[3.1.0]hexan-6-yl]-3-fluorophenyl]phenyl]-2-oxooxazolidin-5-ylmethyl]acetamide The title compound 10 (24.9 mg) was prepared from N-[5(S)-3-[4-(4,4,5,5-tetramethyl-1,3,2-dioxaborolyl)phenyl]-2-oxooxazolidin-5-ylmethyl]acetamide (18.9 mg) and 1-bromo-4-[(1α,5α,6β)-3-t-butoxycarbonyl-6-cyano-3-azabicyclo[3.1.0]hexan-6-yl]-3-fluorobenzene (20.0 mg) in the same manner as described for EXAMPLE 1.

MS (FAB$^+$) m/z: 535 (MH$^+$). HRMS (FAB$^+$) for C$_{29}$H$_{32}$FN$_4$O$_5$ (MH$^+$): calcd, 535.2357; found, 535.2375.

EXAMPLE 11

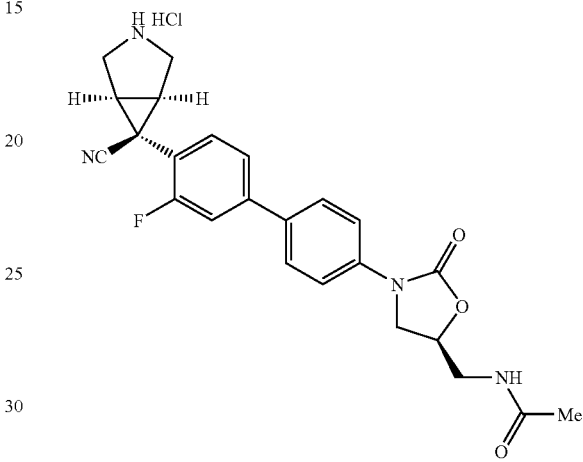

N-[5(S)-3-[4-[4-[(1α,5α,6β)-6-Cyano-3-azabicyclo[3.1.0]hexan-6-yl]-3-fluorophenyl]phenyl]-2-oxooxazolidin-5-ylmethyl]acetamide Hydrochloride The title compound 11 (281 mg) was prepared from N-[5(S)-3-[4-[4-[(1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]acetamide (360 mg) in the same manner as described for EXAMPLE 2.

MS (FAB$^+$) m/z: 435 (MH$^+$) (as free base). HRMS (FAB$^+$) for C$_{24}$H$_{24}$FN$_4$O$_3$ (MH$^+$): calcd, 435.1832; found, 435.1821.

EXAMPLE 12

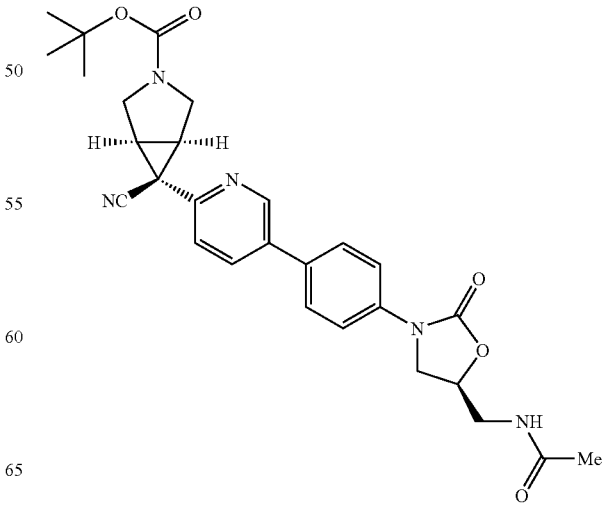

N-[5(S)-3-[4-[2-[(1α,5α,6β)-3-t-Butoxycarbonyl-6-cyano-3-azabicyclo[3.1.0]hexan-6-yl]pyridin-5-yl]phenyl]-2-oxooxazolidin-5-ylmethyl]acetamide The title compound 12 (20.3 mg) was prepared from N-[5(S)-3-[4-(4,4,5,5-tetramethyl-1,3,2-dioxaborolyl)phenyl]-2-oxooxazolidin-5-ylmethyl]acetamide (20.0 mg) and 5-bromo-2-[(1α,5α,6β)-3-t-butoxycarbonyl-6-cyano-3-azabicyclo[3.1.0]hexan-6-yl]pyridine (20.2 mg) in the same manner as described for EXAMPLE 1.

MS (FAB+) m/z: 518 (MH+). HRMS (FAB+) for $C_{28}H_{32}N_5O_5$ (MH+): calcd, 518.2403; found, 518.2412.

EXAMPLE 13

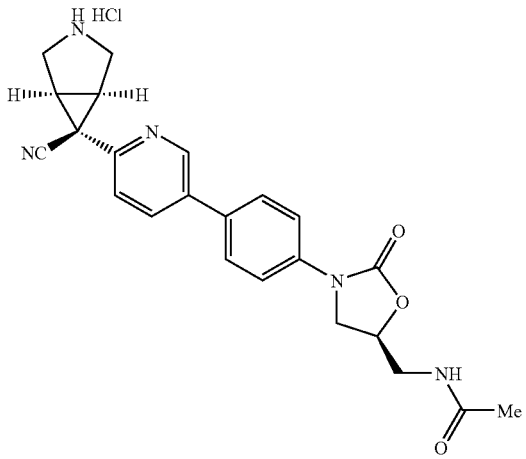

N-[5(S)-3-[4-[2-[(1α,5α,6β)-6-Cyano-3-azabicyclo[3.1.0]hexan-6-yl]pyridin-5-yl]phenyl]-2-oxooxazolidin-5-ylmethyl]acetamide Hydrochloride The title compound 13 (254 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]acetamide (366 mg) in the same manner as described for EXAMPLE 2.

MS (FAB+) m/z: 418 (MH+) (as free base). HRMS (FAB+) for $C_{23}H_{24}N_5O_3$ (MH+): calcd, 418.1879; found, 418.1885.

EXAMPLE 14

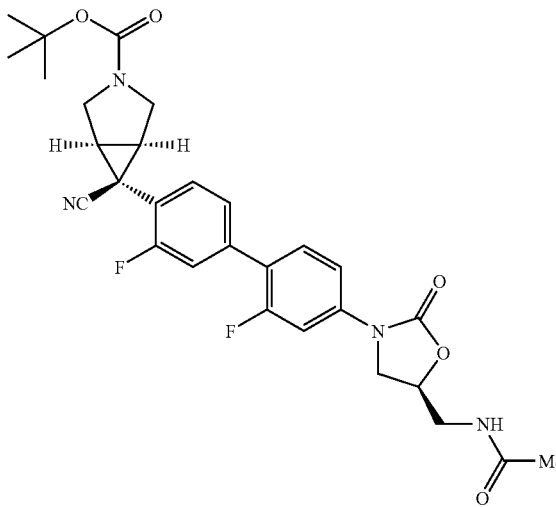

N-[5(S)-3-[4-[4-[(1α,5α,6β)-3-t-Butoxycarbonyl-6-cyano-3-azabicyclo[3.1.0]hexan-6-yl]-3-fluorophenyl]-3-fluorophenyl]-2-oxooxazolidin-5-ylmethyl]acetamide The title compound 14 (24.9 mg) was prepared from N-[5(S)-3-[3-fluoro-4-(4,4,5,5-tetramethyl-1,3,2-dioxaborolyl)phenyl]-2-oxooxazolidin-5-ylmethyl]acetamide (20.0 mg) and 1-bromo-4-[(1α,5α,6β)-3-t-butoxycarbonyl-6-cyano-3-azabicyclo[3.1.0]hexan-6-yl]-3-fluorobenzene (20.2 mg) in the same manner as described for EXAMPLE 1.

MS (FAB+) m/z: 553 (MH+). HRMS (FAB+) for $C_{29}H_{31}F_2N_4O_5$ (MH+): calcd, 553.2263; found, 553.2250.

EXAMPLE 15

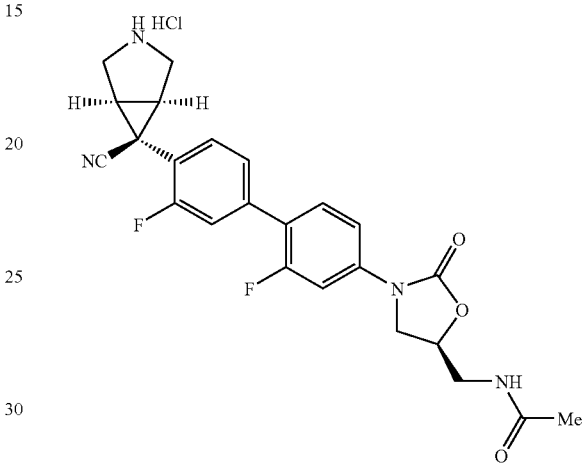

N-[5(S)-3-[4-[4-[(1α,5α,6β)-6-Cyano-3 azabicyclo[3.1.0]hexan-6-yl]-3-fluorophenyl]-3-fluorophenyl]-2-oxooxazolidin-5-ylmethyl]acetamide Hydrochloride The title compound 15 (290 mg) was prepared from N-[5(S)-3-[4-[2-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]acetamide (367 mg) in the same manner as described for EXAMPLE 2.

MS (FAB+) m/z: 453 (MH+) (as free base). HRMS (FAB+) for $C_{24}H_{23}F_2N_4O_3$ (MH+): calcd, 453.1738; found, 453.1747.

EXAMPLE 16

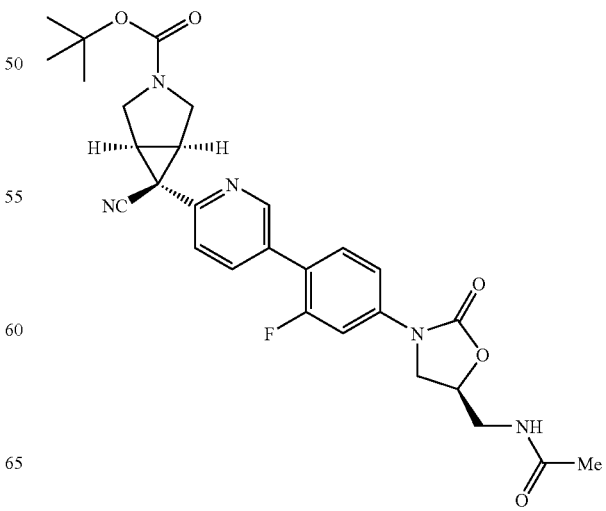

33

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]acetamide The title compound 16 (354 mg) was prepared from N-[5(S)-3-[3-fluoro-4-(4,4,5,5-tetramethyl-1,3,2-dioxaborolyl)phenyl]-2-oxooxazolidin-5-ylmethyl]acetamide (350 mg) and 5-bromo-2-[(1α,5α,6β)-3-t-butoxycarbonyl-6-cyano-3-azabicyclo[3.1.0]hexan-6-yl]pyridine (337 mg) in the same manner as described for EXAMPLE 1.

MS (FAB$^+$) m/z: 536 (MH$^+$). HRMS (FAB$^+$) for $C_{28}H_{31}FN_5O_5$ (MH$^+$): calcd, 536.2309; found, 536.2296.

EXAMPLE 17

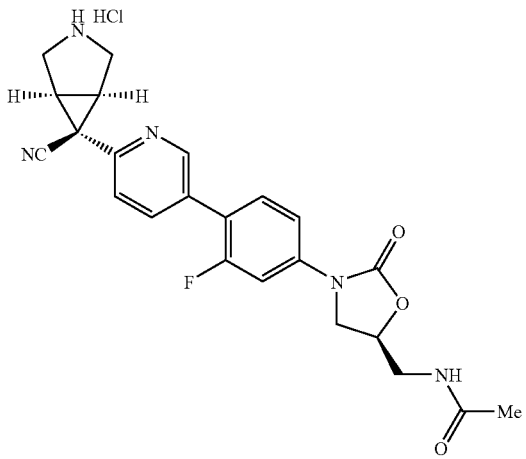

N-[5(S)-3-[4-[2-[(1α,5α,6β)-6-Cyano-3-azabicyclo[3.1.0]hexan-6-yl]pyridin-5-yl]-3-florophenyl]-2-oxooxazolidin-5-ylmethyl]acetamide Hydrochloride The title compound 17 (259 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]acetamide (400 mg) in the same manner as described for EXAMPLE 2.

MS (FAB$^+$) m/z: 436 (MH$^+$) (as free base). HRMS (FAB$^+$) for $C_{23}H_{23}FN_5O_3$ (MH$^+$): calcd, 436.1785; found, 436.1776.

EXAMPLE 18

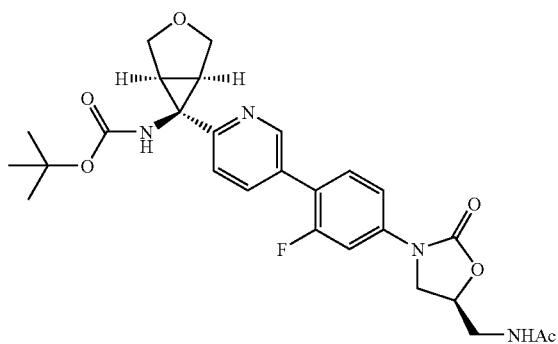

34

N-[5(S)-3-[4-[2-[(1α,5α,6β)-6-t-Butoxycarbonylamino-3-oxabicyclo[3.1.0]hexan-6-yl]pyridin-5-yl]-3-fluorophenyl]-2-oxooxazolidin-5-ylmethyl]acetamide The title compound 18 (62.7 mg) was prepared from N-[5(S)-3-[3-fluoro-4-(4,4,5,5-tetramethyl-1,3,2-dioxaborolyl)phenyl]-2-oxooxazolidin-5-ylmethyl]acetamide (67.2 mg) and 5-bromo-2-[(1α,5α,6β)-6-t-butoxycarbonylamino-3-oxabicyclo[3.1.0]hexan-6-yl]pyridine (63.1 mg) in the same manner as described for EXAMPLE 1.

MS (FAB$^+$) m/z: 527 (MH$^+$). HRMS (FAB$^+$) for $C_{27}H_{32}FN_4O_6$ (MH$^+$): calcd, 527.2306; found, 527.2329.

EXAMPLE 19

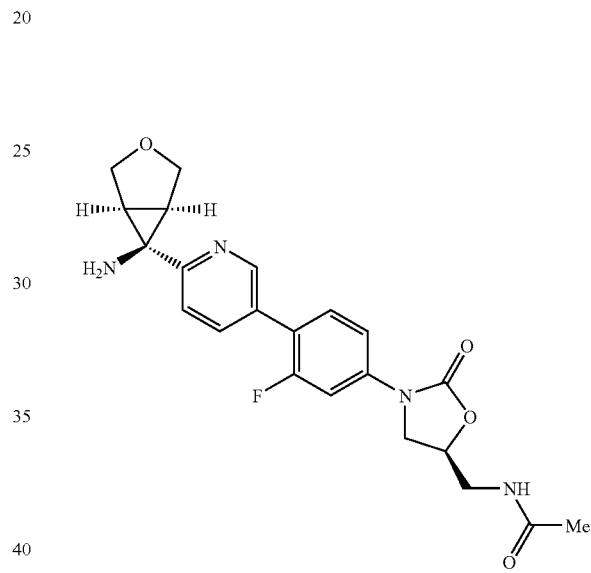

N-[5(S)-3-[4-[2-[(1α,5α,6β)-6-Amino-3-oxabicyclo[3.1.0]hexan-6-yl]pyridin-5-yl]-3-fluorophenyl]-2-oxooxazolidin-5-ylmethyl]acetamide To a solution of N-[5(S)-3-[4-[2-[(1α,5α,6β)-6-t-butoxycarbonylamino-3-oxabicyclo[3.1.0]hexan-6-yl]pyridin-5-yl]-3-fluorophenyl]-2-oxooxazolidin-5-ylmethyl]acetamide (52.0 mg) in dichloromethane (1 mL) was added trifluoroacetic acid (0.5 mL) at 0° C., the mixture was stirred at room temperature for 2 hours. After quenching the reaction by addition of saturated sodium hydrogencarbonate solution, the mixture was extracted with chloroform-methanol (9:1) solution. The organic extracts were dried over anhydrous magnesium sulfate, and then concentrated in vacuo. Flash chromatography (NH silica, dichloromethane:methanol=20:1) of the residue gave title compound 19 (36.7 mg).

MS (EI$^+$) m/z: 426 (M$^+$). HRMS (EI$^+$) for $C_{22}H_{23}FN_4O_4$ (M$^+$): calcd, 426.1703; found, 426.1741.

EXAMPLE 20

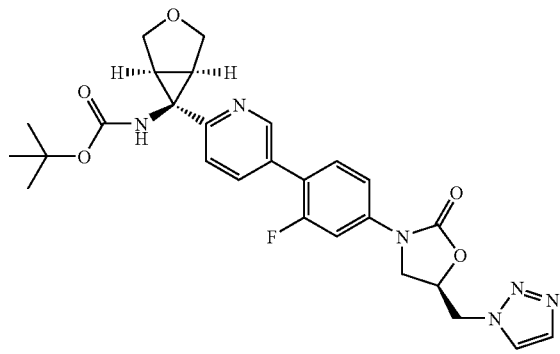

1-[5(R)-3-[4-[2-[(1α,5α,6β)-6-t-Butoxycarbony-
lamino-3-oxabicyclo[3.1.0]hexan-6-yl]pyridin-5-yl]-
3-fluorophenyl]-2-oxooxazolidin-5-ylmethyl]-1,2,3-
triazole The title compound 20 (71.1 mg) was prepared from 1-[5 (R)-3-[3-fluoro-4-(4,4,5,5-tetramethyl-1,3,2-dioxaborolyl) phenyl]-2-oxooxazolidin-5-ylmethyl]-1,2,3-triazole (65.6 mg) and 5-bromo-2-[(1α,5α,6β)-6-t-butoxycarbonylamino-3-oxabicyclo[3.1.0]hexan-6-yl]pyridine (60.0 mg) in the same manner as described for EXAMPLE 1.

MS (FAB$^+$) m/z: 537 (MH$^+$). HRMS (FAB$^+$) for C$_{27}$H$_{30}$FN$_6$O$_5$ (MH$^+$): calcd, 537.2262; found, 537.2276.

EXAMPLE 21

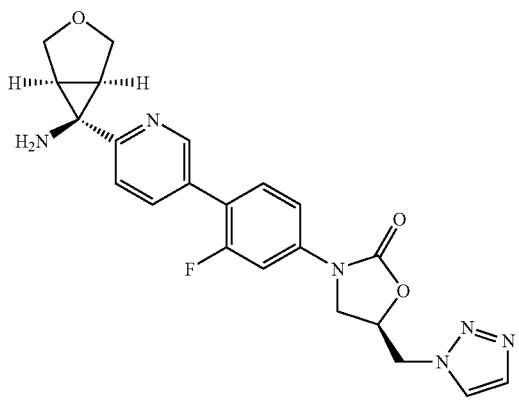

1-[5(R)-3-[4-[2-[(1α,5α,6β)-6-Amino-3-oxabicyclo
[3.1.0]hexan-6-yl]pyridin-5-yl]-3-fluorophenyl]-2-
oxooxazolidin-5-ylmethyl]-1,2,3-triazole The title compound 21 (238 mg) was prepared from 1-[5 (R)-3-[4-[2-[(1α,5α,6β)-6-t-butoxycarbonylamino-3-oxabi-cyclo[3.1.0]hexan-6-yl]pyridin-5-yl]-3-fluorophenyl]-2-oxooxazolidin-5-ylmethyl]-1,2,3-triazole (433 mg) in the same manner as described for EXAMPLE 18.

MS (FAB$^+$) m/z: 437 (MH$^+$). HRMS (FAB$^+$) for C$_{22}$H$_{22}$FN$_6$O$_3$ (MH$^+$): calcd, 437.1737; found, 437.1755.

EXAMPLE 22

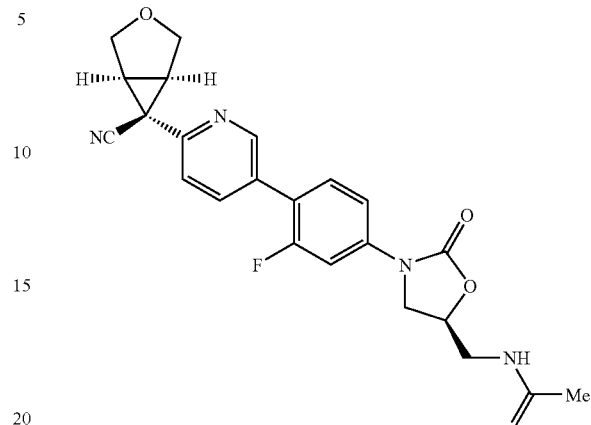

N-[5(S)-3-[4-[2-[(1α,5α,6≈)-6-Cyano-3-oxabicyclo
[3.1.0]hexan-6-yl]pyridin-5-yl]-3-fluorophenyl]-2-
oxooxazolidin-5-ylmethyl]acetamide The title compound 22 (302 mg) was prepared from N-[5 (S)-3-[3-fluoro-4-(4,4,5,5-tetramethyl-1,3,2-dioxaborolyl) phenyl]-2-oxooxazolidin-5-ylmethyl]acetamide (378 mg) and 5-bromo-2-[(1α,5α,6β)-6-cyano-3-oxabicyclo[3.1.0] hexan-6-yl]pyridine (337 mg) in the same manner as described for EXAMPLE 1.

MS (EI$^+$) m/z: 436 (M$^+$). HRMS (EI$^+$) for C$_{23}$H$_{21}$FN$_4$O$_4$ (M$^+$): calcd, 436.1547; found, 436.1516.

EXAMPLE 23

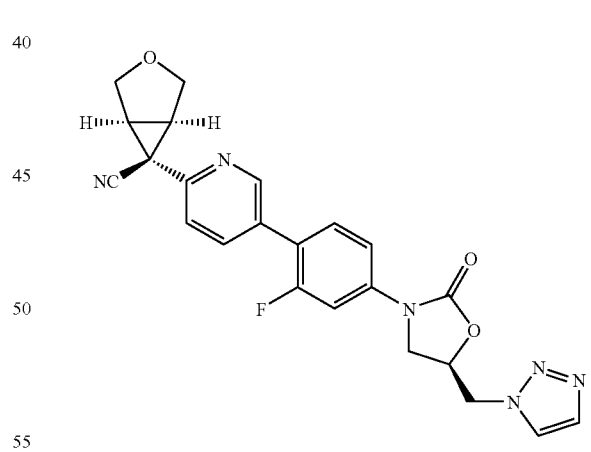

1-[5(R)-3-[4-[2-[(1α,5α,6β)-6-Cyano-3-oxabicyclo
[3.1.0]hexan-6-yl]pyridin-5-yl]-3-fluorophenyl]-2-
oxooxazolidin-5-ylmethyl]-1,2,3-triazole The title compound 23 (353 mg) was prepared from 1-[5 (R)-3-[3-fluoro-4-(4,4,5,5-tetramethyl-1,3,2-dioxaborolyl) phenyl]-2-oxooxazolidin-5-ylmethyl]-1,2,3-triazole (388 mg) and 5-bromo-2-[(1α,5α,6β)-6-cyan-3-oxabicyclo [3.1.0]hexan-6-yl]pyridine (265 mg) in the same manner as described for EXAMPLE 1.

EXAMPLE 24

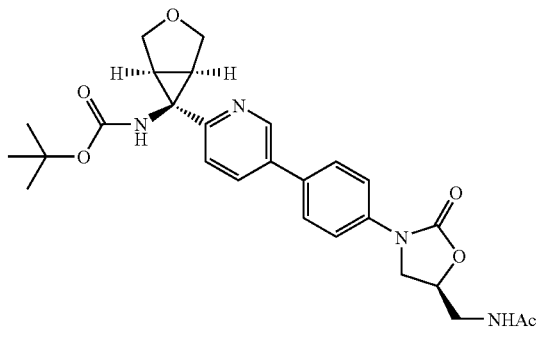

N-[5(S)-3-[4-[2-[(1α,5α,6β)-6-t-Butoxycarbony-lamino-3-oxabicyclo[3.1.0]hexan-6-yl]pyridin-5-yl]phenyl]-2-oxooxazolidin-5-ylmethyl]acetamide The title compound 24 (387 mg) was prepared from N-[5(S)-3-[4-(4,4,5,5-tetramethyl-1,3,2-dioxaborolyl)phenyl]-2-oxooxazolidin-5-ylmethyl]acetamide (406 mg) and 5-bromo-2-[(1α,5α,6β)-6-t-butoxycarbonylamino-3-oxabicyclo[3.1.0]hexan-6-yl]pyridine (400 mg) in the same manner as described for EXAMPLE 1.

MS (FAB$^+$) m/z: 509 (MH$^+$). HRMS (FAB$^+$) for $C_{27}H_{33}N_4O_6$ (MH$^+$): calcd, 509.2400; found, 509.2384.

EXAMPLE 25

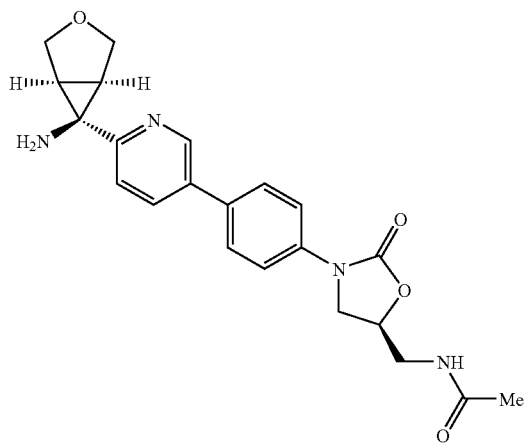

N-[5(S)-3-[4-[2-[(1α,5α,6β)-6-Amino-3-oxabicyclo[3.1.0]hexan-6-yl]pyridin-5-yl]phenyl]-2-oxooxazolidin-5-ylmethyl]acetamide The title compound 25 (262 mg) was prepared from N-[5(S)-3-[4-[2-[(1α,5α,6β)-6-t-butoxycarbonylamino-3-oxabicyclo[3.1.0]hexan-6-yl]pyridin-5-yl]phenyl]-2-oxooxazolidin-5-ylmethyl]acetamide (380 mg) in the same manner as described for EXAMPLE 18.

MS (FAB$^+$) m/z: 409 (MH$^+$). HRMS (FAB$^+$) for $C_{22}H_{25}N_4O_4$ (MH$^+$): calcd, 409.1876; found, 409.1838.

EXAMPLE 26

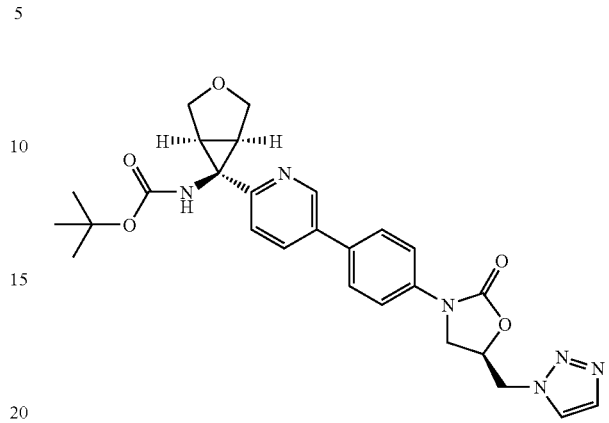

1-[5(R)-3-[4-[2-[(1α,5α,6β)-6-t-Butoxycarbony-lamino-3-oxabicyclo[3.1.0]hexan-6-yl]pyridin-5-yl]phenyl]-2-oxooxazolidin-5-ylmethyl]-1,2,3-triazole The title compound 26 (313 mg) was prepared from 1-[5(R)-3-[4-(4,4,5,5-tetramethyl-1,3,2-dioxaborolyl)phenyl]-2-oxooxazolidin-5-ylmethyl]-1,2,3-triazole (418 mg) and 5-bromo-2-[(1α,5α,6β)-6-t-butoxycarbonylamino-3-oxabicyclo[3.1.0]hexan-6-yl]pyridine (400 mg) in the same manner as described for EXAMPLE 1.

MS (FAB$^+$) m/z: 519 (MH$^+$). HRMS (FAB$^+$) for $C_{27}H_{31}N_6O_5$ (MH$^+$): calcd, 519.2356; found, 519.2382.

EXAMPLE 27

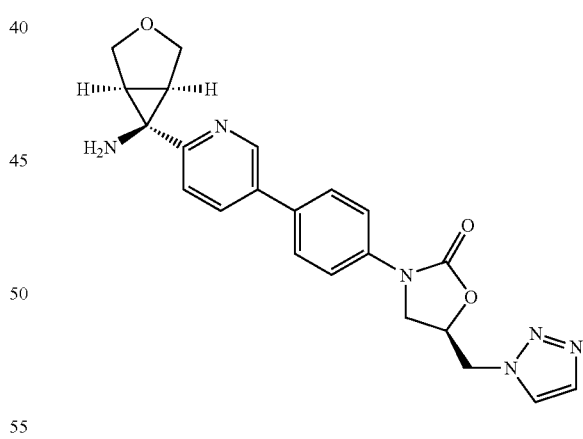

1-[5(R)-3-[4-[2-[(1α,5α,6β)-6-Amino-3-oxabicyclo[3.1.0]hexan-6-yl]pyridin-5-yl]phenyl]-2-oxooxazolidin-5-ylmethyl]-1,2,3-triazole The title compound 27 (210 mg) was prepared from 1-[5(R)-3-[4-[2-[(1α,5α,6β)-6-t-butoxycarbonylamino-3-oxabicyclo[3.1.0]hexan-6-yl]pyridin-5-yl]phenyl]-2-oxooxazolidin-5-ylmethyl]-1,2,3-triazole (310 mg) in the same manner as described for EXAMPLE 18.

MS (FAB$^+$) mnz: 419 (MH$^+$). HRMS (FAB$^+$) for $C_{22}H_{23}N_6O_3$ (MH$^+$): calcd, 419.1832; found, 419.1835.

EXAMPLE 28

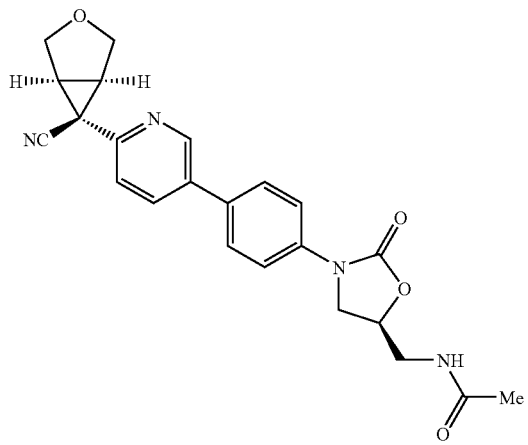

N-[5(S)-3-[4-[2-[(1α,5α,6β)-6-Cyano-3-oxabicyclo[3.1.0]hexan-6-yl]pyridin-5-yl]phenyl]-2-oxooxazolidin-5-ylmethyl]acetamide The title compound 28 (318 mg) was prepared from N-[5(S)-3-[4-(4,4,5,5-tetramethyl-1,3,2-dioxaborolyl)phenyl]-2-oxooxazolidin-5-ylmethyl]acetamide (360 mg) and 5-bromo-2-[(1α,5α,6β)-6-cyano-3-oxabicyclo[3.1.0]hexan-6-yl]pyridine (265 mg) in the same manner as described for EXAMPLE 1.

MS (FAB$^+$) m/z: 419 (MH$^+$). HRMS (FAB$^+$) for $C_{23}H_{23}N_4O_4$ (MH$^+$): calcd, 419.1719; found, 419.1712.

EXAMPLE 29

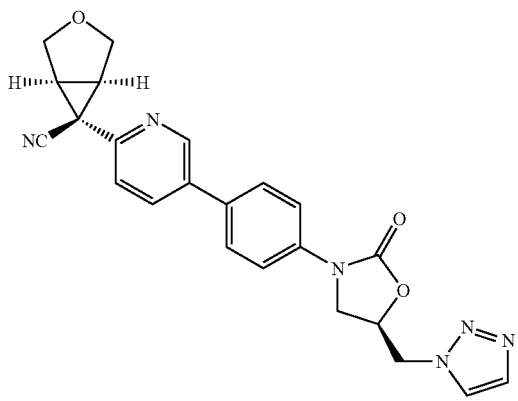

1-[5(R)-3-[4-[2-[(1α,5α,6β)-6-Cyano-3-oxabicyclo[3.1.0]hexan-6-yl]pyridin-5-yl]phenyl]-2-oxooxazolidin-5-ylmethyl]-1,2,3-triazole The title compound 29 (344 mg) was prepared from 1-[5(R)-3-[4-(4,4,5,5-tetramethyl-1,3,2-dioxaborolyl)phenyl]-2-oxooxazolidin-5-ylmethyl]-1,2,3-triazole (419 mg) and 5-bromo-2-[(1α,5α,6β)-6-cyano-3-oxabicyclo[3.1.0]hexan-6-yl]pyridine (300 mg) in the same manner as described for EXAMPLE 1.

MS (FAB$^+$) m/z: 429 (MH$^+$). HRMS (FAB$^+$) for $C_{23}H_{21}N_6O_3$ (MH$^+$): calcd, 429.1675; found, 429.1677.

EXAMPLE 30

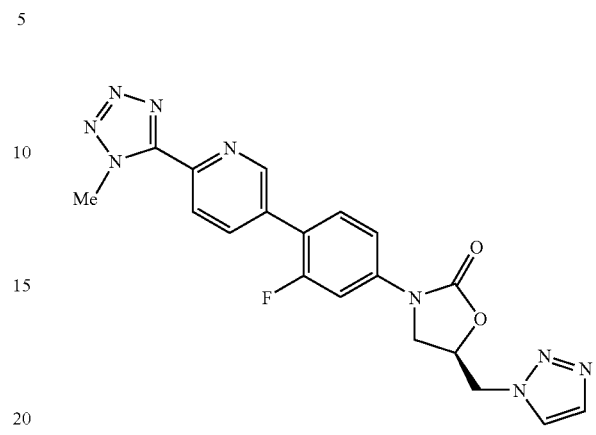

1-[5(R)-3-[3-Fluoro-4-[2-(1-methyltetrazol-5-yl)pyridin-5-yl]phenyl]-2-oxooxazolidin-5-ylmethyl]-1,2,3-triazole The title compound 30 (480 mg) was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (500 mg) and 5-bromo-2-(1-methyltetrazol-5-yl)pyridine (309 mg) in the same manner as described for EXAMPLE 1.

MS (FAB$^+$) m/z: 422 (MH$^+$). HRMS (FAB$^+$) for $C_{19}H_{17}FN_9O_2$(MH$^+$): calcd, 422.1489; found, 422.1508.

EXAMPLE 31

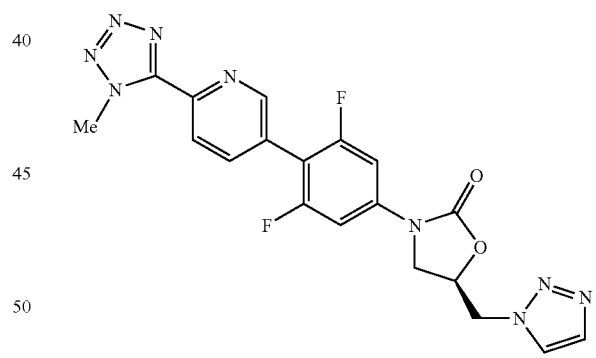

1-[5(R)-3-[3,5-Difluoro-4-[2-(1-methyltetrazol-5-yl)pyridin-5-yl]phenyl]-2-oxooxazolidin-5-ylmethyl]-1,2,3-triazole The mixture of 5-bromo-2-(1-methyltetrazol-5-yl)pyridine (312 mg), bis(pinacolato)diboron (363 mg), potassium 2-ethylhexanoate (355 mg) and [1,1'-bis(diphenylphosphino)ferrocene]palladium(II) dichloride-dichloromethane adduct (53.1 mg) in dioxane (13 mL) was stirred at 80° C. for 1.5 hours and concentrated in vacuo. To a solution of the resulting residue in dioxane (29 mL) was added 1-[5(R)-3-[3,5-difluoro-4-(trifluoromethanesulfonyl)oxyphenyl]-2-oxooxazolidin-5-ylmethyl]-1,2,3-triazole (500 mg), tetrakis(triphenylphosphine)palladium (0) (135 mg),and 2M sodium carbonate solution (2.9 mL), the mixture was stirred at 90° C. for 6 hours. Flash chromatography (NH silica, ethyl acetate) of the mixture gave title compound 31 (246 mg).

MS (FAB$^+$) m/z: 440 (MH$^+$). HRMS (FAB$^+$) for $C_{19}H_{16}F_2N_9O_2$(MH$^+$): calcd, 440.1395; found, 440.1395.

EXAMPLE 32

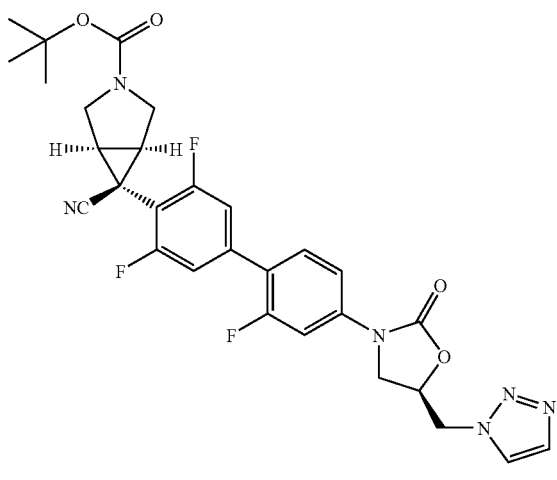

1-[5(R)-3-[4-[4-[(1α,5α,6β)-3-t-Butoxycarbonyl-6-cyano-3-azabicyclo[3.1.0]hexan-6-yl]-3,5-difluorophenyl]-3-fluorophenyl]-2-oxooxazolidin-5-ylmethyl]-1,2,3-triazole Title compound 32 (362 mg) was prepared from 1-[5(R)-3-[3-fluoro-4-(4,4,5,5-tetramethyl-1,3,2-dioxaborolyl)-phenyl]-2-oxooxazolidin-5-ylmethyl]-1,2,3-triazole (260 mg) and 1-bromo-4-[(1α,5α,6β)-3-t-butoxycarbonyl-6-cyano-3-azabicyclo[3.1.0]hexan-6-yl]-3,5-difluorobenzene (267 mg) in the same manner as described for EXAMPLE 1.

MS (FAB$^+$) m/z: 581 (MH$^+$). HRMS (FAB$^+$) for $C_{29}H_{28}F_3N_6O_4$ (MH$^+$): calcd, 581.2124; found, 581.2149.

EXAMPLE 33

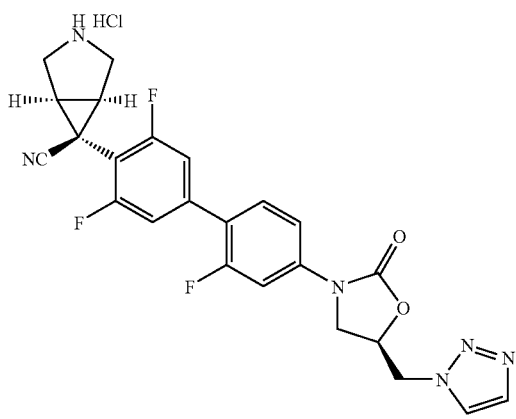

1-[5(R)-3-[4-[4-[(1α,5α,6β)-6-Cyano-3-azabicyclo[3.1.0]hexan-6-yl]-3,5-difluorophenyl]-3-fluorophenyl]-2-oxooxazolidin-5-ylmethyl]-1,2,3-triazole Hydrochloride Title Compound 33 (281 mg) was prepared from 1-[5(R)-3-[4-[4-[(1α,5α,6β)-3-t-butoxycarbonyl-6-cyano-3-azabicyclo[3.1.0]hexan-6-yl]-3,5-difluorophenyl]-3-fluorophenyl]-2-oxooxazolidin-5-ylmethyl]-1,2,3-triazole (360 mg) in the same manner as described for EXAMPLE 2.

MS (FAB$^+$) m/z: 481 (MH$^+$) (as free base). HRMS (FAB$^+$) for $C_{24}H_{20}F_3N_6O_2$ (MH$^+$): calcd, 481.1600; found, 481.1598.

EXAMPLE 34

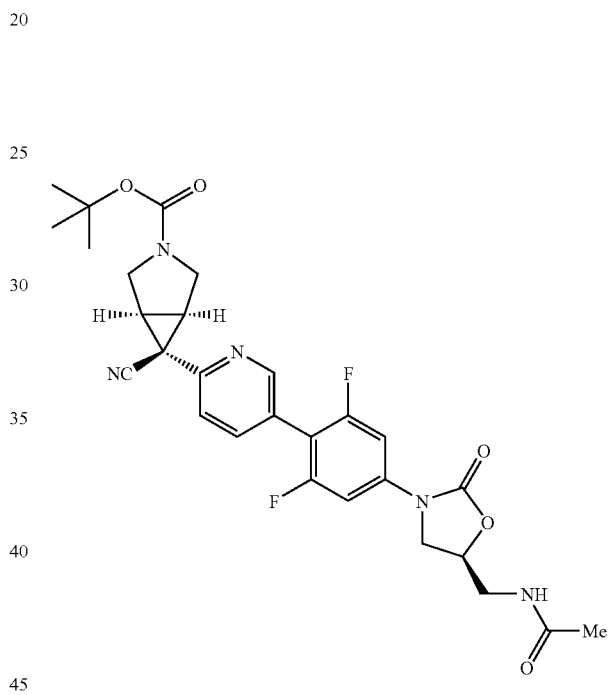

N-[5(S)-3-[4-[2-[(1α,5α,6β)-3-t-Butoxycarbonyl-6-cyano-3-azabicyclo[3.1.0]hexan-6-yl]pyridin-5-yl]-3,5-difluorophenyl]-2-oxooxazolidin-5-ylmethyl] acetamide Title Compound 34 (15.5 mg) was prepared from N-[5(S)-3-[3,5-difluoro-4-(trifluoromethane-sulfonyl)oxyphenyl]-2-oxooxazolidin-5-ylmethyl]acetamide (19.6 mg) and 5-bromo-2-[(1α,5α,6β)-3-t-butoxycarbonyl-6-cyano-3-azabicyclo[3.1.0]hexan-6-yl]pyridine (20.0 mg) in the same manner as described for EXAMPLE 31.

MS (FAB$^+$) m/z: 554 (MH$^+$). HRMS (FAB$^+$) for $C_{28}H_{30}F_2N_5O_5$ (MH$^+$): calcd, 554.2215; found, 554.2201.

EXAMPLE 35

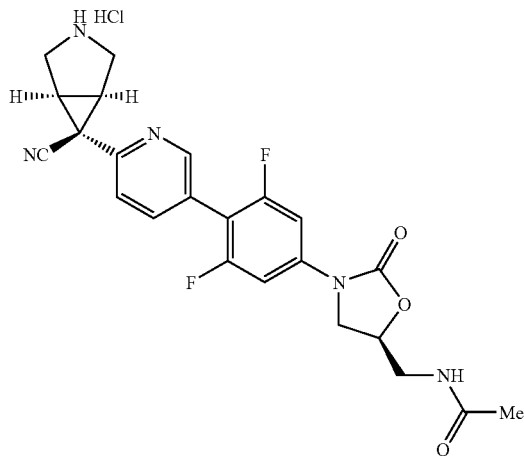

N-[5(S)-3-[4-[2-[(1α,5α,6β)-6-Cyano-3-azabicyclo[3.1.0]hexan-6-yl]pyridin-5-yl]-3,5-difluorophenyl]-2-oxooxazolidin-5-ylmethyl]acetamide Hydrochloride Title Compound 35 (185 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]acetamide (235 mg) in the same manner as described for EXAMPLE 2.

MS (FAB$^+$) m/z: 454 (MH$^+$) (as free base). HRMS (FAB$^+$) for $C_{23}H_{22}F_2N_5O_3$ (MH$^+$): calcd, 454.1691,; 454.1651.

EXAMPLE 36

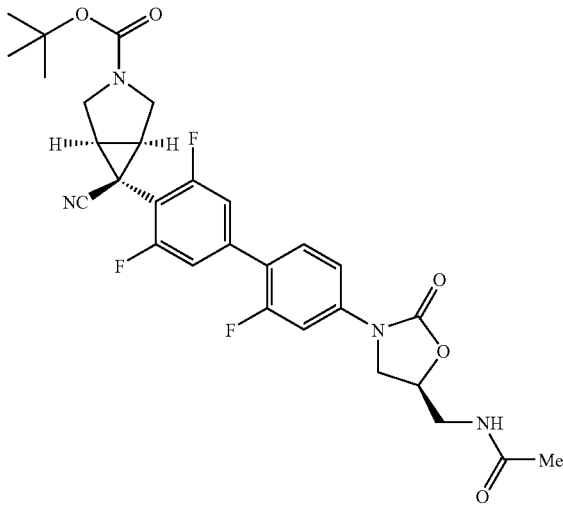

N-[5(S)-3-[4-[4-[(1α,5α,6β)-3-t-Butoxycarbonyl-6-cyano-3-azabicyclo[3.1.0]hexan-6-yl]-3,5-difluorophenyl]-3-fluorophenyl]-2-oxooxazolidin-5-ylmethyl]acetamide Title Compound 36 (347 mg) was prepared from N-[5(S)-3-[4-(4,4,5,5-tetramethyl-1,3,2-dioxaborolyl)-3-fluorophenyl]-2-oxooxazolidin-5-ylmethyl]acetamide (300 mg) and 1-bromo-4-[(1α,5α,6β)-3-t-butoxycarbonyl-6-cyano-3-azabicyclo[3.1.0]hexan-6-yl]-3,5-difluorobenzene (317 mg) in the same manner as described for EXAMPLE 1.

MS (FAB$^+$) m/z: 571 (MH$^+$). HRMS (FAB$^+$) for $C_{29}H_{30}F_3N_4O_5$(MH$^+$): calcd;, 571.2168; found, 571.2159.

EXAMPLE 37

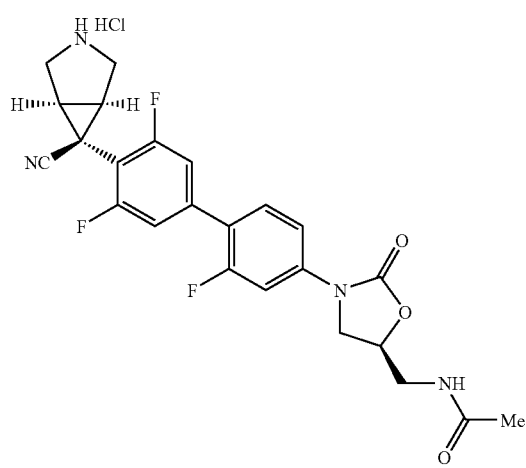

N-[5(S)-3-[4-[4-[(1α,5α,6β)-6-Cyano-3-azabicyclo[3.1.0]hexan-6-yl]-3,5-difluorophenyl]-3-fluorophenyl]-2-oxooxazolidin-5-ylmethyl]acetamide Hydrochloride Title Compound 37 (251 mg) was prepared from N-[5(S)-3-[4-[4-[(1α,5α,6β)-3-t-butoxycarbonyl-6-cyano-3-azabicyclo-[3.1.0]hexan-6-yl]-3,5-difluorophenyl]-3-fluorophenyl]-2-oxooxazolidin-5-ylmethyl]acetamide (347 mg) in the same manner as described for EXAMPLE 2.

MS (EI$^+$) m/z: 470 (M$^+$) (as free base). HRMS (EI$^+$) for $C_{24}H_{21}F_3N_4O_3$ (M$^+$): calcd, 470.1566; found, 470.1551.

EXAMPLE 38

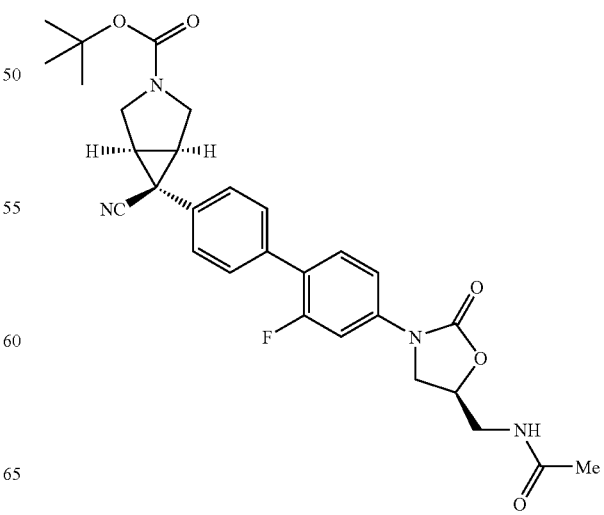

N-[5(S)-3-[4-[4-[(1α,5α,6β)-3-t-Butoxycarbonyl-6-cyano-3-azabicyclo[3.1.0]hexan-6-yl]phenyl]-3-fluorophenyl]-2-oxooxazolidin-5-ylmethyl]acetamide Title Compound 38 (274 mg) was prepared from N-[5(S)-3-[4-(4,4,5,5-tetramethyl-1,3,2-dioxaborolyl)-3-fluorophenyl]-2-oxooxazolidin-5-ylmethyl]acetamide (300 mg) and 1-bromo-4-[(1α,5α,6β)-3-t-butoxycarbonyl-6-cyano-3-azabicyclo[3.1.0]hexan-6-yl]benzene (288 mg) in the same manner as described for EXAMPLE 1.

MS (FAB$^+$) m/z: 535 (MH$^+$). HRMS (FAB$^+$) for $C_{29}H_{32}FN_4O_5$ (MH$^+$): calcd, 535.2357; found, 535.2325.

EXAMPLE 39

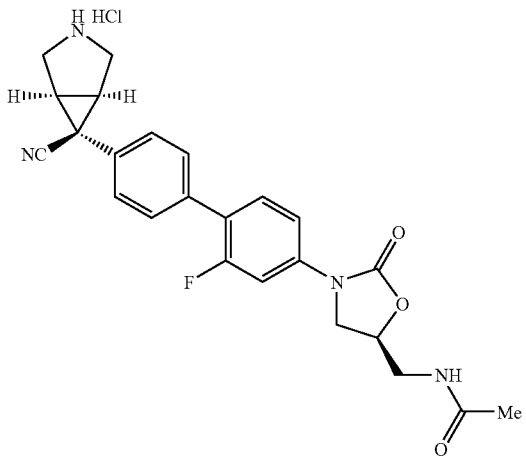

N-[5(S)-3-[4-[4-[(1α,5α,6β)-6-Cyano-3-azabicyclo[3.1.0]hexan-6-yl]phenyl]-3-fluorophenyl]-2-oxooxazolidin-5-ylmethyl]acetamide Hydrochloride Title Compound 39 (212 mg) was prepared from N-[5(S)-3-[4-[4-[(1α,5α,6β)-3-t-butoxycarbonyl-6-cyano-3-azabicyclo[3.1.0]hexan-6-yl]phenyl]-3-fluorophenyl]-2-oxooxazolidin-5-ylmethyl]acetamide (274 mg) in the same manner as described for EXAMPLE 2.

MS (FAB$^+$) m/z: 435 (MH$^+$) (as free base). HRMS (FAB$^+$) for $C_{24}H_{24}FN_4O_3$ (MH$^+$): calcd, 435.1832; found, 435.1818.

EXAMPLE 40

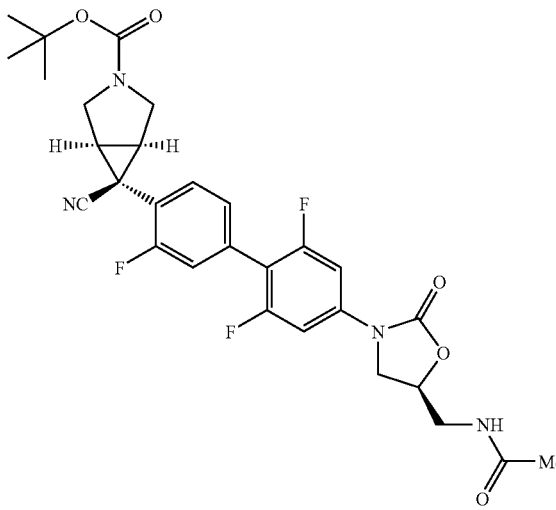

N-[5(S)-3-[4-[4-[(1α,5α,6β)-3-t-Butoxycarbonyl-6-cyano-3-azabicyclo[3.1.0]hexan-6-yl]-3-fluorophenyl]-3,5-difluorophenyl]-2-oxooxazolidin-5-ylmethyl]acetamide Title Compound 40 (427 mg) was prepared from N-[5(S)-3-[3,5-difluoro-4-(trifluoromethanesulfonyl)oxyphenyl]-2-oxooxazolidin-5-ylmethyl]acetamide (641 mg) and 1-bromo-4-[(1α,5α,6β)-3-t-butoxycarbonyl-6-cyano-3-azabicyclo[3.1.0]hexan-6-yl]-3-fluorobenzene (700 mg) in the same manner as described for EXAMPLE 31.

MS (FAB$^+$) m/z: 571 (MH$^+$). HRMS (FAB$^+$) for $C_{29}H_{30}F_3N_4O_5$ (MH$^+$): calcd, 571.2168; found, 571.2134.

EXAMPLE 41

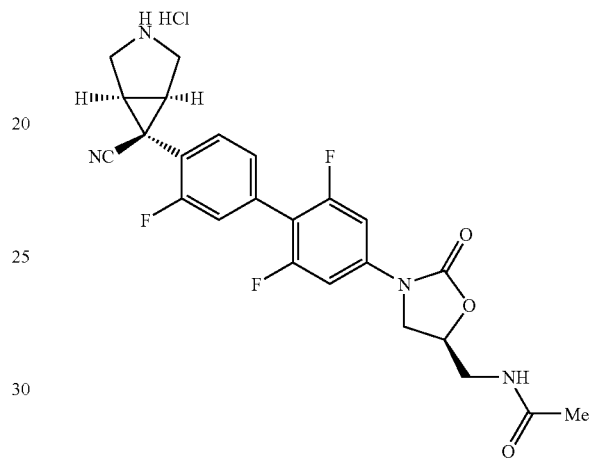

N-[5(S)-3-[4-[4-[(1α,5α,6β)-6-Cyano-3-azabicyclo[3.1.0]hexan-6-yl]-3-fluorophenyl]-3,5-difluorophenyl]-2-oxooxazolidin-5-ylmethyl]acetamide Hydrochloride Title Compound 41 (340 mg) was prepared from N-[5(S)-3-[4-[4-[(1α,5α,6b)-3-t-butoxycarbonyl-6-cyano-3-azabicyclo[3.1.0]hexan-6-yl]-3-fluorophenyl]-3,5-difluorophenyl]-2-oxooxazolidin-5-ylmethyl]acetamide (420 mg) in the same manner as described for EXAMPLE 2.

MS (FAB$^+$) m/z: 471 (MH$^+$) (as free base). HRMS (FAB$^+$) for $C_{24}H_{22}F_3N_4O_3$ (MH$^+$): calcd, 471.1644; found, 471.1611.

EXAMPLE 42

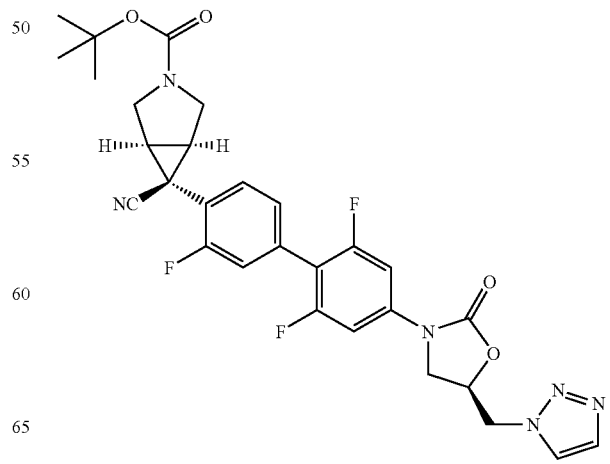

1-[5(R)-3-[4-[4-[(1α,5α,6β)-3-t-Butoxycarbonyl-6-cyano-3-azabicyclo[3.1.0]hexan-6-yl]-3-fluorophenyl]-3,5-difluorophenyl]-2-oxooxazolidin-5-ylmethyl]-1,2,3-triazole Title Compound 42 (273 mg) was prepared from 1-[5(R)-3-[3,5-difluoro-4-(trifluoromethanesulfonyl)oxyphenyl]-2-oxooxazolidin-5-ylmethyl]-1,2,3-triazole (561 mg) and 1-bromo-4-[(1α,5α,6β)-3-t-butoxycarbonyl-6-cyano-3-azabicyclo[3.1.0]hexan-6-yl]-3-fluorobenzene (600 mg) in the same manner as described for EXAMPLE 31.

MS (FAB$^+$) m/z: 581 (MH$^+$). HRMS (FAB$^+$) for $C_{29}H_{28}F_3N_6O_4$(MH$^+$): calcd, 581.2124; found, 581.2141.

1-[5(R)-3-[4-[2-[(1α,5α,6β)-3-t-Butoxycarbonyl-6-cyano-3-azabicyclo[3.1.0]hexan-6-yl]pyridin-5yl]-3,5-difluorophenyl]-2-oxooxazolidin-5-ylmethyl]-1,2,3-triazole Title Compound 44 (14.5 mg) was prepared from 1-[5(R)-3-[3,5-difluoro-4-(trifluoromethanesulfonyl)oxyphenyl]-2-oxooxazolidin-5-ylmethyl]-1,2,3-triazole (19.6 mg) and 5-bromo-2-[(1α,5α,6β)-3-t-butoxycarbonyl-6-cyano-3-azabicyclo[3.1.0]hexan-6-yl]pyridine (20.0 mg) in the same manner as described for EXAMPLE 31.

MS (FAB$^+$) m/z: 564 (MH$^+$). HRMS (FAB$^+$) for $C_{28}H_{28}F_2N_7O_4$ (MH$^+$): calcd, 564.2171; found, 564.2147.

EXAMPLE 43

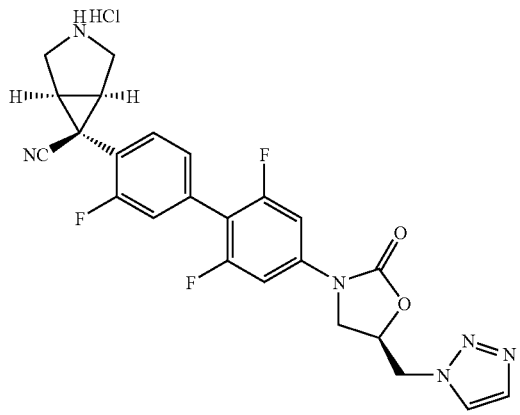

1-[5(R)-3-[4-[4-[(1α,5α,6β)-6-Cyano-3-azabicyclo[3.1.0]hexan-6-yl]-3-fluorophenyl]-3,5-difluorophenyl]-2-oxooxazolidin-5-ylmethyl]-1,2,3-triazole Hydrochloride Title Compound 43 1-[5(R)-3-[4-[4-[(1α,5α,6β)-6-cyano-3-azabicyclo[3.1.0]hexan-6-yl]-3-fluorophenyl]-3,5-difluorophenyl]-2-oxooxazolidin-5-ylmethyl]-1,2,3-triazole hydrochloride (223 mg) was prepared from (270 mg) in the same manner as described for EXAMPLE 2.

MS (FAB$^+$) m/z: 481 (MH$^+$) (as free base). HRMS (FAB$^+$) for $C_{24}H_{20}F_3N_6O_2$ (MH$^+$): calcd, 481.1600; found, 481.1624.

EXAMPLE 45

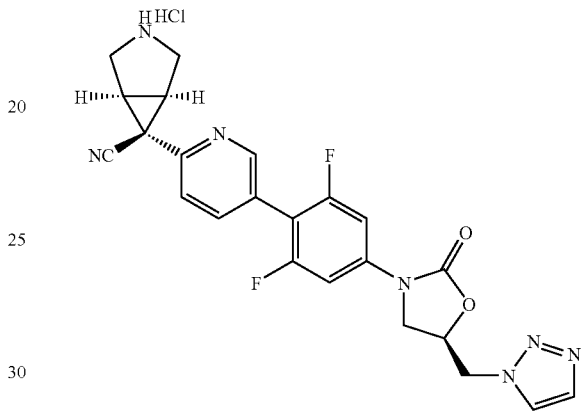

1-[5(R)-3-[4-[2-[(1α,5α,6β)-6-Cyano-3-azabicyclo[3.1.0]hexan-6-yl]pyridin-5-yl]-3,5-difluorophenyl]-2-oxooxazolidin-5-ylmethyl]-1,2,3-triazole Hydrochloride Title Compound 45 (294 mg) was prepared from 1-[5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]-1,2,3-triazole (360 mg) in the same manner as described for EXAMPLE 2.

MS (FAB$^+$) m/z: 464 (MH$^+$) (as free base). HRMS (FAB$^+$) for $C_{23}H_{20}F_2N_7O_2$ (MH$^+$): calcd, 464.1647; found, 464.1648.

EXAMPLE 44

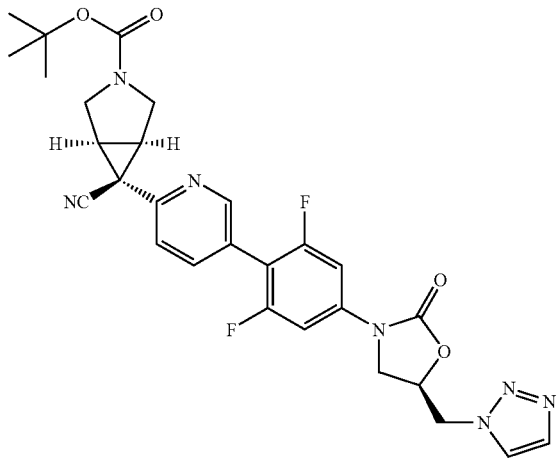

EXAMPLE 46

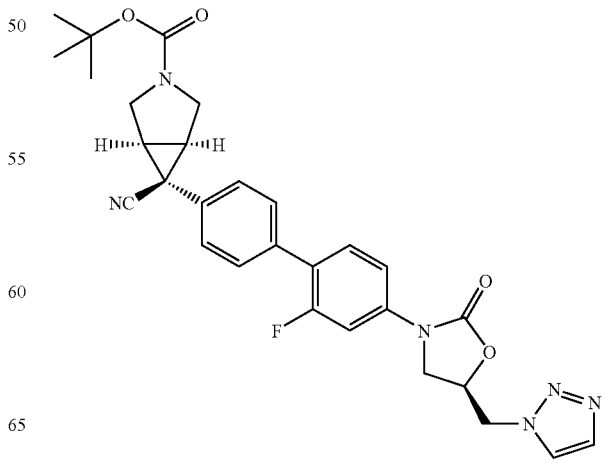

1-[5(R)-3-[4-[4-[(1α,5α,6β)-3-t-Butoxycarbonyl-6-cyano-3-azabicyclo[3.1.0]hexan-6-yl]phenyl]-3-fluorophenyl]-2-oxooxazolidin-5-ylmethyl]-1,2,3-triazole Title Compound 46 (305 mg) was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (300 mg) and 1-bromo-4-[(1α,5α,6β)-3-t-butoxycarbonyl-6-cyano-3-azabicyclo[3.1.0]hexan-6-yl]benzene (281 mg) in the same manner as described for EXAMPLE 1.

MS (FAB$^+$) m/z: 545 (MH$^+$). HRMS (FAB$^+$) for $C_{29}H_{30}FN_6O_4$ (MH$^+$): calcd, 545.2313; found, 545.2318.

EXAMPLE 47

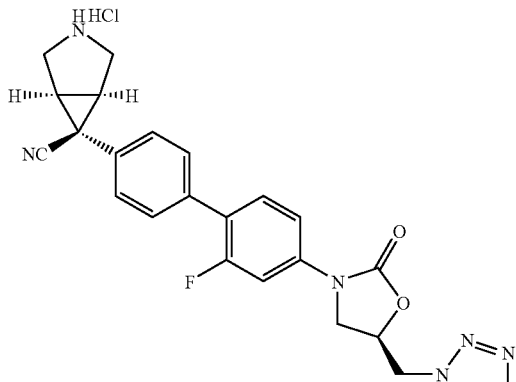

1-[5(R)-3-[4-[4-[(1α,5α,6β)-6-Cyano-3-azabicyclo[3.1.0]hexan-6-yl]phenyl]-3-fluorophenyl]-2-oxooxazolidin-5-ylmethyl]-1,2,3-triazole Hydrochloride Title Compound 47 (265 mg) was prepared from 1-[5(R)-3-[4-[4-[( 1α,5α,6β)-3-t-butoxycarbonyl-6-cyano-3-azabicyclo[3.1.0]hexan-6-yl]phenyl]-3-fluorophenyl]-2-oxooxazolidin-5-ylmethyl]-1,2,3-triazole (305 mg) in the same manner as described for EXAMPLE 2.

MS (FAB$^+$) m/z: 445 (MH$^+$) (as free base). HRMS (FAB$^+$) for $C_{24}H_{22}FN_6O_2$ (MH$^+$): calcd, 445.1788; found, 445.1826.

EXAMPLE 48

1-[5(R)-3-[4-[2-[(1α,5α,6β)-6-t-Butoxycarbonylamino-3-oxabicyclo[3.1.0]hexan-6-yl]pyridin-5-yl]-3,5-difluorophenyl]-2-oxooxazolidin-5-ylmethyl]-1,2,3-triazole Title Compound 48 (482 mg) was prepared from 1-[5(R)-3-[3,5-difluoro-4-(trifluoromethanesulfonyl)oxyphenyl]-2-oxooxazolidin-5-ylmethyl]-1,2,3-triazole (750 mg) and 5-bromo-2-[(1α,5α,6β)-6-t-butoxycarbonylamino-3-oxabicyclo[3.1.0]hexan-6-yl]pyridine (684 mg) in the same manner as described for EXAMPLE 31.

MS (FAB$^+$) m/z: 555 (MH$^+$). HRMS (FAB$^+$) for $C_{27}H_{29}F_2N_6O_5$(MH$^+$): calcd, 555.2167; found, 555.2159.

EXAMPLE 49

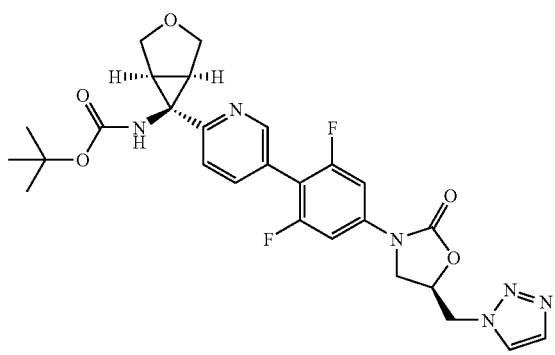

1-[5(R)-3-[4-[2-[(1α,5α,6β)-6-Amino-3-oxabicyclo[3.1.0]hexan-6-yl]pyridin-5-yl]-3,5-difluorophenyl]-2-oxooxazolidin-5-ylmethyl]-1,2,3-triazole To a solution of 1-[5(R)-3-[4-[2-[(1α,5α,6β)-6-t-butoxycarbonylamino-3-oxabicyclo[3.1.0]hexan-6-yl]pyridine-5-yl]-3,5-difluorophenyl]-2-oxooxazolidin-5-ylmethyl]-1,2,3-triazole (465 mg) in dichloromethane was added trifluoroacetic acid (4 mL) at room temperature, the mixture was stirred at the same temperature for 1 hour and concentrated in vacuo. After addition of aqueous sodium hydrogencarbonate solution, the mixture was extracted with dichloromethane-methanol (10:1). The organic extracts were dried over anhydrous magnesium sulfate, filtered, and then concentrated in vacuo. Flash chromatography (NH silica, chloroform:methanol=9:1) of the residue gave 1-[5(R)-3-[4-[2-[(1α,5α,6β)-6-amino-3-oxabicyclo[3.1.0]hexan-6-yl]pyridin-5-yl]-3,5-difluorophenyl]-2-oxooxazolidin-5-ylmethyl]-1,2,3-triazole (299 mg).

MS (FAB$^+$) m/z: 455 (MH$^+$). HRMS (FAB$^+$) for $C_{22}H_{21}F_2N_6O_3$ (MH$^+$): calcd, 455.1643; found, 455.1649.

EXAMPLE 50

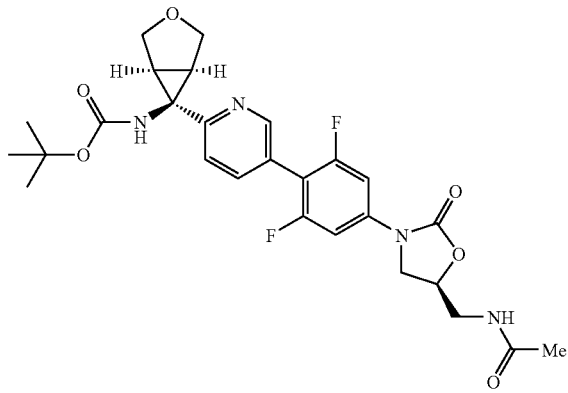

N-[5(S)-3-[4-[2-[(1α,5α,6β)-6-t-Butoxycarbony-lamino-3-oxabicyclo[3.1.0]hexan-6-yl]pyridin-5-yl]-3,5-difluorophenyl]-2-oxooxazolidin-5-ylmethyl]acetamide Title Compound 50 (269 mg) was prepared from N-[5(S)-3-[3,5-difluoro-4-(trifluoromethanesulfonyl)oxyphenyl]-2-oxooxazolidin-5-ylmethyl]acetamide (500 mg) and 5-bromo-2-[(1α,5α,6β)-6-t-butoxycarbonylamino-3-oxabicyclo[3.1.0]hexan-6-yl]pyridine (467 mg) in the same manner as described for EXAMPLE 31.

MS (FAB$^+$) m/z: 545 (MH$^+$). HRMS (FAB$^+$) for $C_{27}H_{31}F_2N_4O_6$(MH$^+$): calcd, 545.2212; found, 545.2224.

EXAMPLE 51

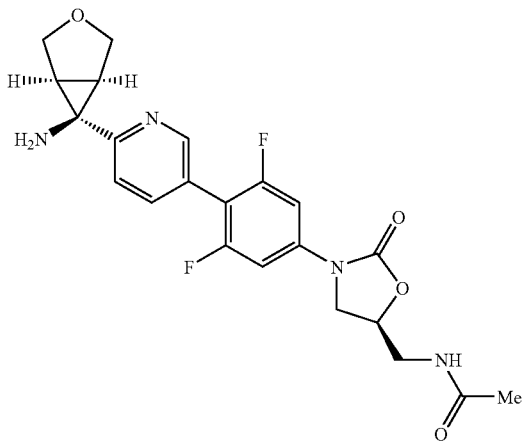

N-[5(S)-3-[4-[2-[(1α,5α,6β)-6-Amino-3-oxabicyclo[3.1.0]hexan-6-yl]pyridin-5-yl]-3,5-difluorophenyl]-2-oxooxazolidin-5-ylmethyl]acetamide Title Compound 51 (278 mg) was prepared from N-[5(S)-3-[4-[2-[(1α,5α,6β)-6-t-butoxycarbonylamino-3-oxabicyclo-[3.1.0]hexan-6-yl]pyridin-5-yl]-3,5-difluorophenyl]-2-oxooxazolidin-5-ylmethyl]acetamide (442 mg) in the same manner as described for EXAMPLE 49.

MS (FAB$^+$) m/z: 445 (MH$^+$). HRMS (FAB$^+$) for $C_{22}H_{23}F_2N_4O_4$ (MH$^+$): calcd, 445.1687; found, 445.1699.

EXAMPLE 52

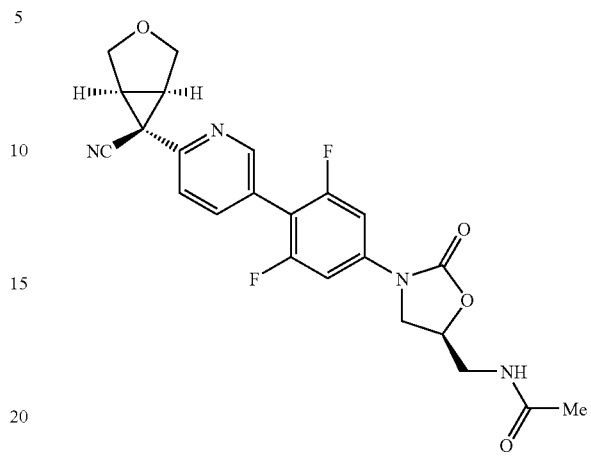

N-[5(S)-3-[4-[2-[(1α,5α,6β)-6-Cyano-3-oxabicyclo[3.1.0]hexan-6-yl]pyridin-5-yl]-3,5-difluorophenyl]-2-oxooxazolidin-5-ylmethyl]acetamide Title Compound 52 (349 mg) was prepared from N-[5(S)-3-[3,5-difluoro-4-(trifluoromethanesulfonyl)oxyphenyl]-2-oxooxazolidin-5-ylmethyl]acetamide (600 mg) and 5-bromo-2-[(1α,5α,6β)-6-cyano-3-oxabicyclo[3.1.0]-hexan-6-yl]pyridine (419 mg) in the same manner as described for EXAMPLE 31.

MS (FAB$^+$) m/z: 455 (MH$^+$). HRMS (FAB$^+$) for $C_{23}H_{21}F_2N_4O_4$ (MH$^+$): calcd, 455.1531; found, 455.1505.

EXAMPLE 53

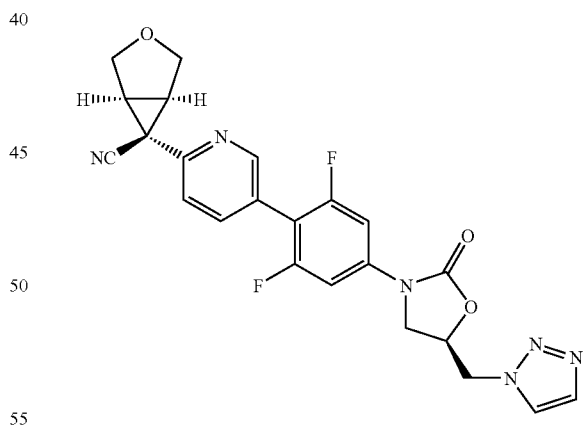

1-[5(R)-3-[4-[2-[(1α,5α,6β)-6-Cyano-3-oxabicyclo[3.1.0]hexan-6-yl]pyridin-5-yl]-3,5-difluorophenyl]-2-oxooxazolidin-5-ylmethyl]-1,2,3-triazole Title Compound 53 (319 mg) was prepared from 1-[5(R)-3-[3,5-difluoro-4-(trifluoromethanesulfonyl)oxyphenyl]-2-oxooxazolidin-5-ylmethyl]-1,2,3-triazole (612 mg) and 5-bromo-2-[(1α,5α,6β)-6-cyano-3-oxabicyclo[3.1.0]-hexan-6-yl]pyridine (419 mg) in the same manner as described for EXAMPLE 31.

MS (FAB+) m/z: 465 (MH+). HRMS (FAB+) for C$_{23}$H$_{19}$F$_2$N$_6$O$_3$ (MH+): calcd, 465.1487; found, 465.1460.

EXAMPLE 54

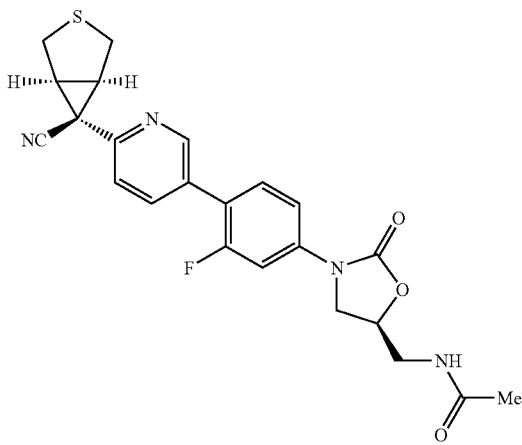

N-[5(S)-3-[4-[2-[(1α,5α,6β)-6-Cyano-3-thiabicyclo[3.1.0]hexan-6-yl]pyridin-5-yl]-3-fluorophenyl]-2-oxooxazolidin-5-ylmethyl]acetamide Title Compound 54 (1.32 g) was prepared from N-[5(S)-3-[4-(4,4,5,5-tetramethyl-1,3,2-dioxaborolyl)-3-fluorophenyl]-2-oxooxazolidin-5-ylmethyl]acetamide (1.51 g) and 5-bromo-2-[(1α,5α,6β)-6-cyano-3-thiabicyclo-[3.1.0]hexan-6-yl]pyridine (1.13 g) in the same manner as described for EXAMPLE 1.

MS (FAB+) m/z: 453 (MH+). HRMS (FAB+) for C$_{23}$H$_{22}$FN$_4$O$_3$S (MH+): calcd, 453.1397; found, 453.1402.

EXAMPLE 55

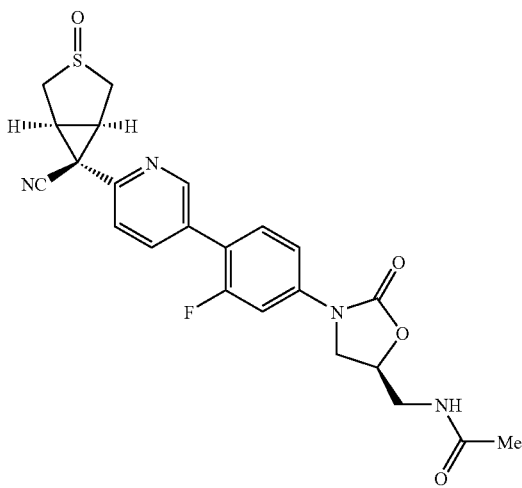

N-[5(S)-3-[4-[2-[(1α,5α,6β)-6-Cyano-3-thiabicyclo[3.1.0]hexan-6-yl]pyridin-5-yl]-3-fluorophenyl]-2-oxooxazolidin-5-ylmethyl]acetamide S-Oxide Title Compound 55 (233 mg) was prepared from N-[5(S)-3-[4-[2-[(1α,5α,6β-cyano-3-thiabicyclo[3.1.0]hexan-6-yl]pyridin-5-yl]-3-fluorophenyl]-2-oxooxazolidin-5-ylmethyl]acetamide (294 mg) in the same manner as described for EXAMPLE 58.

MS (FAB+) m/z: 469 (MH+). HRMS (FAB+) for C$_{23}$H$_{22}$FN$_4$O$_4$S (MH+): calcd, 469.1346; found, 469.1359.

EXAMPLE 56

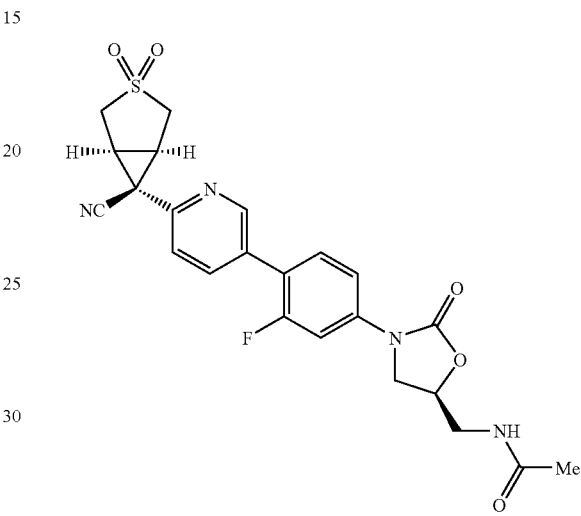

N-[5(S)-3-[4-[2-[(1α,5α,6β)-6-Cyano-3-thiabicyclo[3.1.0]hexan-6-yl]pyridin-5yl]-3-fluorophenyl]-2-oxooxazolidin-5-ylmethyl]acetamide S,S-Dioxide Title Compound 56 (292 mg) was prepared from N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide (317 mg) in the same manner as described for EXAMPLE 59.

MS (FAB+) m/z: 485 (MH+). HRMS (FAB+) for C$_{23}$H$_{22}$FN$_4$O$_5$S (MH+): calcd, 485.1295; found, 485.1282.

EXAMPLE 57

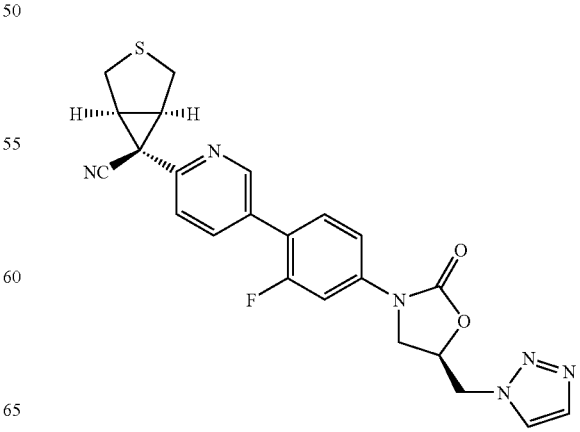

1-[5(R)-3-[4-[2-[(1α,5α,6β)-6-Cyano-3-thiabicyclo[3.1.0]hexan-6-yl]pyridin-5-yl]-3-fluorophenyl]-2-oxooxazolidin-5-ylmethyl]-1,2,3-triazole Title Compound 57 (546 mg) was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (582 mg) and 5-bromo-2-[(1α,5α,6β)-6-cyano-3-thiabicyclo-[3.1.0]hexan-6-yl]pyridine (422 mg) in the same manner as described for EXAMPLE 1.

MS (FAB$^+$) m/z: 463 (MH$^+$). HRMS (FAB$^+$) for $C_{23}H_{20}FN_6O_2S$ (MH$^+$): calcd, 463.1352; found, 463.1355.

EXAMPLE 58

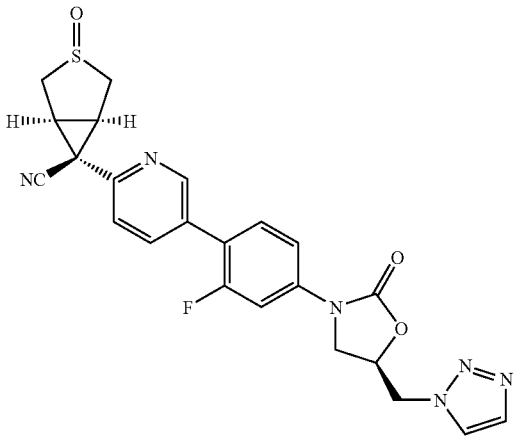

1-[5(R)-3-[4-[2-[(1α,5α,6β)-6-Cyano-3-thiabicyclo[3.1.0]hexan-6-yl]pyridin-5-yl]-3-fluorophenyl]-2-oxooxazolidin-5-ylmethyl]-1,2,3-triazole S-Oxide To a solution of 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole (118 mg) in dichloromethane-methanol (5:1, 8 mL) was added a solution of m-chloroperoxybenzoic acid (74.5 mg) in dichloromethane-methanol (5:1, 1 mL) at −19° C., the mixture was stirred at 0° C. for 70 minutes. Flash chromatography (NH silica, dichloromethane:tetrahydrofuran=7:3) of the mixture gave 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S-oxide (111 mg).

MS (FAB$^+$) m/z: 479 (MH$^+$). HRMS (FAB$^+$) for $C_{23}H_{20}FN_6O_3S$ (MH$^+$): calcd, 479.1302; found, 479.1306.

EXAMPLE 59

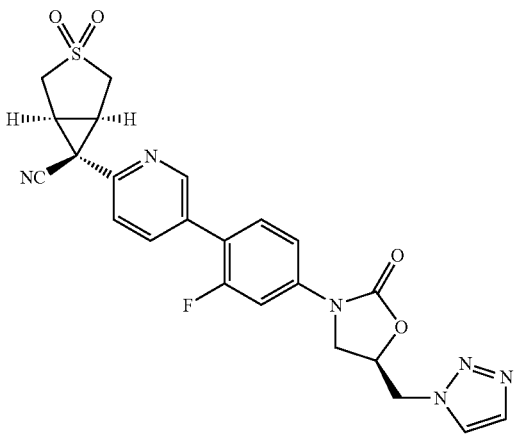

1-[5(R)-3-[4-[2-[(1α,5α,6β)-6-Cyano-3-thiabicyclo[3.1.0]hexan-6-yl]pyridin-5-yl]-3-fluorophenyl]-2-oxooxazolidin-5-ylmethyl]-1,2,3-triazole S,S-Dioxide To a solution of 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole (254 mg) in dichloromethane-methanol (5:1, 14 mL) was added a solution of m-chloroperoxybenzoic acid (438 mg) in dichloromethane-methanol (5:1, 2.0 mL) at 0° C., the mixture was stirred at room temperature for 1.25 hours. After addition of m-chloroperoxybenzoic acid (146 mg) in dichloromethane-methanol (5:1, 0.7 mL) to the mixture, the mixture was stirred at room temperature for 2 hours. Flash chromatography (NH silica, dichloromethane:tetrahydrofuran=2:1) of the mixture gave 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S,S-dioxide (261 mg).

MS (FAB$^+$) m/z: 495 (MH$^+$). HRMS (FAB$^+$) for $C_{23}H_{20}FN_6O_4S$ (MH$^+$): calcd, 495.1251; found, 495.1256.

EXAMPLE 60

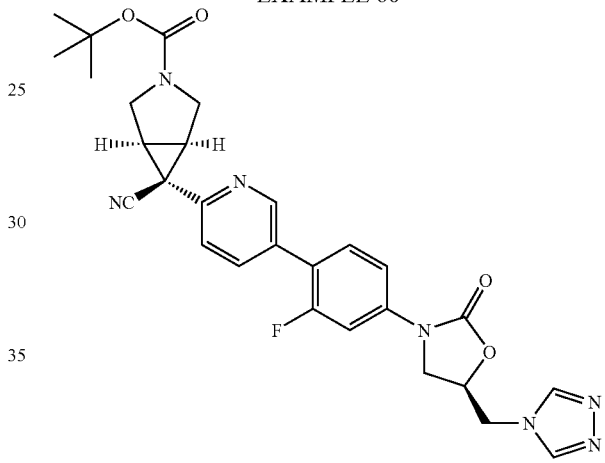

4-[5(R)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]-1,2,4-triazole Title Compound 60 (64.0 mg) was prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (700 mg) in the same manner as described for EXAMPLE 83.

Rf value (TLC): 0.26 (dichloromethane:methanol=10:1).

EXAMPLE 61

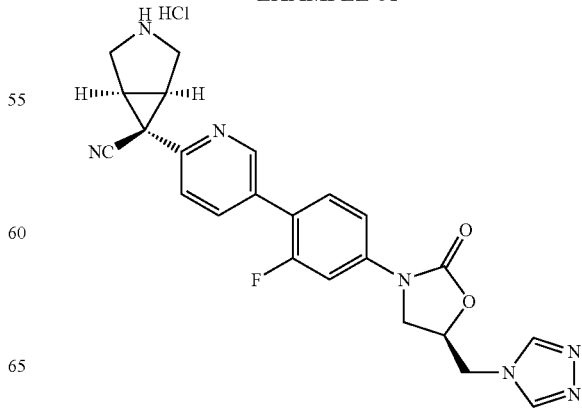

4-[5(R)-3-[4-[2-[(1α,5α,6β)-6-Cyano-3azabicyclo[3.1.0]hexan-6-yl]pyridin-5-yl]-3-fluorophenyl]-2-oxooxazolidin-5-ylmethyl]-1,2,4-triazole Hydrochloride Title Compound 61 (37.9 mg) was prepared from 4-[5(R)-3-[4-[2-[(1a ,5b ,6b )-3-t-butoxycarbonyl-6-cyano-3-azabicyclo[3.1.0]hexan-6-yl]pyridin-5-yl]-3-fluorophenyl]-2-oxooxazolidin-5-ylmethyl]-1,2,4-triazole (64.0 mg) in the same manner as described for EXAMPLE 2.

MS (FAB$^+$) m/z: 446 (MH$^+$) (as free base). HRMS (FAB$^+$) for $C_{23}H_{21}FN_7O_2$(MH$^+$): calcd, 446.1741; found, 446.1756.

EXAMPLE 62

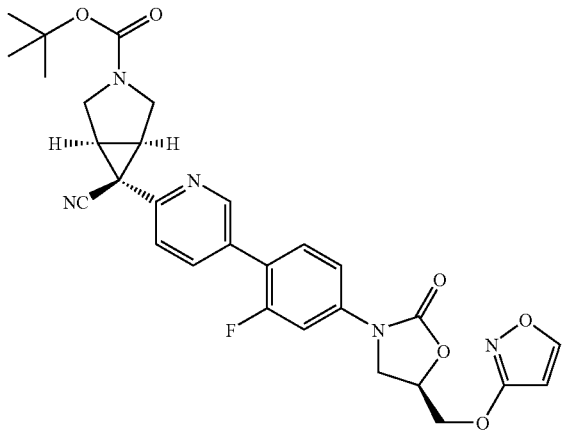

5(R)-3-[4-[2-[(1α,5α,6β)-3-t-Butoxycarbonyl-6-cyano-3-azabicyclo[3.1.0]hexan-6-yl]pyridin-5-yl]-3-fluorophenyl]-5-[(isoxazol-3-yl)oxy]methyloxazolidin-2-one Title Compound 62 (53.8 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-5-hydroxymethyloxazolidin-2-one (50.0 mg) in the same manner as described for EXAMPLE 66.

MS (FAB$^+$) m/z: 562 (MH$^+$). HRMS (FAB$^+$) for $C_{29}H_{29}FN_5O_6$(MH$^+$): calcd, 562.2102; found, 562.2074.

EXAMPLE 63

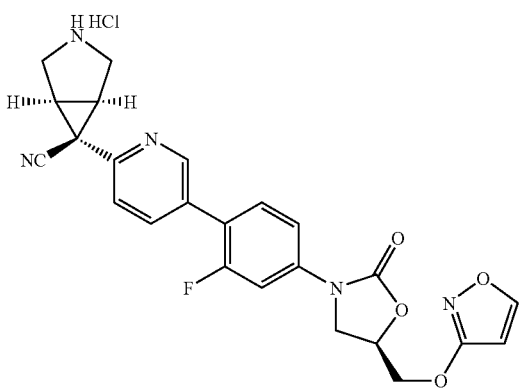

5(R)-3-[4-[2-[(1α,5α,6β)-6-Cyano-3-azabicyclo[3.1.0]hexan-5-yl]pyridin-5-yl]-3-fluorophenyl]-5-[(isoxazol-3-yl)oxy]methyloxazolidin-2-one Hydrochloride Title Compound 63 (303 mg) was prepared from 5(R)-3-[4-[2-[(1α,5α,6β)-3-t-butoxycarbonyl-6-cyano-3-Azabicyclo-[3.1.0]hexan-6-yl]pyridin-5-yl]-3-fluorophenyl]-5-[(isoxazol-3-yl)oxy]methyloxazolidin-2-one (400 mg) in the same manner as described for EXAMPLE 2.

MS (FAB$^+$) m/z: 462 (MH$^+$) (as free base). HRMS (FAB$^+$) for $C_{24}H_{21}FN_5O_4$(MH$^+$): calcd, 462.1578; found, 462.1534.

EXAMPLE 64

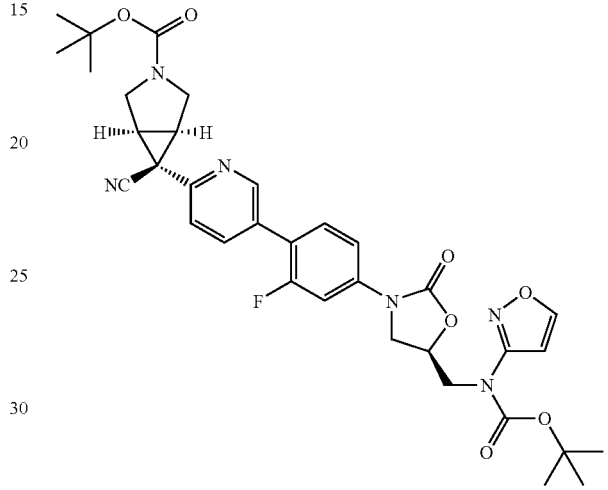

5(R)-3-[4-[2-[(1α,5α,6β)-3-t-Butoxycarbonyl-6-cyano-3-azabicyclo[3.1.0]hexan-6-yl]pyridin-5-yl]-3-fluorophenyl]-5-[N-(t-butoxycarbonyl)N-(isoxazol-3-yl)]aminomethyloxazolidin-2-one Title Compound 64 (58.2 mg) was prepared from N-[5(S)-3-[4-[2-[(1α,5α,6β)-3-t-butoxycarbonyl-6-cyano-3-azabicyclo-[3.1.0]hexan-6-yl]pyridin-5-yl]-3-fluorophenyl]-5-hydroxymethyloxazolidin-2-one (50.0 mg) in the same manner as described for EXAMPLE 67.

MS (FAB$^+$) m/z: 661 (MH$^+$). HRMS (FAB$^+$) for $C_{34}H_{38}FN_6O_7$ (MH$^+$): calcd, 661.2786; found, 661.2760.

EXAMPLE 65

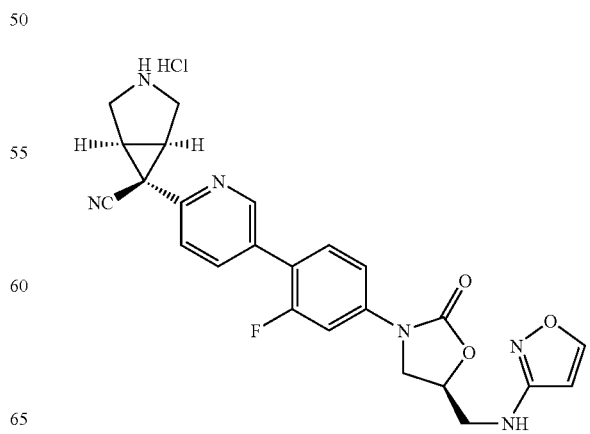

5(R)-3-[4-[2-[(1α,5α,6β)-6-Cyano-3-azabicyclo[3.1.0]hexan-6-yl]pyridin-5-yl]-3-fluorophenyl]-5-[N-(isoxazol-3-yl)]aminomethyloxazolidin-2-one Hydrochloride Title Compound 65 (280 mg) was prepared from 5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-5-[N-(t-butoxycarbonyl)-N-(isoxazol-3-yl)]aminomethyloxazolidin-2-one (600 mg) in the same manner as described for EXAMPLE 2.

MS (FAB⁺) m/z: 461 (MH⁺) (as free base). HRMS (FAB⁺) for $C_{24}H_{22}FN_6O_3$ (MH⁺): calcd, 461.1737; found, 461.1712.

EXAMPLE 66

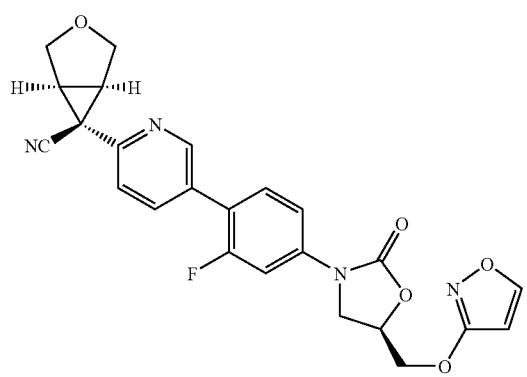

5(R)-3-[4-[2-[(1α,5α,6β)-6-Cyano-3-oxabicyclo[3.1.0]hexan-6-yl]pyridin-5-yl]-3-fluorophenyl]-5-[(isoxazol-3-yl)oxy]methyloxazolidin-2-one To a suspension of N-[5(S)-3-[4-[2-[(1α,5α,6β)-6-cyano-3-oxabicyclo[3.1.0]hexan-6-yl]pyridin-5-yl]-3-fluorophenyl]-5-hydroxymethyloxazolidin-2-one (200 mg), 3-hydroxyisoxazole (55.9 mg) and triphenylphosphine (199 mg) in tetrahydrofuran (5 mL) was added diisopropyl azodicarboxylate (133 mg), the mixture was stirred at room temperature for 1 hour, and concentrated in vacuo. After treatment of the residue with ethyl acetate and ether, the resulting residue was dissolved in chloroform, insoluble materials were filtered off, and filtrate was concentrated in vacuo to give 5(R)-3-[4-[2-[(1α,5α,6β)-6-cyano-3-oxabicyclo[3.1.0]hexan-6-yl]pyridin-5-yl]-3-fluorophenyl]-5-[(isoxazol-3-yl)oxy]methyloxazolidin-2-one (205 mg).

MS (FAB⁺) m/z: 463 (MH⁺). HRMS (FAB⁺) for $C_{24}H_{20}FN_4O_5$ (MH⁺): calcd, 463.1418; found, 463.1439.

EXAMPLE 67

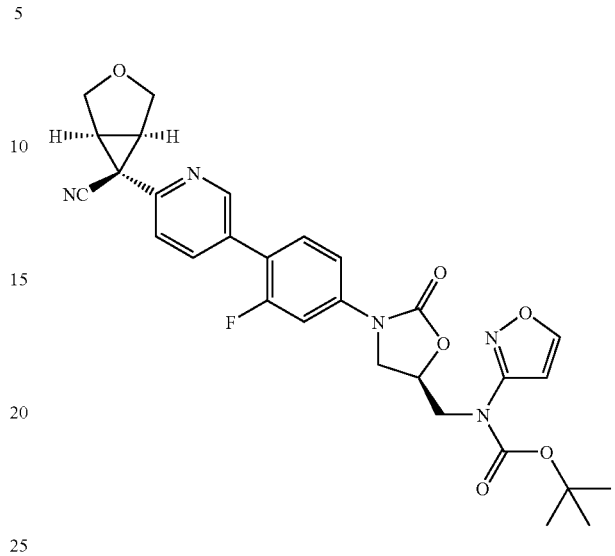

5(R)-5-[N-(t-Butoxycarbonyl)-N-(isoxazol-3-yl)]aminomethyl-3-[4-[2-[(1α,5α,6β)-6-cyano-3-oxabicyclo[3.1.0]hexan-6-yl]pyridin-5-yl]-3-fluorophenyl]oxazolidin-2-one To a suspension of N-[5(S)-3-[4-[2-[(1α,5α,6β)-6-cyano-3-oxabicyclo[3.1.0]pyridin-5-yl]-3-fluorophenyl]-5-hydroxymethyloxazolidin-2-one (300 mg), 3-N-(t-butoxycarbonyl) aminoisoxazole (168 mg), and tetramethylazodicarboxamide (196 mg) in toluene (7.5 mL) was added tributylphosphine (230 mg), and the mixture was stirred at 50° C. for 2 hours. Flash chromatography (silica, hexane:ethyl acetate=1:1) of the mixture gave 5(R)-5-[N-(t-butoxycarbonyl)-N-(isoxazol-3-yl)]aminomethyl-3-[4-[2-[(1α,5α,6β)-6-cyano-3-oxabicyclo[3.1.0]hexan-6-yl]-3-fluorophenyl]oxazolidin-2-one (392 mg).

MS (FAB⁺) m/z: 562 (MH⁺). HRMS (FAB⁺) for $C_{29}H_{29}FN_5O_6$ (MH⁺): calcd, 562.2102; found, 562.2123.

EXAMPLE 68

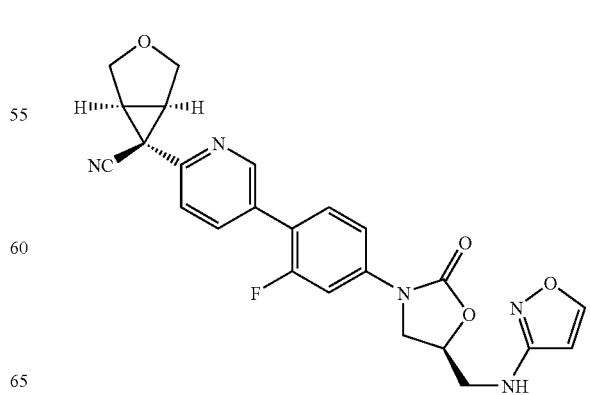

5(R)-3-[4-[2-[(1α,5α,6β)-6-Cyano-3-oxabicyclo[3.1.0]hexan-6-yl]pyridin-5-yl]-3-fluorophenyl]5-[N-(isoxazol-3-yl)]aminomethyloxazolidin-2-one To a solution of 5(R)-5-[N-(t-butoxycarbonyl)-N-(isoxazol-3-yl)]aminomethyl-3-[4-[2-[(1α,5=,6β)-6-cyano-3-oxabicyclo[3.1.0]hexan-6-yl]pyridin-5-yl]-3-fluorophenyl]oxazolidin-2-one (375 mg) in dichloromethane (4.0 mL) was added trifluoroacetic acid (2.0 mL) at 0° C., the mixture was stirred at room temperature for 2 hours and then concentrated in vacuo. After dilution of the residue with ethyl acetate, the mixture was washed with 5% potassium carbonate solution, dried over anhydrous magnesium sulfate, and then concentrated in vacuo to give 5(R-3-[4-[2-[(1α,5α,6β)-6-cyano-3-oxabicyclo[3.1.0]hexan-6-yl]pyridin-5-yl]-3-fluorophenyl]-5-[N-(isoxazol-3-yl)]aminomethyloxazolidin-2-one (189 mg).

MS (FAB⁺) m/z: 462 (MH⁺). HRMS (FAB⁺) for $C_{24}H_{21}FN_5O_4$(MH⁺): calcd, 462.1578; found, 462.1602.

EXAMPLE 69

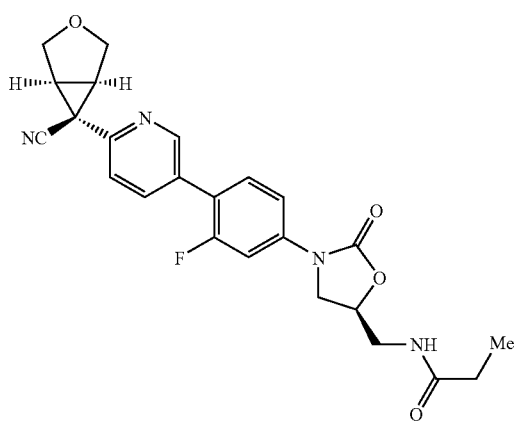

N-[5(S)-3-[4-[2-[(1α,5α,6β)-6-Cyano-3-oxabicyclo[3.1.0]hexan-6-yl]pyridin-5-yl]-3-fluorophenyl]-2-oxooxazolidin-5-ylmethyl]propionamide The title Compound 69 (213 mg) was prepared from 5(S)-aminomethyl-3-[4-[2-[(1α,5α,6β)-6-cyano-3-oxabicyclo[3.1.0]hexan-6-yl]pyridin-5-yl]-3-fluorophenyl]oxazolidin-2-one (200 mg) in the same manner as described for EXAMPLE 70.

MS (FAB⁺) m/z: 451 (MH⁺). HRMS (FAB⁺) for $C_{24}H_{24}FN_4O_4$(MH⁺): calcd, 451.1782; found, 451.1753.

EXAMPLE 70

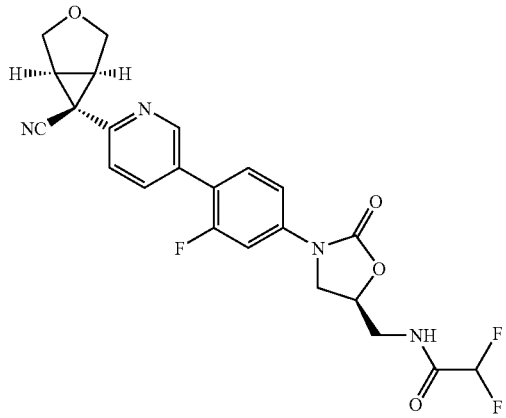

N-[5(S)-3-[4-[2-[(1α,5α,6β)-6-Cyano-3-oxabicyclo[3.1.0]hexan-6-yl]pyridin-5-yl]-3-fluorophenyl]-2-oxooxazolidin-5-ylmethyl]difluoroacetamide To a suspension of 5(S)-aminomethyl-3-[4-[2-[(1α,5α,6β)-6-cyano-3-oxabicyclo[3.1.0]hexan-6-yl]pyridin-5-yl]-3-fluorophenyl]oxazolidin-2-one (200 mg) in pyridine (5 mL) was added difluoroacetic anhydride (159 mg) at 0° C., the mixture was stirred at room temperature for 2 hours and then concentrated in vacuo. After dilution of the residue with dichloromethane, the mixture was washed with 3% hydrochloric acid and 5% sodium hydrogencarbonate solution, dried over anhydrous magnesium sulfate, and then concentrated in vacuo. Flash chromatography (silica, dichloromethane:methanol=15:1) of the residue gave N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]difluoroacetamide (230 mg).

MS (FAB⁺) m/z: 473 (MH⁺). HRMS (FAB⁺) for $C_{23}H_{20}F_3N_4O_4$ (MH⁺): calcd, 473.1437; found, 473.1426.

EXAMPLE 71

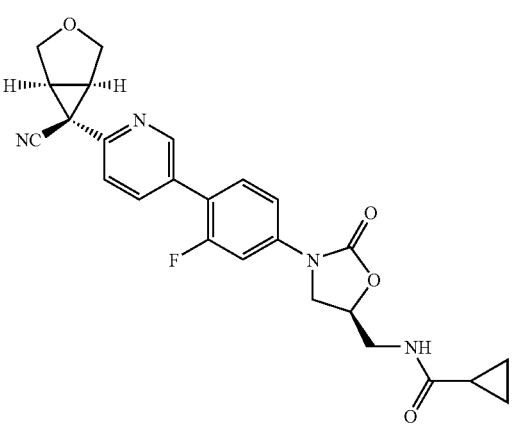

N-[5(S)-3-[4-[2-[(1α,5α,6β)-6-Cyano-3-oxabicyclo[3.1.0]hexan-6-yl]pyridin-5-yl]-3-fluorophenyl]-2-oxooxazolidin-5-ylmethyl]cyclopropanecarboxamide To a solution of 5(S)-aminomethyl-3-[4-[2-[(1α,5α,6β)-6-cyano-3-oxabicyclo[3.1.0]hexan-6-yl]pyridin-5-yl]-3-fluorophenyl]oxazolidin-2-one (200 mg) and cyclopropanecarboxylic acid (56.8 mg) in dichloromethane (10 mL) was added 1-[3-(dimethylamino)propyl]-3-ethylcarbodiimide hydrochloride (146 mg) at room temperature, the mixture was stirred at the same temperature for 2 hours. The mixture was washed with water and 5% sodium hydrogencarbonate solution, dried over anhydrous magnesium sulfate, and then concentrated in vacuo. Flash chromatography (silica, dichloromethane:methanol=15:1) of the residue gave N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]cyclopropanecarboxamide (167 mg).

MS (FAB$^+$) m/z: 463 (MH$^+$). HRMS (FAB$^+$) for $C_{25}H_{24}FN_4O_4$ (MH$^+$): calcd, 463.1782; found, 463.1774.

EXAMPLE 72

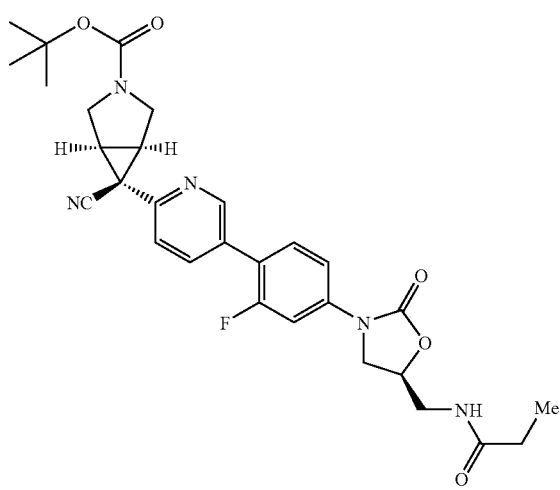

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]propionamide Title Compound 72 (305 mg) was prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (300 mg) and propionyl chloride (58 μL) in the same manner as described for EXAMPLE 92.

MS (FAB$^+$) m/z: 550 (MH$^+$).

EXAMPLE 73

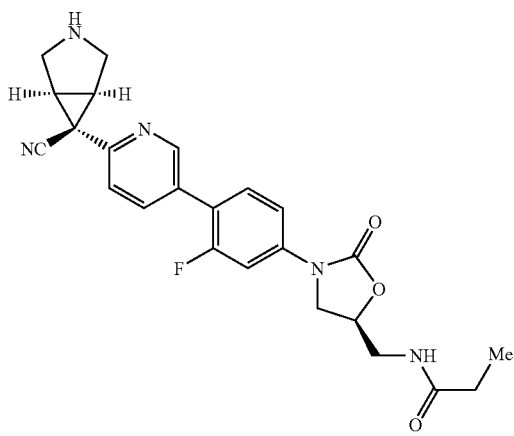

N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]propionamide Title Compound 73 (165 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]propionamide (295 mg) in the same manner as described for EXAMPLE 49.

MS (FAB$^+$) m/z: 450 (MH$^+$). HRMS (FAB$^+$) for $C_{24}H_{25}FN_5O_3$(MH$^+$): calcd, 450.1941; found, 450.1905.

EXAMPLE 74

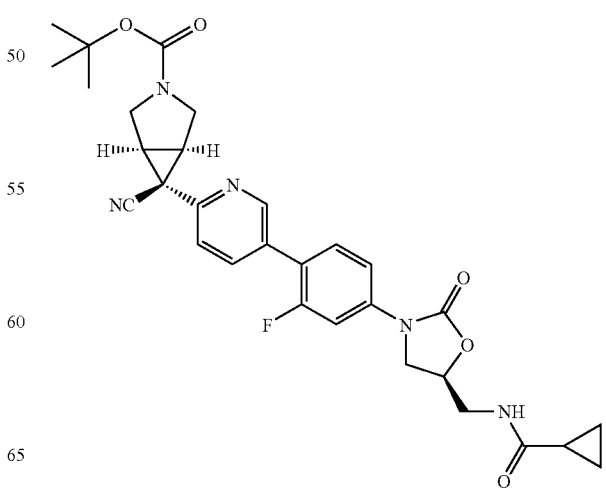

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]cyclopropanecarboxamide Title Compound 74 (260 mg) was prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (300 mg) in the same manner as described for EXAMPLE 71.
MS (FAB⁺) m/z: 562 (MH⁺).

EXAMPLE 75

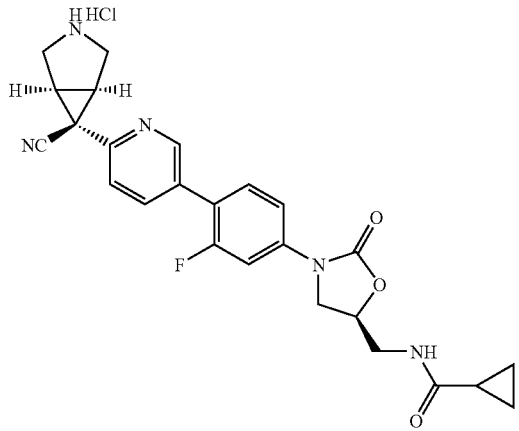

N-[5(S)-3-[4-[2-[(1α,5α,6β)-6-Cyano-3-azabicyclo[3.1.0]hexan-6-yl]-3-fluorophenyl]-2-oxooxazolidin-5-ylmethyl]cyclopropanecarboxamide Hydrochloride Title Compound 75 (183 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]cyclopropanecarboxamide (250 mg) in the same manner as described for EXAMPLE 2.
MS (FAB⁺) m/z: 462 (MH⁺) (as free base). HRMS (FAB⁺) for $C_{25}H_{25}FN_5O_3$ (MH⁺): calcd, 462.1941; found, 462.1938.

EXAMPLE 76

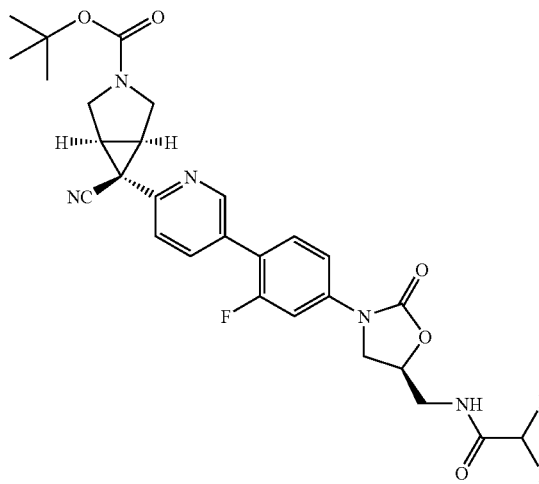

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]difluoroacetamide Title Compound 76 (258 mg) was prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (300 mg) in the same manner as described for EXAMPLE 70.
MS (FAB⁺) m/z: 572 (MH⁺).

EXAMPLE 77

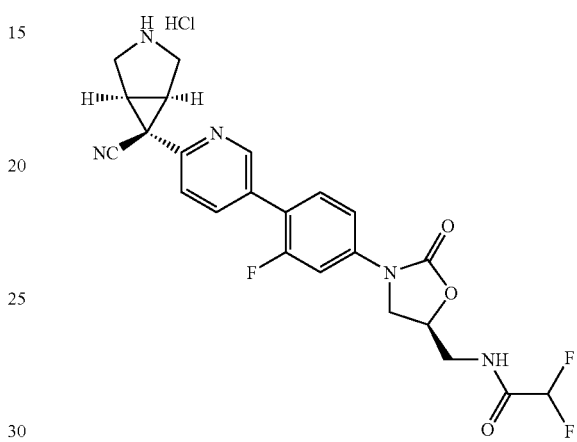

N-[5(S)-3-[4-[2-[(1α,5α,6β)-6-Cyano-3-azabicyclo[3.1.0]hexan-6-yl]-3-fluorophenyl]-2-oxooxazolidin-5-ylmethyl]difluoroacetamide Hydrochloride Title Compound 77 (170 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]difluoroacetamide (250 mg) in the same manner as described for EXAMPLE 2.
MS (FAB⁺) m/z: 472 (MH⁺) (as free base). HRMS (FAB⁺) for $C_{23}H_{21}F_3N_5O_3$ (MH⁺): calcd, 472.1596; found, 472.1590.

EXAMPLE 78

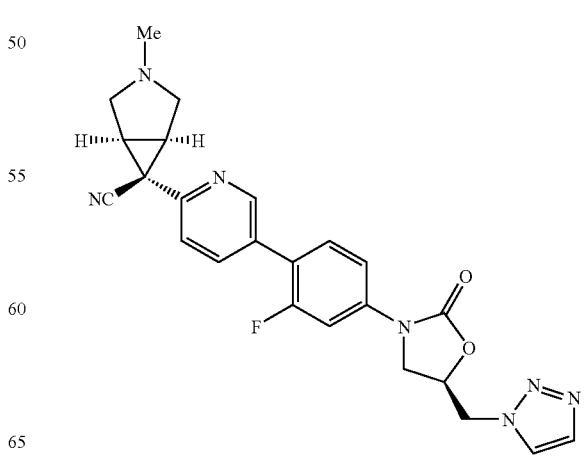

1-[5(R)-3-[4-[2-[(1α,5α,6β)-6-Cyano-3-methyl-3-azabicyclo[3.1.0]hexan-6-yl]pyridin-5-yl]-3-fluorophenyl]-2-oxooxazolidin-5-ylmethyl-]-1,2,3-triazole To a suspension of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) in tetrahydrofuran (0.45 mL) was added acetic acid (5.1 μL), 35% formaldehyde solution (35.6 μL), and sodium triacetoxyborohydride (20.0 mg) at room temperature, the mixture was stirred at the same temperature for 3 hours. After quenching the reaction by addition of saturated sodium hydrogencarbonate solution at 0° C., the mixture was extracted with dichloromethane-methanol (5:1) solution. The organic extracts were washed with brine, dried over anhydrous magnesium sulfate, and then concentrated in vacuo. Preparative thin-layer chromatography (silica, dichloromethane:methanol=10:1) of the residue gave 1-[5(R)-3-[4-[2-[(1α,5α,6β)-6-cyano-3-methyl-3-azabicyclo[3.1.0]hexan-6-yl]pyridin-5-yl]-3-fluorophenyl]-2-oxooxazolidin-5-ylmethyl]-1,2,3-triazole (15.0 mg).

MS (FAB+) m/z: 460 (MH+). HRMS (FAB+) for $C_{24}H_{23}FN_7O_2$ (MH+): calcd, 460.1897; found, 460.1888.

EXAMPLE 79

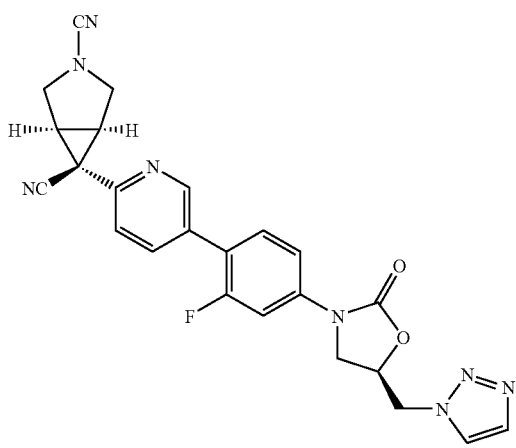

1-[5(R)-3-[4-[2-[(1α,5α,6β)-3,6-Dicyano-3-azabicyclo[3.1.0]hexan-6-yl]pyridin-5-yl]-3-fluorophenyl]-2-oxooxazolidin-5-ylmethyl]-1,2,3-triazole A suspension of 1-[5(R)-3-[4-[2-[(1α,5α,6β)-6-cyano-3-azabicyclo[3.1.0hexan-6-yl]pyridin-5-yl]-3-fluorophenyl]-2-oxooxazolidin-5-ylmethyl]-1,2,3-triazole (300 mg) and sodium acetate (390 mg) in methanol (20 mL) was stirred at room temperature for 30 minutes. To the resulting suspension was added a solution of cyanogens bromide in dichloromethane (5 M, 0.4 mL) at 0° C., the mixture was stirred at the same temperature for 8 hours. After insoluble materials were filtered off, the filtrate was concentrated in vacuo. Treatment of the residue with water and methanol gavel-[5(R)-3-[4-[2-[(1α,5α,6β)-3,6-dicyano-3-azabicyclo[3.1.0]hexan-6-yl]pyridin-5-yl]-3-fluorophenyl]-2-oxooxazolidin-5-ylmethyl]-1,2,3-triazole (138 mg).

MS (FAB+) m/z: 471 (MH+). HRMS (FAB+) for $C_{24}H_{20}FN_8O_2$ (MH+): calcd, 471.1693; found, 471.1709.

EXAMPLE 80

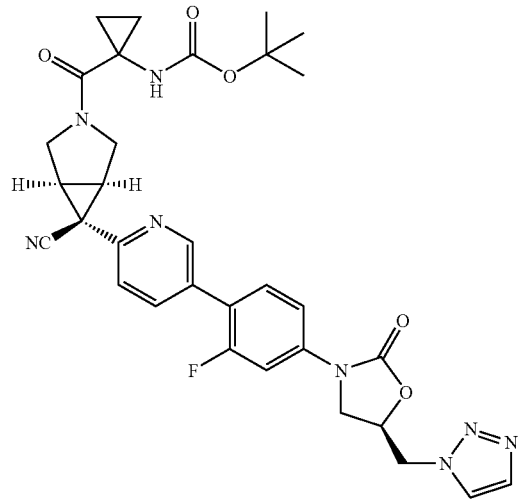

1-[5(R)-3-[4-[2-[(1α,5α,6β)-3-[(1-t-Butoxycarbonylaminocyclopropan-1-yl)carbonyl-6-cyano-3-azabicyclo[3.1.0]hexan-6-yl]pyridin-5-yl]-3-fluorophenyl]-2-oxooxazolidin-5-ylmethyl]-1,2,3-triazole A mixture of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg), 1-(t-butoxycarbonylamino) cyclopropane-1-carboxylic acid (13.6 mg), 1-[3-(dimethylamino)propyl]-3-ethylcarbodiimide hydrochloride (12.9 mg), and 4-(dimethylamino)pyridine (8.2 mg) in dichloromethane was stirred at room temperature for 5 hours. After dilution of the mixture with water, the mixture was washed with brine, dried over anhydrous magnesium sulfate, and then concentrated in vacuo. Flash chromatography (silica, dichloromethane:methanol=10:1) of the residue gave title compound 80(28.6 mg).

MS (FAB+) m/z: 629 (MH+). HRMS (FAB+) for $C_{32}H_{34}FN_8O_5$ (MH+): calcd, 629.2636; found, 629.2633.

EXAMPLE 81

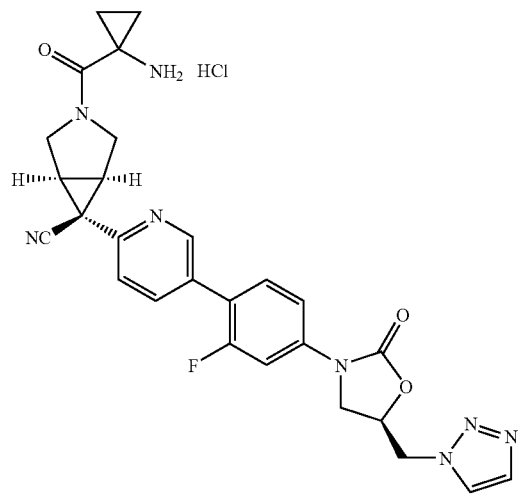

1-[5(R)-3-[4-[2-[(1α,5α,6β)-3-[(1-Aminocyclopropan-1-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole Hydrochloride Title Compound 81 (18.4 mg) was prepared from 1-[5(R)-3-[4-[2-[(1α,5α,6β)-3-[(1-t-butoxycarbonylaminocyclopropan-1-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole (26.6 mg) in the same manner as described for EXAMPLE 2.

MS (FAB$^+$) m/z: 529 (MH$^+$) (as free base). HRMS (FAB$^+$) for $C_{27}H_{26}FN_8O_3$ (MH$^+$): calcd, 529.2112; found, 529.2105.

EXAMPLE 82

MS (FAB$^+$) m/z: 619 (MH$^+$). HRMS (FAB$^+$) for $C_{33}H_{28}FN_8O_4$ (MH$^+$): calcd, 619.2218; found, 619.2214.

Step 2.

Title Compound 82

A mixture of the compound of Step 1 of Example 82 (20.0 mg) and methylhydrazine (34.4 μL) in ethanol was heated under reflux for 2 days. After dilution of the mixture with brine, the mixture was extracted with ethyl acetate. The organic extracts were dried over anhydrous magnesium sulfate, and then concentrated in vacuo. Preparative thin-layer chromatography (NH silica, ethyl acetate:methanol=10:1) of the residue gave title compound 82 (10.8 mg).

MS (FAB$^+$) m/z: 489 (MH$^+$). HRMS (FAB$^+$) for $C_{25}H_{26}FN_8O_2$ (MH$^+$): calcd, 489.2163; found, 489.2195.

EXAMPLE 83

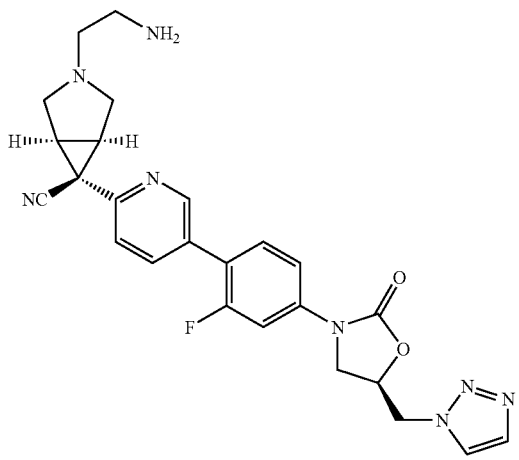

1-[5(R)-3-[4-[2-[(1α,5α,6β)-3-(2-Aminoethyl)-6-cyano-3-azabicyclo[3.1.0]hexan-6-yl]pyridin-5-yl]-3-fluorophenyl]-2-oxooxazolidin-5-ylmethyl]-1,2,3-triazole Step 1.

1-[5(R)-3-[4-[2-[(1α,5α,6β)-6-Cyano-3-[2-(phthalimid-2-yl)ethyl]-3-azabicyclo[3.1.0]hexan-6-yl]pyridin-5-yl]-3-fluorophenyl]-2-oxooxazolidin-5-ylmethyl]-1,2,3-triazole A suspension of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg), 2-bromoethylphthalimide (11.4 mg) and potassium carbonate (9.3 mg) in acetonitrile (0.2 mL) was heated under reflux for overnight and concentrated in vacuo. Flash chromatography (silica, dichloromethane:methanol=10:1) of the residue gave compound of Step 1 of Example 82 (25.2 mg).

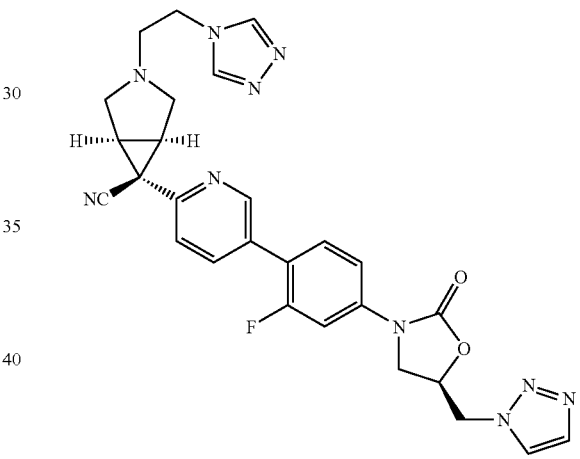

1-[5(R)-3-[4-[2-[(1α,5α,6β)-6-Cyano-3-[2-(1,2,4-triazol-4-yl)ethyl]-3-azabicyclo[3.1.0]hexan-6-yl]pyridin-5-yl]-3-fluorophenyl]-2-oxooxazolidin-5-ylmethyl]-1,2,3-triazole A mixture of 1-[5(R)-3-[4-[2-[(1α,5α,6β)-3-(2-aminoethyl)-6-cyano-3-azabicyclo[3.1.0]hexan-6-yl]pyridin-5-yl]-3-fluorophenyl]-2-oxooxazolidin-5-ylmethyl]-1,2,3-triazole (29.7 mg), dimethylformamide azine (8.6 mg) and p-toluenesulfonic acid (0.6 mg) in toluene was heated under reflux for 16 hours and concentrated in vacuo. Preparative thin-layer chromatography (silica, dichloromethane:methanol=10:1) of the residue gave title compound 83 (10.9 mg).

MS (FAB$^+$) m/z: 541 (MH$^+$). HRMS (FAB$^+$) for $C_{27}H_{26}FN_{10}O_2$ (MH$^+$): calcd, 541.2224; found, 541.2203.

EXAMPLE 84

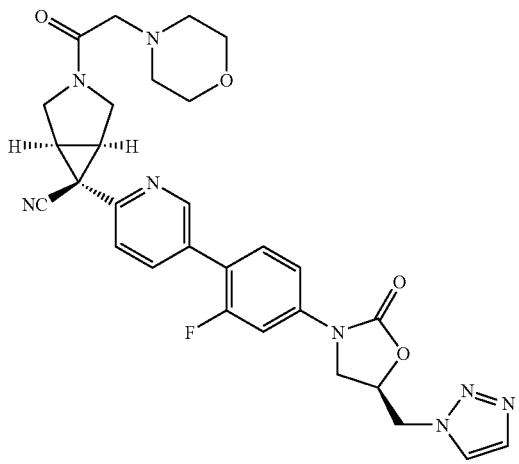

1-[5(R)-3-[4-[2-[(1α,5α,6β)-6-Cyano-3-(morpholin-4-yl)acetyl-3-azabicyclo[3.1.0]hexan-6-yl]pyridin-5-yl]-3-fluorophenyl]-2-oxooxazolidin-5-ylmethyl]-1,2,3-triazole Step 1.

1-[5(R)-3-[4-[2-[(1α,5α,6β)-3-Bromoacetyl-6-cyano-3-azabicyclo[3.1.0]hexan-6-yl]pyridin-5-yl]-3-fluorophenyl]-2-oxooxazolidin-5-ylmethyl]-1,2,3-triazole To a solution of bromoacetyl bromide (9.8 μL) in dichloromethane (0.3 mL) was added a solution of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (50.0 mg) and triethylamine (15.6 μL) in dichloromethane (1.5 mL) at 0° C., the mixture was stirred at the same temperature for 3 hours, and concentrated in vacuo. After dilution of the residue with dichloromethane-methanol (10:1) solution, the mixture was washed with 2 N hydrochloric acid, dried over anhydrous magnesium sulfate, and then concentrated in vacuo to give compound of Step 1 of example 84 (88.1 mg).

Step 2.

Title Compound 84.

To a solution of morpholine (29.3 μL) in acetonitrile (1.0 mL) was added a solution of the crude compound of Step 1 of Example 84 (88.1 mg) in acetonitrile (1.5 mL) at 0° C., the mixture was stirred at the same temperature for 5 hours. After dilution of the residue with water, the mixture was washed with dichloromethane-methanol (10:1) solution. The organic extracts were washed with brine, dried over anhydrous magnesium sulfate, and then concentrated in vacuo. Preparative thin-layer chromatography (silica, dichloromethane:methanol=5:1) of the residue gave title compound 84 (17.5 mg).

MS (FAB$^+$) m/z: 573 (MH$^+$). HRMS (FAB$^+$) for C$_{29}$H$_{30}$FN$_8$O$_4$ (MH$^+$): calcd, 573.2374; found, 573.2381.

EXAMPLE 85

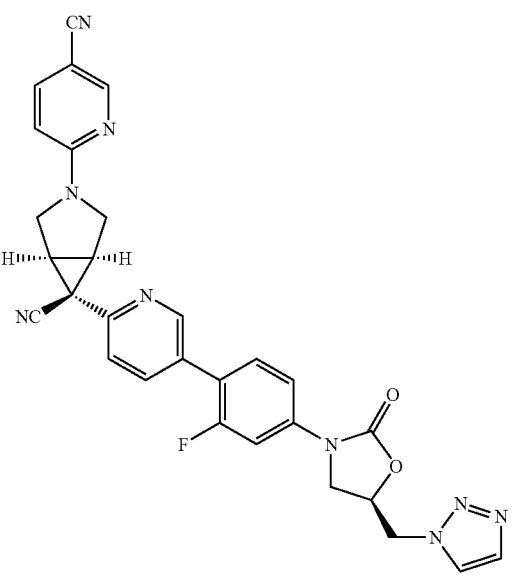

1-[5(R)-3-[4-[2-[(1α,5α,6β)-6-Cyano-3-(5-cyanopyridin-2-yl)-3-azabicyclo[3.1.0]hexan-6-yl]pyridin-5-yl]-3-fluorophenyl]-2-oxooxazolidin-5-ylmethyl]-1,2,3-triazole To a suspension of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) in dimethyl sulfoxide (0.5 mL) was added diisopropylethylamine (78 μL), the mixture was stirred at room temperature for 5 minutes. To the resulting mixture was added 2-bromo-5-cyanopyridine (16.4 mg), the mixture was stirred at 60° C. for 9 hours. After dilution of the mixture with ethyl acetate and water, the mixture was extracted with ethyl acetate. The organic extracts were washed with water and brine, dried over anhydrous magnesium sulfate, filtered, and then concentrated in vacuo. Flash chromatography (silica, dichloromethane:methanol=20:1) of the residue gave title compound 85 (12.8 mg).

MS (FAB$^+$) m/z: 548 (MH$^+$). HRMS (FAB$^+$) for C$_{29}$H$_{23}$FN$_9$O$_2$ (MH$^+$): calcd, 548.1959; found, 548.1984.

EXAMPLE 86

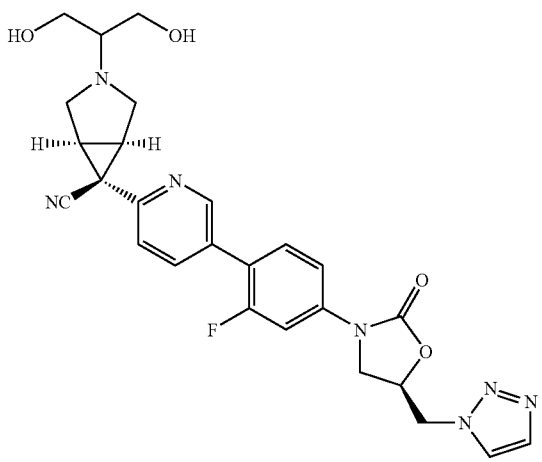

1-[5(R)-3-[4-[2-[(1α,5α,6β)-6-Cyano-3-(1,3-dihydroxypropan-2-yl)-3-azabicyclo[3.1.0]hexan-6-yl]pyridin-5-yl]-3-fluorophenyl]-2-oxooxazolidin-5-ylmethyl]-1,2,3-triazole To a solution of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (50.0 mg) in dichloromethane-methanol (10:1, 1.0 mL) was added 1,3-dihydroxyacetone dimmer (60.7 mg), methanol (4.0 mL), acetic acid (0.5 mL), and sodium cyanoborohydride (21.2 mg), the mixture was stirred at room temperature for 7.5 hours. After addition of 2 N hydrochloric acid, the mixture was stirred at room temperature for 1 hour. The mixture was diluted with brine and extracted with dichloromethane-methanol (10:1). The organic extracts were dried over anhydrous potassium carbonate, filtered, and then concentrated in vacuo. Preparative thin-layer chromatography (silica, dichloromethane:methanol=10:1) of the residue gave title compound 86 (13.2 mg).

MS (FAB$^+$) m/z: 520 (MH$^+$). HRMS (FAB$^+$) for $C_{26}H_{27}FN_7O_4$ (MH$^+$): calcd, 520.2109; found, 520.2086.

EXAMPLE 87

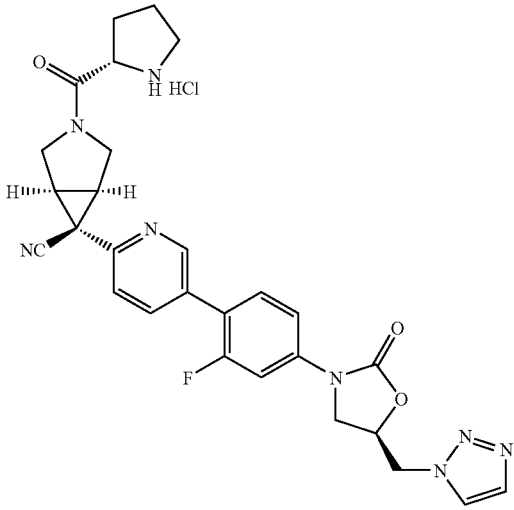

1-[5(R)-3-[4-[2-[(1α,5α,6β)-6-Cyano-3-[((2S)-pyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole Hydrochloride Step 1.

1-[5(R)-3-[4-[2-[(1α,5α,6β)-3-[((2S)-1-t-Butoxycarbonylpyrrolidin-2-yl)carbonyl]-6-cyano-3-azabicyclo[3.1.0]-hexan-6-yl]pyridin-5-yl]-3-fluorophenyl]-2-oxooxazolidin-5-ylmethyl]-1,2,3-triazole The compound of Step 1 in Example 87 (27.1 mg) was prepared from 1-[5(R)-3-[4-[2-[(1α,5α,6β)-6-cyano-3-azabicyclo[3.1.0]-hexan-6-yl]pyridin-5-yl]-3-fluorophenyl]-2-oxooxazolidin-5-ylmethyl]-1,2,3-triazole (20.0 mg) and N-Boc-L-proline (11.6 mg) in the same manner as described for EXAMPLE 71.

MS (FAB$^+$) m/z: 643 (MH$^+$). HRMS (FAB$^+$) for $C_{33}H_{36}FN_8O_5$ (MH$^+$): calcd, 643.2793; found, 643.2744.

Step 2.

1-[5(R)-3-[4-[2-[(1α,5α,6β)-6-Cyano-3-[((2S)-pyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole Hydrochloride The compound of Step 2 in Example 87 (16.8 mg) was prepared from 1-[5(R)-3-[4-[2-[(1α,5α,6β)-3-[((2S)-1-t-butoxycarbonylpyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole (26.9 mg) in the same manner as described for EXAMPLE 2.

MS (FAB$^+$) m/z: 543 (MH$^+$) (as free base). HRMS (FAB$^+$) for $C_{28}H_{28}FN_8O_3$ (MH$^+$): calcd, 543.2268; found, 543.2243.

EXAMPLE 88

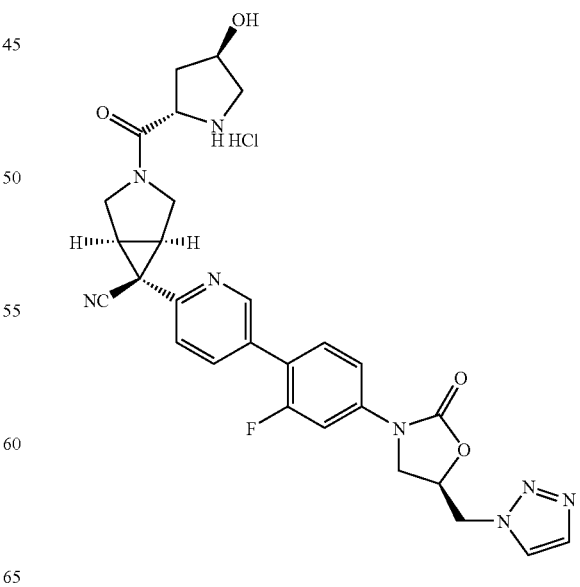

1-[5(R)-3-[4-[2-[(1α,5α,6β)-6-Cyano-3-[((2S,4R)-4-hydroxypyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole Hydrochloride Step 1.

1-[5(R)-3-[4-[2-[(1α,5α,6β)-3-[((2S,4R)-1-t-Butoxycarbonyl-4-hydroxypyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole The compound of Step 1 of Example 88 (28.4 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and N-Boc-4-hydroxy-L-proline (12.3 mg) in the same manner as described for EXAMPLE 71.

MS (FAB$^+$) m/z: 659 (MH$^+$). HRMS (FAB$^+$) for $C_{33}H_{36}FN_8O_6$ (MH$^+$): calcd, 659.2742; found, 659.2775.

Step 2.

Compound 88 (15.6 mg) was prepared from the compound of Step 1 of Example 88 (27.4 mg) in the same manner as described for EXAMPLE 2.

MS (FAB$^+$) m/z: 559 (MH$^+$). HRMS (FAB$^+$) for $C_{28}H_{28}FN_8O_4$ (MH$^+$): calcd, 559.2218; found, 559.2247.

EXAMPLE 89

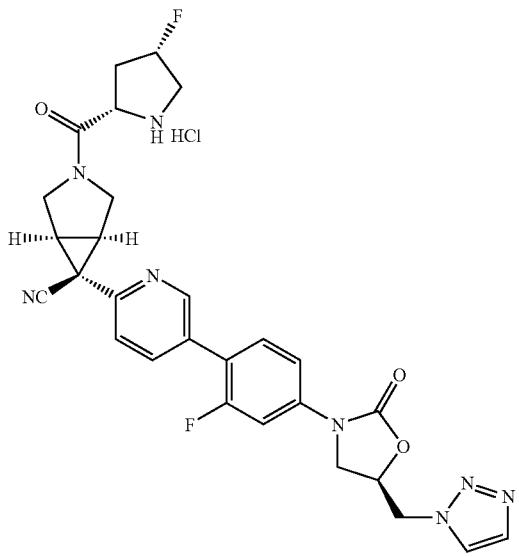

1-[5(R)-3-[4-[2-[(1α,5α,6β)-6-Cyano-3-[((2S,4S)-4-fluoropyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole Hydrochloride Step. 1

1-[5(R)-3-[4-[2-[(1α,5α,6β)-3-[((2S,4S)-1-t-Butoxycarbonyl-4-fluoropyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole The compound of Step 1 of Example 89 (73.6 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (50.0 mg) and N-Boc-(4S)-fluoro-L-proline (31.5 mg) in the same manner as described for EXAMPLE 71.

MS (FAB$^+$) m/z: 661 (MH$^+$). HRMS (FAB$^+$) for $C_{33}H_{35}F_2N_8O_5$ (MH$^+$): calcd, 661.2698; found, 661.2656.

Step 2.

The compound of Example 89 (44.0 mg) was prepared from the compound of Step 1 of Example 89 (69.3 mg) in the same manner as described for EXAMPLE 2.

MS (FAB$^+$) m/z: 561 (MH$^+$). HRMS (FAB$^+$) for $C_{28}H_{27}F_2N_8O_3$ (MH$^+$): calcd, 561.2174; found, 561.2142.

EXAMPLE 90

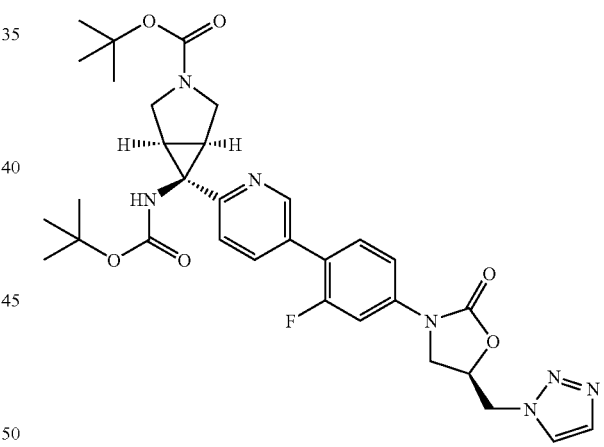

1-[5(R)-3-[4-[2-[(1α,5α,6β)-3-t-Butoxycarbonyl-6-(t-butoxycarbonyl)amino-3-azabicyclo[-3.1.0]hexan-6-yl]pyridin-5-yl]-3-fluorophenyl]-2-oxooxazolidin-5-ylmethyl]-1,2,3-trazole Title Compound 90 (473 mg) was prepared from 1-[5(R)-3-[3-fluoro-4-(4,4,5,5-tetramethyl-1,3,2-dioxaborolyl)-phenyl]-2-oxooxazolidin-5-ylmethyl]-1,2,3-triazole (600 mg) and 5-bromo-2-[(1α,5α,6β)-3-t-butoxycarbonyl-6-(t-butoxycarbonyl)amino-3-azabicyclo[3.1.0]hexan-6-yl]pyridine (702 mg) in the same manner as described for EXAMPLE 1.

MS (FAB$^+$) m/z: 636 (MH$^+$). HRMS (FAB$^+$) for $C_{32}H_{39}F7O_6$ (MH$^+$): calcd, 636.2946; found, 636.2931.

EXAMPLE 91

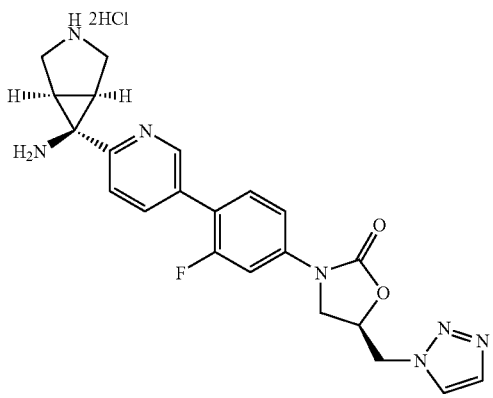

1-[5(R)-3-[4-[4-[(1α,5α,6β)-6-Amino-3-azabicyclo[3.1.0]hexan-6-yl]pyridin-5-yl]-3-fluorophenyl]-2-oxooxazolidin-5-ylmethyl]-1,2,3-triazole Dihydrochloride Title Compound 91 (305 mg) was prepared from 1-[5(R)-3-[4-[4-[(1α,5α,6β)-3-t-butoxycarbonyl-6-(t-butoxycarbonyl)-amino-3-azabicyclo[3.1.0]hexan-6-yl]pyridin-5-yl]-3-fluorophenyl]-2-oxooxazolidin-5-ylmethyl]-1,2,3-triazole (397 mg) in the same manner as described for EXAMPLE 2.

MS (FAB$^+$) m/z: 436 (MH$^+$). HRMS (FAB$^+$) for $C_{22}H_{23}FN_7O_2$ (MH$^+$): calcd, 436.1897; found, 436.1898.

EXAMPLE 92

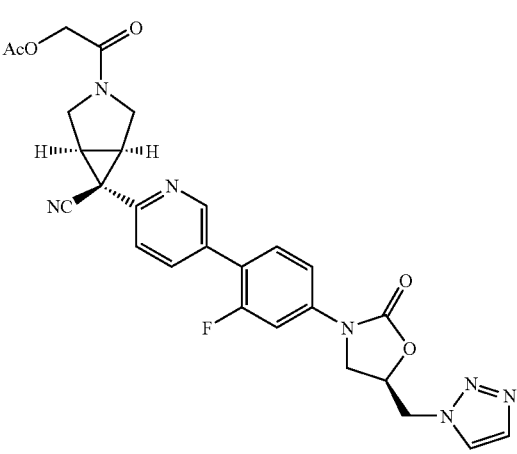

1-[5(R)-3-[4-[2-[(1α,5α,6β)-3-Acetoxyacetyl-6-cyano-3-azabicyclo[3.1.0]hexan-6-cyano-3-azabicyclo[3.1.0]hexan-6pyridin-5-yl]-3-fluorophenyl]-2-oxooxazolidin-5-ylmethyl]-1,2,3-triazole To a suspension of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (30.0 mg) in dichloromethane (0.7 mL) was added triethylamine (28 μL) and acetoxyacetyl chloride (7.0 μL) at 0° C., the mixture was stirred at the same temperature for 1 hour. After dilution of the mixture with water, the mixture was extracted with dichloromethane. The organic extracts were washed with water and brine, dried over anhydrous sodium sulfate, filtered, and then concentrated in vacuo. Flash chromatography (silica, dichloromethane:methanol=10:1) of the residue gave the title compound of 92 (34.7 mg).

MS (FAB$^+$) m/z: 546 (MH$^+$). HRMS (FAB$^+$) for $C_{27}H_{25}FN_7O_5$ (MH$^+$): calcd, 546.1901; found, 546.1888.

EXAMPLE 93

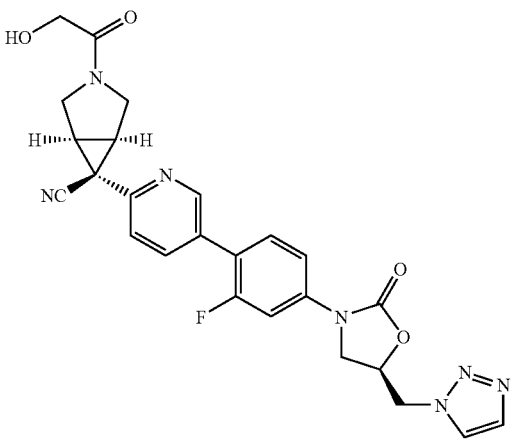

1-[5(R)-3-[4-[2-[(1α,5α,6β)-6-Cyano-3-hydroxyacetyl-3-azabicyclo[3.1.0]hexan-6-yl]pyridin-5-yl]-3-fluorophenyl]-2-oxooxazolidin-5-ylmethyl]-1,2,3-triazole To a solution of 1-[5(R)-3-[4-[2-[(1α,5α,6β)-3-acetoxyacetyl-6-cyano-3-azabicyclo]3.1.0]hexan-6-yl]pyridin-5-yl]-3-fluorophenyl]-2-oxooxazolidin-5-ylmethyl]-1,2,3-triazole (255 mg) in methanol (4.5 mL) and tetrahydrofuran (1.3 mL) was added potassium carbonate (130 mg) at room temperature, the mixture was stirred at the same temperature for 2 hours, and concentrated in vacuo. After dilution of the residue with dichloromethane-methanol (5:1) solution, the mixture was washed with brine. The organic extracts were dried over anhydrous magnesium sulfate, filtered, and then concentrated in vacuo. Flash chromatography (silica, dichloromethane:methanol=5:1) of the residue gave the title compound of Example 93 (137 mg).

MS (FAB$^+$) m/z: 504 (MH$^+$). HRMS (FAB$^+$) for $C_{25}H_{23}FN_7O_4$ (MH$^+$): calcd, 504.1796; found, 504.1800.

EXAMPLE 94

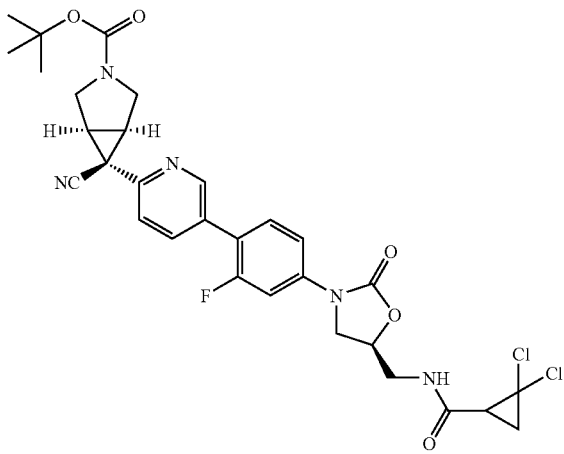

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide Diastereomer A and Diastereomer B Title Compound 94 (diastereomer A: 100 mg, diastereomer B: 76.6 mg) were prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (269 mg) and 2,2-dichlorocyclopropanecarboxylic acid (110 mg) in the same manner as described for EXAMPLE 71.

Diastereomer A (Less Polar):
  MS (FAB$^+$) m/z: 630 (MH$^+$).

Diastereomer B (More Polar):
  MS (FAB$^+$) m/z: 630 (MH$^+$).

EXAMPLE 95

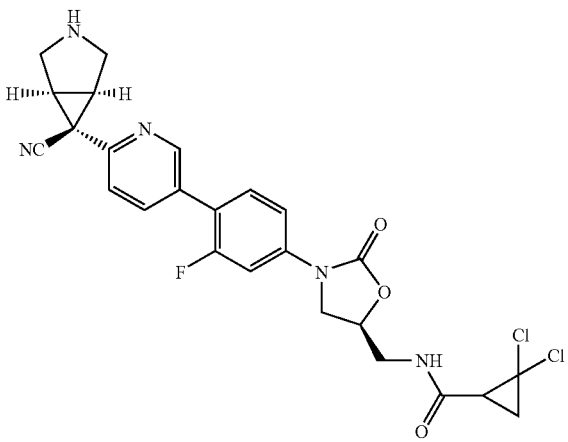

N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-S-ylmethyl]-(2,2-dichlorocyclopropane)-1-carboxamide Diastereomer A'

Title Compound 95 (diastereomer A': 78.9 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide (diastereomer A: 97.0 mg) in the same manner as described for EXAMPLE 49.
  MS (FAB$^+$) m/z: 530 (MH$^+$). HRMS (FAB$^+$) for $C_{25}H_{23}Cl_2FN_5O_3$ (MH$^+$): calcd, 530.1162; found, 530.1198.

EXAMPLE 96

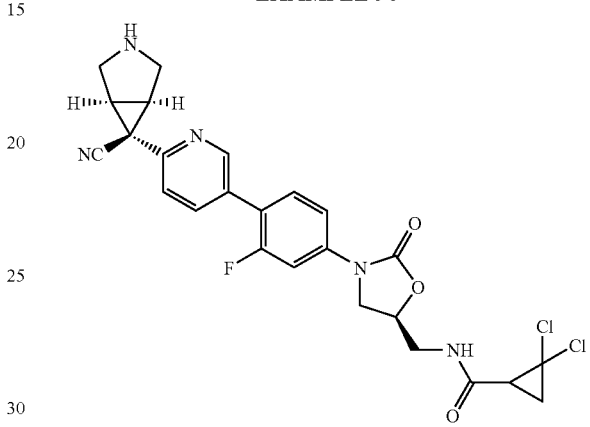

N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide Diastereomer B'

Title Compound 96 (diastereomer B': 57.2 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide (diastereomer B: 73.0 mg) in the same manner as described for EXAMPLE 49.
  MS (FAB$^+$) m/z: 530 (MH$^+$). HRMS (FAB$^+$) for $C_{25}H_{23}Cl_2FN_5O_3$ (MH$^+$): calcd, 530.1162; found, 530.1137.

EXAMPLE 97

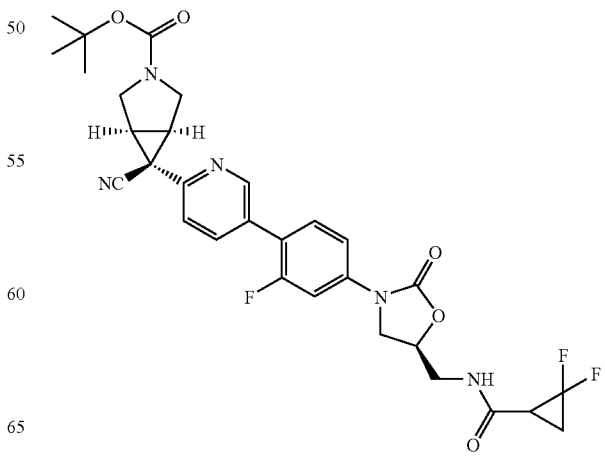

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide Diastereomer C and Diastereomer D Title Compound 97 (diastereomer C: 125 mg, diastereomer D: 125 mg) were prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (300 mg) and 2,2-difluorocyclopropanecarboxylic acid (96.5 mg) in the same manner as described for EXAMPLE 71.

EXAMPLE 98

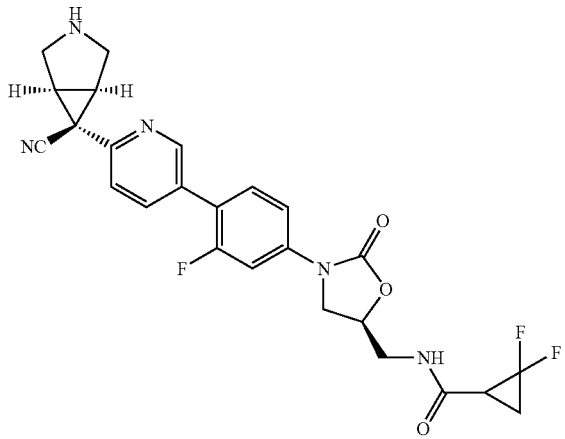

N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide Diastereomer C'

Title Compound 98 (diastereomer C': 75.8 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide (diastereomer C: 122 mg) in the same manner as described for EXAMPLE 49.

MS (FAB$^+$) m/z: 498 (MH$^+$). HRMS (FAB$^+$) for $C_{25}H_{23}F_3N_5O_3$ (MH$^+$): calcd, 498.1753; found, 498.1783.

EXAMPLE 99

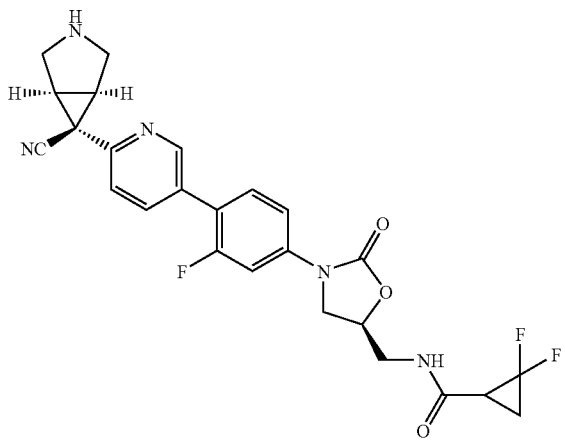

N-[5(S)-3-[4-[2-[(1α,5α,6β)-6-Cyano-3-azabicyclo[3.1.0]hexan-6-yl]pyridin-5-yl]fluorophenyl]-2-oxooxazolidin-5-ylmethyl]-(2,2-difluorocyclopropane)-1-carboxamide Diastereomer D'

Title Compound 99 (diastereomer D': 62.2 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide (diastereomer D: 122 mg) in the same manner as described for EXAMPLE 49.

MS (FAB$^+$) m/z: 498 (MH$^+$). HRMS (FAB$^+$) for $C_{25}H_{23}F_3N_5O_3$ (MH$^+$): calcd, 498.1753; found, 498.1740.

EXAMPLE 100

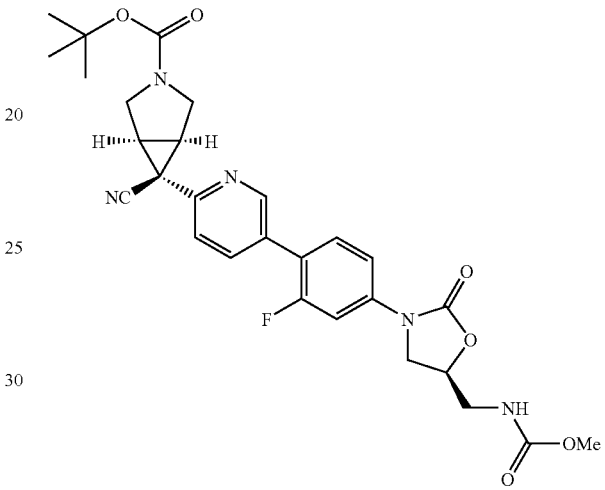

O-Methyl-N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]carbamate Title Compound 100 (53.2 mg) was prepared from 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (200 mg) and methyl chloroformate (37 μL) in the same manner as described for EXAMPLE 92.

MS (FAB$^+$) m/z: 552 (MH$^+$).

EXAMPLE 101

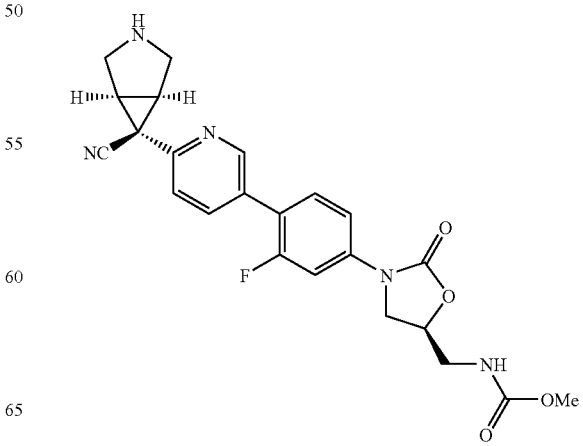

O-Methyl-N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]carbamate Title Compound 101 (32.7 mg) was prepared from O-methyl N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]carbamate (50.0 mg) in the same manner as described for EXAMPLE 49.

MS (FAB$^+$) m/z: 452 (MH$^+$). HRMS (FAB$^+$) for $C_{23}H_{23}FN_5O_4$ (MH$^+$): calcd, 452.1734; found, 452.1729.

EXAMPLE 102

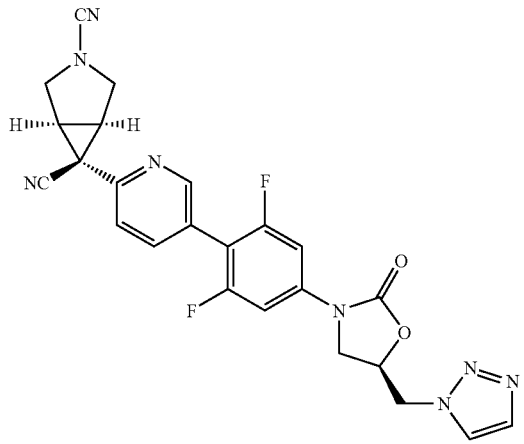

1-[5(R)-3-[4-[2-[(1α,5α,6β)-3,6-Dicyano-3-azabicyclo[3.1.0]hexan-6-yl]pyridin-5-yl]-3,5-difluorophenyl]-2-oxooxazolidin-5-ylmethyl]-1,2,3-triazole Title Compound 102 (12.2 mg) was prepared from 1-[5(R)-3-[4-[4-[(1α,5α,6β)-6-cyano-3-azabicyclo[3.1.0]-hexan-6-yl]pyridin-5-yl]-3,5-difluorophenyl]-2-oxooxazolidin-5-ylmethyl]-1,2,3-triazole (15.0 mg) in the same manner as described for EXAMPLE 79.

MS (FAB$^+$) m/z: 489 (MH$^+$). HRMS (FAB$^+$) for $C_{24}H_{19}F_2N_8O_2$ (MH$^+$): calcd, 489.1599; found, 489.1634.

EXAMPLE 103

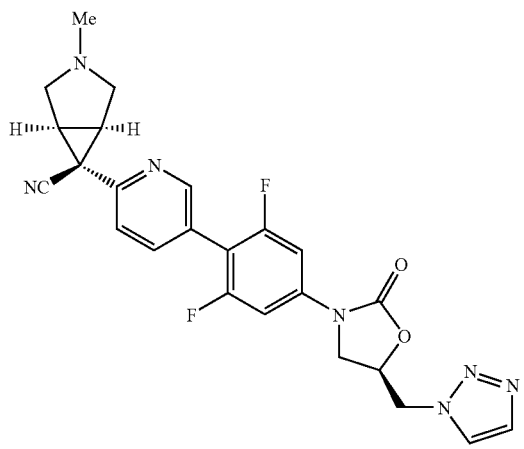

1-[5(R)-3-[4-[2-[(1α,5α,6β)-6-Cyano-3-methyl-3-azabicyclo[3.1.0]hexan-6-yl]pyridin-5-yl]-3,5-difluorophenyl]-2-oxooxazolidin-5-ylmethyl]-1,2,3-triazole Title Compound 103 (14.8 mg) was prepared from 1-[5(R)-3-[4-[4-[(1α,5α,6β)-6-cyano-3-azabicyclo[3.1.0]hexan-6-yl]pyridin-5-yl]-3,5-difluorophenyl]-2-oxooxazolidin-5-ylmethyl]-1,2,3-triazole (15.0 mg) in the same manner as described for EXAMPLE 78.

MS (FAB$^+$) m/z: 478 (MH$^+$). HRMS (FAB$^+$) for $C_{24}H_{22}F_2N_7O_2$ (MH$^+$): calcd, 478.1803; found, 478.1825.

EXAMPLE 104

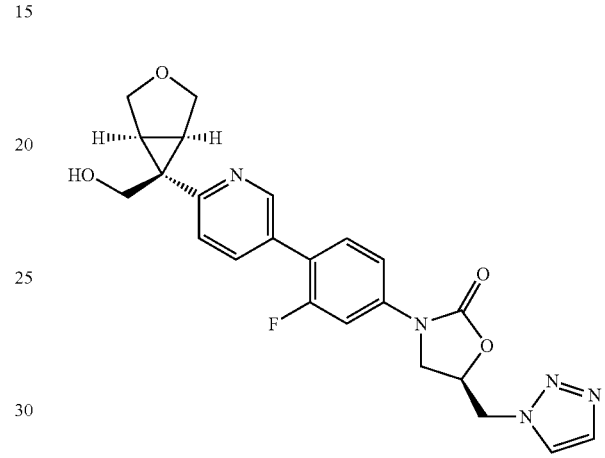

1-[5(R)-3-[3-Fluoro-4-[2-[(1α,5α,6β)-6-hydroxymethyl-3-oxabicyclo[3.1.0]hexan-6-yl]pyridin-5-yl]phenyl]-2-oxooxazolidin-5-ylmethyl]-1,2,3-triazole Title Compound 104 (73.2 mg) was prepared from 1-[5(R)-3-[3-fluoro-4-(4,4,5,5-tetramethyl-1,3,2-dioxaborolyl)-phenyl]-2-oxooxazolidin-5-ylmethyl]-1,2,3-triazole (83.4 mg) and 5-bromo-2-[(1α,5α,6β)-6-hydroxymethyl-3-oxabicyclo[3.1.0]hexan-6-yl]pyridine (58.0 mg) in the same manner as described for EXAMPLE 1.

MS (FAB$^+$) m/z: 452 (MH$^+$). HRMS (FAB$^+$) for $C_{23}H_{23}FN_5O_4$ (MH$^+$): calcd, 452.1734; found, 452.1735.

EXAMPLE 105

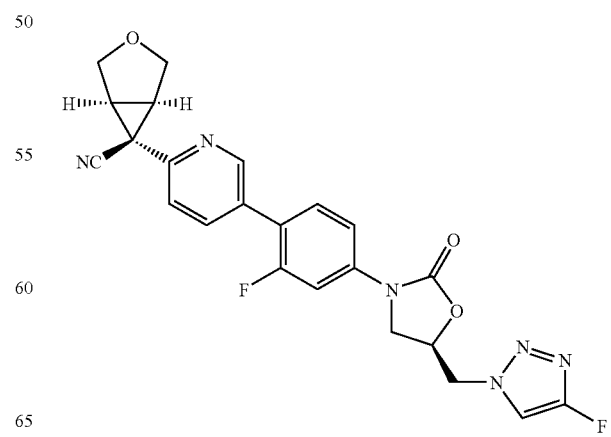

1-[5(R)-3-[4-[2-[(1α,5α,6β)-6-Cyano-3-oxabicyclo[3.1.0]hexan-6-yl]pyridin-5-yl]-3-fluorophenyl]-2-oxooxazolidin-5-ylmethyl]-4-fluoro-1,2,3-triazole Title Compound 105 (101 mg) was prepared from 4-fluoro-1-[5(R)-3-(3-fluoro-4-iodophenyl)-2-oxooxazolidin-5-ylmethyl]-1,2,3-triazole (125 mg) and 5-bromo-2-[(1α,5α,6β)-6-cyano-3-oxabicyclo[3.1.0]hexan-6-yl]pyridine (122 mg) in the same manner as described for EXAMPLE 31.

MS (FAB+) m/z: 465 (MH+). HRMS (FAB+) for $C_{23}H_{19}F_2N_6O_3$ (MH+): calcd, 465.1487; found, 465.1514.

EXAMPLE 106

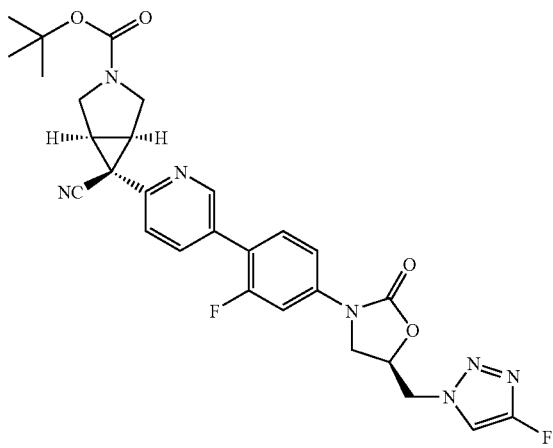

1-[5(R)-3-[4-[-2-[(1α,5α,6β)-3-t-Butoxycarbonyl-6-cyano-3-azabicyclo[3.1.0]hexan-6-yl]pyridin-5-yl]-2-fluorophenyl]-2-oxooxazolidin-5-ylmethyl]-4-fluoro-1,2,3-triazole Title Compound 106 (301 mg) was prepared from 4-fluoro-1-[5(R)-3-[3-fluoro-4-(4,4,5,5-tetramethyl-1,3,2-dioxaborolyl)phenyl]-2-oxooxazolidin-5-ylmethyl]-1,2,3-triazole (370 mg) and 5-bromo-2-[(1α,5α,6β-3-t-butoxycarbonyl-6-cyano-3-azabicyclo[3.1.0]hexan-6-yl]pyridine (332 mg) in the same manner as described for EXAMPLE 1.

MS (FAB+) m/z: 564 (MH+). HRMS (FAB+) for $C_{28}H_{28}F_2N_7O_4$ (MH+): calcd, 564.2171; found, 564.2168.

EXAMPLE 107

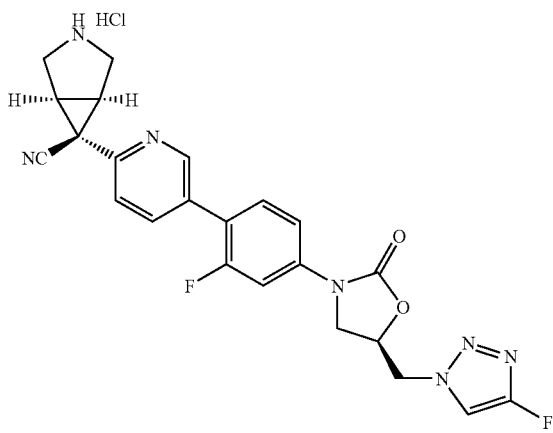

1-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-4-fluoro-1,2,3-triazole Hydrochloride Title Compound 107 (231 mg) was prepared from 1-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole (290 mg) in the same manner as described for EXAMPLE 2.

MS (FAB+) m/z: 464 (MH+) (as free base). HRMS (FAB+) for $C_{23}H_{20}F_2N_7O_2$ (MH+): calcd, 464.1647; found, 464.1645.

EXAMPLE 108

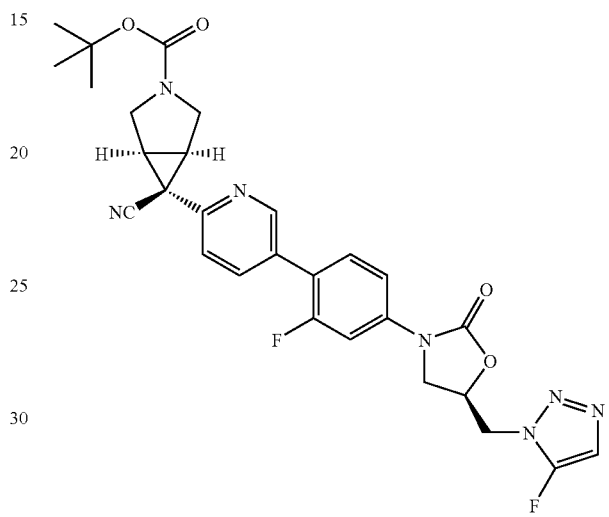

1-[5(R)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole Title Compound 108 (169 mg) was prepared from 1-[5(R)-3-(3-fluoro-4-iodophenyl)-2-oxooxazolidin-5-ylmethyl]-5-fluoro-1,2,3-triazole (150 mg) and 5-bromo-2-[(1α,5α,6β)-3-t-butoxycarbonyl-6-cyano-3-azabicyclo-[3.1.0]hexan-6-yl]pyridine (202 mg) in the same manner as described for EXAMPLE 31.

MS (FAB+) m/z: 564 (MH+). HRMS (FAB+) for $C_{28}H_{28}F_2N_7O_4$ (MH+): calcd, 564.2171; found, 564.2189.

EXAMPLE 109

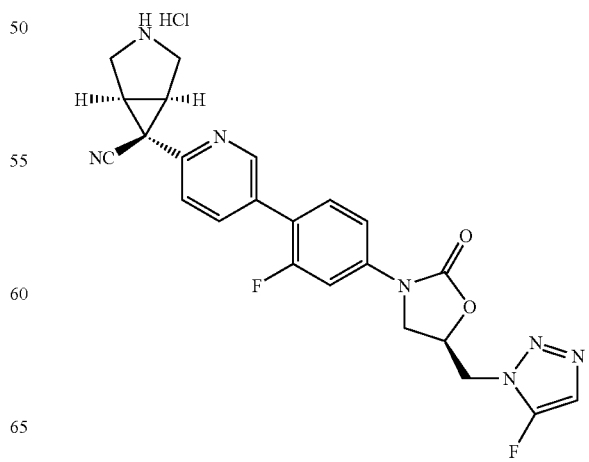

1-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-5-fluoro-1,2,3-triazole Hydrochloride Title Compound 109 (118 mg) was prepared from 1-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole (151 mg) in the same manner as described for EXAMPLE 2.

MS (FAB$^+$) m/z: 464 (MH$^+$) (as free base). HRMS (FAB$^+$) for $C_{23}H_{20}F_2N_7O_2$ (MH$^+$): calcd, 464.1647; found, 464.1679.

EXAMPLE 110

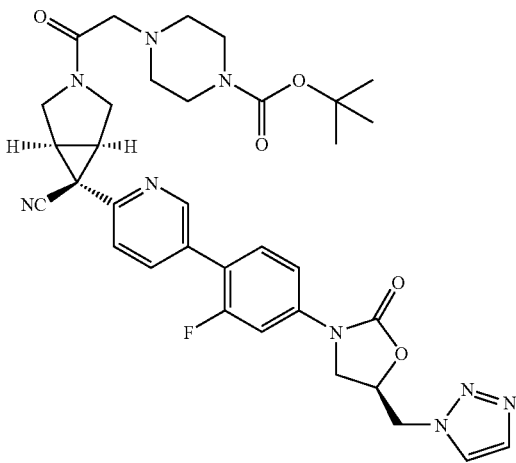

1-[5(R)-3-[4-[2-[(1α,5α,6β)-3-(4-t-Butoxycarbonylpiperazin-1-yl)acetyl-6-cyano-3-azabicyclo[3.1.0]hexan-6-yl]pyridin-5-yl]-3-fluorophenyl]-2-oxooxazolidin-5-ylmethyl]-1,2,3-triazole Title compound 110 (60.7 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (50.0 mg) and 1-t-butoxycarbonylpiperazine (62.6 mg) in the same manner as described for EXAMPLE 78.

MS (FAB$^+$) m/z: 672 (MH$^+$). HRMS (FAB$^+$) for $C_{34}H_{39}FN_9O_5$ (MH$^+$): calcd, 672.3058; found, 672.3040.

EXAMPLE 111

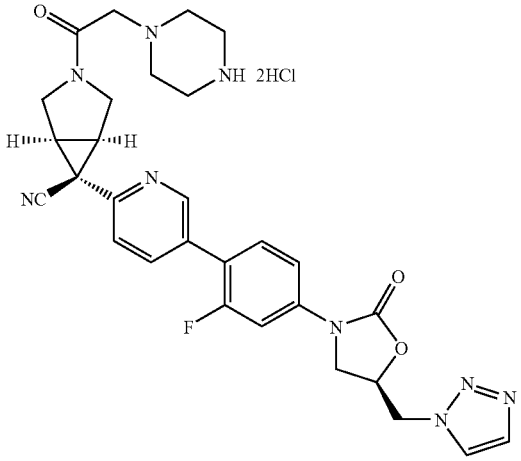

1-[5(R)-3-[4-[2-[(1α,5α,6β)-6-Cyano-3-(piperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole Dihydrochloride Title Compound 111 (57.0 mg) was prepared from 1-[5(R)-3-[4-[2-[(1α,5α,6β)-3-(4-t-butoxycarbonylpiperazin-1-yl)-acetyl-6-cyano-3-azabicyclo[3.1.0]hexan-6-yl]pyridin-5-yl]-3-fluorophenyl]-2-oxooxazolidin-5-ylmethyl]-1,2,3-triazole (59.7 mg) in the same manner as described for EXAMPLE 2.

MS (FAB$^+$) m/z: 572 (MH$^+$) (as free base). HRMS (FAB$^+$) for $C_{29}H_{31}FN_9O_3$ (MH$^+$): calcd, 572.2534; found, 572.2535.

EXAMPLE 112

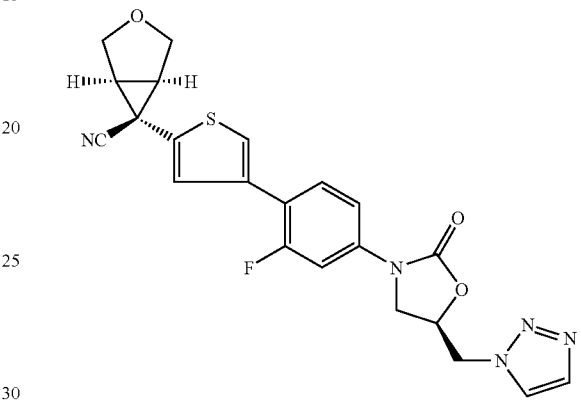

1-[5(R)-3-[4-[2-[(1α,5α,6β)-6-Cyano-3-oxabicyclo[3.1.0]hexan-6-yl]thiophen-4-yl]-3-fluorophenyl]-2-oxooxazolidin-5-ylmethyl]-1,2,3-triazole Title Compound 112 (261 mg) was prepared from 1-[5(R)-3-[3-fluoro-4-(4,4,5,5-tetramethyl-1,3,2-dioxaborolyl)-phenyl]-2-oxooxazolidin-5-ylmethyl]-1,2,3-triazole (388 mg) and 4-bromo-2-[(1α,5α,6β)-6-cyano-3-oxabicyclo[3.1.0]hexan-6-yl]thiophene (270 mg) in the same manner as described for EXAMPLE 1.

MS (FAB$^+$) m/z: 452 (MH$^+$). HRMS (FAB$^+$) for $C_{22}H_{19}FN_5O_3S$ (MH$^+$): calcd, 452.1193; found, 452.1180.

EXAMPLE 113

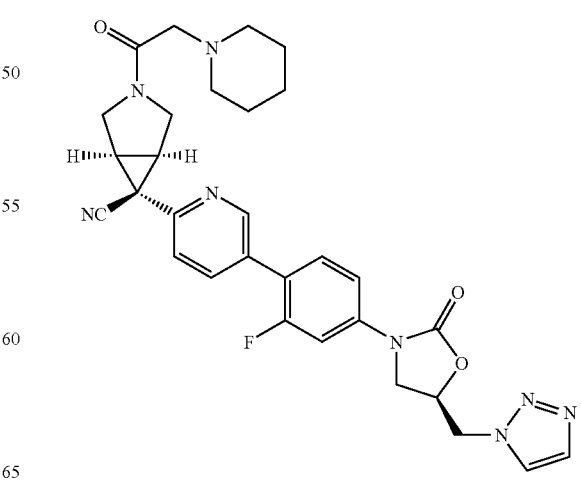

1-[5(R)-3-[4-[2-[(1α,5α,6β)-6-Cyano-3-(piperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole Title Compound 113 (15.7 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and piperidine (17.8 μL) in the same manner as described for EXAMPLE 84.
MS (FAB$^+$) m/z: 571 (MH$^+$). HRMS (FAB$^+$) for $C_{30}H_{32}FN_8O_3$ (MH$^+$): calcd, 571.2581; found, 571.2579.

EXAMPLE 114

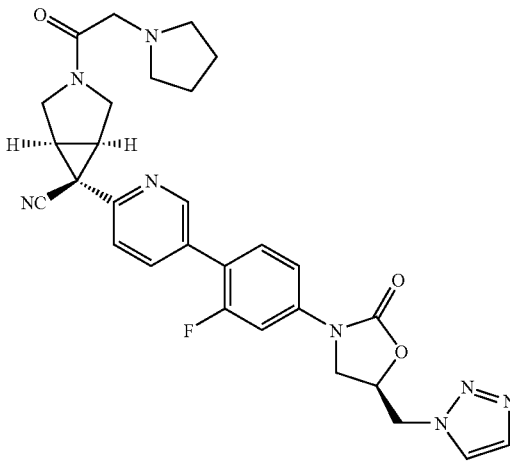

1-[5(R)-3-[4-[2-[(1α,5α,6β)-6-Cyano-3-(pyrrolidin-1-yl)acetyl-3-azabicyclo[3.1.0]hexan-6-yl]pyridin-5-yl]-3-fluorophenyl]-2-oxooxazolidin-5-ylmethyl]-1,2,3-triazole Title Compound 114 (20.7 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and pyrrolidine (15 μL) in the same manner as described for EXAMPLE 84.
MS (FAB$^+$) m/z: 557 (MH$^+$). HRMS (FAB$^+$) for $C_{30}H_{32}FN_8O_3$ (MH$^+$): calcd, 557.2425; found, 557.2467.

EXAMPLE 115

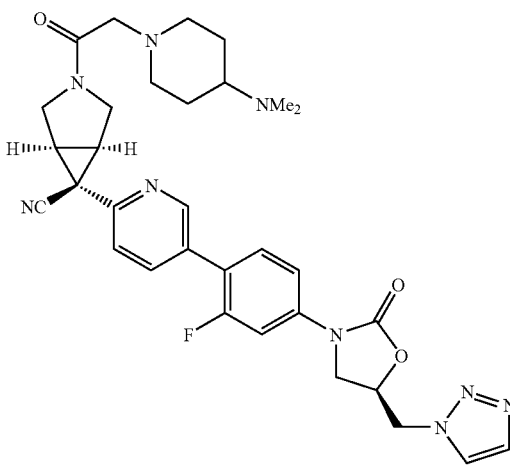

1-[5(R)-3-[4-[2-[(1α,5α,6β)-6-Cyano-3-(4-dimethylaminopiperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole Title Compound 115 (22.0 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and 4-dimethylaminopiperidine dihydrochloride (36.2 mg) in the same manner as described for EXAMPLE 84.
MS (FAB$^+$) m/z: 614 (MH$^+$). HRMS (FAB$^+$) for $C_{32}H_{37}FN_9O_3$ (MH$^+$): calcd, 614.3003; found, 614.3049.

EXAMPLE 116

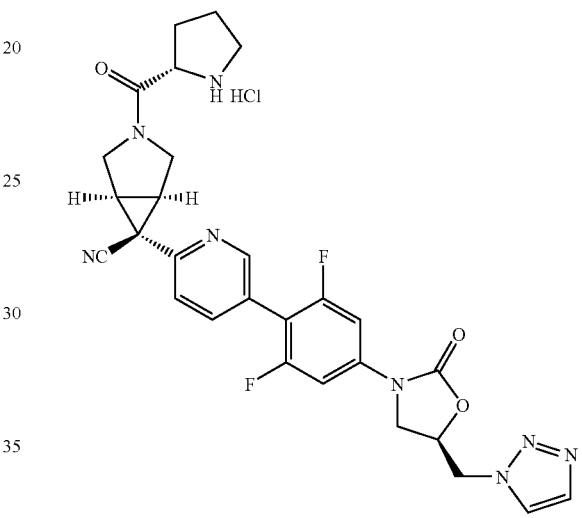

1-[5(R)-3-[4-[2-[(1α,5α,6β)-6-Cyano-3-[((2S)-pyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole Hydrochloride Step 1.

1-[5(R)-3-[4-[2-[(1α,5α,6β)-3-[((2S)-1-t-Butoxycarbonylpyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole The compound of Step 1 of Example 116 (13.3 mg) was prepared from 1-[5(R)-3-[4-[2-[(1α,5α,6β)-6-cyano-3-azabicyclo[3.1.0]-hexan-6-yl]pyridin-5-yl]-3,5-difluorophenyl]-2-oxooxazolidin-5-ylmethyl]-1,2,3-triazole (10.0 mg) and N-Boc-L-proline (5.6 mg) in the same manner as described for EXAMPLE 71
MS (FAB$^+$) m/z: 661 (MH$^+$). HRMS (FAB$^+$) for $C_{33}H_{35}F_2N_8O_5$ (MH$^+$): calcd, 661.2698; found, 661.2691.
Step 2.
Title Compound 116 (8.4 mg) was prepared from the compound of Step 1 of title Example 116 (13.3 mg) in the same manner as described for and EXAMPLE 2.
MS (FAB$^+$) m/z: 561 (MH$^+$) (as free base). HRMS (FAB$^+$) for $C_{28}H_{27}F_2N_8O_3$ (MH$^+$): calcd, 561.2174; found, 561.2220.

EXAMPLE 117

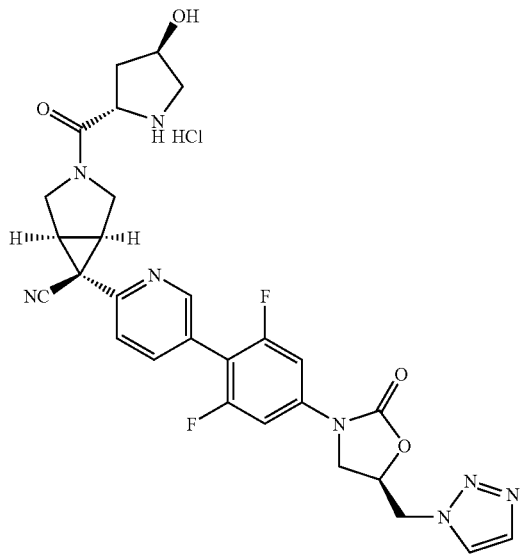

1-[5(R)-3-[4-[2-[(1α,5α,6β)-6-Cyano-3-[((2S,4R)-4-hydroxypyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole Hydrochloride Step 1.

1-[5(R)-3-[4-[2-[(1α,5α,6β)-3-[((2S,4R)-1-t-Butoxycarbonyl-4-hydroxypyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole The compound of Step 1 of Example 117 (12.9 mg) was prepared from 1-[5(R)-3-[4-[2-[(1α,5α,6β)-6-cyano-3-azabicyclo[3.1.0]hexan-6-yl]pyridin-5-yl]-3,5-difluorophenyl]-2-oxooxazolidin-5-ylmethyl]-1,2,3-triazole (10.0 mg) and N-Boc-4-hydroxy-L-proline (6.0 mg) in the same manner as described for EXAMPLE 71.

MS (FAB$^+$) m/z: 677 (MH$^+$). HRMS (FAB$^+$) for C$_{33}$H$_{35}$F$_2$N$_8$O$_6$ (MH$^+$): calcd, 677.2698; found, 677.2691.

Step 2.

Title Compound 117 (2.7 mg) was prepared from the compound of Step 1 of Example 117 (11.7 mg) in the same manner as described for EXAMPLE 2.

MS (FAB$^+$) m/z: 577 (MH$^+$) (as free base). HRMS (FAB$^+$) for C$_{28}$H$_{27}$F$_2$N$_8$O$_4$(MH$^+$): calcd, 577.2123; found, 577.2123.

EXAMPLE 118

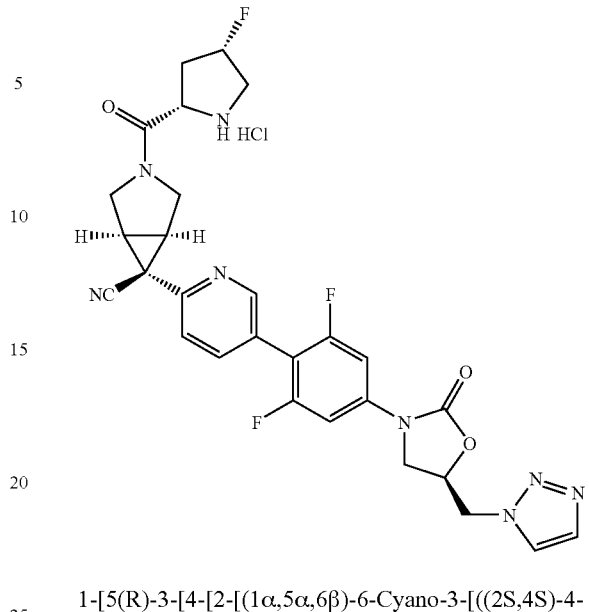

1-[5(R)-3-[4-[2-[(1α,5α,6β)-6-Cyano-3-[((2S,4S)-4-fluoropyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole Hydrochloride Step 1.

1-[5(R)-3-[4-[2-[(1α,5α,6β)-3-[((2S,4S)-1-t-Butoxycarbonyl-4-fluoropyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole The compound of Step 1 of Example 118(12.8 mg) was prepared from 1-[5(R)-3-[4-[2-[(1α,5α,6β)-6-cyano-3-azabicyclo[3.1.0]hexan-6-yl]pyridin-5-yl]-3,5-difluorophenyl]-2-oxooxazolidin-5-ylmethyl]-1,2,3-triazole (10.0 mg) and N-Boc-(4S)-fluoro-L-proline (6.0 mg) in the same manner as described for EXAMPLE 71.

MS (FAB$^+$) m/z: 679 (MH$^+$). HRMS (FAB$^+$) for C$_{33}$H$_{34}$F$_3$N$_8$O$_5$ (MH$^+$): calcd, 679.2604; found, 679.2625.

Step 2.

Title Compound 118 (8.8 mg) was prepared from the compound of Step 1 of Example 118 (12.6 mg) EXAMPLE 2.

MS (FAB$^+$) m/z: 579 (MH$^+$) (as free base). HRMS (FAB$^+$) for C$_{28}$H$_{26}$F$_3$N$_8$O$_3$ (MH$^+$): calcd, 579.2080; found, 579.2055.

EXAMPLE 119

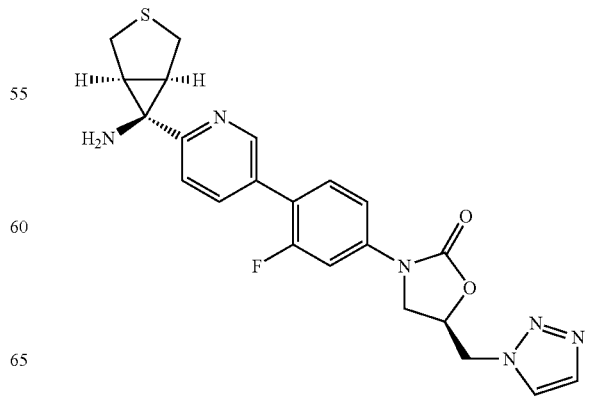

1-[5(R)-3-[4-[2-[(1α,5α,6β)-6-Amino-3-thiabicyclo[3.1.0]hexan-6-yl]pyridin-5-yl]-3-fluorophenyl]-2-oxooxazolidin-5-ylmethyl]-1,2,3-triazole Step 1.

1-[5(R)-3-[4-[2-[(1α,5α,6β)-6-t-Butoxycarbonylamino-3-thiabicyclo[3.1.0]hexan-6-yl]pyridin-5-yl]-3-fluorophenyl]-2-oxooxazolidin-5-ylmethyl]-1,2,3-triazole The compound of Step 1 of Example 119 (9.8 mg) was prepared from 1-[5(R)-3-[3-fluoro-4-(4,4,5,5-tetramethyl-1,3,2-dioxaborolyl)phenyl]-2-oxooxazolidin-5-ylmethyl]-1,2,3-triazole (22.3 mg) and 5-bromo-2-[(1α,5α,6β)-6-t-butoxycarbonylamino-3-thiabicyclo[3.1.0]hexan-6-yl]pyridine (18.4 mg) in the same manner as described for EXAMPLE 1.

MS (FAB$^+$) m/z: 553 (MH$^+$). HRMS (FAB$^+$) for $C_{27}H_{30}FN_6O_4S$ (MH$^+$): calcd, 553.2033; found, 553.2039.

Step 2.

Title Compound 119 (1.2 mg) was prepared from the compound of Step 1 of Example 119 (4.0 mg) in the same manner as described for EXAMPLE 49.

MS (FAB$^+$) m/z: 453 (MH$^+$). HRMS (FAB$^+$) for $C_{22}H_{22}FN_6O_2S$ (MH$^+$): calcd, 453.1509; found, 453.1520.

EXAMPLE 120

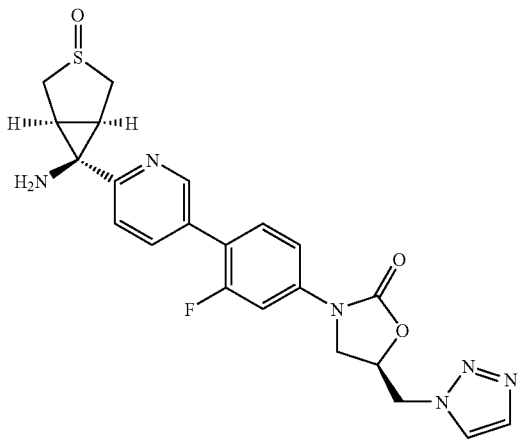

1-[5(R)-3-[4-[2-[(1α,5α,6β)-6-Amino-3-thiabicyclo[3.1.0]hexan-6-yl]pyridin-5-yl]-3-fluorophenyl]-2-oxooxazolidin-5-ylmethyl]-1,2,3-triazole S-Oxide Diastereomer E' and Diastereomer F'

Step 1.

1-[5(R)-3-[4-[2-[(1α,5α,6β)-6-t-Butoxycarbonylamino-3-thiabicyclo[3.1.0]hexan-6-yl]pyridin-5-yl]-3-fluorophenyl]-2-oxooxazolidin-5-ylmethyl]-1,2,3-triazole S-Oxide Diastereomer E and Diastereomer F The compound of Step 1 of Example 120 diastereomer E (4.8 mg) and diastereomer F (10.2 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole (20.0 mg) in the same manner as described for EXAMPLE 58.

Diastereomer E (Less Polar):
MS (FAB$^+$) m/z: 569 (MH$^+$). HRMS (FAB$^+$) for $C_{27}H_{30}FN_6O_5S$ (MH$^+$): calcd, 569.1982; found, 569.1945.

Diastereomer F (More Polar):
MS (FAB$^+$) m/z: 569 (MH$^+$). HRMS (FAB$^+$) for $C_{27}H_{30}FN_6O_5S$ (MH$^+$): calcd, 569.1982; found, 569.1947.

Step 2.

Title Compound 120 diastereomer E'(2.4 mg) was prepared from the compound of Step 1 of Example 120 diastereomer E (3.7 mg) in the same manner as described for EXAMPLE 49.

MS (FAB$^+$) m/z: 469 (MH$^+$). HRMS (FAB$^+$) for $C_{23}H_{20}FN_6O_2S$ (MH$^+$): calcd, 469.1458; found, 469.1411.

EXAMPLE 121

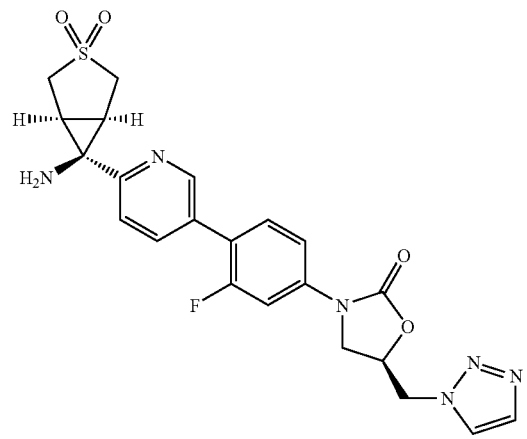

1-[5(R)-3-[4-[2-[(1α,5α,6β)-6-Amino-3-thiabicyclo[3.1.0]hexan-6-yl]pyridin-5-yl]-3-fluorophenyl]-2-oxooxazolidin-5-ylmethyl]-1,2,3-triazole S,S-Dioxide Step 1.

1-[5(R)-3-[4-[2-[(1α,5α,6β)-6-t-Butoxycarbonylamino-3-thiabicyclo[3.1.0]hexan-6-yl]pyridin-5-yl]-3-fluorophenyl]-2-oxooxazolidin-5-ylmethyl]-1,2,3-triazole S,S-Dioxide The compound of Step 1 of Example 121 (10.6 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole (20.0 mg) in the same manner as described for EXAMPLE 59.

MS (FAB$^+$) m/z: 585 (MH$^+$). HRMS (FAB$^+$) for $C_{27}H_{30}FN_6O_6S$ (MH$^+$): calcd, 585.1932; found, 585.1923.

Step 2.

Title Compound 121 (2.3 mg) was prepared from the compound of Step 1 of Example 121 (3.0 mg) in the same manner as described for EXAMPLE 49.

MS (FAB$^+$) m/z: 485 (MH$^+$). HRMS (FAB$^+$) for $C_{22}H_{22}FN_6O_4S$ (MH$^+$): calcd, 485.1407; found, 485.1397.

EXAMPLE 122

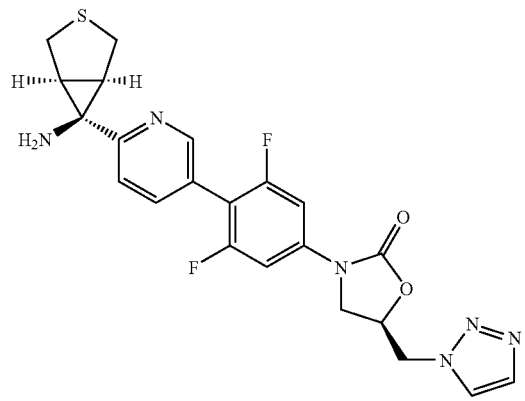

1-[5(R)-3-[4-[2-[(1α,5α,6β)-6-Amino-3-thiabicyclo[3.1.0]hexan-6-yl]pyridin-5-yl]-3,5-difluorophenyl]-2-oxooxazolidin-5-ylmethyl]-1,2,3-triazole Step 1.

1-[5(R)-3-[4-[2-[(1α,5α,6β)-6-t-Butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole The compound of Step 1 of Example 122 (141 mg) was prepared from 1-[5(R)-3-(3,5-difluoro-4-iodophenyl)-2-oxooxazolidin-5-ylmethyl]-1,2,3-triazole (188 mg) an 5-bromo-2-[(1α,5α,6β)-6-t-butoxycarbonylamino-3-thiabicyclo[3.1.0]hexan-6-yl]pyridine (200 mg) in the same manner as described for EXAMPLE 31.

MS (FAB$^+$) m/z: 571 (MH$^+$). HRMS (FAB$^+$) for $C_{27}H_{29}F_2N_6O_4S$ (MH$^+$): calcd, 571.1939; found, 571.1899.

Step 2.

Title Compound 122 (4.2 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole (10.0 mg) in the same manner as described for EXAMPLE 49.

MS (FAB$^+$) m/z: 471 (MH$^+$). HRMS (FAB$^+$) for $C_{22}H_{21}F_2N_6O_2S$ (MH$^+$): calcd, 471.1415; found, 471.1436.

EXAMPLE 123

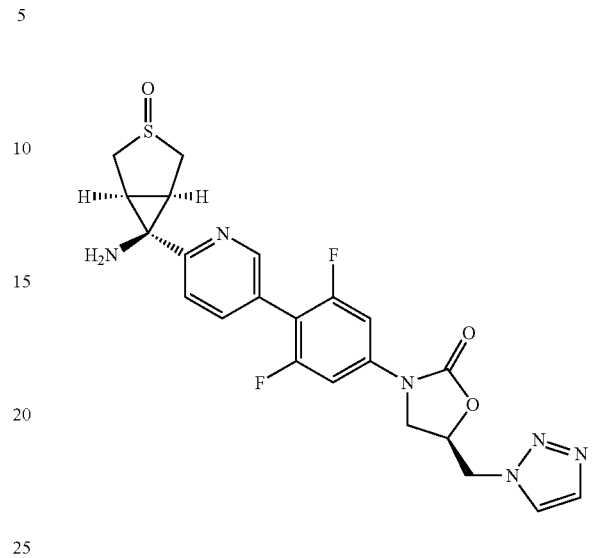

1-[5(R)-3-[4-[2-[(1α,5α,6β)-6-Amino-3-thiabicyclo[3.1.0]hexan-6-yl]pyridin-5-yl]-3,5-difluorophenyl]-2-oxooxazolidin-5-ylmethyl]-1,2,3-triazole S-Oxide Diastereomer G' and Diastereomer H'

Step 1.

1-[5(R)-3-[4-[2-[(1α,5α,6β)-6-t-Butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole S-Oxide Diastereomer G and Diastereomer H The compound of Step 1 of Example 123 diastereomer G (10.2 mg) and diastereomer H (18.6 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole (30.0 mg) in the same manner as described for EXAMPLE 58.

Diastereomer G (Less Polar):

MS (FAB$^+$) m/z: 587 (MH$^+$). HRMS (FAB$^+$) for $C_{27}H_{29}F_2N_6O_5S$ (MH$^+$): calcd, 587.1888; found, 587.1860.

Diastereomer H (More Polar):

MS (FAB$^+$) m/z: 587 (MH$^+$). HRMS (FAB$^+$) for $C_{27}H_{29}F_2N_6O_5S$ (MH$^+$): calcd, 587.1888; found, 587.1921.

Step 2.

Title Compound 123 diastereomer G'(0.8 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole diastereomer G (2.2 mg) in the same manner as described for EXAMPLE 49.

MS (FAB+) m/z: 487 (MH+). HRMS (FAB+) for C22H21F2N6O3S (MH+): calcd, 487.1364; found, 487.1348.

EXAMPLE 124

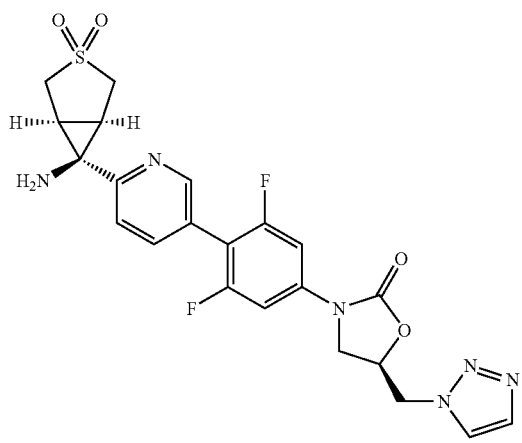

Step 1.

1-[5(R)-3-[4-[2-[(1α,5α,6β)-6-t-Butoxycarbonylamino-3-thiabicyclo[3.1.0]hexan-6-yl]pyridin-5-yl]-3,5-difluorophenyl]-2-oxooxazolidin-5-ylmethyl]-I, 2,3-triazole S,S-Dioxide The compound of Step 1 of Example 124 (19.2 mg) was prepared from 1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole (20.0 mg) in the same manner as described for EXAMPLE 59.

MS (FAB+) m/z: 603 (MH+). HRMS (FAB+) for C27H29F2N6O6S (MH+): calcd, 603.1837; found, 603.1873.

Step 2.

Title Compound 124 (2.7 mg) was prepared from the compound of Step 1 of Example 124 (4.0 mg) in the same manner as described for EXAMPLE 49.

MS (FAB+) m/z: 503 (MH+). HRMS (FAB+) for C22H21F2N6O4S (MH+): calcd, 503.1313; found, 503.1306.

EXAMPLE 125

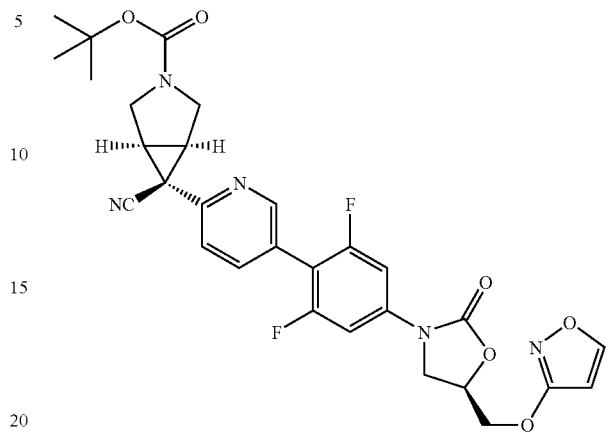

5(R)-3-[4-[2-[(1α,5α,6β)-3-t-Butoxycarbonyl-6-cyano-3-azabicyclo[3.1.0]hexan-6-yl]pyridin-5-yl]-3,5-difluorophenyl]-5-[(isoxazol-3-yl)oxy]methyloxazolidin-2-one Title Compound 125 (47.8 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-hydroxymethyloxazolidin-2-one (50.0 mg) in the same manner as described for EXAMPLE 66.

MS (FAB+) m/z: 580 (MH+). HRMS (FAB+) for C29H28F2N5O6(MH+): calcd, 580.2008; found, 580.1965.

EXAMPLE 126

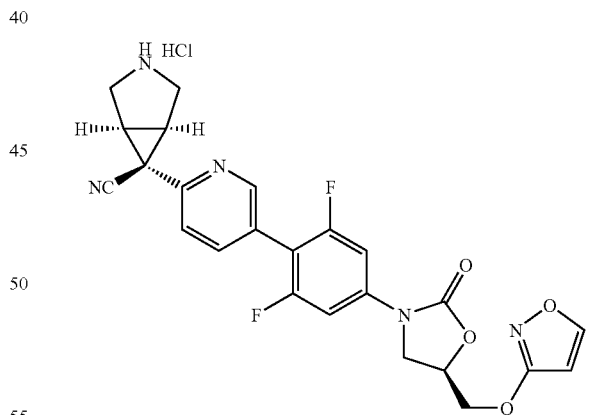

5(R)-3-[4-[2-[(1α,5α,6β)-6-Cyano-3-azabicyclo[3.1.0]hexan-6-yl]pyridin-5-yl]-3,5-difluorophenyl]-5-[(isoxazol-3-yl)oxy]methyloxazolidin-2-one Hydrochloride Title Compound 126 (26.5 mg) was prepared from 5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[(isoxazol-3-yl)oxy]methyloxazolidin-2-one (47.0 mg) in the same manner as described for EXAMPLE 2.

MS (FAB+) m/z: 480 (MH+) (as free base). HRMS (FAB+) for $C_{24}H_{20}F_2N_5O_4$ (MH+): calcd, 480.1483; found, 480.1449.

EXAMPLE 127

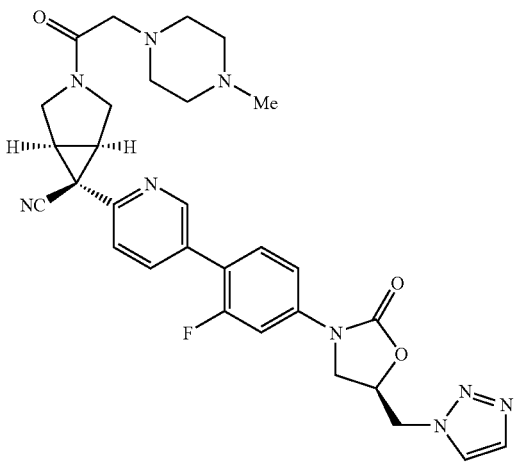

1-[5(R)-3-[4-[2-[(1α,5α,6β)-6-Cyano-3-(4-methylpiperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole Title Compound 127 (17.9 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and N-methylpiperazine (20 μL) in the same manner as described for EXAMPLE 84.

MS (FAB+) m/z: 586 (MH+). HRMS (FAB+) for $C_{30}H_{33}FN_9O_3$ (MH+): calcd, 586.2690; found, 586.2642.

EXAMPLE 128

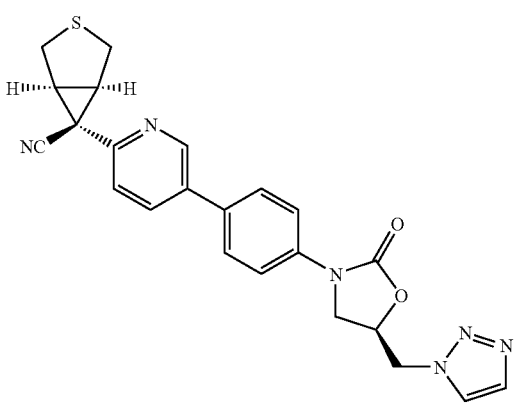

1-[5(R)-3-[4-[2-[(1α,5α,6β)-6-Cyano-3-thiabicyclo[3.1.0]hexan-6-yl]pyridin-5-yl]phenyl]-2-oxooxazolidin-5-ylmethyl]-1,2,3-triazole Title Compound 128 (201 mg) was prepared from 1-[5(R)-3-[4-(4,4,5,5-tetramethyl-1,3,2-dioxaborolyl)phenyl]-2-oxooxazolidin-5-ylmethyl]-1,2,3-triazole (263 mg) and 5-bromo-2-[(1α,5α,6β)-6-cyano-3-thiabicyclo-[3.1.0]hexan-6-yl]pyridine (200 mg) in the same manner as described for EXAMPLE 1.

MS (FAB+) m/z: 445 (MH+). HRMS (FAB+) for $C_{23}H_{21}N_6O_2S$ (MH+): calcd, 445.1447; found, 445.1434.

EXAMPLE 129

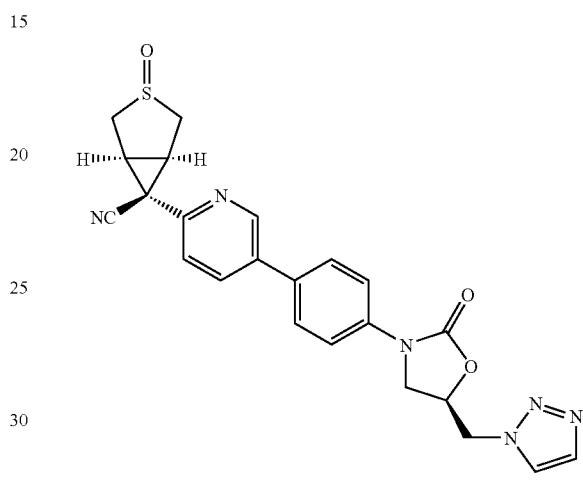

1-[5(R)-3-[4-[2-[(1α,5α,6β)-6-Cyano-3-thiabicyclo[3.1.0]hexan-6-yl]pyridin-5-yl]phenyl]-2-oxooxazolidin-5-ylmethyl]-1,2,3-triazole S-Oxide Title Compound 129 (21.9 mg) was prepared from 1-[5(R)-3-[4-[2-[(1α,5α,6β-6-cyano-3-thiabicyclo[3.1.0]hexan-6-yl]pyridin-5-yl]phenyl]-2-oxooxazolidin-5-ylmethyl]-1,2,3-triazole (22.3 mg) in the same manner as described for EXAMPLE 58.

MS (FAB+) m/z: 461 (MH+). HRMS (FAB+) for $C_{23}H_{21}N_6O_3S$ (MH+): calcd, 461.1396; found, 461.1390.

EXAMPLE 130

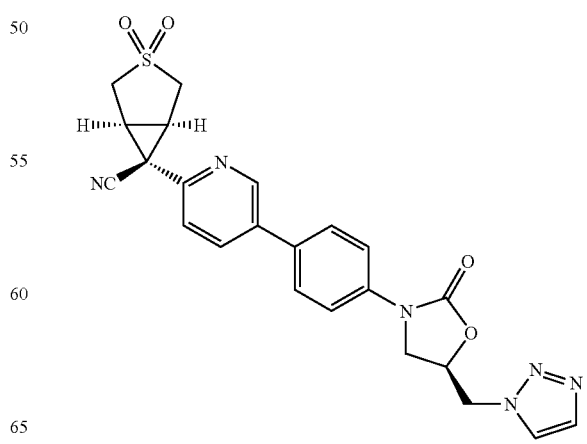

1-[5(R)-3-[4-[2-[(1α,5α,6β)-6-Cyano-3-thiabicyclo[3.1.0]hexan-6-yl]pyridin-5-yl]phenyl]-2-oxooxazolidin-5-ylmethyl]-1,2,3-triazole S,S-Dioxide Title Compound 130 (18.2 mg) was prepared from 1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole (22.3 mg) in the same manner as described for EXAMPLE 58.

MS (FAB$^+$) m/z: 477 (MH$^+$). HRMS (FAB$^+$) for $C_{23}H_{21}N_6O_4S$ (MH$^+$): calcd, 477.1345; found, 477.1329.

EXAMPLE 131

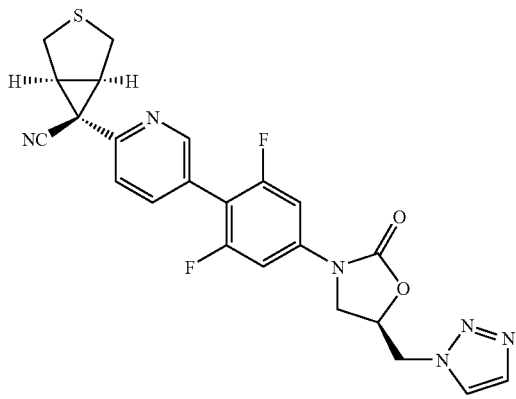

1-[5(R)-3-[4-[2-[(1α,5α,6β)-6-Cyano-3-thiabicyclo[3.1.0]hexan-6-yl]pyridin-5-yl]-3,5-difluorophenyl]-2-oxooxazolidin-5-ylmethyl]-1,2,3-triazole Title Compound 131 (142 mg) was prepared from 1-[5(R)-3-[3,5-difluoro-4(trifluoromethanesulfonyl)-oxyphenyl]-2-oxooxazolidin-5-ylmethyl]-1,2,3-triazole (254 mg) and 5-bromo-2-[(1α,5α,6β)-6-cyano-3-thiabicyclo[3.1.0]hexan-6-yl]pyridine (200 mg) in the same manner as described for EXAMPLE 31.

MS (FAB$^+$) m/z: 481 (MH$^+$). HRMS (FAB$^+$) for $C_{23}H_{19}F_2N_6O_2S$ (MH$^+$): calcd, 481.1258; found, 481.1241.

EXAMPLE 132

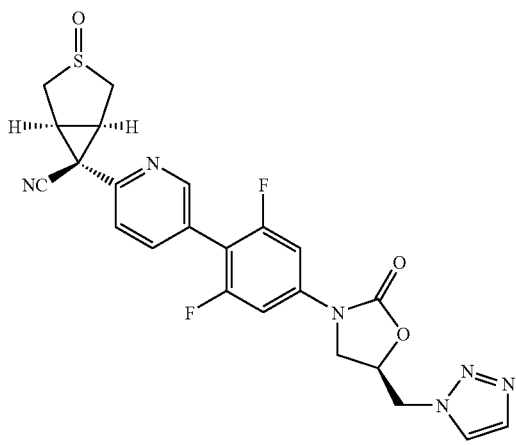

1-[5(R)-3-[4-[2-[(1α,5α,6β)-6-Cyano-3-thiabicyclo[3.1.0]hexan-6-yl]pyridin-5-yl]-3,5-difluorophenyl]-2-oxooxazolidin-5-ylmethyl]-1,2,3-triazole S-Oxide Title Compound 132 (18.5 mg) was prepared from 1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole (20.0 mg) in the same manner as described for EXAMPLE 58.

MS (FAB$^+$) m/z: 497 (MH$^+$). HRMS (FAB$^+$) for $C_{23}H_{19}F_2N_6O_3S$ (MH$^+$): calcd, 497.1207; found, 497.1251.

EXAMPLE 133

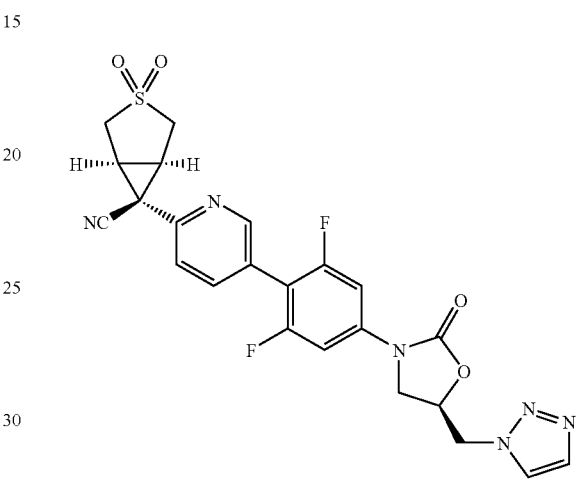

1-[5(R)-3-[4-[2-[(1α,5α,6β)-6-Cyano-3-thiabicyclo[3.1.0]hexan-6-yl]pyridin-5-yl]-3,5-difluorophenyl]-2-oxooxazolidin-5-ylmethyl]-1,2,3-triazole S,S-Dioxide Title Compound 133 (18.9 mg) was prepared from 1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole (20.0 mg) in the same manner as described for EXAMPLE 58.

MS (FAB$^+$) m/z: 513 (MH$^+$). HRMS (FAB$^+$) for $C_{23}H_{19}F_2N_6O_4S$ (MH$^+$): calcd, 513.1157; found, 513.1181.

EXAMPLE 134

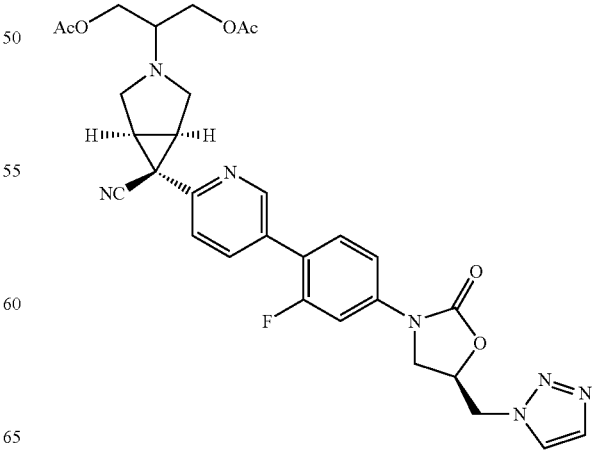

1-[5(R)-3-[4-[2-[(1α,5α,6β)-6-Cyano-3-(1,3-diacetoxypropan-2-yl)-3-azabicyclo[3.1.0]hexan-6-yl]pyridin-5-yl]-3-fluorophenyl]-2-oxooxazolidin-5-ylmethyl]-1,2,3-triazole To a solution of 1-[5(R)-3-[4-[2-[(1α,5α,6β)-6-cyano-3-(1,3-dihydroxypropan-2-yl)-3-azabicyclo[3.1.0]hexan-6-yl]pyridin-5-yl]-3-fluorophenyl]-2-oxooxazolidin-5-ylmethyl]-1,2,3-triazole (7.7 mg) in dichloromethane (0.2 mL) was added acetic anhydride at room temperature, the mixture was stirred at the same temperature for 5 hours. To the mixture was added 4-(dimethylamino)pyridine (9.0 mg), the mixture was stirred at room temperature for 1 hour and concentrated in vacuo. Preparative thin-layer chromatography (silica, dichloromethane:methanol=10:1) of the residue gave title compound 134 (5.8 mg).

MS (FAB$^+$) m/z: 604 (MH$^+$). HRMS (FAB$^+$) for $C_{30}H_{31}FN_7O_6$ (MH$^+$): calcd, 604.2320; found, 604.2300.

EXAMPLE 135

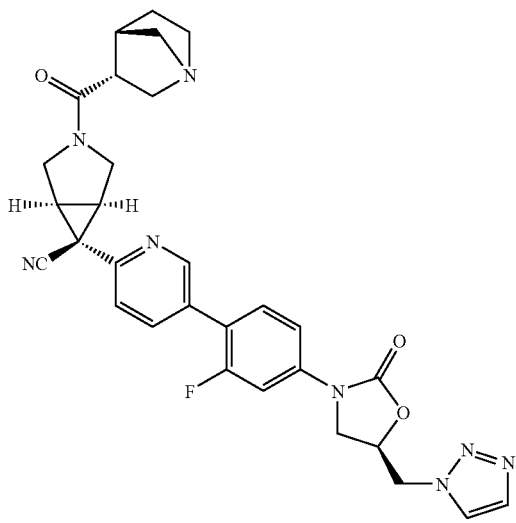

1-[5(R)-3-[4-[2-[(1α,5α,6β)-3-[(3R,4S)-1-Azabicyclo[2.2.1]hepan-3-yl]carbonyl-6-cyano-3-azabicyclo[3.1.0]hexan-6-yl]pyridin-5-yl]-3-fluorophenyl]-2-oxooxazolidin-5-ylmethyl]-1,2,3-triazole Title Compound 135 (3.9 mg) was prepared from 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (20.0 mg) and (3R,4S)-1-azabicycloheptane-3-carboxylic acid hydrochloride (9.5 mg) in the same manner as described for EXAMPLE 71.

MS (FAB$^+$) m/z: 569 (MH$^+$). HRMS (FAB$^+$) for $C_{30}H_{30}FN_8O_3$ (MH$^+$): calcd, 569.2425; found, 569.2380.

EXAMPLE 136

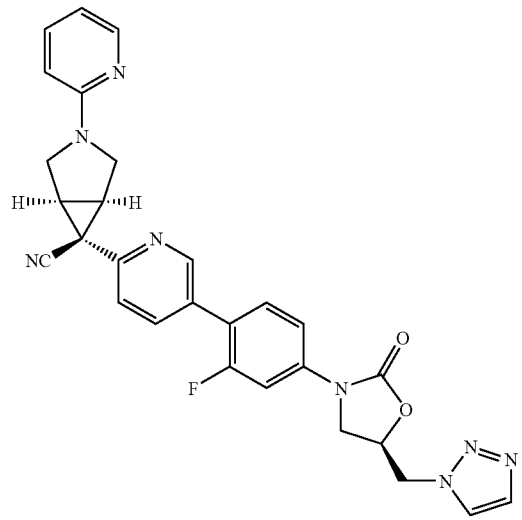

1-[5(R)-3-[4-[2-[(1α,5α,6β)-6-Cyano-3-(pyridin-2-yl)-3-azabicyclo[3.1.0]hexan-6-yl]pyridin-5-yl]-3-fluorophenyl]-2-oxooxazolidin-5-ylmethyl]-1,2,3-triazole A suspension of 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole (50.0 mg) and 2-pyridyl trifluoromethnesulfonate (0.86 mL) in diisopropylethylamine (0.2 mL) was stirred at 90° C. for 44 hours. Flash chromatography (silica, ethyl acetate:methanol=5:1) of the mixture gave title compound 136(18.6 mg).

MS (FAB$^+$) m/z: 523 (MH$^+$). HRMS (FAB$^+$) for $C_{28}H_{24}FN_8O_2$ (MH$^+$): calcd, 523.2006; found, 523.1978.

EXAMPLE 137

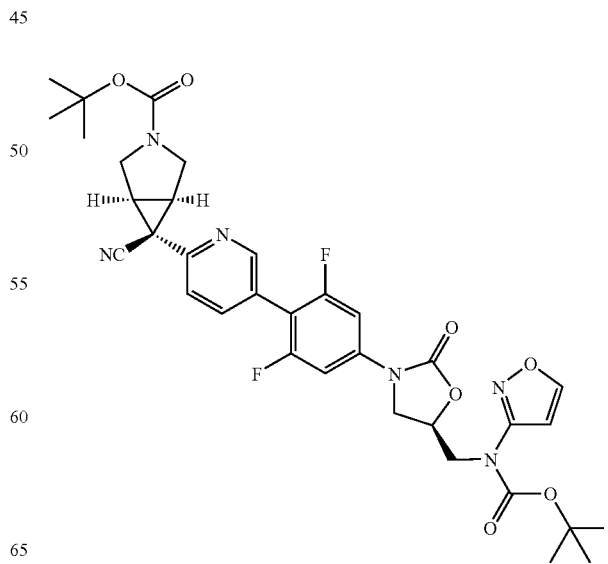

5(R)-3-[4-[2-[(1α,5α,6β)-3-t-Butoxycarbonyl-6-cyano-3-azabicyclo[3.1.0]hexan-6-yl]pyridin-5-yl]-3,5-difluorophenyl]-5-[N-(t-butoxycarbonyl)-N-(isoxazol-3-yl)]aminomethyloxazolidin-2-one Title Compound 137 (54.9 mg) was prepared from N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-5-hydroxymethyloxazolidin-2-one (50.0 mg) in the same manner as described for EXAMPLE 67.

MS (FAB$^+$) m/z: 679 (MH$^+$). HRMS (FAB$^+$) for $C_{34}H_{37}F_2N_6O_7$ (MH$^+$): calcd, 679.2692; found, 679.2672.

EXAMPLE 138

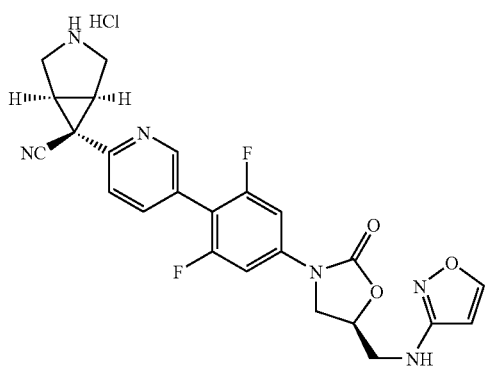

5(R)-3-[4-[2-[(1α,5α,6β)-6-Cyano-3-azabicyclo[3.1.0]hexan-6-yl]pyridin-5-yl]-3,5-difluorophenyl]-5-[N-(isoxazol-3-yl)]aminomethyloxazolidin-2-one Hydrochloride Title Compound 138 (20.7 mg) was prepared from 5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[N-(t-butoxycarbonyl)-N-(isoxazol-3-yl)]aminomethyloxazolidin-2-one (51.8 mg) in the same manner as described for EXAMPLE 2.

$^1$H NMR (DMSO-d6) δ 3.03-3.09 (m, 2H), 3.40-3.47 (m, 4H), 3.85 (dd, J=9.2 Hz, 6.1 Hz, 1H), 3.90-4.00 (m, 2H), 4.20 (t, J=9.2 Hz, 1H), 4.90-4.98 (m, 1H), 6.00 (d, J=1.8 Hz, 1H), 6.57 (t, J=6.1 Hz, 1H), 7.45-7.53 (m, 2H), 7.72 (d, J=7.9 Hz, 1H), 8.01 (d, J=7.9 Hz, 1H), 8.39 (d, J=1.8 Hz, 1H), 8.64 (s, 1H).

EXAMPLE 139

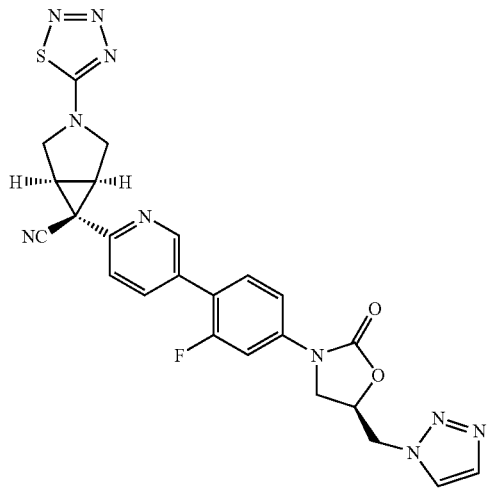

1-[5(R)-3-[4-[2-[(1α,5α,6β)-6-Cyano-3-(thiatriazol-2-yl)-3-azabicyclo[3.1.0]hexan-6-yl]pyridin-5-yl]-3-fluorophenyl]-2-oxooxazolidin-5-ylmethyl]-1,2,3-triazole To a solution of 1,1'-thiocarbonyldiimidazole (21.6 mg) in acetonitrile (1.0 mL) was added 1-[5(R)-3-[4-[2-[(1α,5α,6β)-6-cyano-3-azabicyclo[3.1.0]hexan-6-yl]pyridin-5yl]-3-fluorophenyl]-2-oxooxazolidin-5-ylmethyl]-1,2,3-triazole (50.0 mg) at room temperature, the mixture was stirred at the same temperature for 1 hour. To the mixture was added iodomethane (67.9 μL), the mixture was stirred at room temperature for overnight, and concentrated in vacuo. A suspension of the residue and sodium azide (21.3 mg) in acetonitrile (1.0 mL) was stirred at room temperature for overnight. After dilution of the mixture with water, the insoluble materials were collected by filtration. Preparative thin-layer chromatography (silica, dichloromethane:methanol=10:1) of the insoluble materials title compound 139 (13.7 mg).

MS (FAB$^+$) m/z: 531 (MH$^+$). HRMS (FAB$^+$) for $C_{24}H_{20}FN_{10}O_2S$ (MH$^+$): calcd, 531.1475; found, 531.1466.

EXAMPLE 140

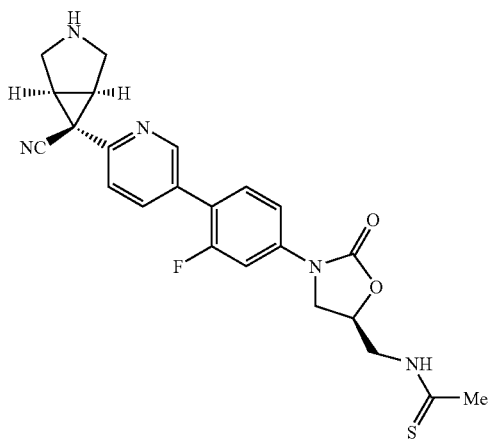

N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]thioacetamide Step 1.

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]thioacetamide A mixture of 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (100 mg), ethyl dithioacetate (28.0 μL), triethylamine (62.2 μL), and tetrahydrofuran (3 mL) was stirred at room temperature for overnight and concentrated in vacuo Flash chromatography (silica, dichloromethane:methanol=10:1) of the residue gave N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]thioacetamide (82.0 mg).

MS (FAB$^+$) m/z: 552 (MH$^+$).

Step 2.

Title Compound 140 (46.2 mg) was prepared from the compound of Step 1 of Example 140 (77.0 mg) in the same manner as described for EXAMPLE 49.

MS (FAB$^+$) m/z: 452 (MH$^+$). HRMS (FAB$^+$) for $C_{23}H_{23}FN_5O_2S$ (MH$^+$): calcd, 452.1557; found, 452.1531.

EXAMPLE 141

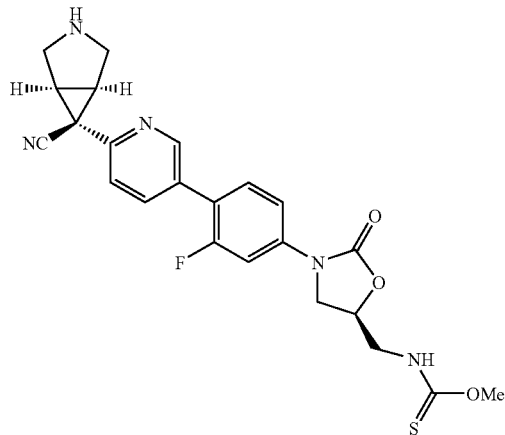

O-Methyl N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]thiocarbamate Step 1.

N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl]isothiocyanate To a solution of 5(S)-aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (150 mg) in tetrahydrofuran (2.0 mL) was added carbon disulfide (36.6 μL) and triethylamine (42.4 μL) at 0° C., the mixture was stirred at the same temperature for 4 hours. To the mixture was added ethyl chloroformate (29.1 μL) at 0° C., the mixture was stirred at the same temperature for 30 minutes and concentrated in vacuo. Treatment of the residue with water gave crude product. A solution of the crude product in dichloromethane was dried over anhydrous sodium sulfate, filtered, and then concentrated in vacuo. Flash chromatography (silica, ethyl acetate) of the residue gave the compound of Step 1 of Example 141 (125 mg).

MS (FAB$^+$) m/z: 536 (MH$^+$).

Step 2.

O-Methyl N-[5(S)-3-[4-[2-[(1α,5α,6β)-3-t-Butoxycarbonyl-6-cyano-3-azabicyclo[3.1.0]hexan-6-yl]pyridin-5-yl]-3-fluorophenyl]-2-oxooxazolidin-5-ylmethyl] thiocarbamate To a solution of sodium methoxide in methanol (prepared from sodium hydride (26.5 mg) and methanol (1.0 mL)) was added a suspension of the compound of Step 1 of Example 141 (119 mg) in methanol (1.0 mL) at 0° C., the mixture was stirred at room temperature for 5 hours and concentrated in vacuo. After dilution of the residue with water, the mixture was extracted with dichloromethane-methanol (10:1). The organic extracts were dried over anhydrous sodium sulfate, filtered, and then concentrated in vacuo. Flash chromatography (silica, dichloromethane:ethyl acetate=1:1) of the residue gave the compound of Step 2 of Example 141 (93.5 mg).

MS (FAB$^+$) m/z: 568 (MH$^+$).

Step 3.

Title Compound 141 (43.6 mg) was prepared from the compound of Step 2 of Example 141 (85.0 mg) in the same manner as described for EXAMPLE 49.

MS (FAB$^+$) m/z: 468 (MH$^+$). HRMS (FAB$^+$) for $C_{23}H_{23}FN_5O_3S$ (MH$^+$): calcd, 468.1506; found, 468.1524.

REFERENCE EXAMPLE 1

N-[5(S)-3-[3-Fluoro-4-(4,4,5,5-tetramethyl-1,3,2-dioxaborolyl)phenyl]-2-oxooxazolidin-5-ylmethyl]acetamide The mixture of N-[5(S)-3-(3-fluoro-4-iodophenyl)-2-oxooxazolidin-5-ylmethyl]acetamide (2.00 g), bis(pinacolato)diboron (1.61 g), potassium acetate (1.56 g) and [1,1'-bis(diphenylphosphino)ferrocene]palladium(II) dichloride-dichloromethane adduct (432 mg) in dimethyl sulfoxide (50 mL) was heated at 80° C. for 1 hour. The mixture was diluted with water and extracted with ethyl acetate. The organic extracts were washed with brine, dried over anhydrous magnesium sulfate, and then concentrated in vacuo. Flash chromatography (silica, ethyl acetate:acetone=9:1) of the residue gave N-[5(S)-3-[3-fluoro-4-(4,4,5,5-tetramethyl-1,3,2-dioxaborolyl)phenyl]-2-oxooxazolidin-5-ylmethyl]acetamide (889 mg).

MS (EI$^+$) m/z: 378 (M$^+$). HRMS (EI$^+$) for $C_{18}H_{24}BFN_2O_5$ (M$^+$): calcd, 378.1762; found, 378.1779.

REFERENCE EXAMPLE 2

N-[5(S)-3-[4-(4,4,5,5-Tetramethyl-1,3,2-dioxaborolyl)phenyl]-2-oxooxazolidin-5-ylmethyl]acetamide Reference Example 2 (92.5 mg) was prepared from N-[5(S)-3-(4-iodophenyl)-2-oxooxazolidin-5-ylmethyl]acetamide (108 mg) and bis(pinacolato)diboron (855 mg) in the same manner as described for REFERENCE EXAMPLE 1.
MS (EI$^+$) m/z: 360 (M$^+$). HRMS (EI$^+$) for $C_{18}H_{25}BN_2O_5$ (M$^+$): calcd, 360.1857; found, 360.1875.

REFERENCE EXAMPLE 3

1-[5(R)-3-[3-Fluoro-4-(4,4,5,5-tetramethyl-1,3,2-dioxaborolyl)phenyl]-2-oxooxazolidin-5-ylmethyl]-1,2,3-triazole Reference Example 3 (1.53 g) was prepared from 1-[5(R)-3-(3-fluoro-4-iodophenyl)-2-oxooxazolidin-5-ylmethyl]-1,2,3-triazole (2.69 g) and bis(pinacolato)diboron (1.86 g) in the same manner as described for REFERENCE EXAMPLE 1.
MS (EI$^+$) m/z: 388 (M$^+$). HRMS (EI$^+$) for $C_{18}H_{22}BFN_4O_4$ (M$^+$): calcd, 388.1718; found, 388.1752.

REFERENCE EXAMPLE 4

1-[5(R)-3-[4-(4,4,5,5-Tetramethyl-1,3,2-dioxaborolyl)phenyl]-2-oxooxazolidin-5-ylmethyl]-1,2,3-triazole Reference Example 4 (147 mg) was prepared from 1-[5(R)-3-(4-iodophenyl)-2-oxooxazolidin-5-ylmethyl]-1,2,3-triazole (200 mg) and bis(pinacolato)diboron (151 mg) in the same manner as described for REFERENCE EXAMPLE 1.
MS (EI$^+$) m/z: 370 (M$^+$). HRMS (EI$^+$) for $C_{18}H_{23}BN_4O_4$ (M$^+$): calcd, 370.1812; found, 370.1814.

REFERENCE EXAMPLE 5

5(R)-5-(t-Butyldimethylsilyloxy)methyl-3-(3-fluoro-4-iodophenyl)oxazolidin-2-one To a solution of 5(R)-3-(3-fluoro-4-iodophenyl)-5-hydroxymethyloxazolidin-2-one (3.00 g) in dichloromethane (30 mL) was added imidazole (1.33 g) and t-butyidimethylsilyl chloride (1.48 g) at 0° C., the mixture was stirred at room temperature for 2 hours. The mixture was washed with water, 2N hydrochloric acid, saturated sodium hydrogencarbonate solution and brine, dried over anhydrous magnesium sulfate, and then concentrated in vacuo to give Reference Example 5 (3.66 g).
MS (EI$^+$) m/z: 451 (M$^+$). HRMS (EI$^+$) for $C_{16}H_{23}FINO_3Si$ (M$^+$): calcd, 451.0476; found, 451.0511.

REFERENCE EXAMPLE 6

5(R)-5-(t-Butyldimethylsilyloxy)methyl-3-[3-fluoro-4-(4,4,5,5-tetramethyl-1,3,2-dioxaborolyl)phenyl]oxazolidin-2-one Reference Example 6 (64.4 mg) was prepared from 5(R)-5-(t-butyldimethylsilyloxy)methyl-3-(3-fluoro-4-iodophenyl)oxazolidin-2-one (100 mg) and bis(pinacolato)diboron (67.0 mg) in the same manner as described for Reference Example 1.
MS (CI$^+$) m/z: 452 (MH$^+$). HRMS (CI$^+$) for $C_{22}H_{36}BFNO_5Si$ (MH$^+$): calcd, 452.2440; found, 452.2394.

REFERENCE EXAMPLE 7

3,5-Difluoro-4-(methoxymethyl)oxynitrobenzene

To a solution of 2,6-difluoro-4-nitrophenol (35.0 g) in dichloromethane (300 mL) was added diisopropylethylamine (50.2 mL) and methoxymethyl chloride (17.5 mL) at 0° C., the mixture was stirred at room temperature for 2 hours. The mixture was washed with water, 5% sodium hydrogencarbonate solution and brine, dried over anhydrous magnesium sulfate, and then concentrated in vacuo. Flash chromatography (silica, hexane: ethyl acetate=9:1) of the residue gave Reference Example 7(35.2 g).
$^1$H NMR (CDCl$_3$) δ 3.59 (d, J=1.5 Hz, 3H), 5.30 (s, 2H), 7.83-7.91 (m, 2H).

REFERENCE EXAMPLE 8

4-Benzyloxycarbonylamino-2,6-difluoro-1-(methoxymethyl)oxybenzene

A suspension of 3,5-difluoro-4-(methoxymethyl)oxynitrobenzene (35.0 g) and palladium catalyst (10% on charcoal, 3.00 g) in methanol (250 mL) ) was hydrogenated at 1 atm for 2 hours at room temperature. After filtration of the catalyst, the filtrate was concentrated in vacuo to give 4-amino-2,6-difluoro-1-(methoxymethyl)oxybenzene. This was used in the next step without further purification. To a solution of crude 4-amino-2,6-difluoro-1-(methoxymethyl)oxybenzene thus obtained in tetrahydrofuran (500 mL) was successively added sodium hydrogencarbonate (17.4 g), water (100 mL) and benzyl chloroformate (30.0 g) at 0° C., and the mixture was stirred at room temperature for 15 minutes. The mixture was diluted with saturated sodium hydrogencarbonate solution and extracted with ethyl acetate. The organic extracts were washed with brine, dried over anhydrous magnesium sulfate, and then concentrated in vacuo. Flash chromatography (silica, hexane:ethyl acetate=6:1) of the residue gave Reference Example 8 (49.10 g).
MS (EI$^+$) m/z: 323 (M$^+$). HRMS (EI$^+$) for $C_{16}H_{15}F_2NO_4$ (M$^+$): calcd, 323.0969; found, 323.0963.

REFERENCE EXAMPLE 9

5(R)-3-[3,5-Difluoro-4-(methoxymethyl)oxyphenyl]-5-hydroxymethyloxazolidin-2-one To a solution of 4-benzyloxycarbonylamino-2,6-difluoro-1-(methoxymethyl)oxybenzene (46.3 g) in dry tetrahydrofuran (400 mL) was added a solution of n-butyllithium in hexane (1.6 M, 90.0 mL) at −78° C., and the mixture was stirred at the same temperature for 30 minutes. (R)-Glycidyl butyrate (20.3 mL) was added to the mixture at −78° C. and the mixture was allowed to stand at room temperature for 3 hours. After quenching the reaction with the addition of aqueous ammonium chloride solution, the mixture was extracted with ethyl acetate. The organic extracts were washed with brine, dried over anhydrous magnesium sulfate, filtered, and then concentrated in vacuo. To a solution of the residue in methanol (300 mL) was added potassium carbonate (20.0 g), the mixture was stirred at room temperature for 30 minutes, and then concentrated in vacuo. After dilution of the residue with water, the mixture was extracted with ethyl acetate. The organic extracts were washed with brine, dried over anhydrous magnesium sulfate, filtered, and then concentrated in vacuo. Flash chromatography (silica, hexane: ethyl acetate=1:4) of the residue gave Reference Example 9 (36.1 g).

MS (EI$^+$) m/z: 289 (M$^+$). HRMS (EI$^+$) for $C_{12}H_{13}F_2NO_5$ (M$^+$): calcd, 289.0762; found, 289.0743.

REFERENCE EXAMPLE 10

N-[5(S)-3-[3,5-Difluoro-4-(methoxymethyl)oxyphenyl]-2-oxooxazolidin-5-ylmethyl]acetamide To a solution of 5(R)-3-[3,5-difluoro-4-(methoxymethyl)oxyphenyl]-5-hydroxymethyloxazolidin-2-one (5.00 g) in dichloromethane (20 mL) were successively added triethylamine (4.82 mL) and methanesulfonyl chloride (2.53 mL) at 0° C., and the mixture was stirred at the same temperature for 1 hour. The mixture was washed with water, dried over anhydrous magnesium sulfate, filtered, and then concentrated in vacuo to give 5(R)-3-[3,5-difluoro-4-(methoxymethyl)oxyphenyl]-5-methanesulfonyloxymethyloxazolidin-2-one. This was used in the next step without further purification. The mixture of crude 5(R)-3-[3,5-difluoro-4-(methoxymethyl)oxyphenyl]-5-methanesulfonyloxymethyloxazolidin-2-one thus obtained and sodium azide (3.93 g) in N,N-dimethylformamide (20 mL) was heated at 60° C. for 8 hours, and then concentrated in vacuo. The residue was diluted with ethyl acetate and washed with water and brine. The organic extracts were dried over anhydrous magnesium sulfate, filtered, and then concentrated in vacuo to give 5(R)-azidomethyl-3-[3,5-difluoro-4-(methoxymethyl)oxyphenyl]oxazolidin-2-one (5.43 g). This was used in the next step without further purification. A suspension of 5(R)-azidomethyl-3-[3,5-difluoro-4-(methoxymethyl)oxyphenyl]oxazolidin-2-one (3.53 g) and Lindlar catalyst (5% palladium on CaCO3 partially poisoned with lead, 700 mg) in methanol (110 mL) was hydrogenated at 1 atm for 6 hours at room temperature. After filtration of the catalyst, the filtrate was concentrated in vacuo. To a solution of the residue in tetrahydrofuran (15 mL) was added triethylamine (6.30 mL) and acetic anhydride (2.10 mL) at room temperature, and the mixture was stirred at the same temperature for 2 hours. After quenching the reaction by the addition of saturated sodium hydrogencarbonate solution, the mixture was extracted with ethyl acetate. The organic extracts were dried over anhydrous magnesium sulfate, filtered, and then concentrated in vacuo. Flash chromatography (silica, ethyl acetate) of the residue gave Reference Example 10 (3.45 g).

MS (EI$^+$) m/z: 330 (M$^+$). HRMS (EI$^+$) for $C_{14}H_{16}F_2N_2O_5$ (M$^+$): calcd, 330.1027; found, 330.1001.

REFERENCE EXAMPLE 11

N-[5(S)-3-(3,5-Difluoro-4-hydroxyphenyl)-2-oxooxazolidin-5-ylmethyl]acetamide

To a solution of N-[5(S)-3-[3,5-difluoro-4-(methoxymethyl)oxyphenyl]-2-oxooxazolidin-5-ylmethyl]acetamide (200 mg) in methanol (5 mL) was added concentrated hydrochloric acid (0.50 mL), the mixture was stirred at room temperature for 1 day, and then concentrated in vacuo. Treatment with water of the residue gave Reference Example 11 (144 mg).

MS (EI$^+$) m/z: 286 (M$^+$). HRMS (EI$^+$) for $C_{12}H_{12}F_2N_2O_4$ (M$^+$): calcd, 286.0765; found, 286.0747.

REFERENCE EXAMPLE 12

N-[5(S)-3-[3,5-Difluoro-4-(trifluoromethanesulfonyl)oxyphenyl]-2-oxooxazolidin-5-ylmethyl]acetamide To a solution of N-[5(S)-3-(3,5-difluoro-4-hydroxyphenyl)-2-oxooxazolidin-5-ylmethyl]acetamide (2.70 g) in pyridine (15 mL) was added triflic anhydride (2.38 mL) at 0° C., the mixture was stirred at room temperature for 12 hours. After dilution of the mixture with water, the mixture was extracted with ethyl acetate. The organic extracts were washed with 5% hydrochloric acid and brine, dried over anhydrous magnesium sulfate, filtered, and then concentrated in vacuo. Flash chromatography (silica, ethyl acetate: methanol=19:1) of the residue gave Reference Example 12 (3.48 g).

MS (EI$^+$) m/z: 418 (M$^+$). HRMS (EI$^+$) for $C_{13}H_{11}F_5N_2O_6S$ (M$^+$): calcd, 418.0258; found, 418.0210.

REFERENCE EXAMPLE 13

1-[5(R)-3-(3-Fluoro-4-iodophenyl)-2-oxooxazolidin-5-ylmethyl]-1,2,3-triazole

Step 1.

5(R)-Acetoxymethyl-3-(3-fluorophenyl)oxazolidin-2-one

To a solution of 5(R)-3-(3-fluorophenyl)-5-hydroxymethyloxazolidin-2-one (5.28 g) in tetrahydrofuran (53 mL) was added triethylamine (3.83 mL), acetic anhydride (2.55 mL) and (4-dimethylamino)pyridine (152 mg), and the mixture was stirred at room temperature for 1 hour. After quenching the reaction by the addition of 1 N hydrochloric acid, the mixture was extracted with ethyl acetate. The organic extracts were washed with brine, dried over anhydrous sodium sulfate, filtered, and then concentrated in vacuo to give crude 5(R)-acetoxymethyl-3-(3-fluorophenyl)oxazolidin-2-one (6.33 g).

Step 2.

5(R)-Acetoxymethyl-3-(3-fluoro-4-iodophenyl)oxazolidin-2-one

To a solution of 5(R)-acetoxymethyl-3-(3-fluorophenyl)oxazolidin-2-one (6.33 g) in acetic acid (40 mL) was added iodine monochloride (1.91 mL), the mixture was stirred at room temperature for 18 hours, and then concentrated in vacuo. The resulting residue was dissolved with ethyl acetate, the mixture was washed with aqueous sodium hydrogencarbonate solution, 20% sodium sulfite solution and brine, dried over anhydrous sodium sulfate, filtered, and then concentrated in vacuo to give crude 5(R)-acetoxymethyl-3-(3-fluoro-4-iodophenyl)oxazolidin-2-one (9.48 g).

Step 3.

5(R)-3-(3-Fluoro-4-iodophenyl)-5-hydroxymethyloxazolidin-2-one

To a solution of crude 5(R)-acetoxymethyl-3-(3-fluoro-4-iodophenyl)oxazolidin-2-one (9.48 g) in methanol (95 mL) was added potassium carbonate (6.91 g), and the mixture was stirred at room temperature for 2.5 hours. After insoluble materials were filtered off, the filtrate was concentrated in vacuo. The residue was dissolved with ethyl acetate, the mixture was washed with brine, dried over anhydrous sodium sulfate, filtered, and then concentrated in vacuo. After treating of the residue with isopropanol, the resulting precipitates were collected by filtration to give 5(R)-3-(3-fluoro-4-iodophenyl)-5-hydroxymethyloxazolidin-2-one, and the filtrate was concentrated in vacuo. Flash chromatography (silica, ethyl acetate) of the residue gave further amount of the product (total 6.24 g).

MS (EI$^+$) m/z: 337 (M$^+$). $^1$H NMR (CDCl$_3$) δ 2.15 (t, J=6.4Hz, 1H), 3.74-4.80 (m, 5H), 7.07 (dd, J=8.8, 2.4Hz, 1H), 7.48 (dd, J=10.3, 2.4 Hz, 1H), 7.70 (dd, J=8.8, 6.8 Hz, 1H).

Step 4.

5(R)-Azidomethyl-3-(3-fluoro-4-iodophenyl)oxazolidin-2-one

To a solution of 5(R)-3-(3-fluoro-4-iodophenyl)-5-hydroxymethyloxazolidin-2-one (2.00 g) in dichloromethane (30 mL) was added triethylamine (1.24 mL) and methanesulfonyl chloride (551 µL) at 0° C., the mixture was stirred at the same temperature for 30 minutes. The mixture was washed with ice water, dried over anhydrous magnesium sulfate, filtered, and then concentrated in vacuo. The mixture of the residue and sodium azide (964 mg) in N,N-dimethylformamide (30 mL) was stirred at 80° C. for 2 hours and concentrated in vacuo. After dilution of the residue with water, the mixture was extracted with ethyl acetate. The organic extracts were dried over anhydrous magnesium sulfate, filtered, and then concentrated in vacuo to give 5(R)-azidomethyl-3-(3-fluoro-4-iodophenyl)oxazolidin-2-one (2.18 g).

MS (EI$^+$) m/z: 361 (M$^+$). HRMS (EI$^+$) for C$_{10}$H$_8$FIN$_4$O$_2$ (M$^+$): calcd, 361.9676; found, 361.9698.

Step 5.

1-[5(R)-3-(3-Fluoro-4-iodophenyl)-2-oxooxazolidin-5-ylmethyl]-1,2,3-triazole

The mixture of 5(R)-azidomethyl-3-(3-fluoro-4-iodophenyl)oxazolidin-2-one (2.18 g) and 2,5-norbornadiene (6.40 mL) in dioxane (45.6 mL) was stirred at 80° C. for 2 hours, 110° C. for 4 hours, and then concentrated in vacuo to give Reference Example 13 (1.70 g).

MS (EI$^+$) m/z: 388 (M$^+$). HRMS (EI$^+$) for C$_{12}$H$_{10}$FIN$_4$O$_2$ (M$^+$): calcd, 387.9833; found, 387.9835.

REFERENCE EXAMPLE 14

5(R)-Azidomethyl-3-(4-iodophenyl)oxazolidin-2-one

Reference Example 14 (75.3 g) was prepared from 5(R)-3-(4-iodophenyl)-5-hydroxymethyloxazolidin-2-one (70.0 g) in the same manner as described for REFERENCE EXAMPLE 13.

MS (EI$^+$) m/z: 344 (M$^+$). HRMS (EI$^+$) for C$_{10}$H$_9$IN$_4$O$_2$ (M$^+$): calcd, 343.9770; found, 343.9740.

REFERENCE EXAMPLE 15

1-[5(R)-3-(4-Iodophenyl)-2-oxooxazolidin-5-ylmethyl]-1,2,3-triazole

Reference Example 15 (62.5 mg) was prepared from 5(R)-azidomethyl-3-(4-iodophenyl)oxazolidin-2-one (100 mg) in the same manner as described for REFERENCE EXAMPLE 13.

MS (EI$^+$) m/z: 370 (M$^+$). HRMS (EI$^+$) for C$_{12}$H$_{11}$N$_4$O$_2$ (M$^+$): calcd, 369.9927; found, 369.9919.

REFERENCE EXAMPLE 16

5(R)-5-(t-Butyldimethylsilyloxy)methyl-3-(4-iodophenyl)oxazolidin-2-one

Reference Example 16 (2.66 g) was prepared from 5(R)-3-(4-iodophenyl)-5-hydroxymethyloxazolidin-2-one (2.00 g) in the same manner as described for REFERENCE EXAMPLE 5.

MS (EI$^+$) m/z: 433 (M$^+$). HRMS (EI$^+$) for C$_{16}$H$_{24}$INO$_3$Si (M$^+$): calcd, 433.0570; found, 433.0544.

REFERENCE EXAMPLE 17 cis-N-t-Butoxycarbonylpyrrolidine-3,4-diol

To a solution of N-t-butoxycarbonyl-3-pyrroline (69.3 g) and NMO (72.2 g) in tetrahydrofuran (340 mL), t-butanol (210 mL) and water (100 mL) was added OsO$_4$ (2.5% solution in t-butanol, 4.8 mL), the mixture was heated under reflux for 2.5 hours, and then concentrated in vacuo. After dilution of the residue with brine, the mixture was extracted with ethyl acetate. The organic extracts were concentrated in vacuo. Flash chromatography (silica, hexane:ethyl acetate=1:1) of the residue gave Reference Example 17 (55.0 g).

MS (FAB$^+$) m/z: 204 (MH$^+$). HRMS (FAB$^+$) for C$_9$H$_{18}$NO$_4$ (MH$^+$): calcd, 204.1236; found, 204.1240.

REFERENCE EXAMPLE 18 cis-N-t-Butoxycarbonylpyrrolidine-3,4-cyclic Sulfate

To a solution of cis-N-t-butoxycarbonylpyrrolidine-3,4-diol (406 mg) and triethylamine (1.1 mL) in dichloromethane (10 mL) was added thionyl chloride (220 µL) at 0° C., the mixture was stirred at the same temperature for 10 minutes. After quenching the reaction by addition of water (1 mL), the mixture was diluted hexane and water. The organic extracts were washed with water, saturated sodium hydrogencarbonate solution and brine, dried over anhydrous magnesium sulfate, filtered, and then concentrated in vacuo to give crude cyclic sulfite (482 mg). To a solution of the crude cyclic sulfite (482 mg) in carbon tetrachloride (6 mL), acetonitrile (6 mL), and water (9 mL) was added ruthenium(III) chloride hydrate (6.0 mg) and sodium periodate (856 mg) at 0° C., the mixture was stirred at the same temperature for 2 hours. After dilution of the mixture with hexane and ether, the mixture was extracted with hexane. The organic extracts were washed with brine, dried over anhydrous magnesium sulfate, filtered, and then concentrated in vacuo. Flash chromatography (silica, hexane:ethyl acetate=1:1) of the residue gave Reference Example 18 (438 mg).

MS (FAB$^+$) m/z: 266 (MH$^+$). HRMS (FAB$^+$) for C$_9$H$_{16}$NO$_6$S (MH$^+$): calcd, 266.0698; found, 266.0730.

REFERENCE EXAMPLE 19

5-Bromo-2-[(1α,5α,6β)-3-t-butoxycarbonyl-6-cyano-3-azabicyclo[3.1.0]hexan-6-yl]pyridine To a suspension of sodium hydride (60% oil dispersion, 2.24 g) in dimethoxyethane (110 mL) was added a solution of 5-bromo-2-pyridylacetonitrile (5.0 g) in dimethoxyethane (20 mL) and a solution of cis-N-t-butoxycarbonylpyrrolidine-3,4-cyclic sulfate (7.41 g) in dimethoxyethane (20 mL) at 0° C., the mixture was stirred at room temperature for 3 hours. After dilution of the mixture with brine, the mixture was extracted with ethyl acetate. The organic extracts were dried over anhydrous magnesium sulfate, filtered, and then concentrated in vacuo. Flash chromatography (silica, hexane:ethyl acetate=4:1) of the residue gave Reference Example 19 (7.50 g).

MS (EI$^+$) m/z: 363 (M$^+$). HRMS (EI$^+$) for $C_{16}H_{18}BrN_3O_2$ (M$^+$): calcd, 363.0582; found, 363.0582.

REFERENCE EXAMPLE 20

1-Bromo-4-[(1α,5α,6β)-3-t-butoxycarbonyl-6-cyano-3-azabicyclo[3.1.0]hexan-6-yl]-3-fluorobenzene Reference Example 20 (334 mg) was prepared from 4-bromo-2-fluorophenylacetonitrile (214 mg) and cis-N-t-butoxycarbonylpyrrolidine-3,4-cyclic sulfate (292 mg) in the same manner as described for REFERENCE EXAMPLE 19.

MS (FAB$^+$) m/z: 381 (MH$^+$). HRMS (FAB$^+$) for $C_{17}H_{19}BrFN_2O_2$ (MH$^+$): calcd, 381.0614; found, 381.0622.

REFERENCE EXAMPLE 21

5-Bromo-2-chloro-3-fluoropyridine

A suspension of 5-bromo-3-fluoro-2-hydroxypyridine (10.0 g) in phosphoryl chloride (50 mL) was heated at 150° C. for 4 hours. The mixture was poured into ice, the resulting mixture was adjusted to pH 10 by addition of potassium carbonate and extracted with dichloromethane. The organic extracts were dried over anhydrous magnesium sulfate, filtered, and then concentrated in vacuo to give Reference Example 21 (10.9 g).

MS (EI$^+$) m/z: 209 (M$^+$). HRMS (EI$^+$) for $C_5H_2BrClFN$ (M$^+$): calcd, 208.9043; found, 208.9064.

REFERENCE EXAMPLE 22

5-Bromo-3-fluoro-2pyridineacetonitrile

The mixture of 5-bromo-2-chloro-3-fluoropyridine (700 mg) and potassium fluoride (773 mg) in dimethyl sulfoxide (14 mL) was heated at 150° C. for 12 hours. To the resulting mixture was added a solution of sodium anion of t-butyl cyanoacetate [prepared from t-butyl cyanoacetate (1.27 g) and sodium hydride (346 mg) in dimethyl sulfoxide (14 mL)] in dimethyl sulfoxide (14 mL), the mixture was stirred at room temperature for 2.5 days. After dilution of the mixture with saturated ammonium chloride solution, the mixture was extracted with ethyl acetate. The organic extracts were washed with brine, dried over anhydrous magnesium sulfate, filtered, and then concentrated in vacuo. Flash chromatography (silica, hexane:ethyl acetate=5:1) of the residue gave crude t-butyl 5-bromo-3-fluoro-2pyridinecyanoacetate. To a solution of the crude t-butyl 5-bromo-3-fluoro-2pyridinecyanoacetate in acetonitrile (5 mL) was added trifluoroacetic acid (5 mL) at 0° C., the mixture was stirred at room temperature for 2 hours, and poured into ice water and potassium carbonate. The mixture was extracted with ethyl acetate. The organic extracts were washed with brine, dried over anhydrous magnesium sulfate, filtered, and then concentrated in vacuo. Flash chromatography (silica, hexane:ethyl acetate=4:1) of the residue gave Reference Example 22 (179 mg).

MS (EI$^+$) m/z: 214 (M$^+$). HRMS (EI$^+$) for $C_7H_4BrFN_2$ (M$^+$): calcd, 213.9542; found, 213.9558.

REFERENCE EXAMPLE 23

5-Bromo-2-pyrimidineacetonitrile

To a suspension of sodium hydride (3.76 g) in dimethyl sulfoxide (200 mL) was added t-butyl cyanoacetate (13.9 mL) at 10 ° C., the mixture was stirred at room temperature for 1 hour. To the mixture was added 5-bromo-2-chloropyrimidine (7.00 g), the mixture was stirred at room temperature for 2 hours, and poured into ice water and ammonium chloride. The mixture was extracted with ethyl acetate. The organic extracts were dried over anhydrous magnesium sulfate, filtered, and then concentrated in vacuo to give crude t-butyl 5-bromo-2-pyrimidinecyanoacetate. To a suspension of the crude t-butyl 5-bromo-2-pyrimidinecyanoacetate (3.9 g) in dichloromethane (75 mL) was added trifluoroacetic acid (75 mL) at 0° C., the mixture was stirred at room temperature for 18 hours, and concentrated in vacuo. After dilution of the residue with saturated sodium hydrogencarbonate solution, the mixture was extracted with ethyl acetate. The organic extracts were dried over anhydrous magnesium sulfate, filtered, and then concentrated in vacuo. Flash chromatography (silica, hexane:ethyl acetate=2:1) of the residue gave Reference Example 23 (3.71 g).

MS (EI$^+$) m/z: 197 (M$^+$). HRMS (EI$^+$) for $C_6H_4BrN_3$ (M$^+$): calcd, 196.9589; found, 196.9572.

REFERENCE EXAMPLE 24

1-[5(R)-3-(3,5-Difluoro-4-iodophenyl)-2-oxooxazolidin-5-ylmethyl]-4-methyl-1,2,3-triazole To a solution of 5(R)-aminomethyl-3-(3,5-difluoro-4-iodophenyl)oxazolidin-2-one (100 mg) in methanol (2 mL) was added diisopropylethylamine (262 μL) and asym-dichloroacetone tosylhydrazone (108 mg) at 0° C., the mixture was stirred at room temperature for 20 hours, and concentrated in vacuo. Flash chromatography (silica, ethyl acetate) of the residue gave Reference Example 24 (110 mg).

MS (EI$^+$) m/z: 420 (M$^+$). HRMS (EI$^+$) for $C_{13}H_{11}F_2IN_4O_2$ (M$^+$): calcd, 420.9895; found, 420.9904.

REFERENCE EXAMPLE 25 cis-Tetrahydrofuran-3,4-cyclic Sulfate

To a suspension of 1,4-anhydroerythritol (5.00 g) in carbon tetrachloride (48 mL) was added thionyl chloride (4.2 mL), the mixture was heated under reflux for 1 hour. The mixture was cooled to 0° C., and diluted with acetonitrile (48 mL). The mixture was added sodium periodate (15.4 g), ruthenium trichloride n-hydrate (49.8 mg), and then water at 0° C., the mixture stirred at room temperature for 3 hours. After dilution of the mixture with ether, the mixture was washed with water. The organic extracts were washed with water, dried over anhydrous magnesium sulfate, filtered, and then concentrated in vacuo. Flash chromatography (silica, hexane:ethyl acetate=1:1) of the residue gave Reference Example 25 (6.70 g).

MS (CI$^+$) m/z: 167 (MH$^+$). HRMS (CI$^+$) for C$_4$H$_7$O$_5$S (MH$^+$): calcd, 167.0014; found, 166.9993.

REFERENCE EXAMPLE 26

5-Bromo-2-[(1α,5α,6β)-6-cyano-3-oxabicyclo[3.1.0]hexan-6-yl]pyridine

Reference Example 26 (187 mg) was prepared from 5-bromo-2-pyridylacetonitrile (197 mg) and cis-tetrahydrofuran-3,4-cyclic sulfate (183 mg) in the same manner as described for REFERENCE EXAMPLE 19.

MS (CI$^+$) m/z: 265 (MH$^+$). HRMS (CI$^+$) for C$_{11}$H$_{10}$BrN$_2$O (MH$^+$): calcd, 264.9976; found, 264.9981.

REFERENCE EXAMPLE 27

6-(5-Bromopyridin-2-yl)-(1α,5α,6β)-3-oxabicyclo[3.1.0]hexane-6-carboxamide

The mixture of 5-bromo-2-[(1α,5α,6β)-6-cyano-3-oxabicyclo[3.1.0]hexan-6-yl]pyridine (4.00 g) and 25% sodium hydroxide solution (66 mL) in ethanol (200 mL) was heated under reflux for 6 hours and concentrated in vacuo. Treatment of the residue with water gave Reference Example 27 (4.20 g).

MS (EI$^+$) m/z: 282 (M$^+$). HRMS (EI$^+$) for C$_{11}$H$_{11}$BrN$_2$O$_2$ (M$^+$): calcd, 282.0004; found, 281.9966.

REFERENCE EXAMPLE 28

5-Bromo-2-[(1α,5α,6β)-6-t-butoxycarbonylamino-3-oxabicyclo[3.1.0]hexan-6-yl]pyridine The mixture of 6-(5-bromopyridin-2-yl)-(1α,5α,6β)-3-oxabicyclo[3.1.0]hexane-6-carboxamide (2.50 g) and lead tetraacetate (7.83 g) in t-butanol (125 mL) was heated under reflux for 8 hours. After quenching the reaction by addition of saturated sodium hydrogencarbonate solution, the mixture was diluted with ethyl acetate. After the insoluble materials were filtered off, the filtrate was extracted with ethyl acetate. The organic extracts were washed with brine, dried over anhydrous magnesium sulfate, filtered, and then concentrated in vacuo. Flash chromatography (NH silica, hexane:ethyl acetate=7:3) of the residue gave Reference Example 28 (2.10 g).

MS (FAB$^+$) m/z: 355 (MH$^+$). HRMS (FAB$^+$) for C$_{15}$H$_{20}$BrN$_2$O$_3$ (MH$^+$): calcd, 355.0657; found, 355.0656.

REFERENCE EXAMPLE 29

1-Bromo-4-[(1α,5α,6β)-3-t-butoxycarbonyl-6-cyano-3-azabicyclo[3.1.0]hexan-6-yl]-3,5-difluorobenzene Reference Example 29 (1.06 g) was prepared from 4-bromo-3,5-difluorophenylacetonitrile (1.50 g) and cis-N-t-butoxycarbonylpyrrolidine-3,4-cyclic sulfate (1.89 g) in the same manner as described for Reference Example 19.

MS (FAB$^+$) m/z: 399 (MH$^+$). HRMS (FAB$^+$) for C$_{17}$H$_{18}$BrF$_2$N$_2$O$_2$ (MH$^+$): calcd, 399.0520; found, 399.0522.

REFERENCE EXAMPLE 30

1-Bromo-4-[(1α,5α,6β)-3-t-butoxycarbonyl-6-cyano-3-azabicyclo[3.1.0]hexan-6-yl]benzene Reference Example 30 (809 mg) was prepared from 4-bromophenylacetonitrile (1.00 g) and cis-N-t-butoxycarbonylpyrrolidine-3,4-cyclic sulfate (1.49 g) in the same manner as described for Reference Example 19.

MS (FAB$^+$) m/z: 363 (MH$^+$). HRMS (FAB$^+$) for C$_{17}$H$_{20}$BrN$_2$O$_2$ (MH$^+$): calcd, 363.0708; found, 363.0730.

REFERENCE EXAMPLE 31

5-Bromo-2-[(1α,5α,6β)-6-cyano-3-thiabicyclo[3.1.0]hexan-6-yl]pyridine

Reference Example 31 (5.5 mg) was prepared from 5-bromo-2-pyridylacetonitrile (32.3 mg) and cis-tetrahydrothiophene-3,4-cyclic sulfate (32.9 mg) in the same manner as described for Reference Example 19.

MS (FAB$^+$) m/z: 281 (MH$^+$). HRMS (FAB$^+$) for C$_{11}$H$_{10}$BrN$_2$S (MH$^+$): calcd, 280.9748; found, 280.9743.

REFERENCE EXAMPLE 32 cis-Tetrahydrothiophene-3,4-cyclic sulfate

To a solution of cis-tetrahydrothiophene-3,4-diol (48.8 mg) and triethylamine (22.6 μL) in dichloromethane (2 mL) was added a solution of sulfuryl chloride (48.9 μL) in dichloromethane (0.4 mL) at −78° C., the mixture was stirred at the same temperature for 1.5 hours. After quenching the reaction by addition of ice, the mixture was extracted with ethyl acetate. The organic extracts were washed with brine, dried over anhydrous sodium sulfate, filtered, and then concentrated in vacuo. Flash chromatography (silica, ethyl acetate) of the residue gave Reference Example 32 (14.6 mg).

MS (EI$^+$) m/z: 182 (M$^+$). HRMS (EI$^+$) for C$_4$H$_6$O$_4$S$_2$ (M$^+$): calcd, 182.0582; found, 182.0582.

REFERENCE EXAMPLE 33

Step 1.

5-Bromo-2-[(1α,5α,6β)-6-carboxyl-3-oxabicyclo[3.1.0]hexan-6-yl]pyridine

To a solution of 6-(5-bromopyridin-2-yl)-(1α,5α,6β)-3-oxabicyclo[3.1.0]hexane-6-carboxamide (100 mg) in concentrated sulfuric acid (1.0 mL) and water (0.5 mL) was added sodium nitrite (73.1 mg) at 0° C., the mixture was stirred at room temperature for 30 minutes. After addition of ice water (1.5 mL), the mixture was stirred at room temperature for 30 minutes. The mixture was adjusted to pH 7 by the addition of potassium carbonate at 0° C. The mixture was adjusted to pH 4 by the addition of 5% hydrochloric acid, the mixture was extracted with chloroform. The organic extracts were dried over anhydrous magnesium sulfate, filtered, and then concentrated in vacuo to give 5-bromo-2-[(1α,5α,6β)-6-carboxyl-3-oxabicyclo[3.1.0]hexan-6-yl]pyridine (87.9 mg).

MS (EI$^+$) m/z: 283 (M$^+$). HRMS (EI$^+$) for C$_{11}$H$_{10}$BrNO$_3$ (M$^+$): calcd, 282.9844; found, 282.9874.

Step 2.

5-Bromo-2-[(1α,5α,6β)-6-hydroxymethyl-3-oxabicyclo[3.1.0]hexan-6-yl]pyridine To a solution of 5-bromo-2-[(1α,5α,6β)-6-carboxyl-3-oxabicyclo[3.1.0]hexan-6-yl]pyridine (150 mg) in tetrahydrofuran (5.3 mL) was added a solution of diisobutylalminum hydride in toluene (1.0 M, 1.32 mL) at 0° C., the mixture was stirred at room temperature for 1 hour, and stirred at 60° C. for 1 hour. After quenching the reaction by addition of saturated ammonium chloride solution, the mixture was stirred at room temperature for 30 minutes. The mixture was extracted with ethyl acetate. The organic extracts were dried over anhydrous magnesium sulfate, filtered, and then concentrated in vacuo. Flash chromatography (silica, hexane:ethyl acetate=1:3) of the residue gave 5-bromo-2-[(1α,5α,6β)-6-hydroxymethyl-3-oxabicyclo[3.1.0]hexan-6-yl]pyridine (62.3 mg).

MS (EI$^+$) m/z: 269 (M$^+$). HRMS (EI$^+$) for $C_{11}H_{12}BrNO_2$ (M$^+$): calcd, 269.0051; found, 269.0045.

REFERENCE EXAMPLE 34

4-Bromo-2-[(1α,5α,6β)-6-cyano-3-oxabicyclo[3.1.0]hexan-6-yl]thiophene

Reference Example 34 (104 mg) was prepared from 4-bromo-2-thiopheneacetonitrile (100 mg) and cis-tetrahydrofuran-3,4-cyclic sulfate (90.4 mg) in the same manner as described for Reference Example 26.

MS (EI$^+$) m/z: 269 (M$^+$). HRMS (EI$^+$) for $C_{10}H_8BrNOS$ (M$^+$): calcd, 268.9510; found, 268.9519.

REFERENCE EXAMPLE 35

5-Bromo-2-[(1α,5α,6β)-3-t-butoxycarbonyl-6-(t-butoxycarbonyl)amino-3-azabicyclo[3.1.0]hexan-6-yl]pyridine Step 1.

5-Bromo-2-[(1α,5α,6β)-3-t-butoxycarbonyl-6-carbamoyl-3-azabicyclo[3.1.0]hexan-6-yl]pyridine A mixture of 5-bromo-2-[(1α,5α,6β)-3-t-butoxycarbonyl-6-cyano-3-azabicyclo[3.1.0]hexan-6-yl]pyridine (4.00 g) and 25% sodium hydroxide solution (70 mL) in ethanol (210 mL) was heated under reflux for 8 hours and concentrated in vacuo. Treatment of the residue with ice water gave the compound of Step 1 of Reference Example 35 (3.88 g).

MS (FAB$^+$) m/z: 382 (MH$^+$). HRMS (FAB$^+$) for $C_{16}H_{21}BrN_3O_3$ (MH$^+$): calcd, 382.0766; found, 382.0776.

Step 2.

Reference Example 35 (2.42 g) was prepared from the compound of Step 1 of Reference Example 35 (3.50 g) in the same manner as described for Reference Example 28.

MS (FAB$^+$) m/z: 454 (MH$^+$). HRMS (FAB$^+$) for $C_{20}H_{29}BrN_3O_4$ (MH$^+$): calcd, 454.1341; found, 454.1323.

REFERENCE EXAMPLE 36

5(R)-5-(t-Butyldimethylsilyloxy)methyl-3-[4-[2-[(1α,5α,6β)-6-cyano-3-oxabicyclo[3.1.0]hexan-6-yl]pyridin-5-yl]-3-fluorophenyl]oxazolidin-2-one Reference Example 36 (5.42 g) was prepared from 5(R)-5-(t-butyldimethylsilyloxy)methyl-3-[3-fluoro-4-(4,4,5,5-tetramethyl-1,3,2-dioxaborolyl)phenyl]oxazolidin-2-one (5.00 g) and 5-bromo-2-[(1α,5α,6β)-6-cyano-3-oxabicyclo[3.1.0]hexan-6-yl]pyridine (2.94 g) in the same manner as described for EXAMPLE 1.

MS (FAB$^+$) m/z: 510 (MH$^+$). HRMS (FAB$^+$) for $C_{27}H_{33}FN_3O_4Si$ (MH$^+$): calcd, 510.2224; found, 510.2204.

REFERENCE EXAMPLE 37

5(R)-3-[4-[2-[(1α,5α,6β)-6-Cyano-3-oxabicyclo[3.1.0]hexan-6-yl]-3-fluorophenyl]-5-hydroxymethyloxazolidin-2-one To a solution of 5(R)-5-(t-butyldimethylsilyloxy)methyl-3-[4-[2-[(1α,5α,6β)-6-cyano-3-oxabicyclo[3.1.0]hexan-6-yl]pyridin-5-yl]-3-fluorophenyl]oxazolidin-2-one (4.75 g) in tetrahydrofuran (93 mL) was added a solution of tetrabutylammonium fluoride in tetrahydrofuran (1.0 M, 11.2 mL) at 0° C., the mixture was stirred at room temperature for 1 hour. After quenching the reaction by addition of saturated ammonium chloride solution, the mixture was extracted with ethyl acetate. The organic extracts were washed with brine, dried over anhydrous magnesium sulfate, filtered, and then concentrated in vacuo. Treatment of the residue with ether gave 5(R)-3-[4-[2-[(1α,5α,6β)-6-cyano-3-oxabicyclo[3.1.0]hexan-6-yl]pyridin-5-yl]-3-fluorophenyl]-5-hydroxymethyloxazolidin-2-one (3.07 g).

MS (EI$^+$) m/z: 395 (M$^+$). HRMS (EI$^+$) for $C_{21}H_{18}FN_3O_4$ (M$^+$): calcd, 395.1281; found, 395.1261.

REFERENCE EXAMPLE 38

5(R)-Azidomethyl-3-[4-[2-[(1α,5α,6β)-6-cyano-3-oxabicyclo[3.1.0]hexan-6-yl]pyridin-5-yl]-3-fluorophenyl]oxazolidin-2-one Reference Example 38 (1.72 g) was prepared from 5(R)-3-[4-[2-[(1α,5α,6β)-6-cyano-3-oxabicyclo[3.1.0] hexan-6-yl]pyridin-5-yl]-3-fluorophenyl]-5-hydroxymethyloxazolidin-2-one (1.90 g) in the same manner as described for Reference Example 13.

MS (FAB$^+$) m/z: 421 (MH$^+$). HRMS (FAB$^+$) for $C_{21}H_{18}FN_6O_3$ (MH$^+$): calcd, 421.1424; found, 421.1431.

REFERENCE EXAMPLE 39

5(S)-Aminomethyl-3-[4-[2-[(1α,5α,6β)-6-cyano-3-oxabicyclo[3.1.0]hexan-6-yl]-3-fluorophenyl]oxazolidin-2-one Reference Example 39 (1.40 g) was prepared from 5(R)-azidomethyl-3-[4-[2-[(1α,5α,6β)-6-cyano-3-oxabicyclo[3.1.0]hexan-6-yl]pyridin-5-yl]-3-fluorophenyl]oxazolidin-2-one (1.60 g) in the same manner as described for Reference Example 10.

MS (FAB$^+$) m/z: 395 (MH$^+$). HRMS (FAB$^+$) for $C_{21}H_{20}FN_4O_3$ (MH$^+$): calcd, 395.1519; found, 395.1513.

REFERENCE EXAMPLE 40

5(R)-5-(t-Butyldimethylsilyloxy)methyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one Reference Example 40 (109 mg) was prepared from 5(R)-5-(t-butyldimethylsilyloxy)methyl-3-[3-fluoro-4-(4,4,5,5-tetramethyl-1,3,2-dioxaborolyl)phenyl]oxazolidin-2-one (100 mg) and 5-bromo-2-[(1α,5α,6β)-3-t-butoxycarbonyl-6-cyano-3-azabicyclo[3.1.0]hexan-6-yl]pyridine (80.9 mg) in the same manner as described for EXAMPLE 1.

MS (FAB$^+$) m/z: 609 (MH$^+$). HRMS (FAB$^+$) for $C_{32}H_{42}FN_4O_5Si$ (MH$^+$): calcd, 609.2909; found, 609.2886.

REFERENCE EXAMPLE 41

5(R)-3-[4-[2-[(1α,5α,6β)-3-t-Butoxycarbonyl-6-cyano-3-azabicyclo[3.1.0]hexan-6-yl]-3-fluorophenyl]-5-hydroxymethyloxazolidin-2-one Reference Example 41 (3.21 g) was prepared from 5(R)-5-(t-butyldimethylsilyloxy)methyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one (4.24 g) in the same manner as described for Reference Example 36.

MS (FAB$^+$) m/z: 495 (MH$^+$). HRMS (FAB$^+$) for $C_{26}H_{28}FN_4O_5$ (MH$^+$): calcd, 495.2044; found, 495.2048.

REFERENCE EXAMPLE 42

5(R)-Azidomethyl-3-[4-[2-[(1α,5α,6β)-3-t-butoxycarbonyl-6-cyano-3-azabicyclo[3.1.0]hexan-6-yl]-3-fluorophenyl]oxazolidin-2-one Reference Example 42 (1.88 g) was prepared from 5(R)-3-[4-[2-[(1α,5α,6β)-3-t-butoxycarbonyl-6-cyano-3-azabicyclo[3.1.0]hexan-6-yl]-3-fluorophenyl]-5-hydroxymethyloxazolidin-2-one (2.00 g) in the same manner as described for Reference Example 13.

MS (FAB$^+$) m/z: 520 (MH$^+$). HRMS (FAB$^+$) for $C_{26}H_{27}FN_7O_4$ (MH$^+$): calcd, 520.2109; found, 520.2137.

REFERENCE EXAMPLE 43

5(S)-Aminomethyl-3-[4-[2-[(1α,5α,6β)-3-t-butoxycarbonyl-6-cyano-3-azabicyclo[3.1.0]hexan-6-yl]pyridin-5-yl]-3-fluorophenyl]oxazolidin-2-one Reference Example 43 (48.0 mg) was prepared from 5(R)-azidomethyl-3-[4-[2-[(1α,5α,6β)-3-t-butoxycarbonyl-6-cyano-3-azabicyclo[3.1.0]hexan-6-yl]-3-fluorophenyl]oxazolidin-2-one (100 mg) in the same manner as described for Reference Example 10.

MS (FAB$^+$) m/z: 494 (MH$^+$). HRMS (FAB$^+$) for $C_{26}H_{29}FN_5O_4$ (MH$^+$): calcd, 494.2204; found, 494.2197.

REFERENCE EXAMPLE 44

5-Bromo-2-(4-cyanotetrahydropyran-4-yl)pyridine

A mixture of 5-bromo-2pyridineacetonitrile (400 mg), triethylbenzylammonium chloride (462 mg), bis(2-bromoethyl)ether (281 μL), and 50% sodium hydroxide solution (10 mL) was stirred at 70° C. for 1 hour. After decantation of aqueous layer, the residue was diluted with saturated ammonium chloride solution and extracted with ethyl acetate. The organic extracts were dried over anhydrous magnesium sulfate, filtered, and then concentrated in vacuo. Flash chromatography (silica, hexane:ethyl acetate=7:3) of the residue gave 5-bromo-2-(4-cyanotetrahydropyran-4-yl)pyridine (104 mg).

MS (EI$^+$) m/z: 266 (M$^+$). HRMS (EI$^+$) for $C_{11}H_{11}BrN_2O$ (M$^+$): calcd, 266.0055; found, 266.0038.

REFERENCE EXAMPLE 45

5(R)-3-[4-[2-[(1α,5α,6β)-3-t-Butoxycarbonyl-6-cyano-3-azabicyclo[3.1.0]hexan-6-yl]-3,5-difluorophenyl]-5-hydroxymethyloxazolidin-2-one Reference Example 45 (105 mg) was prepared from 5(R)-3-(3,5-difluoro-4-iodophenyl)-5-hydroxymethyloxazolidin-2-one (813 mg) and 5-bromo-2-[(1α,5α,6β)-6-cyano-3-oxabicyclo[3.1.0]hexan-6-yl]pyridine (1.00 g) in the same manner as described for Reference Example 31.

MS (FAB$^+$) m/z: 513 (MH$^+$). HRMS (FAB$^+$) for $C_{26}H_{27}F_2N_4O_5$ (MH$^+$): calcd, 513.1950; found, 513.1978.

REFERENCE EXAMPLE 46

5(R)-3-(3,5-Difluoro-4-iodophenyl)-5-hydroxymethyloxazolidin-2-one

Reference Example 46 (1.91 g) was prepared from 5(R)-3-(3,5-difluorophenyl)-5-hydroxymethyloxazolidin-2-one (2.00 g) in the same manner as described for Reference Example 13.

MS (EI$^+$) m/z: 354 (M$^+$). HRMS (EI$^+$) for $C_{10}H_8F_2INO_3$ (M$^+$): calcd, 354.9517; found, 354.9522.

REFERENCE EXAMPLE 47

5(R)-Azidomethyl-3-(3,5-difluoro-4-iodophenyl)oxazolidin-2-one

Reference Example 47 (2.44 g) was prepared from 5(R)-3-(3,5-difluoro-4-iodophenyl)-5-hydroxymethyl-oxazolidin-2-one (2.30 g) in the same manner as described for REFERENCE EXAMPLE 13.

MS (FAB$^+$) m/z: 381 (MH$^+$). HRMS (FAB$^+$) for $C_{10}H_8F_2IN_4O_2$ (MH$^+$): calcd, 380.9660; found, 380.9685.

REFERENCE EXAMPLE 48

1-[5(R)-3-(3,5-Difluoro-4-iodophenyl)-2-oxooxazolidin-5-ylmethyl]-1,2,3-triazole Reference Example 48 (876 mg) was prepared from 5(R)-azidomethyl-3-(3,5-difluoro-4-iodophenyl)oxazolidin-2-one (875 mg) in the same manner as described for REFERENCE EXAMPLE 13.

MS (EI$^+$) m/z: 406 (M$^+$). HRMS (EI$^+$) for $C_{12}H_9F_2IN_4O_2$ (M$^+$): calcd, 405.9738; found, 405.9750.

REFERENCE EXAMPLE 49

4-Fluoro-1-[5(R)-3-(3-fluoro-4-iodophenyl)-2-oxooxazolidin-5-ylmethyl]-1,2,3-triazole and 5-Ffluoro-1-[5(R)-3-(3-fluoro-4-iodophenyl)-2-oxooxazolidin-5-ylmethyl]-1,2,3-triazole A mixture of 5(R)-azidomethyl-3-(3-fluoro-4-iodophenyl)oxazolidin-2-one (700 mg) and 1-fluoro-1-ethenyl phenyl sulfoxide (987 mg) was heated at 110° C. for 15 hours. Flash chromatography (silica, toluene:ethyl acetate=2:1) of the residue gave 4-fluoro-1-[5(R)-3-(3-fluoro-4-iodophenyl)-2-oxooxazolidin-5-ylmethyl]-1,2,3-triazole (125 mg) and 5-fluoro-1-[5(R)-3-(3-fluoro-4-iodophenyl)-2-oxooxazolidin-5-ylmethyl]-1,2,3-triazole (258 mg). 4-Fluoro-1-[5(R)-3-(3-fluoro-4-iodophenyl)-2-oxooxazolidin-5-ylmethyl]-1,2,3-triazole:

MS (EI+) m/z: 406 (M+). HRMS (EI+) for $C_{12}H_9F_2IN_4O_2$ (M+): calcd, 405.9738; found, 405.9744. 5-Fluoro-1-[5(R)-3-(3-fluoro-4-iodophenyl)-2-oxooxazolidin-5-ylmethyl]-1,2,3-triazole:

MS (EI+) m/z: 406 (M+). HRMS (EI+) for $C_{12}H_9F_2IN_4O_2$ (M+): calcd, 405.9738; found, 405.9753.

REFERENCE EXAMPLE 50

4-Fluoro-1-[5(R)-3-[3-fluoro-4-(4,4,5,5-tetramethyl-1,3,2-dioxaborolyl)phenyl]-2-oxooxazolidin-5-ylmethyl]-1,2,3-triazole Reference Example 50 (380 mg) was prepared from 4-fluoro-1-[5(R)-3-(3-fluoro-4-iodophenyl)-2-oxooxazolidin-5-ylmethyl]-1,2,3-triazole (430 mg) in the same manner as described for Reference Example 1.

MS (FAB+) m/z: 407 (MH+). HRMS (FAB+) for $C_{18}H_{22}BF_2N_4O_4$ (MH+): calcd, 407.1702; found, 407.1693.

REFERENCE EXAMPLE 51

5-Bromo-2-[(1α,5α,6β)-6-carboxyl-3-thiabicyclo[3.1.0]hexan-6-yl]pyridine

A mixture of 5-bromo-2-[(1α,5α,6β)-6-cyano-3-thiabicyclo[3.1.0]hexan-6-yl]pyridine (1.77 g) and concentrated hydrochloric acid (17 mL) was heated at 80° C. for 70 minutes and concentrated in vacuo. Treatment of the residue with water gave Reference Example 51 (1.81 g).

MS (FAB+) m/z: 299 (MH+). HRMS (FAB+) for $C_{11}H_{10}BrNO_2S$ (MH+): calcd, 298.9616; found, 298.9612.

REFERENCE EXAMPLE 52

5-Bromo-2-[(1α,5α,6β)-6-t-butoxycarbonylamino-3-thiabicyclo[3.1.0]hexan-6-yl]pyridine To a suspension of 5-bromo-2-[(1α,5α,6β)-6-carboxyl-3-thiabicyclo[3.1.0]hexan-6-yl]pyridine (760 mg) in toluene (10 mL) was added diphenylphosphoryl azide (0.60 mL) and triethylamine (0.46 mL) at room temperature, the mixture was stirred at the same temperature for 75 minutes. The mixture was washed with water and brine. The organic extracts were dried over anhydrous magnesium sulfate, filtered, and then concentrated in vacuo. A solution of the residue in t-butanol (5 mL) was stirred at 120° C. for 9.5 hours and concentrated in vacuo. Flash chromatography (silica, hexane:ethyl acetate=9:1) of the residue gave Reference Example 52 (502 mg).

MS (FAB+) m/z: 371 (MH+). HRMS (FAB+) for $C_{15}H_{20}BrN_2O_2S$ (MH+): calcd, 371.0429; found, 371.0407.

REFERENCE EXAMPLE 53

5-Bromo-2-pyridylacetonitrile

Step 1.

t-Butyl (5-Bromo-2(1H)-pyridinylidene)cyanoacetate

To a suspension of NaH (66.4 g, 60% oil dispersion) in dry DMSO (1.5 L) was added t-butyl cyanoacetate (243 mL) at 18-25° C. for 1 hour, the mixture was stirred at room temperature for 2 hours. 2,5-Dibromopyridine (150 g) was added to the resulting mixture, the mixture was stirred at 120° C. for 6.5 hours. After cooling, the mixture was poured into saturated ammonium chloride solution, the resulting precipitates were collected by filtration, washed with water and cooled EtOH to give t-butyl (5-bromo-2(1H)-pyridinylidene)cyanoacetate (166 g).

$^1$H NMR (CDCl$_3$) δ 1.53 (s, 9H), 7.20 (dd, J=9.8, 1.8Hz, 1H), 7.53 (dd, J=9.8, 2.4 Hz, 1H), 7.64 (dd, J=6.1, 1.8 Hz, 1H), 14.15 (brs, 1H).

Step 2.

Reference Example 53—A suspension of the compound Step 1 of Reference Example 53 (120 g) and KSF clay (80 g) in acetonitrile (800 mL) was heated under reflux for 6 hours. After insoluble materials were filtered off, the filtrate was concentrated in vacuo. Flash chromatography (silica, hexane:ethyl acetate=4:1) of the residue gave Reference Example 53 (57.2 g).

MS (EI+) m/z: 197 (M+).

ANTIBACTERIAL ACTIVITY

The pharmaceutically-acceptable compounds of the present invention are useful antibacterial agents having a good spectrum of activity in vitro against standard bacterial strains, which are used to screen for activity against pathogenic bacteria. Notably, the pharmaceutically-acceptable compounds of the present invention show activity against vancomycin-resistant *enterococci, streptococci* including penicillin-resistant *S. pneumoniae*, methicillin-resistant *S. aureus, M catarrhalis*, and *C. pneumoniae*. The antibacterial spectrum and potency of a particular compound may be determined in a standard test system.

The following in vitro results were obtained based on an agar dilution method except for *C. pneumoniae*. The activity is presented as the minimum inhibitory concentration (MIC).

*S. aureus* and *M. catarrhalis* were tested on Mueller-Hinton agar, using an approximate inoculum of $1\times10^4$ cfu/spot an incubation temperature of 35° C. for 24 hours. The MIC was defined as the lowest concentration at which no visible bacterial growth was observed.

*Streptococci* and *enterococci* were tested on Mueller-Hinton agar supplemented with 5% defibrinated horse blood, using an approximate inoculum of $1\times10^4$ cfu/spot an incubation temperature of 35° C. in an atmosphere of 5% $CO_2$ for 24 hours. The MIC was defined as the lowest concentration at which no visible bacterial growth was observed.

*C. pneumoniae* was tested using minimum essential medium supplemented with 10% heat-inactivated fetal bovine serum, 2 mM L-glutamine, 1 mg/ml cycloheximide and non essential amino acid. HeLa 229 cells were inoculated with $10^4$ inclusion-forming units of *C. pneumoniae* strain per mL. Infected cells were incubated with test compounds in complete medium at 35° C. in an atmosphere of 5% $CO_2$ for 72 hours. Cells monolayers were fixed in methanol, stained for chlamydial inclusions with an fluorescein-conjugated anti-*Chlamydia* monoclonal antibody, and were observed with fluorescence microscope. The MIC was defined as the lowest concentration at which no inclusion was observed.

| | MIC (μg/ml) | | | |
|---|---|---|---|---|
| Strains | example 13 | example 15 | example 23 | Linezolid |
| | *Staphylococcus aureus* | | | |
| Smith | 0.125 | 0.25 | 0.06 | 1 |
| CR | 0.5 | 1 | 0.5 | 16 |
| MR | 0.125 | 0.25 | 0.06 | 1 |

-continued

| | MIC (μg/ml) | | | |
|---|---|---|---|---|
| Strains | example 13 | example 15 | example 23 | Linezolid |
| *Staphylococcus pneumoniae* | | | | |
| IID553 | 0.125 | 0.25 | 0.06 | 2 |
| PRQR | 0.06 | 0.25 | 0.06 | 1 |
| *Streptococcus pyogenes* | | | | |
| IID692 | 0.06 | 0.25 | 0.06 | 1 |
| *Enterococcus faecium* | | | | |
| VRQR | 0.125 | 0.5 | 0.06 | 2 |
| *Moraxella catarrhalis* | | | | |
| ATCC25238 | 1 | 4 | 0.5 | 4 |

CR = chloramphenicol resistant
MR = methicillin resistant
PRQR = penicillin resistant, quinolone resistant
VRQR = vancomycin resistant, quinolone resistant
NT = not tested The invention described herein is exemplified by the following non-limiting examples. The compound data is designated in accordance to *General Guidelines for Manuscript Preparation*, J. Org. Chem. Vol. 66, pg. 19A, Issue 1, 2001.

What is claimed is:

1. A compound of formula I:

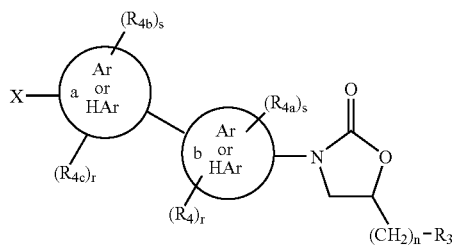

or an enantiomer, diastereomer, pharmaceutically acceptable salt, hydrate or prodrug thereof, wherein:

$R_1$ represents:
  i) hydrogen,
  ii) $(CH_2)_n NR_5 R_6$,
  iii) $CR_7 R_8 R_9$, $C(R)_2 OR_{14}$, $CH_2 NHR_{14}$,
  iv) $C(=O)R_{13}$, $C(=NOH)H$, $C(=NOR_{13})H$, $C(=NOR_{13})R_{13}$, $C(=NOH)R_{13}$, $C(=O)N(R_{13})_2$, $C(=NOH)N(R_{13})_2$, $NHC(=X_1)N(R_{13})_2$, $NRCO_2 R$, $(C=NH)R_7$, $N(R_{13})C(=X_1)N(R_{13})_2$, $COOR_{13}$, $SO_2 R_{14}$, $N(R_{13})SO_2 R_{14}$, $N(R_{13})COR_{14}$,
  v) $(C_{1-6}alkyl)CN$, CN, $CH=C(R)_2$, $(CH_2)_p OH$, $C(=O)CHR_{13}$, $C(=NR_{13})R_{13}$, $NR_{10}C(=X_1)R_{13}$; or
  vi) $C_{5-10}$ heterocycle optionally substituted with 1-3 groups of $R_7$, which may be attached through either a carbon or a heteroatom;

X represents

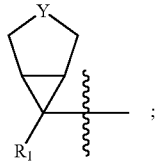

Y represents NR*, O, or S(O)p;

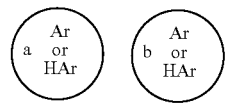

represents aryl or heteroaryl;
$R_3$ represents $NR(C=X_2)R_{12}$, $NR*R_{12}$, $C_{6-10}$ aryl, $-(O)_n C_{5-10}$ heterocyclyl that may be attached through either a carbon or a heteroatom, $C_{5-10}$ heteraryl or a $C_{5-10}$ heteraryl represented by that represents an optionally substituted aromatic heterocyclic heterocyclyl group containing 1 to 4 nitrogen atoms and at least one double bond and that is connected through a bond on any nitrogen; said aryl, heteroayl and heterocyclyl optionally substituted with 1-3 groups of $R_7$;

$R_4$, $R_{4a}$, $R_{4b}$, and $R_{4c}$ independently represent:
  i) hydrogen,
  ii) halogen,
  iii) $C_1$-6 alkoxy, or
  iv) $C_{1-6}$ alkyl;
r and s independently are 1-3, with the provision that when $(R_{4a})_s$, $(R_4)_s$ or $(R_{4b})$ and $(R_{4c})_s$ are attached to an Ar or HAr ring the sum of r and s is less than or equal to 4;

$R_5$ and $R_6$ independently represent:
  i) hydrogen,
  ii) $C_{1-6}$ alkyl optionally substituted with 1-3 groups of halogen, CN, OH, $C_{1-6}$ alkoxy, amino, imino, hydroxyamino, alkoxyamino, $C_{1-6}$ acyloxy, $C_{1-6}$ alkylsulfenyl, $C_{1-6}$ alkylsulfinyl, $C_{1-6}$ alkylsulfonyl, aminosulfonyl, $C_{1-6}$ alkylaminosulfonyl, $C_{1-6}$ dialkylaminosulfonyl, 4-morpholinylsulfonyl, phenyl, pyridine, 5-isoxazolyl, ethylenyloxy, or ethynyl, said phenyl and pyridine optionally substituted with 1-3 halogen, CN, OH, $CF_3$, $C_{1-6}$ alkyl or $C_{1-6}$ alkoxy;
  iii) $C_{1-6}$ acyl optionally substituted with 1-3 groups of halogen, OH, SH, $C_{1-6}$ alkoxy, naphthalenoxy, phenoxy, amino, $C_{1-6}$ acylamino, hydroxylamino, alkoxylamino, $C_{1-6}$ acyloxy, aralkyloxy, phenyl, pyridine, $C_{1-6}$ alkylcarbonyl, $C_{1-6}$ alkylamino, $C_{1-6}$ dialkylamino, $C_{1-6}$ hydroxyacyloxy, $C_{1-6}$ alkylsulfenyl, phthalimido, maleimido, succinimido, said phenoxy, phenyl and pyridine optionally substituted with 1-3 groups of halo, OH, CN, $C_{1-6}$ alkoxy, amino, $C_{1-6}$ acylamino, $CF_3$ or $C_{1-6}$ alkyl;
  iv) $C_{1-6}$ alkylsulfonyl optionally substituted with 1-3 groups of halogen, OH, $C_{1-6}$ alkoxy, amino, hydroxylamino, alkoxylamino, $C_{1-6}$ acyloxy, or phenyl; said phenyl optionally substituted with 1-3 groups of halo, OH, $C_{1-6}$ alkoxy, amino, $C_{1-6}$ acylamino, $CF_3$ or $C_{1-6}$ alkyl;

v) arylsulfonyl optionally substituted with 1-3 of halogen, $C_{1-6}$ alkoxy, OH or $C_{1-6}$ alkyl;

vi) $C_{1-6}$ alkoxycarbonyl optionally substituted with 1-3 of halogen, OH, $C_{1-6}$ alkoxy, $C_{1-6}$ acyloxy, or phenyl, said phenyl optionally substituted with 1-3 groups of halo, OH, $C_{1-6}$ alkoxy, amino, $C_{1-6}$ acylamino, $CF_3$ or $C_{1-6}$ alkyl;

vii) aminocarbonyl, $C_{1-6}$ alkylaminocarbonyl or $C_{1-6}$ dialkylaminocarbonyl, said alkyl groups optionally substituted with 1-3 groups of halogen, OH, $C_{1-6}$ alkoxy or phenyl viii) five to six-membered heterocycles optionally substituted with 1-3 groups of halogen, OH, CN, amino, $C_{1-6}$ acylamino, $C_{1-6}$ alkylsulfonylamino, $C_{1-6}$ alkoxycarbonylamino, $C_{1-6}$ alkoxy, $C_{1-6}$ acyloxy or $C_{1-6}$ alkyl, said alkyl optionally substituted with 1-3 groups of halogen, or $C_{1-6}$ alkoxy;

ix) $C_{3-6}$ cycloalkylcarbonyl optionally substituted with 1-3 groups of halogen, OH, $C_{1-6}$ alkoxy or CN;

x) benzoyl optionally substituted with 1-3 groups of halogen, OH, $C_{1-6}$ alkoxy, $C_{1-6}$ alkyl, $CF_3$, $C_{1-6}$ alkanoyl, amino or $C_{1-6}$ acylamino;

xi) pyrrolylcarbonyl optionally substituted with 1-3 groups of $C_{1-6}$ alkyl;

xii) $C_{1-2}$ acyloxyacetyl where the acyl is optionally substituted with amino, $C_{1-6}$ alkylamino, $C_{1-6}$ dialkylaniino, 4-morpholino, 4-aniinophenyl, 4-(dialkylamino)phenyl, 4-(glycylamino)phenyl; or $R_5$ and $R_6$ taken together with any intervening atoms can form a 3- to 7-membered heterocyclic ring containing carbon atoms and 1-2 heteroatoms independently chosen from O, S, SO, $SO_2$, N, or $NR_8$;

$R_7$ represents:

i) hydrogen, halogen, $(CH_2)pC_{5-10}$ heterocyclyl, CN, $CO_2R$, $CON(R)_2$, CHO, $(CH_2)_{0-3}NHAc$, $C(=NOR)$, OH, $C_{1-6}$ alkoxy, $C_{1-6}$ alkyl, alkenyl, hydroxy $C_{1-6}$ alkyl, $(CH_2)_{1-3}NHC(O)C_{1-6}$ alkyl, $(CH_2)_{0-3}N(C_{1-6}$ alkyl$)_2$, $NHCO2R$, —$OCOC_{1-6}$ alkyl;

ii) $(CH_2)_n$amino, $(CH_2)_nC1-6$ alkylamino, $C_{1-6}$ acylamino, $C_{1-6}$ dialkylamino, hydroxylamino or $C_{1-2}$ alkoxyamino, all of which can be optionally substituted on the nitrogen with $C_{1-6}$ acyl, $C_{1-6}$ alkylsulfonyl or $C_{1-6}$ alkoxycarbonyl, said acyl and alkylsulfonyl optionally substituted with 1-2 of halogen or OH;

$R_8$ and $R_9$ independently represents:

i) H, CN, ii) $C_{1-6}$ alkyl optionally substituted with 1-3 halogen, CN, OH, $C_{1-6}$ alkoxy, $C_{1-6}$ acyloxy, or ammo, iii) phenyl optionally substituted with 1-3 groups of halogen, OH, $C_{1-6}$ alkoxy; or $R_7$ and $R_8$ taken together can form a 3-to 7 - membered carbon ring optionally interrupted with 1-2 heteroatoms chosen from O, S, SO, $SO_2$, NH, and $NR_8$;

$X_1$ represents O, S or $NR_{13}$, NCN, $NCO_2R_{16}$, or $NSO_2R_{14}$;

$X_2$ represents O, S, NH or $NSO_2R_{14}$;

$R_{10}$ represents hydrogen, $C_{1-6}$ alkyl or $CO_2R_{15}$;

$R_{12}$ represents hydrogen, $C_{1-6}$ alkyl, $NH_2$, OR, $CHF_2$, $CHCl_2$, $C(R)_2Cl$, $(CH_2)_nSR$, $(CH_2)_nN$, $(CH_2)_nSO_2R$, $(CH_2)_nS(O)R$, $C_{1-6}$ alkylamino, $C_{3-6}$ cycloalkyl, $C_{5-10}$ heterocyclyl or $C_{1-6}$ dialkylamino, where said alkyl, and cycloalkyl may be substituted with 1-3 groups of halo, CN, OH or $C_{1-6}$ alkoxy, said heterocyclyl optionally substituted with 1-3 groups of $R_7$;

each $R_{13}$ represents independently hydrogen, $C_{1-6}$ alkyl, $C_{6-10}$ aryl, $NR_5R_6$, $SR_8$, $S(O)R_8$, $S(O)_2 R_8$, CN, OH, $C_{1-6}$ alkylS(O)R, $C_{1-6}$ alkoxycarbonyl, hydroxycarbonyl, —OCOaryl, $C_{1-6}$ acyl, $C_{3-7}$ -membered carbon ring optionally interrupted with 1-4 heteroatoms chosen from O, S, SO, $SO_2$, NH and $NR_8$, where said $C_{1-6}$ alkyl, aryl or $C_{1-6}$ acyl groups may be independently substituted with 0-3 groups halogens, hydroxy, $N(R)_2$, $CO_2R$, $C_{6-10}$ aryl, $C_{5-10}$ heteroaryl, or $C_{1-6}$ alkoxy groups;

when two $R_{13}$ groups are attached to the same atom or two adjacent atoms they may be taken together to form a 3-to7-membered carbon ring optionally interrupted with 1-2 heteroatoms chosen from O, S, SO, $SO_2$, NH, and $NR_8$;

R represents hydrogen or $C_{1-6}$ alkyl;

R* represents hydrogen, CN, $C(=O)R_{14}$, $(CH_2)_pCO_2C_{1-6}$ alkyl, $(CH_2)_pC_{5-10}$ heterocyclyl, or $C_{1-6}$ alkyl, said alkyl and heterocyclyl optionally substituted with 1 to 3 groups of $R_7$;

$R_{14}$ represents amino, $C_{1-6}$ alkyl, $C_{3-6}$ cycloalkyl, $(CH_2)_p C_{5-10}$ heterocyclyl, $C_{1-6}$ haloalkyl, phenyl, said alkyl, cycloalkyl, phenyl, heterocyclyl optionally substituted with 1 to 3 groups of $R_7$, when $R_7$ is an amino or hydroxyl group or a nitrogen that forms part of the heterocycle, said amino and hydroxy optionally protected with an amino or hydroxy protecting group;

$R_{15}$ is $C_{1-6}$ alkyl or benzyl said benzyl optionally substituted with 1-3 groups of halo, OH, $C_{1-6}$ alkoxy, amino, $C_{1-6}$ acylamino, or $C_{1-6}$ alkyl;

$R_{16}$ is hydrogen, $C_{5-10}$ heteroaryl, $C_{6-10}$aryl, said heteroaryl and aryl optionally substituted with 1-3 groups of $R_7$;

p represents 0-2 and n represents 0-1.

2. The compound according to claim 1 wherein Ar and HAr of

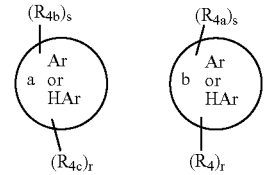

independently are phenyl, pyridyl, pyrimidinyl, or piperidinyl, and r+s for a nd b combined $\leq 3$.

3. The compound according to claim 2 wherein X is

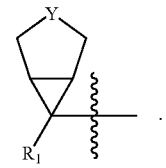

4. The compound according to claim 3 wherein Y is NR* and $R_1$ is H, $NR_5R_6$, CN, OH, or $CR_7R_8R_9$.

5. The compound according to claim 4 wherein $R_1$ is $NR_5R_6$, or CN.

6. The compound according to claim 5 wherein $R_3$ is $C_{5-10}$ heteroaryl, said heteroaryl optionally substituted with 1-3 groups of $R_7$.

7. The compound according to claim 1 of the structural formula IV:

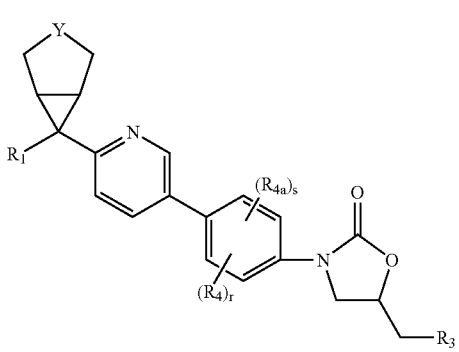

Formula IV wherein $R_4$, $R_{4a}$, are as described and $R_3$ and (N)

independently are 1,2,3-triazole, 1,2,4-triazole, 1,2,5-triazole, tetrazole, pyrazole or imidazole, any of which may contain 1 to 3 substitutents selected from $R_7$.

8. A compound which is:

1-[5(R)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]-1,2,3-triazole, 1-[5(R)-3-[4-[2-[(1α,5α,6β)-6-cyano-3-azabicyclo[3.1.0]hexan-6-yl]pyridin-5-yl]phenyl]-2-oxooxazolidin-5-ylmethyl]-1,2,3-triazole hydrochloride, 1-[5(R)-3-[4-[4-[(1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3-fluorophenyl]phenyl]-2-oxooxazolidin-5-ylmethyl]-1,2,3-triazole hydrochloride, 1-[5(R)-3-[4-[4-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3-fluorophenyl]-3-fluorophenyl]-2-oxooxazolidin-5-ylmethyl]-1,2,3-triazole hydrochloride, 1-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,3-triazole hydrochloride, N-[5(S)-3-[4-[4-[((1α,5α,6β)-3-t-butoxycarbonyl-6-cyano-3-azabicyclo[3.1.0]hexan-6-yl]-3-fluorophenyl]phenyl]-2-oxooxazolidin-5-ylmethyl]acetamide, N-[5(S)-3-[4-[4-[(1α,5α,6β)-6-cyano-3-azabicyclo[3.1.0]hexan-6-yl]-3-fluorophenyl]phenyl]-2-oxooxazolidin-5-ylmethyl]acetamide hydrochloride, N-[5(S)-3-[4-[2-[(1α,5α,6β)-3-t-butoxycarbonyl-6-cyano-3-azabicyclo[3.1.0]hexan-6-yl]pyridin-5-yl]phenyl]-2-oxooxazolidin-5-ylmethyl]acetamide, N-[5(S)-3-[4-[2-[(1α,5α,6β)-6-cyano-3-azabicyclo[3.1.0]hexan-6-yl]pyridin-5-yl]phenyl]-2-oxooxazolidin-5-ylmethyl]acetamide hydrochloride, N-[5(S)-3-[4-[4-[(1α,5α,6β)-3-t-butoxycarbonyl-6-cyano-3-azabicyclo[3.1.0]hexan-6-yl]-3-fluorophenyl]-3-fluorophenyl]-2-oxooxazolidin-5-ylmethyl]acetamide, N-[5(S)-3-[4-[2-[(1α,5α,6β)-6-cyano-3-azabicyclo[3.1.0]hexan-6-yl]-3-fluorophenyl]-3-fluorophenyl]-2-oxooxazolidin-5-ylmethyl]acetamide hydrochloride, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]acetamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]acetamide hydrochloride, N-[5(S)-3-[4-[2-[(1α,5α,6β)-6-t-butoxycarbonylamino-3-oxabicyclo[3.1.0]hexan-6-yl]pyridin-5-yl]-3-fluorophenyl]-2-oxooxazolidin-5-ylmethyl]acetamide, N-[5(S)-3-[4-[2-[(1α,5α,6β)-6-amino-3-oxabicyclo[3.1.0]hexan-6-yl]pyridin-5-yl]-3-fluorophenyl]-2-oxooxazolidin-5-ylmethyl]acetamide, 1-[5(R)-3-[4-[2-[(1α,5α,6β)-6-t-butoxycarbonylamino-3-oxabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-amino-3-oxabicyclo[3.1.0]hexan-6-yl]pyridin-5-yl]-3-fluorophenyl]-2-oxooxazolidin-5-ylmethyl]-1,2,3-triazole, N-[5(S)-3-[4-[4-[(1α,5α,6β)-6-cyano-3-oxabicyclo[3.1.0]hexan-6-yl]pyridin-5-yl]-3-fluorophenyl]-2-oxooxazolidin-5-ylmethyl]acetamide, 1-[5(R)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]-1,2,3-triazole, N-[5(S)-3-[4-[2-[(1α,5α,6β)-6-t-butoxycarbonylamino-3-oxabicyclo[3.1.0]hexan-6-yl]pyridin-5-yl]phenyl]-2-oxooxazolidin-5-ylmethyl]acetamide, N-[5(S)-3-[4-[2-[(1α,5α,6β)-6-amino-3-oxabicyclo[3.1.0]hexan-6-yl]pyridin-5-yl]phenyl]-2-oxooxazolidin-5-ylmethyl]acetamide, 1-[5(R)-3-[4-[2-[(1α,5α,6β)-6-t-butoxycarbonylamino-3-oxabicyclo[3.1.0]hexan-6-yl]pyridin-5-yl]phenyl]-2-oxooxazolidin-5-ylmethyl]-1,2,3-triazole, 1-[5(R)-3-[4-[2-[(1α,5α,6β)-6-amino-3-oxabicyclo[3.1.0]hexan-6-yl]pyridin-5-yl]phenyl]-2-oxooxazolidin-5-ylmethyl]-1,2,3-triazole, N-[5(S)-3-[4-[4-[(1α,5α,6β)-6-cyano-3-oxabicyclo[3.1.0]hexan-6-yl]pyridin-5-yl]phenyl]-2-oxooxazolidin-5-ylmethyl]acetamide, 1-[5(R)-3-[4-[2-[(1α,5α,6β)-6-cyano-3-oxabicyclo[3.1.0]hexan-6-yl]pyridin-5-yl]phenyl]-2-oxooxazolidin-5-ylmethyl]-1,2,3-triazole, 1-[5(R)-3-[4-[4-[(1α,5α,6β)-3-t-butoxycarbonyl-6-cyano-3-azabicyclo[3.1.0]hexan-6-yl]-3,5-difluorophenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3,5-difluorophenyl]-3-fluorophenyl]-2-oxooxazolidin-5-ylmethyl]-1,2,3-triazole, N-[5(S)-3-[4-[4-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]acetamide, N-[5(S)-3-[4-[4-[(1α,5α,6β)-6-cyano-3-azabicyclo[3.1.0]hexan-6-yl]pyridin-5-yl]-3,5-difluorophenyl]-2-oxooxazolidin-5-ylmethyl]acetamide hydrochloride, N-[5(S)-3-[4-[4-[(1α,5α,6β)-3-t-butoxycarbonyl-6-cyano-3-azabicyclo[3.1.0]hexan-6-yl]-3,5-difluorophenyl]-3-fluorophenyl]-2-oxooxazolidin-5-ylmethyl]acetamide, N-[5(S)-3-[4-[4-[(1α,5α,6β)-6-cyano-3-azabicyclo[3.1.0]hexan-6-yl]-3,5-difluorophenyl]-3-fluorophenyl]-2-oxooxazolidin-5-ylmethyl]acetamide hydrochloride, N-[5(S)-3-[4-[4-[(1α,5α,6β)-3-t-butoxycarbonyl-6-cyano-3-azabicyclo[3.1.0]hexan-6-yl]phenyl]-3-fluorophenyl]-2-oxooxazolidin-5-ylmethyl]acetamide, N-[5(S)-3-[4-[4-[(1α,5α,6β)-6-cyano-3-azabicyclo[3.1.0]hexan-6-yl]phenyl]-3-fluorophenyl]-2-oxooxazolidin-5-ylmethyl]acetamide, N-[5(S)-3-[4-[4-[(1α,5α,6β)-3-t-butoxycarbonyl-6-cyano-3-azabicyclo[3.1.0]hexan-6-yl]-3-fluorophenyl]-3,5-difluorophenyl]-2-oxooxazolidin-5-ylmethyl]acetamide, N-[5(S)-3-[4-[4-[(1α,5α,6β)-6-cyano-3-azabicyclo[3.1.0]hexan-6-yl]-3-fluorophenyl]-3,5-difluorophenyl]-2-oxooxazolidin-5-ylmethyl]acetamide, 1-[5(R)-3-[4-[4-[(1α,5α,6β)-3-t-butoxycarbonyl-6-cyano-3-azabicyclo[3.1.0]hexan-6-yl]-3-fluorophenyl]-3,5-difluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3-fluorophenyl]-3,5-difluorophenyl]-2-oxooxazolidin-5-ylmethyl]-1,2,3-triazole hydrochloride, 1-[5(R)-3-[4-[4-[(1α,5α,6β)-3-t-butoxycarbonyl-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[4-[(1α,5α,6β)-3-t-butoxycarbonyl-6-cyano-3-azabicyclo[3.1.0]hexan-6-yl]phenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]phenyl]-3-fluorophenyl]-2-oxooxazolidin-5-ylmethyl]-1,2,3-triazole, 1-[5(R)-3-[4-[2-[(1α,5α,6β)-6-t-butoxycarbonylamino-3-oxabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-amino-3-oxabicyclo[3.1.0]hexan-6-yl]pyridin-5-yl]-3,5-difluorophenyl]-2-oxooxazolidin-5-ylmethyl]-1,2,3-triazole, N-[5(S)-3-[4-[2-[(1α,5α,6β)-6-t-butoxycarbonylamino-3-oxabicyclo[3.1.0]hexan-6-yl]pyridin-5-yl]-3,5-difluorophenyl]-2-oxooxazolidin-5-ylmethyl]acetamide, N-[5(S)-3-[4-[2-[(1α,5α,6β)-6-amino-3-oxabicyclo[3.1.0]hexan-6-yl]pyridin-5-yl]-3,5-difluorophenyl]-2-oxooxazolidin-5-ylmethyl]acetamide, N-[5(S)-3-[4-[2-[(1α,5α,6β)-6-cyano-3-oxabicyclo[3.1.0]hexan-6-yl]pyridin-5-yl]-3,5-difluorophenyl]-2-oxooxazolidin-5-ylmethyl]acetamide, 1-[5(R)-3-[4-[2-[(1α,5α,6β)-6-cyano-3-oxabicyclo[3.1.0]hexan-6-yl]pyridin-5-yl]-3,5-difluorophenyl]-2-oxooxazolidin-5-ylmethyl]-1,2,3-triazole, N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide, N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide S-oxide, N-[5(S)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]acetamide S,S-dioxide, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-cyano-3-thiabicyclo[3.1.0]hexan-6-yl]pyridin-5-yl]-3-fluorophenyl]-2-oxooxazolidin-5-ylmethyl]-1,2,3-triazole S,S-dioxide, 4-[5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-1,2,4-triazole, 4-[5(R)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-1,2,4-triazole, 5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-5-[(isoxazol-3-yl)oxy]methyloxazolidin-2-one, 5(R)-3-[4-[2-[(1α,5α,6β)-6-cyano-3-azabicyclo[3.1.0]hexan-6-yl]pyridin-5-yl]-3-fluorophenyl]-5-[(isoxazol-3-yl)oxy]methyloxazolidin-2-one, 5(R)-3-[4-[2-[(1α,5α,6β)-3-t-butoxycarbonyl-6-cyano-3-azabicyclo[3.1.0]hexan-6-yl]pyridin-5-yl]-3-fluorophenyl]-5-[N-(t-butoxycarbonyl)-N-(isoxazol-3-yl)]aminomethyloxazolidin-2-one, 5(R)-3-[4-[2-[(1α,5α,6β)-6-cyano-3-azabicyclo[3.1.0]hexan-6-yl]pyridin-5-yl]-3-fluorophenyl]-5-[N-(isoxazol-3-yl)]aminomethyloxazolidin-2-one, 5(R)-3-[4-[2-[(1α,5α,6β)-6-cyano-3-oxabicyclo[3.1.0]hexan-6-yl]pyridin-5-yl]-3-fluorophenyl]-5-[(isoxazol-3-yl)oxy]methyloxazolidin-2-one, 5(R)-5-[N-(t-butoxycarbonyl)-N-(isoxazol-3-yl)]aminomethyl-3-[4-[2-[(1α,5α,6β)-6-cyano-3-oxabicyclo[3.1.0]hexan-6-yl]pyridin-5-yl]-3-fluorophenylloxazolidin-2-one, 5(R)-3-[4-[2-[(1α,5α,6β)-6-cyano-3-oxabicyclo[3.1.0]hexan-6-yl]pyridin-5-yl]-3-fluorophenyl]-5-[N-(isoxazol-3-yl)]aminomethyloxazolidin-2-one, N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]propionamide, N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]difluoroacetamide, N-[5(S)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]propionamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]propionamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]difluoroacetamide,
N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]difluoroacetamide,
1-[5(R)-3-[4-[2-[(1α,5α,6β)-6-cyano-3-methyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3,6-dicyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[(1-t-butoxycarbonylaminocyclopropan-1-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[(1-aminocyclopropan-1-yl)carbonyl]-6-cyano-3-azabicyclo[3.1.0]hexan-6-yl]pyridin-5-y]-3-fluorophenyl]-2-oxooxazolidin-5-ylmethyl]-1,2,3-triazole,
1-[5(R)-3-[4-[2-[(1α,5α,6β)-6-cyano-3-[2-(phthalimid-2-yl)ethyl]-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-(2-aminoethyl)-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-[2-(1,2,4-triazol-4-yl)ethyl]-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-bromoacetyl-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(morpfiolin-4-yl)acetyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(5-cyanopyridin-2-yl)-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(1,3-dihydroxypropan-2-yl)-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-[((2S)-pyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[((2S,4R)-1-t-butoxycabonyl-4-hydroxypyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-[((2S,4R)-4-hydroxypyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-[((2S,4S)-4-fluoropyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[4-[(1α,5α,6β)-3-t-butoxycarbonyl-6-(t-butoxycarbonyl)amino-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[4-[(1α,5α,6β)-6-amino-3-azabicyclo[3.1.0]hexan-6-yl]pyridin-5-yl]-3-fluorophenyl]-2-oxooxazolidin-5-ylmethyl]-1,2,3-triazole dihydrochloride,
1-[5(R)-3-[4-[2-[(1α,5α,6β)-3-acetoxyacetyl-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-hydroxyacetyl-3-azabicyclo[3.1.0]hexan-6-yl]pyridin-5-yl]-3-fluorophenyl]-2-oxooxazolidin-5-ylmethyl]-1,2,3-triazole,
N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide,
N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-dichlorocyclopropane)-1-carboxamide,
N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide,
N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide,
N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]-(2,2-difluorocyclopropane)-1-carboxamide,
O-methyl-N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]carbamate,
O-methyl-N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]carbamate,
1-[5(R)-3-[4-[2-[(1α,5α,6β)-3,6-dicyano-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-cyano-3-methyl-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[3-fluoro-4-[2-[(1α,5α,6β)-6-hydroxymethyl-3-oxabicyclo[3.1.0]hexan-6-yl]pyridin-5-yl]phenyl]-2-oxooxazolidin-5-ylmethyl]-1,2,3-triazole,
1-[5(R)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]-4-fluoro-1,2,3-triazole,
1-[5(R)-3-[4-[4-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[4-[(1α,5α,6β)-6-cyano-3-azabicyclo[3.1.0]hexan-6-yl]-3-fluorophenyl]-2-oxooxazolidin-5-ylmethyl]-4-fluoro-1,2,3-triazole,
1-[5(R)-3-[4-[4-[(1α,5α,6β)-6-t-butoxycarbonyl-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole,
1-[5(R)-3-[4-[4-[(1α,5α,6β)-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole,
1-[5(R)-3-[4-[2-[(1α,5α,6β)-3-(4-t-butoxycarbonylpiperazin-1-yl)acetyl-6-cyano-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(piperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole dihydrochloride,
1-[5(R)-3-[4-[2-[(1α,5α,6β)-6-cyano-3-oxabicyclo[3.1.0]hexan-6-yl]thiophen-4-yl]-3-fluorophenyl]-2-oxooxazolidin-5-ylmethyl]-1,2,3-triazole,
1-[5(R)-3-[4-[2-[(1α,5α,6β)-6-cyano-3-(piperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(pyrrolidin-1-yl)acetyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-(4-dimethylaminopiperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-cyano-3-[((2S)-pyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-cyano-3-[((2S,4R)-4-hydroxypyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole hydrochloride,
1-[5(R)-3-[4-[2-[(1α,5α,6β)-3-[((2S,4R)-1-t-butoxycabonyl-4-hydroxypyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-cyano-3-[((2S,4S)-4-fluoropyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-amino-3-thiabicyclo[3.1.0]hexan-6-yl]pyridin-5-yl]-3-flouorophenyl]-2-oxooxazolidin-5-ylmethyl]-1,2,3-triazole,
1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole S-oxide,
1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole S-oxide,
1-[5(R)-3-[4-[2-[(1α,5α,6β)-6-t-butoxycarbonyl-3-thiabicyclo[3.1.0]hexan-6-yl]pyridin-5-yl]-3-fluorophenyl]-2-oxooxazolidin-5-ylmethyl]-1,2,3-triazole S,S-dioxide,
1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole S,S-dioxide,
1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-amino-3-thiabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole S-oxide,
1-[5(R)-3-[4-[2-[(1α,5α,6β)-6-amino-3-thiabicyclo[3.1.0]hexan-6-yl]-3,5-difluorophenyl]-2-oxooxazolidin-5-ylmethyl]-1,2,3-triazole S-oxide,
1-[5(R)-3-[4-[2-[(1α,5α,6β)-6-t-butoxycarbonylamino-3-thiabicyclo[3.1.0]hexan-6-yl]pyridin-5-yl]-3,5-difluorophenyl]-2-oxooxazolidin-5-ylmethyl]-1,2,3-triazole S,S-dioxide,
1-[5(R)-3-[4-[2-[(1α,5α,6β)-6-amino-3-thiabicyclo[3.1.0]hexan-6-yl]pyridin-5-yl]-3,5-difluorophenyl]-2-oxooxazolidin-5-ylmethyl]-1,2,3-triazole S,S-dioxide,
5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[(isoxazol-3-yl)oxy]methyloxazolidin-2-one,
5(R)-3-[4-[2-[(1α,5α,6β)-6-cyano-3-azabicyclo[3.1.0]hexan-6-yl]pyridin-5-yl]-3,5-diflourophenyl]-5-[(isoxazol-3-yl)oxy]methyloxazolidin-2-one,
1-[5(R)-3-[4-[2-[(1α,5α,6β)-6-cyano-3-(4-methylpiperazin-6-yl)acetyl-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole,
1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole S-oxide,
1-[5(R)-3-[4-[2-[(1α,5α,6β)-6-cyano-3-thiabicyclo[3.1.0]hexan-6-yl]pyridin-5-yl]phenyl]-2-oxooxazolidin-5-ylmethyl]-1,2,3-triazole S,S-dioxide,
1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole,
1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole S-oxide,
1-[5(R)-3-[4-[2-[(1α,5α,6β)-6-cyano-3-thiabicyclo[3.1.0]hexan-6-yl]pyridin-5-yl]-3,5-difluorophenyl]-2-oxooxazolidin-5-ylmethyl]-1,2,3-triazole S,S-dioxide,
1-[5(R)-3-[4-[2-[(1α,5α,6β)-6-cyano-3-(1,3-diacetoxypropan-2-yl)-3-azabicyclo[3.1.0]hexan-6-yl]pyridin-5-yl]-3-fluorophenyl]-2-oxooxazolidin-5-ylmethyl]-1,2,3-triazole,
1-[5(R)-3-[4-[2-[(1α,5α,6β)-3-[(3R,4S)-1-azabicyclo[2.2.1]hepan-3-yl]carbonyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(pyridin-2-yl)-3-azabicyclo[3.1.0]hexan-6-yl]pyridin-5-yl]-3-fluorophenyl]-2-oxooxazolidin-5-ylmethyl]-1,2,3-triazole, 5(R)-3-[4-[2-[(1α,5α,6β)-3-t-butoxycarbonyl-6-cyano-3-azabicyclo[3.1.0]hexan-6-yl]pyridin-5-yl]-3,5-difluorophenyl]-5-[N-(t-butoxycarbonyl]-N-(isoxazol-3-yl)]aminomethyloxazolidin-2-one, 5(R)-3-[4-[2-[(1α,5α,6β)-6-cyano-3-azabicyclo[3.1.0]hexan-6-yl]pyridin-5-yl]-3,5-difluorophenyl]-5-[N-(isoxazol-3-yl)]aminomethyloxazolidin-2-one, 1-[5(R)-3-[4-[2-[(1α,5α,6β)-6-cyano-3-(thiatriazol-2-yl)-3-azabicyclo[3.1.0]hexan-6-yl]pyridin-5-yl]-3-fluorophenyl]-2-oxooxazolidin-5-ylmethyl]-1,2,3-triazole, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]thioacetamide, N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]thioacetamide, N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]isothiocyanate, O-methyl-N-[5(S)-3-[4-[2-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]thiocarbamate, O-methyl-N-[5(S)-3-[4-[2-[(1α,5α,6β)-6-cyano-3-azabicyclo[3.1.0]hexan-6-yl]pyridin-5-yl]-3-fluorophenyl]-2-oxooxazolidin-5-ylmethyl]thiocarbamate, an enantiomer, diastereomer, pharmaceutically acceptable salt, hydrate or prodrug thereof.

9. A compound according to claim 8, which is:

1-[5(R)-3-[4-[4-[(1α,5α,6β)-6-Cyano-3-azabicyclo[3.1.0]hexan-6-yl]-3-fluorophenyl]-3-fluorophenyl]-2-oxooxazolidin-5-ylmethyl]-1,2,3-triazole, 1-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-1,2,3-triazole, N-[5(S)-3-[4-[4-[(1α,5α,6β)-6-Cyano-3-azabicyclo[3.1.0]hexan-6-yl]-3-fluorophenyl]phenyl]-2-oxooxazolidin-5-ylmethyl]acetamide, N-[5(S)-3-[4-[2-[(1α,5α,6β)-6-Cyano-3-azabicyclo[3.1.0]hexan-6-yl]pyridin-5-yl]phenyl]-2-oxooxazolidin-5-ylmethyl]acetamide, N-[5(S)-3-[4-[2-[(1α,5α,6β)-6-Cyano-3-azabicyclo[3.1.0]hexan-6-yl]pyridin-5-yl]-3-fluorophenyl]-3-fluorophenyl]-2-oxooxazolidin-5-ylmethyl]acetamide, N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]acetamide, 1-[5(R)-3-[4-[2-[(1α,5α,6β)-6-Amino-3-oxabicyclo[3.1.0]hexan-6-yl]pyridin-5-yl]-3-fluorophenyl]-2-oxooxazolidin-5-ylmethyl]-1,2,3-triazole, 1-[5(R)-3-[4-[4-[(1α,5α,6β)-6-Cyano-3-azabicyclo[3.1.0]hexan-6-yl]-3,5-difluorophenyl]-3-fluorophenyl]-2-oxooxazolidin-5-ylmethyl]-1,2,3-triazole, N-[5(S)-3-[4-[4-[(1α,5α,6β)-6-Cyano-3-azabicyclo[3.1.0]hexan-6-yl]pyridin-5-yl]-3,5-difluorophenyl]-2-oxooxazolidin-5-ylmethyl]acetamide, N-[5(S)-3-[4-[4-[(1α,5α,6β)-6-Cyano-3-azabicyclo[3.1.0]hexan-6-yl]-3,5-difluorophenyl]-3-fluorophenyl]-2-oxooxazolidin-5-ylmethyl]acetamide, N-[5(S)-3-[4-[4-[(1α,5α,6β)-6-Cyano-3-azabicyclo[3.1.0]hexan-6-yl]phenyl]-3-fluorophenyl]-2-oxooxazolidin-5-ylmethyl]acetamide, 1-[5(R)-3-[4-[4-[(1α,5α,6β)-6-Cyano-3-azabicyclo[3.1.0]hexan-6-yl]phenyl]-3-fluorophenyl]-2-oxooxazolidin-5-ylmethyl]-1,2,3-triazole, 4-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-1,2,4-triazole, 5(R)-3-[4-[2-[(1α,5α,6β)-6-Cyano-3-azabicyclo[3.1.0]hexan-6-yl]pyridin-5-yl]-3-fluorophenyl]-5-[(isoxazol-3-yl)oxy]methyloxazolidin-2-one, 5(R)-3-[4-[2-[(1α,5α,6β)-6-Cyano-3-azabicyclo[3.1.0]hexan-6-yl]pyridin-5-yl]-3-fluorophenyl]-5-[N-(isoxazol-3-yl)]aminomethyloxazolidin-2-one, N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]cyclopropanecarboxamide, N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]difluoroacetamide, 1-[5(R)-3-[4-[2-[(1α,5α,6β)-3-[(1-Aminocyclopropan-1-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, enantiomer, diastereomer, or pharmaceutically acceptable salt, hydrate or prodrug thereof.

10. The compound according to claim 9, which is:

1-[5(R)-3-[4-[4-[(1α,5α,6β)-6-Cyano-3-azabicyclo[3.1.0]hexan-6-yl]-3-fluorophenyl]-3-fluorophenyl]-2-oxooxazolidin-5-ylmethyl]-1,2,3-triazole hydrochloride, 1-[5(R)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]-1,2,3-triazole hydrochloride, N-[5(S)-3-[4-[4-[(1α,5α,6β)-6-Cyano-3-azabicyclo[3.1.0]hexan-6-yl]-3-fluorophenyl]phenyl]-2-oxooxazolidin-5-ylmethyl]acetamide hydrochloride, N-[5(S)-3-[4-[2-[(1α,5α,6β)-6-Cyano-3-azabicyclo[3.1.0]hexan-6-yl]pyridin-5-yl]phenyl]-2-oxooxazolidin-5-ylmethyl]acetamide hydrochloride, N-[5(S)-3-[4-[2-[(1α,5α,6β)-6-Cyano-3-azabicyclo[3.1.0]hexan-6-yl]-3-fluorophenyl]-3-fluorophenyl]-2-oxooxazolidin-5-ylmethyl]acetamide hydrochloride, or N-[5(S)-3-[4-[2-[(1α,5α,6β)-6-Cyano-3-azabicyclo[3.1.0]hexan-6-yl]pyridin-5-yl]-3-fluorophenyl]-2-oxooxazolidin-5-ylmethyl]acetamide hydrochloride.

11. A pharmaceutical composition comprised of a compound in accordance with claim 1 in combination with a pharmaceutically acceptable carrier, said composition optionally in combination with a vitamin selected from the group consisting vitamin B2, vitamin B6, vitamin B12 and folic acid.

12. The compound according to claim 1 wherein $R_3$ is 1,2,3-triazole, 1,2,4- triazole, 1,2,5-triazole, tetrazole, pyrazole or imidazole, any of which may contain 1 to 3 substitutents selected from $R_7$.

13. The compound according to claim 12 which is:

1-[5(R)-3-[4-[2-[(1α,5α,6β)-3t-butoxycarbonyl-6-cyano-3-azabicyclo[3.1.0]hexan-6- yl]pyridin-5-yl]phenyl]-2-oxooxazolidin-5-ylmethyl]- 1,2,3-triazole, 1-[5(R)-3-[4-[2-[(1α,5α,6β)-6-cyano-3-azabicyclo[3.1.0]hexan-6-yl]pyridin-5-yl]phenyl]- 2-oxooxazolidin-5-ylmethyl]-1,2,3-triazole hydrochloride, 1-[5(R)-3-[4-[4-[(1α,5α,6β)-3-t-butoxycarbonyl-6-cyano-3-azabicyclo3.1.0]hexan-6-yl]- 3-fluorophenyl]phenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3- fluorophenyl]phenyl]-2-oxooxazolidin-5 -ylmethyl]-1,2,3-triazole hydrochloride, 1-[5(R)-3-[4-[4-[(1α,5α,6β)-3-t-butoxycarbonyl-6-cyano-3-azabicyclolj3.1.0]hexan-6-yl]- 3-fluorophenyl]-3-fluorophenyl]-2-oxooxazolidin-5 -ylmethyl]-1,2,3-triazole, 1-[5(R)-3-[4-[4-[(1α,5α,6β)-6-cyano-3-azabicyclo[3.1.0]hexan-6-yl]-3-fluorophenyl]-3- fluorophenyl]-2-oxooxazolidin-5-ylmethyl]-1,2,3-triazole hydrochloride, 1-[5(R)-3-[4-[2-[(1α,5α,6β)-3-t-butoxycarbonyl-6-cyano-3-azabicyclo[3.1.0]hexan-6- yl]pyridin-5-yl]-3-fluorophenyl]-2-oxooxazolidin-5-ylmethyl]- 1,2,3-triazole, 1-[5(R)-3-[4-[2-[(1α,5α, 6β)-6-cyano-3-azabicyclo[3.1.0]hexan-6-yl]pyridin-5-yl]-3- fluorophenyl]-2-oxooxazolidin-5-ylmethyl]- 1,2,3-triazole hydrochloride, 1-[5(R)-3-[4-[2-[(1α,5α,6β)-6-t-butoxycarbonylamino-3-oxabicyclo[3.1.0]hexan-6- yl]pyridin-5-yl]-3-fluorophenyl]-2-oxooxazolidin-5-ylmethyl]-1,2,3-triazole, 1-[5(R)-3-[4-[2-[(1α,5α,6β)-6-amino-3-oxabicyclo [3.1.0]hexan-6-yl]pyridin-5-yl]-3- fluorophenyl]-2-oxooxazolidin-5-ylmethyl]-1,2,3-triazole, 1-[5(R)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]-1,2,3-triazole, 1-[5(R)-3-[4-[2-[(1α,5α,6β)-6-t-butoxycarbonylamino-3-oxabicyclo[3.1.0]hexan-6- yl]pyridin-5-yl]phenyl]-2-oxooxazolidin-5-ylmethyl]-1,2,3-triazole, 1-[5(R)-3-[4-[2-[(1α,5α,6β)-6-amino-3-oxabicyclo [3.1.0]hexan-6-yl]pyridin-5- yl]phenyl]-2-oxooxazolidin-5-ylmethyl]1,2,3-triazole, 1-[5(R)-3-[4-[2-[(1α,5α,6β)-6-cyano-3-oxabicyclo [3.1.0]hexan-6-yl]pyridin-5- yl]phenyl]-2-oxooxazolidin-5-ylmethyl]-1,2,3-triazole, 1-[5(R)-3-[4-[4-[(1α,5α,6β)-3-t-butoxycarbonyl-6-cyano-3-azabicyclo[3.1.0]hexan-6-yl]- 3,5-difluorophenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3,5-difluorophenyl]- 3-fluorophenyl]-2-oxooxazolidin-5-ylmethyl]- 1,2,3-triazole, 1-[5(R)-3-[4-[4-[(1α,5α,6β)-3-t-butoxycarbonyl-6-cyano-3-azabicyclo[3.1.0]hexan-6-yl]- 3-fluorophenyl]-3, 5-difluorophenyl]-2-oxooxazolidin-5-ylmethyl]-1,2,3-triazole, 1-[5(R)-3-[4-[4-[(1α,5α,6β)-6-cyano-3-azabicyclo[3.1.0]hexan-6-yl]-3-fluorophenyl]-3,5- difluorophenyl]-2-oxooxazolidin-5-ylmethyl]- 1,2,3-triazole hydrochloride, 1-[5(R)-3-[4-[4-[(1α,5α,6β)-3-t-butoxycarbonyl-6-cyano-3-azabicyclo[3.1.0]hexan-6- yl]pyridin-5-yl]-3,5-difluorophenyl]-2-oxooxazolidin-5-ylmethyl]-1,2,3-triazole, 1-[5(R)-3-[4-[4-[(1α,5α,6β)-6-cyano-3-azabicyclo[3.1.0] hexan-6-yl]pyridin-5-yl]-3,5- difluorophenyl]-2-oxooxazolidin-5-ylmethyl]- 1,2,3-triazole, 1-[5(R)-3-[4-[4-[(1α,5α,6β)-3-t-butoxycarbonyl-6-cyano-3-azabicyclo[3.1.0]hexan-6- yl]phenyl]-3-fluorophenyl]-2-oxooxazolidin-5-ylmethyl]-1,2,3-triazole, 1-[5(R)-3-[4-[4-[(1α,5α,6β)-6-cyano-3-azabicyclo[3.1.0] hexan-6-yl]phenyl]-3- fluorophenyl]-2-oxooxazolidin-5-ylmethyl]-1,2,3-triazole, 1-[5(R)-3-[4-[2-[(1α,5α,6β)-6-t-butoxycarbonylamino-3-oxabicyclo[3.1.0]hexan-6- yl]pyridin-5-yl]-3,5-difluorophenyl]-2-oxooxazolidin-5-ylmethyl]-1,2,3-triazole, 1-[5(R)-3-[4-[2-[(1α,5α,6β)-6-amino-3-oxabicyclo [3.1.0]hexan-6-yl]pyridin-5-yl]-3,5- difluorophenyl]-2-oxooxazolidin-5-ylmethyl]-1,2,3-triazole, 1-[5(R)-3-[4-[2-[(1α,5α,6β)-6-cyano-3-oxabicyclo [3.1.0]hexan-6-yl]pyridin-5-yl]-3,5- difluorophenyl]-2-oxooxazolidin-5-ylmethyl]-1,2,3-triazole, 1-[5(R)-3-[4-[2-[(1α,5α,6β)-6-cyano-3-thiabicyclo [3.1.0]hexan-6-yl]pyridin-5-yl]-3- fluorophenyl]-2-oxooxazolidin-5-ylmethyl]-1,2,3-triazole, 1-[5(R)-3-[4-[2-[(1α,5α,6β)-6-cyano-3-thiabicyclo [3.1.0]hexan-6-yl]pyridin-5-yl]-3- fluorophenyl]-2-oxooxazolidin-5-ylmethyl]-1,2,3-triazole S-oxide, 1-[5(R)-3-[4-[2-[(1α,5α,6β)-6-cyano-3-thiabicyclo [3.1.0]hexan-6-yl]pyridin-5-yl]-3- fluorophenyl]-2-oxooxazolidin-5-ylmethyl]-1,2,3-triazole S,S-dioxide, 4-[5(R)-3-[4-[2-[(1α,5α,6β)-3-t-butoxycarbonyl-6-cyano-3-azabicyclo[3.1.0]hexan-6- yl]pyridin-5-yl]-3-fluorophenyl]-2-oxooxazolidin-5-ylmethyl]- 1,2,4-triazole, 4-[5(R)-3-[4-[2-[(1α,5α,6β)-6-cyano-3-azabicyclo [3.1.0]hexan-6-yl]pyridin-5-yl]-3- fluorophenyl]-2-oxooxazolidin-5-ylmethyl]-1,2,4-triazole, 1-[5(R)-3-[4-[2-[(1α,5α,6β)-6-cyano-3-methyl-3-azabicyclo [3.1.0]hexan-6-yl]pyridin-5- yl]-3-fluorophenyl]-2-oxooxazolidin-5-ylmethyl]-1,2,3-triazole, 1-[5(R)-3-[4-[2-[(1α,5α,6β)-3,6-dicyano-3-azabicyclo [3.1.0]hexan-6-yl]pyridin-5-yl]-3- fluorophenyl]-2-oxooxazolidin-5-ylmethyl]-1,2,3-triazole, 1-[5(R)-3-[4-[2-[(1α,5α,6β)-3-[(1-t-butoxycarbonylaminocyclopropan-1-yl)carbonyl]-6- cyano-3-azabicyclo [3.1.0]hexan-6-yl]pyridin-5-y]3-fluorophenyl]-2-oxooxazolidin-5- ylmethyl]-1,2,3-triazole, 1-[5(R)-3-[4-[2-[(1α,5α,6β)-3-[(1-aminocyclopropan-1-yl)carbonyl]-6-cyano-3- azabicyclo [3.1.0]hexan-6-yl]pyridin-5-yl]-3 -fluorophenyl]-2-oxooxazolidin-5-ylmethyl]-1,2,3- triazole, 1-[5(R)-3-[4-[2-[(1α,5α,6β)-6-cyano-3-[2-(phthalimid-2-yl)ethyl]-3- azabicyclo[3.1.0]hexan-6-yl]pyridin-5-yl]-3-fluorophenyl]-2-oxooxazolidin-5-ylmethyl]- 1,2,3- triazole, 1-[5(R)-3-[4-[2-[(1α,5α,6β)-3-(2-aminoethyl)-6-cyano-3-azabicyclo[3.1.0]hexan-6- yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[2-(1,2,4-triazol-4-yl)ethyl]-3- azabicyclo[3.1.0]hexan-6-yl]pyridin-5-yl]-3-fluorophenyl]-2-oxooxazolidin-5-ylmethyl]-1,2, 3- triazole, 1-[5(R)-3-[4-[2-[(1α,5α,6β)-3-bromoacetyl-6-cyano-3-azabicyclo[3.1.0]hexan-6- yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(morpholin-4-yl)acetyl-3-azabicyclo[3.1.0]hexan- 6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(5-cyanopyridin-2-yl)-3-azabicyclo[3.1.0]hexan- 6-yl]pyridin-5-yl]-3fluorophenyl]-2-oxooxazolidin-5-ylmethyl]-1,2,3-triazole, 1-[5(R)-3-[4-[2-[(1α,5α,6β)-6-cyano-3-(1,3-dihydroxypropan-2-yl)-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[((2S)-pyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S,4R)-1-t-butoxycabonyl-4-hydroxypyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[((2S,4R)-4-hydroxypyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-[((2S,4S)-4-fluoropyrrolidin-2-yl)carbonyl]-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[4-[(1α,5α,6β)-3-t-butoxycarbonyl-6-(t-butoxycarbonyl)amino-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[4-[(1α,5α,6β)-6-amino-3-azabicyclo[3.1.0]hexan-6-yl]pyridin-5-yl]-3-fluorophenyl]-2-oxooxazolidin-5-ylmethyl]-1,2,3-triazole dihydrochloride, 1-[5(R)-3-[4-[2-[(1α,5α,6β)-3-acetoxyacetyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-hydroxyacetyl-3-azabicyclo[3.1.0]hexan-6-yl]pyridin-5-yl]-3-fluorophenyl]-2-oxooxazolidi-5-ylmethyl]-1,2,3-triazole, 1-[5(R)-3-[4-[2-[(1α,5α,6β)-3,6-dicyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-methyl-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[3-fluoro-4-[2-[(1α,5α,6β)-6-hydroxymethyl-3-oxabicyclo[3.1.0]hexan-6-yl]pyridin-5-yl]phenyl]-2-oxooxazolidin-5-ylmethyl]-1,2,3-triazole, 1-[5(R)-3-[4-[2-[(1α,5α,6β)-6-cyano-3-oxabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[4-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[4-[(1α,5α,6β)-6-cyano-3-azabicyclo[3.1.0]hexan-6-yl]pyridin-5-yl]-3-fluorophenyl]-2-oxooxazolidin-5-ylmethyl]-4-fluoro-1,2,3-triazole, 1-[5(R)-3-[4-[4-[(1α,5α,6β)-3-t-butoxycarbonyl-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole, 1-[5(R)-3-[4-[4-[(1α,5α,6β)-6-cyano-3-azabicyclo[3.1.0]hexan-6-yl]pyridin-5-yl]-3-fluorophenyl]-2-oxooxazolidin-5-ylmethyl]-5-fluoro-1,2,3-triazole, 1-[5(R)-3-[4-[2-[(1α,5α,6β)-3-(4-t-butoxycarbonylpiperazin-1-yl)acetyl-6-cyano-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(piperazin-1-yl)acetyl-3-azabicyclo[3.1.0]hexan-6-yl]pyridin-5-yl]-3-fluorophenyl]-2-oxooxazolidin-5-ylmethyl]-1,2,3-triazole dihydrochloride, 1-[5(R)-3-[4-[2-[(1α,5α,6β)-6-cyano-3-oxabicyclo[3.1.0]hexan-6-yl]thiophen-4-yl]-3-fluorophenyl]-2-oxooxazolidin-5-ylmethyl]-1,2,3-triazole, 1-[5(R)-3-[4-[2-[(1α,5α,6β)-6-cyano-3-(piperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(pyrrolidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(4-dimethylaminopiperidin-1-yl)acetyl-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[((2S)-1-t-butoxycabonylpyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S)-pyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S,4R)-4-hydroxypyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole hydrochloride, 1-[5(R)-3-[4-[2-[(1α,5α,6β)-3-[((2S,4R)-1-t-butoxycabonyl-4-hydroxypyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-3-[((2S,4S)-1-t-butoxycabonyl-4-fluoropyrrolidin-2-yl)carbonyl]-6-cyano-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-cyano-3-[((2S,4S)-4-fluoropyrrolidin-2-yl)carbonyl]-3-azabicyclo[3.1.0]hexan-6-yl]pyridin-5-yl]-3,5-difluorophenyl]-2-oxooxazolidin-5-ylmethyl]-1,2,3-triazole, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-amino-3-thiabicyclo[3.1.0]hexan-6-yl]pyridin-5-yl]-3-fluorophenyl]-2-oxooxazolidin-5-ylmethyl]-1,2,3-triazole S-oxide, 1-[5(R)-3-[4-[2-[(1α,5α,6β)-6-t-butoxycarbonylamino-3-thiabicyclo[3.1.0]hexan-6-yl]pyridin-5-yl]-3-fluorophenyl]-2-oxooxazolidin-5-ylmethyl]1,2,3-triazole S,S-dioxide, 1-[5(R)-3-[4-[2-[(1α,5α,6β)-6-amino-3-thiabicyclo [3.1.0]hexan-6-yl]pyridin-5-yl]-3- fluorophenyl]-2-oxooxazolidin-5-ylmethyl]-1,2,3-triazole S,S-dioxide, 1-[5(R)-3-[4-[2-[(1α,5α,6β)-6-t-butoxycarbonylamino-3-thiabicyclo[3.1.0]hexan-6- yl]pyridin-5-yl]-3,5-difluorophenyl]-2-oxooxazolidin-5-ylmethyl]-1,2,3-triazole, 1-[5(R)-3-[4-[2-[(1α,5α,6β)-6-amino-3-thiabicyclo [3.1.0]hexan-6-yl]pyridin-5-yl]-3,5- difluorophenyl]-2-oxooxazolidin-5-ylmethyl]-1,2,3-triazole, 1-[5(R)-3-[4-[2-[(1α,5α,6β)-6-t-butoxycarbonylamino-3-thiabicyclo[3.1.0]hexan-6- yl]pyridin-5-yl]-3,5-difluorophenyl]-2-oxooxazolidin-5-ylmethyl]- 1,2,3-triazole S-oxide, 1-[5(R)-3-[4-[2-[(1α,5α,6β)-6-amino-3-thiabicyclo [3.1.0]hexan-6-yl]pyridin-5-yl]-3,5- difluorophenyl]-2-oxooxazolidin-5-ylmethyl]-1,2,3-triazole S-oxide, 1-[5(R)-3-[4-[2-[(1α,5α,6β)-6-t-butoxycarbonylamino-3-thiabicyclo[3.1.0]hexan-6- yl]pyridin-5-yl]-3,5-difluorophenyl]-2-oxooxazolidin-5-ylmethyl]-1,2,3-triazole S,S-dioxide, 1-[5(R)-3-[4-[2-[(1α,5α,6β)-6-amino-3-thiabicyclo [3.1.0]hexan-6-yl]pyridin-5-yl]-3,5- difluorophenyl]-2-oxooxazolidin-5-ylmethyl]-1,2,3-triazole S,S-dioxide, 1-[5(R)-3-[4-[2-[(1α,5α,6β)-6-cyano-3-(4-methylpiperazin- 1-yl)acetyl-3- azabicyclo[3.1.0]hexan-6-yl]pyridin-5-yl]-3-fluorophenyl]-2-oxooxazolidin-5-ylmethyl]-1,2,3- triazole, 1-[5(R)-3-[4-[2-[(1α,5α,6β)-6-cyano-3-thiabicyclo [3.1.0]hexan-6-yl]pyridin-5- yl]phenyl]-2-oxooxazolidin-5-ylmethyl]-1,2,3-triazole, 1-[5(R)-3-[4-[2-[(1α,5α,6β)-6-cyano-3-thiabicyclo [3.1.0]hexan-6-yl]pyridin-5- yl]phenyl]-2-oxooxazolidin-5-ylmethyl]-1,2,3-triazole S-oxide, 1-[5(R)-3-[4-[2-[(1α,5α,6β)-6-cyano-3-thiabicyclo [3.1.0]hexan-6-yl]pyridin-5- yl]phenyl]-2-oxooxazolidin-5-ylmethyl]- 1,2,3-triazole S,S-dioxide, 1-[5(R)-3-[4-[2-[(1 α,5α,6β)-6-cyano-3-thiabicyclo [3.1.0]hexan-6-yl]pyridin-5-yl]-3,5- difluorophenyl]-2-oxooxazolidin-5-ylmethyl]-1,2,3-triazole, 1-[5(R)-3-[4-[2-[(1α,5α,6β)-6-cyano-3-thiabicyclo [3.1.0]hexan-6-yl]pyridin-5-yl]-3,5- difluorophenyl]-2-oxooxazolidin-5-ylmethyl]-1,2,3-triazole S-oxide, 1-[5(R)-3-[4-[2-[(1α,5α,6β)-6-cyano-3-thiabicyclo [3.1.0]hexan-6-yl]pyridin-5-yl]-3,5- difluorophenyl]-2-oxooxazolidin-5-ylmethyl]-1,2,3-triazole S,S-dioxide, 1-[5(R)-3-[4-[2-[(1α,5α,6β)-6-cyano-3-(1,3-diacetoxypropan-2-yl)-3-azabicyclo[3.1.0]hexan-6-yl]pyridin-5-yl]-3-fluorophenyl]-2-oxooxazolidin-5-ylmethyl]-1,2,3-triazole, 1-[5(R)-3-[4-[2-[(1α,5α,6β)-3-[(3R,4S)- 1-azabicyclo[2.2.1]hepan-3-yl]carbonyl-6-cyano- 3-azabicyclo[3.1.0]hexan-6-yl]pyridin-5-yl]-3-fluorophenyl]-2-oxooxazolidin-5-ylmethyl]- 1,2,3-triazole, 1-[5(R)-3-[4-[2-[(1α,5α,6β)-6-cyano-3-(pyridin-2-yl)-3-azabicyclo[3.1.0]hexan-6- yl]pyridin-5-yl]-3-fluorophenyl]-2-oxooxazolidin-5-ylmethyl]-1,2,3-triazole, 1-[5(R)-3-[4-[2-[(1α,5α,6β)-6-cyano-3-(thiatriazol-2-yl)-3-azabicyclo[3.1.0]hexan-6- yl]pyridin-5-yl]-3-fluorophenyl]-2-oxooxazolidin-5-ylmethyl]-1,2,3-triazole, or an enantiomer, diastereomer, pharmaceutically acceptable salt, hydrate or prodrug thereof.

14. The compound according to claim 8, which is:

N-[5(S)-3-[4-[2-[(1α,5α,6β)-6-t-butoxycarbonylamino-3-oxabicyclo[3.1.0]hexan-6- yl]pyridin-5 -yl]-3-fluorophenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5-yl]-3- fluorophenyl]-2-oxooxazolidin-5-ylmethyl]acetamide, 1-[5(R)-3-[4-[2-[(1α,5α,6β)-6-t-butoxycarbonylamino-3-oxabicyclo[3.1.0]hexan-6- yl]pyridin-5-yl]-3-fluorophenyl]-2-oxooxazolidin-5-ylmethyl]-1,2,3-triazole, 1-[5(R)-3-[4-[2-[(1α,5α,6β)-6-amino-3-oxabicyclo [3.1.0]hexan-6-yl]pyridin-5-yl]-3- fluorophenyl]-2-oxooxazolidin-5-ylmethyl]-1,2,3-triazole, N-[5(S)-3-[4-[4-[(1α,5α,6β)-6-cyano-3-oxabicyclo [3.1.0]hexan-6-yl]pyridin-5-yl]-3- fluorophenyl]-2-oxooxazolidin-5-ylmethyl]acetamide, 1-[5(R)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]-1,2,3-triazole, N-[5(S)-3-[4-[2-[(1α,5α,6β)-6-t-butoxycarbonylamino-3-oxabicyclo[3.1.0]hexan-6- yl]pyridin-5-yl]phenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5- yl]phenyl]-2-oxooxazolidin-5-ylmethyl]acetamide, 1-[5(R)-3-[4-[2-[(1α,5α,6β)-6-t-butoxycarbonylamino-3-oxabicyclo[3.1.0]hexan-6- yl]pyridin-5 -yl]phenyl]-2-oxooxazolidin-5-ylmethyl]-1,2,3-triazole, 1-[5(R)-3-[4-[2-[(1α,5α,6β)-6-amino-3-oxabicyclo [3.1.0]hexan-6-yl]pyridin-5-

N-[5(S)-3-[4-[4-[(1α,5α,6β)-6-cyano-3-oxabicyclo [3.1.0]hexan-6-yl]pyridin-5- yl]phenyl]-2-oxooxazolidin-5-ylmethyl]acetamide, 1-[5(R)-3-[4-[2-[(1α,5α,6β)-6-cyano-3-oxabicyclo [3.1.0]hexan-6-yl]pyridin-5- yl]phenyl]-2-oxooxazolidin-5-ylmethyl]-1,2,3-triazole, 1-[5(R)-3-[4-[2-[(1α,5α,6β)-6-t-butoxycarbonylamino-3-oxabicyclo[3.1.0]hexan-6- yl]pyridin-5-yl]-3,5-difluorophenyl]-2-oxooxazolidin-5-ylmethyl]- 1,2,3-triazole, 1-[5(R)-3-[4-[2-[(1α,5α,6β)-6-amino-3-oxabicyclo [3.1.0]hexan-b-yl]pyridin-5-yl]-3,5- difluorophenyl]-2-oxooxazolidin-5-ylmethyl]-1,2,3-triazole, N-[5(S)-3-[4-[2-[(1α,5α,6β)-6-t-butoxycarbonylamino-3-oxabicyclo[3.1.0]hexan-6- yl]pyridin-5-yl]-3,5-difluorophenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5-yl]-3,5- difluorophenyl]-2-oxooxazolidin-5-ylmethyl]acetamide, N-[5(S)-3-[4-[2-[(1α,5α,6β)-6-cyano-3-oxabicyclo [3.1.0]hexan-6-yl]pyridin-5-yl]-3,5- difluorophenyl]-2-oxooxazolidin-5-ylmethyl]acetamide, 1-[5(R)-3-[4-[2-[(1α,5α,6β)-6-cyano-3-oxabicyclo [3.1.0]hexan-6-yl]pyridin-5-yl]-3,5- difluorophenyl]-2-oxooxazolidin-5-ylmethyl]-1,2,3-triazole, 5(R)-3-[4-[2-[(1α,5α,6β)-6-cyano-3-oxabicyclo[3.1.0] hexan-6-yl]pyridin-5-yl]-3- fluorophenyl]-5-[(isoxazol-3-yl)oxy]methyloxazolidin-2-one, 5(R)-5-[N-(t-butoxycarbonyl)-N-(isoxazol-3-yl)]aminomethyl-3-[4-[2-[(1α,5α,6β)-6- cyano-3-oxabicyclo [3.1.0]hexan-6-yl]pyridin-5-yl]-3-fluorophenyl]oxazolidin-2-one, 5(R)-3-[4-[2-[(1α,5α,6β)-6-cyano-3-oxabicyclo[3.1.0] hexan-6-yl]pyridin-5-yl]-3- fluorophenyl]-5-[N-(isoxazol-3-yl))aminomethyloxazolidin-2-one, N-[5(S)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]propionamide, N-[5(S)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]difluoroacetamide, N-[5(S)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]cyclopropanecarboxamide, 1-[5 (R)-3-[3-fluoro-4-[2-[(1α,5α,6β)-6-hydroxymethyl-3-oxabicyclo[3.1.0]hexan-6- yl]pyridin-5-yl]phenyl]-2-oxooxazolidin-5-ylmethyl]-1,2,3-triazole, 1-[5(R)-3-[4-[2-[(1α,5α,6β)-6-cyano-3-oxabicyclo [3.1.0]hexan-6-yl]pyridin-5-yl]-3- fluorophenyl]-2-oxooxazolidin-5-ylmethyl]-4-fluoro-1,2,3-triazole, 1-[5(R)-3-[4-[2-[(1α,5α,6β)-6-cyano-3-oxabicyclo [3.1.0]hexan-6-yl]thiophen-4-yl]-3- fluorophenyl]-2-oxooxazolidin-5-ylmethyl]-1,2,3 -triazole, or an enantiomer, diastereomer, pharmaceutically acceptable salt, hydrate or prodrug thereof.

15. The compound according to claim 14, which is:

N-[5(S)-3-[4-[2-[(1α,5α,6β)-6-t-butoxycarbonylamino-3-oxabicyclo[3.1.0]hexan-6- yl]pyridin-5-yl]-3-fluorophenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5-yl]-3- fluorophenyl]-2-oxooxazolidin-5-ylmethyl]acetamide, N-[5(S)-3-[4-[4-[(1α,5α,6β)-6-cyano-3-oxabicyclo [3.1.0]hexan-6-yl]pyridin-5-yl]-3- fluorophenyl]-2-oxooxazolidin-5-ylmethyl]acetamide, N-[5(S)-3-[4-[2-[(1α,5α,6β)-6-t-butoxycarbonylamino-3-oxabicyclo[3.1.0]hexan-6- yl]pyridin-5-yl]phenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5- yl]phenyl]-2-oxooxazolidin-5-ylmethyl]acetamide, N-[5(S)-3-[4-[4-[(1α,5α,6β)-6-cyano-3-oxabicyclo [3.1.0]hexan-6-yl]pyridin-5- yl]phenyl]-2-oxooxazolidin-5-ylmethyl]acetamide, N-[5(S)-3-[4-[2-[(1α,5α,6β)-6-t-butoxycarbonylamino-3-oxabicyclo[3.1.0]hexan-6- yl]pyridin-5-yl]-3,5-difluorophenyl]-2-oxooxazolidin-5-ylmethyl]acetamide, N-[5(S)-3-[4-[2-[(1α,5α,6β)-6-amino-3-oxabicyclo [3.1.0]hexan-6-yl]pyridin-5-yl]-3,5- difluorophenyl]-2-oxooxazolidin-5-ylmethyl]acetamide, N-[5(S)-3-[4-[2-[(1α,5α,6β)-6-cyano-3-oxabicyclo [3.1.0]hexan-6-yl]pyridin-5-yl]-3,5- difluorophenyl]-2-oxooxazolidin-5-ylmethyl]acetamide, or an enantiomer, diastereomer, pharmaceutically acceptable salt, hydrate or prodrug thereof.

16. The compound according to claim 15, which is:

N-[5(S)-3-[4-[4-[(1α,5α,6β)-6-cyano-3-oxabicyclo [3.1.0]hexan-6-yl]pyridin-5-yl]-3- fluorophenyl]-2-oxooxazolidin-5 -ylmethyl]acetamide, N-[5(S)-3-[4-[4-[(1α,5α,6β)-6-cyano-3-oxabicyclo [3.1.0]hexan-6-yl]pyridin-5- yl]phenyl]-2-oxooxazolidin-5-ylmethyl]acetamide, N-[5(S)-3-[4-[2[(1α,5α,6β)-6-cyano-3-oxabicyclo [3.1.0βhexan-6-yl]pyridin-5-yl]-3,5- difluorophenyl]-2-oxooxazolidin-5-ylmethyl]acetamide, or an enantiomer, diastereomer, pharmaceutically acceptable salt, hydrate or prodrug thereof.

17. The compound according to claim 16, which is:

N-[5(S)-3-[4-[4-[(1α,5α,6β)-6-cyano-3-oxabicyclo [3.1.0]hexan-6-yl]pyridin-5-yl]-3- fluorophenyl]-2-oxooxazolidin-5-ylmethyl] acetamide, or a pharmaceutically acceptable salt or hydrate thereof.

18. The compound according to claim 16, which is:

N-[5(S)-3-[4-[4-[(1α,5α,6β)-6-cyano-3-oxabicyclo [3.1.0]hexan-6-yl]pyridin-5- yl]phenyl]-2-oxooxazolidin-5-ylmethyl]acetamide, or a pharmaceutically acceptable salt or hydrate thereof.

19. The compound according to claim 16, which is:

N-[5(S)-3-[4-[2-[(1α,5α,6β)-6-cyano-3-oxabicyclo [3.1.0]hexan-6-yl]pyridin-5-yl]-3,5- difluorophenyl]-2-oxooxazolidin-5-ylmethyl]acetamide, or a pharmaceutically acceptable salt or hydrate thereof.

20. A pharmaceutical composition comprised of a compound in accordance with claim 13 and a pharmaceutically acceptable carrier.

21. A pharmaceutical composition comprised of a compound in accordance with claim 14 and a pharmaceutically acceptable carrier.

22. A pharmaceutical composition comprised of a compound in accordance with claim 17 and a pharmaceutically acceptable carrier.

23. A pharmaceutical composition comprised of a compound in accordance with claim 18 and a pharmaceutically acceptable carrier.

24. A pharmaceutical composition comprised of a compound in accordance with claim 19 and a pharmaceutically acceptable carrier.

25. A pharmaceutical composition comprised of a compound in accordance with claim 13 in combination with a pharmaceutically acceptable carrier, said composition optionally in combination with a vitamin selected from the group consisting vitamin B2, vitamin B6, vitamin B12 and folic acid.

26. A pharmaceutical composition comprised of a compound in accordance with claim 14 in combination with a pharmaceutically acceptable carrier, said composition optionally in combination with a vitamin selected from the group consisting vitamin B2, vitamin B6, vitamin B12 and folic acid.

27. A pharmaceutical composition comprised of a compound in accordance with claim 17 in combination with a pharmaceutically acceptable carrier, said composition optionally in combination with a vitamin selected from the group consisting vitamin B2, vitamin B6, vitamin B12 and folic acid.

28. A pharmaceutical composition comprised of a compound in accordance with claim 18 in combination with a pharmaceutically acceptable carrier, said composition optionally in combination with a vitamin selected from the group consisting vitamin B2, vitamin B6, vitamin B12 and folic acid.

29. A pharmaceutical composition comprised of a compound in accordance with claim 19 in combination with a pharmaceutically acceptable carrier, said composition optionally in combination with a vitamin selected from the group consisting vitamin B2, vitamin B6, vitamin B12 and folic acid.

* * * * *

UNITED STATES PATENT AND TRADEMARK OFFICE
CERTIFICATE OF CORRECTION

PATENT NO.       : 7,462,633 B2
APPLICATION NO.  : 10/878637
DATED            : December 9, 2008
INVENTOR(S)      : Yasumichi Fukuda It is certified that error appears in the above-identified patent and that said Letters Patent is hereby corrected as shown below:

IN THE CLAIMS:

In Column 127, Line 52 (Claim 1), change "ammo" to --amino--;

In Column 133, Lines 48 and 49 (Claim 8), change "butoxycabonylpyrrolidin" to --butoxycarbonylpyrrolidin--;

Lines 56 and 57 (Claim 8), change "butoxycabonyl" to --butoxycarbonyl--;

Lines 64 and 65 (Claim 8), change "butoxycabonyl" to --butoxycarbonyl--;

In Column 135, Line 2 (Claim 8), change "hexan-6-yl]-3-fluorophenyl]" to --hexan-6-yl]pyridine-5-yl]-3-fluorophenyl]--;

Line 34 (Claim 8), change "butoxycabonylpyrrolidin" to --butoxycarbonylpyrrolidin--;

Line 46 (Claim 8), change "butoxycabonyl" to --butoxycarbonyl--;

Line 50 (Claim 8), change "butoxycabonyl" to --butoxycarbonyl--;

In Column 136, Line 22 (Claim 8), change "[3.1.0]hexan-6-yl]-3,5-difluorophenyl]" to --[3.1.0]hexan-6-yl]pyridine-5-yl]-3,5-difluorophenyl--;

In Column 138, Line 27 (Claim 9), change "enantiomer" to --on an enantiomer--;

In Column 141, Line 5 (Claim 13), change "butoxycabonylpyrrolidin" to --butoxycarbonylpyrrolidin--;

Line 13 (Claim 13), change "butoxycabonyl" to --butoxycarbonyl--;

Line 21 (Claim 13), change "butoxycabonyl" to --butoxycarbonyl--;

Line 37 (Claim 13), change "chioride," to --chloride--;

UNITED STATES PATENT AND TRADEMARK OFFICE
CERTIFICATE OF CORRECTION

PATENT NO. : 7,462,633 B2
APPLICATION NO. : 10/878637
DATED : December 9, 2008
INVENTOR(S) : Yasumichi Fukuda It is certified that error appears in the above-identified patent and that said Letters Patent is hereby corrected as shown below:

In Column 142, Line 11 (Claim 13), change "dihydrochioride," to --dihydrochloride--;

Line 27 (Claim 13), change "butoxycabonylpyrrolidin" to --butoxycarbonylpyrrolidin--;

Line 39 (Claim 13), change "butoxycabonyl" to --butoxycarbonyl--;

Line 43 (Claim 13), change "butoxycabonyl" to --butoxycarbonyl--;

In Column 144, Line 26 (Claim 14), change "pyridin-5-" to --pyridin-5-yl]-2-oxooxazolidin-5-ylmethyl]-1,2,3-triazole,--.

Signed and Sealed this

Eighth Day of December, 2009

David J. Kappos
*Director of the United States Patent and Trademark Office*